US009637788B2

(12) United States Patent
Ochoa et al.

(10) Patent No.: US 9,637,788 B2
(45) Date of Patent: May 2, 2017

(54) DISCRIMINATION OF BLOOD TYPE VARIANTS

(75) Inventors: Jorge Ochoa, Derio (ES); Monica Lopez, Derio (ES); Sergio Escorza, Derio (ES); Diego Tejedor, Derio (ES); Antonio Martinez, Derio (ES); Laureano Simon, Derio (ES)

(73) Assignee: Progenika Biopharma, S.A., Derio (ES)

( * ) Notice: Subject to any disclaimer, the term of this patent is extended or adjusted under 35 U.S.C. 154(b) by 466 days.

(21) Appl. No.: 14/126,819

(22) PCT Filed: Jun. 14, 2012

(86) PCT No.: PCT/EP2012/061270

§ 371 (c)(1), (2), (4) Date: Mar. 24, 2014

(87) PCT Pub. No.: WO2012/171990

PCT Pub. Date: Dec. 20, 2012

(65) Prior Publication Data

US 2014/0220567 A1 Aug. 7, 2014

Related U.S. Application Data

(60) Provisional application No. 61/553,726, filed on Oct. 31, 2011, provisional application No. 61/498,317, filed on Jun. 17, 2011.

(51) Int. Cl.
*C12Q 1/68* (2006.01)
*C12P 19/34* (2006.01)

(52) U.S. Cl.
CPC ..... *C12Q 1/6881* (2013.01); *C12Q 2600/156* (2013.01); *C12Q 2600/16* (2013.01); *C12Q 2600/172* (2013.01)

(58) Field of Classification Search
None
See application file for complete search history.

(56) References Cited

U.S. PATENT DOCUMENTS

2012/0172239 A1 7/2012 Ochoa et al.

FOREIGN PATENT DOCUMENTS

| | | | |
|---|---|---|---|
| EP | 1 780 217 | * | 2/2007 |
| EP | 2471949 | | 7/2012 |
| WO | WO 01/32702 | | 5/2001 |
| WO | WO 2006/032897 | | 3/2006 |
| WO | WO 2006/075254 | | 7/2006 |

OTHER PUBLICATIONS

Wagner et al; BMC Genetics, 2:10, 20.*
U.S. Appl. No. 13/791,284, filed Mar. 8, 2013, Ochoa et al.
Chiaroni et al., "Groupes sanguins erythrocytaires Red-cell blood groups," *EMC-Hematologie,* vol. 2, pp. 53-112, 2005.
Hillyer, "Prevalence, donation practices, and risk assessment of blood donors with hemochromatosis," *Transfusion Medicine Reviews,* vol. 16, No. 3, pp. 270-271, 2002.
Liu et al., "Aberrant RNA splicing in *RHD* 7-9 exons of DEL individuals in Taiwan: A mechanism study," *Biochimica et Biophysica Acta,* vol. 1800, pp. 565-573, 2010.
Reid, "RHD positive haplotypes in D negative Europeans," *Transfusion Medicine Reviews,* vol. 16, No. 3, pp. 270, 2002.

* cited by examiner

*Primary Examiner* — Jehanne Sitton
(74) *Attorney, Agent, or Firm* — Klarquist Sparkman, LLP

(57) ABSTRACT

The present invention provides a method for detecting the presence or absence of, or for discriminating between, blood type variants, including RHD*r's, RHD*DIIIa, RHD*DIVa-2, RHCE*$cs^s$ and RHCE*ce733G. The method comprises genotyping a sample obtained from a human subject at one or more positions in intron 7 of the RHD gene and/or in intron 7 of the RHCE gene. The invention also provides products, in particular, probes, primers and kits for use in the method of the invention.

15 Claims, 9 Drawing Sheets

```
                 Intron7                                        Intron7
Position               1110       1120       1130       1140       1150
RHD*00101        GCTTGGGATG AGGAGGGGAT GAGCTGTGTG AAGCAAGGCG CCTCTGTGAT
RHCE*ce_BN000065 .......... .......... .......... ........T. .......A..

                 Intron7                                        Intron7
Position               1160       1170       1180       1190       1200
RHD*00101        GGGTTCCAGT GATGTGTCTG CCACTGTCTT AATAACTGTG CAATTCTAAG
RHCE*ce_BN000065 .......... .......... .......... .......... ..........

                 Intron7                                        Intron7
Position               1210       1220       1230       1240       1250
RHD*00101        CAGAACCTTT CCTGTCTCTG GGCCTGAGAG TTCCCCTCTG AAAGATGAGG
RHCE*ce_BN000065 .......... .......... .......... .......... T.........

                 Intron7                                        Intron7
Position               1260       1270       1280       1290       1300
RHD*00101        ACTTGACCTA GCAAGGTCCT ACTCACATGC CTGTAGAGAA CAGGCAGGGG
RHCE*ce_BN000065 .......... .......... .....G.... .......... ..........

                 Intron7                                        Intron7
Position               1310       1320       1330       1340       1350
RHD*00101        AAGTTAGAAA AAAAAAAAAG CCAGTGAAGG AAGGGAGCTC TTCAGCTTGC
RHCE*ce_BN000065 .......... ........-. .......... .......... ..........

                 Intron7                                        Intron7
Position               1360       1370       1380       1390       1400
RHD*00101        ACCCATCATC ACAGTGCAGG GACCCAGGCT CAGTGTTGCC AGATCCAATG
RHCE*ce_BN000065 .....C.... .......... .......... .......... ..........

                 Intron7                                        Intron7
Position               1410       1420       1430       1440       1450
RHD*00101        ACTTCTCAAG AGCTCAAAAT CTAGAGTTTT GCATGTGCTC TCCCAAGTAC
RHCE*ce_BN000065 .......... .......... .......... .......... ..........

                 Intron7                                        Intron7
Position               1460       1470       1480       1490       1500
RHD*00101        TGGCAGAAAA TTCAAGATTG TTAGTAACAC TGTGTGGCTA AATTCTGCTT
RHCE*ce_BN000065 .......... .......... .......... .......... ..........

                 Intron7                                        Intron7
Position               1510       1520       1530       1540       1550
RHD*00101        GTGGGCTGCC TAGATTCCCA ATTCTGTGAT TCTGTGGTTC TCTGGAAGCA
RHCE*ce_BN000065 .......... .......... .......... .......... ..........

                 Intron7                                        Intron7
Position               1560       1570       1580       1590       1600
RHD*00101        TTGGTTCTCC ACAGCACCTG CATCACTTGG AAACTTGTTA GAAATGCAAG
RHCE*ce_BN000065 .......... .......... .......... .......... ..........

                 Intron7                                        Intron7
Position               1610       1620       1630       1640       1650
RHD*00101        CCCTACCTAC GGCCCCACCC CAGACCTACC CAGTTAGAAA TCTGGGGGTG
RHCE*ce_BN000065 .......... .......... .......... .......... ..........

                 Intron7                                        Intron7
Position               1660       1670       1680       1690       1700
```

FIG. 3A

```
RHD*00101          GGACCTATCA GTCCATGTTT GAACAAGCCC CACAAGTGTT CTCTTGCAAG
RHCE*ce_BN000065 .......... .......... .......... .......... ..........

                   Intron7                                          Intron7
Position                 1710       1720       1730       1740       1750
RHD*00101          CTCAAGTTTT AGAACCACTG ACCTATAGCC AAAAAAGAAA AAGCCAATCA
RHCE*ce_BN000065 .......... .......... .......... .......... ..........

                   Intron7                                          Intron7
Position                 1760       1770       1780       1790       1800
RHD*00101          GTGGTTTTCT GGTAAAGGAT TAACTTAACA AACTGGCTTT CCAAGAAAAT
RHCE*ce_BN000065 .......G.. ....G..... .......... .-........ ...T......

                   Intron7                                          Intron7
Position                 1810       1820       1830       1840       1850
RHD*00101          AAAGCCTTGA TTGGTAGCAC TTGCAATTTC TATGGTACAA ACGCTTCCCG
RHCE*ce_BN000065 .......... .......... .......... .......... .........A

                   Intron7                                          Intron7
Position                 1860       1870       1880       1890       1900
RHD*00101          CATGACTGAG TTCAAGCTGT CAAGGAGACA TCACTATACA TGGACTTGGG
RHCE*ce_BN000065 .......... ........A. .........G .....GC... ..........

                   Intron7                                          Intron7
Position                 1910     F31920       1930       1940       1950
RHD*00101          AAGAGATGAG AACAATCAGC CCACTGAGCC TATGGGAACT GGCTCCAGCA
RHCE*ce_BN000065 .......... .......... .......... .......... ..........

                   Intron7                                          Intron7
Position                 1960       1970       1980       1990       2000
RHD*00101          CATCCCTGCA AGTCAACTCT CATCAGGGTG AGTGAGTTGA GGACCAAGAA
RHCE*ce_BN000065 .......... .......... .......... .......... ..........

                   Intron7                                          Intron7
Position                 2010       2020       2030       2040       2050
RHD*00101          GCAGTTATCC TCTTGCCTTT GCAGGACCCA GGCAAAGGGA AGGGCATAGT
RHCE*ce_BN000065 .......... .......... .......... .......... ..........

                   Intron7                                          Intron7
Position                 2060       2070       2080       2090       2100
RHD*00101          GACAGTGATG ATCTCTCTTC CGGAAGTCTT TGGTTTGCTG AGAGTAAAAG
RHCE*ce_BN000065 .......... .......... .......... .......... ..........

                   Intron7                                          Intron7
Position                 2110       2120       2130       2140       2150
RHD*00101          GCGTGGGCTT CACCAGTGGT GAAGCCAGTC ATGCAGCCTT AGTCCTGGTA
RHCE*ce_BN000065 .......... .......... .......... .......... ..........

                   Intron7                                          Intron7
Position                 2160       2170       2180       2190       2200
RHD*00101          CTGAAACTCT CTAAATCTCA GTTTTCTATC TGTAAAATGG GAAAATAAGA
RHCE*ce_BN000065 ..C......C .......... .......... .......... .........T

                   Intron7                                          Intron7
Position                 2210       2220       2230       2240       2250
RHD*00101          CCTATGTCAC AGGGTTGCTG TGCAGATTTA GCAACAGAAC ATAGCCCCGT
RHCE*ce_BN000065 .......... .......... .......... ....T..... ..........
```

FIG. 3B

```
                  Intron7                                               Intron7
Position                2260       2270       2280       2290       2300
RHD*00101         TCTTTATGAT GACTGATGCT GCATCCGTAT GAGGACATCT CTATGTAATG
RHCE*ce_BN000065  .......... .......... .....A.... .G........ ..........

                  Intron7                                               Intron7
Position                2310       2320       2330       2340       2350
RHD*00101         GAAAGATGGA GAGAGGATTA AGCGCAAAGT CACAACACTT AATGGGAACT
RHCE*ce_BN000065  .......... .......... ..T....... ....G..... ..........

                  Intron7                                               Intron7
Position                2360       2370       2380       2390       2400
RHD*00101         GTGGATTAGC TACTTGGTGG CATTGGGCAA GTCAGTTGAC TTTGCATTAA
RHCE*ce_BN000065  .......... .......... .......... .......... ..........

                  Intron7                                               Intron7
Position                2410       2420       2430       2440       2450
RHD*00101         TTCCACAAAC AATATTTCCC AATTTCCTAT TCAGATGAGC ATATGTGATT
RHCE*ce_BN000065  .......... .......... .......... .......... ........C.

                  Intron7                                               Intron7
Position                2460       2470       2480       2490       2500
RHD*00101         GAGTCAGATG CTGTGATCAG AACCAGGATG GAGCATTTCC CACAAACTGT
RHCE*ce_BN000065  .......... .......... .G........ .......... ..........

                  Intron7                                               Intron7
Position                2510       2520       2530       2540       2550
RHD*00101         GGGATTTTTA AGTAATGGGA AGGCACACTG AAATGGCACT GAATCATGCA
RHCE*ce_BN000065  .......... ...G...... .......... ........T. ..........

                  Intron7                                               Intron7
Position                2560       2570       2580       2590       2600
RHD*00101         GTTGCAGATA CTCTTTTTCA ATTCTCAGTC CTTTGATTAC GTCAGGGAGA
RHCE*ce_BN000065  .......... .......... .......... .......... A.........

                  Intron7                                               Intron7
Position                2610       2620       2630       2640       2650
RHD*00101         AAAGAAAGTC CCCACTTGGC CTGAGAATCT CTGCACCCTT CTAGCTCTTG
RHCE*ce_BN000065  .......... .........G .......... .......... ..........

                  Intron7                                               Intron7
Position                2660       2670       2680       2690       2700
RHD*00101         TTAACCACTC TTTTGAATAG CAGAGAAAAC CTCAGACTGC CATATCTGGG
RHCE*ce_BN000065  .......... .......... .......... .......... ..........

                  Intron7                                               Intron7
Position                2710       2720       2730       2740       2750
RHD*00101         AGAGATTTTA GCAACATTTT GTTTTCATTG TATCTCTTTT TACAGCTACC
RHCE*ce_BN000065  .......... .......... .......... .......... ..........

                  Intron7                                               Intron7
Position                2760       2770       2780       2790       2800
RHD*00101         TCCCATTTCC CTTCTATTTC AAGCTAGTAA CTCAGTTTTC TTTTAAATTC
RHCE*ce_BN000065  .......... .......... .......... .A........ ..........

                  Intron7                                                 Intron7
Position                2810       2820       2830       2840         2850
RHD*00101         AATTATTTAA ATGTAAAAAT AAGTCTATTT GGAGAAAAAA AATTTT-AATA
```

FIG. 3C

```
RHCE*ce_BN000065 .T........ .......... .......... .......... ......T....

                 Intron7                                          Intron7
Position            F4 2860       2870       2880       2890       2900
RHD*00101        GCATCTCTGG AATGCCAGTA TGGCTAAATT CATGAATGTT GTCCTCAAAT
RHCE*ce_BN000065 .......... .......... .......... .......... ..........

                 Intron7                                          Intron7
Position               2910       2920       2930       2940       2950
RHD*00101        GCTGAAATCT GGGAAGCATC TGGCCAAGCT TTGTGGACAG GCCTGCCTAG
RHCE*ce_BN000065 .......... .......... .......... .......... ....T.....

                 Intron7                                          Intron7
Position               2960       2970       2980       2990       3000
RHD*00101        TTTGAATCCC AAGAGCCACC CAGTCCAAGC CACAAAACAT TGGAATTCTT
RHCE*ce_BN000065 .......... .........T ..T...G... .......... ..........

                 Intron7                                          Intron7
Position               3010       3020       3030       3040       3050
RHD*00101        GGTTCACTTC CCTAACCTGA ACTTGCCCTC TGTGAAATAG GGACACTAAT
RHCE*ce_BN000065 .......... .......... .....T.... .......... .....T....

                 Intron7                                          Intron7
Position               3060       3070       3080       3090       3100
RHD*00101        AGCTCACTCA CAGGGCTGCT GTGAGGACAT GTGTTGAGCT GAGGGTCTCG
RHCE*ce_BN000065 .......... .......... .......... .......... ........G.

                 Intron7                                          Intron7
Position               3110       3120       3130       3140       3150
RHD*00101        CCAGGGGAGA CCCTGTGCAG GGAGACTGTT ATCATGGTGA TGGATTTCTG
RHCE*ce_BN000065 .......... .......... .......... .......... ..........

                 Intron7                                          Intron7
Position               3160       3170       3180       3190       3200
RHD*00101        CTTCATTCAT TTCTTTTTCC AGACAGCATC ATATAGAATG AGTTGTGGGG
RHCE*ce_BN000065 .......... .......... .......... .......... ..........

                 Intron7                                          Intron7
Position               3210       3220       3230       3240       3250
RHD*00101        TGGCAGTCAG CAGGTTTGGG TTTATCCTCT ATTCTGCCAC TTATTACTTA
RHCE*ce_BN000065 .......... .......... .......... .......... ..........

                 Intron7                                          Intron7
Position               3260       3270       3280       3290       3300
RHD*00101        AAAAAACCCC AAAAAACCCA ACTTATATAG TATAAGCTAT ATCCAGAAAA
RHCE*ce_BN000065 ......---- --........ .......... .......... ..........

                 Intron7                                          Intron7
Position               3310       3320       3330       3340       3350
RHD*00101        GTGCAAATAT CATACAAGTA CCATTTGATG AATCTTCTGA TATCCCCACA
RHCE*ce_BN000065 .......... .......... .......... .......... ..........

                 Intron7                                          Intron7
Position               3360       3370       3380       3390       3400
RHD*00101        TAACCAACAC CCAGAACCTC TTCTTGTCTC ATTCCAGGAT AACCACTAAC
RHCE*ce_BN000065 .......... .......... .......... .......... ..........

                 Intron7                                          Intron7
```

FIG. 3D

```
Position                  3410       3420       3430       3440       3450
RHD*00101         CTGACTTCTA ACAGCATCAG TCAGTTTTGT CTGTTTTTGT ACATTATATA
RHCE*ce_BN000065 .......... .......... .......... .......... ..........

                  Intron7                                        Intron7
Position                  3460       3470       3480       3490       3500
RHD*00101         TGTGATGGTT TGAATGTGTC CCCCAAATTT CATGTGCTGG AAACTTAATC
RHCE*ce_BN000065 .......... .......... .......... ........A. ..........

                  Intron7                                        Intron7
Position                  3510       3520       3530       3540       3550
RHD*00101         CTTCAATTCA TATGTTGATG GTTTTTGGAG GAAGGGCCTT TGGGAAGTAA
RHCE*ce_BN000065 .......... .......... C.A....... .......... ..........

                  Intron7                                        Intron7
Position                  3560       3570       3580       3590       3600
RHD*00101         TTAGGATTAG ATAAGGTCAT GGGGTGAGGT ATGATGGCAC TGGTGACTTA
RHCE*ce_BN000065 .......... .......... .......... .......... ..........

                  Intron7                                        Intron7
Position                  3610       3620       3630       3640       3650
RHD*00101         TAAGAAGAGA AAGAGAAATC TGAGCTGGCA TGCTCTTGCC CTCTCACTGT
RHCE*ce_BN000065 .......... .......... .......... .......... .......C..

                  Intron7                                        Intron7
Position                  3660       3670       3680       3690       3700
RHD*00101         GTGATGACTT CTCCATGTCA TGATGCAGCA AGAAGGCCCT CACCAGATGG
RHCE*ce_BN000065 .......... .......... .......... .......... ..........

                  Intron7                                        Intron7
Position                  3710       3720       3730       3740       3750
RHD*00101         TGGCACCATG CTTTTGGACT TCCCAGCCTC TAGAACTGTG AGCTAAATCA
RHCE*ce_BN000065 .......... .......... .......... .......... ..........

                  Intron7                                        Intron7
Position                  3760       3770       3780       3790       3800
RHD*00101         ATTTATTTTC TTTATAATCA CCCAGTTTGA TATTTTGTCA TAGCAACAGA
RHCE*ce_BN000065 .......... .......... .......... .......... ..........

                  Intron7                                        Intron7
Position                  3810       3820       3830       3840       3850
RHD*00101         ATATGGACAA AGAAAGAAAA TTAATGCAAG AAGTAGAGTT TTTACTGTAA
RHCE*ce_BN000065 .......... .......... .......... .......... ..........

                  Intron7                                        Intron7
Position                  3860       3870       3880       3890       3900
RHD*00101         CAGATTCCTG AAAATGTGGA AGTGGCTTTG GAACTGGGTG ATGGGAATAG
RHCE*ce_BN000065 .......... .......... .......... .......... ..........

                  Intron7                                        Intron7
Position                  3910       3920       3930       3940       3950
RHD*00101         GTTGGAAGAG TTTTGAGGAG CAGGCTAGAA AAAGCCTGTA TTGTCAAGAA
RHCE*ce_BN000065 .......... .......... .......... .......... ..........

                  Intron7                                        Intron7
Position                  3960       3970       3980       3990       4000
RHD*00101         TGGAGCATTA TGCCAGGCAC GGTGTCTCAG GCTTATAATC CCAGCACTTT
RHCE*ce_BN000065 .......... G......... ....G..... A......... ..........
```

FIG. 3E

```
                  Intron7                                                Intron7
Position                4010        4020        4030        4040        4050
RHD*00101         GGGAGGCCAA AGCAGGTGGA TCACCTGAGG TCAGGAGTTC GAGACCAGCC
RHCE*ce_BN000065 .......... .......... .......... .......... ..........

                  Intron7                                                Intron7
Position                4060        4070        4080        4090        4100
RHD*00101         TAGCTAACAT GGTGAAACGC TGTTTCTACC AAAAATACAA AAAATTAGCT
RHCE*ce_BN000065 .G........ .......... .......... .......... ..........

                  Intron7
Position                4110        4120
RHD*00101         GGGCGTGGTG GCGCACACCT
RHCE*ce_BN000065 ....ACTC.. ..........
```

FIG. 3F

SEQUENCE LISTING

<160> NUMBER OF SEQ ID NOS: 81

<210> SEQ ID NO 1
<211> LENGTH: 3020
<212> TYPE: DNA
<213> ORGANISM: Homo sapiens

<400> SEQUENCE: 1

```
gcttgggatg aggaggggat gagctgtgtg aagcaaggcg cctctgtgat gggttccagt      60

gatgtgtctg ccactgtctt aataactgtg caattctaag cagaaccttt cctgtctctg     120

ggcctgagag ttcccctctg aaagatgagg acttgaccta gcaaggtcct actcacatgc     180

ctgtagagaa caggcagggg aagttagaaa aaaaaaaaag ccagtgaagg aagggagctc     240

ttcagcttgc acccatcatc acagtgcagg gacccaggct cagtgttgcc agatccaatg     300

acttctcaag agctcaaaat ctagagtttt gcatgtgctc tcccaagtac tggcagaaaa     360

ttcaagattg ttagtaacac tgtgtggcta aattctgctt gtgggctgcc tagattccca     420

attctgtgat tctgtggttc tctggaagca ttggttctcc acagcacctg catcacttgg     480

aaacttgtta gaaatgcaag ccctacctac ggccccaccc cagacctacc cagttagaaa     540

tctgggggtg ggacctatca gtccatgttt gaacaagccc cacaagtgtt ctcttgcaag     600

ctcaagtttt agaaccactg acctatagcc aaaaaagaaa aagccaatca gtggttttct     660

ggtaaaggat taacttaaca aactggcttt ccaagaaaat aaagccttga ttggtagcac     720

ttgcaatttc tatggtacaa acgcttcccg catgactgag ttcaagctgt caaggagaca     780

tcactataca tggacttggg aagagatgag aacaatcagc ccactgagcc tatgggaact     840

ggctccagca catccctgca agtcaactct catcagggtg agtgagttga ggaccaagaa     900

gcagttatcc tcttgccttt gcaggaccca ggcaaaggga agggcatagt gacagtgatg     960

atctctcttc cggaagtctt tggtttgctg agagtaaaag gcgtgggctt caccagtggt    1020

gaagccagtc atgcagcctt agtcctggta ctgaaactct ctaaatctca gttttctatc    1080

tgtaaaatgg gaaaataaga cctatgtcac agggttgctg tgcagattta gcaacagaac    1140

atagccccgt tctttatgat gactgatgct gcatccgtat gaggacatct ctatgtaatg    1200

gaaagatgga gagaggatta agcgcaaagt cacaacactt aatgggaact gtggattagc    1260

tacttggtgg cattgggcaa gtcagttgac tttgcattaa ttccacaaac aatatttccc    1320

aatttcctat tcagatgagc atatgtgatt gagtcagatg ctgtgatcag aaccaggatg    1380

gagcatttcc cacaaactgt gggattttta agtaatggga aggcacactg aaatggcact    1440

gaatcatgca gttgcagata ctctttttca attctcagtc ctttgattac gtcagggaga    1500

aaagaaagtc cccacttggc ctgagaatct ctgcaccctt ctagctcttg ttaaccactc    1560

ttttgaatag cagagaaaac ctcagactgc catatctggg agagatttta gcaacatttt    1620

gttttcattg tatctctttt tacagctacc tcccatttcc cttctatttc aagctagtaa    1680

ctcagttttc ttttaaattc aattatttaa atgtaaaaat aagtctattt ggagaaaaaa    1740

aattttaata gcatctctgg aatgccagta tggctaaatt catgaatgtt gtcctcaaat    1800
```

```
gctgaaatct gggaagcatc tggccaagct ttgtggacag gcctgcctag tttgaatccc   1860

aagagccacc cagtccaagc cacaaaacat tggaattctt ggttcacttc cctaacctga   1920

acttgccctc tgtgaaatag ggacactaat agctcactca cagggctgct gtgaggacat   1980

gtgttgagct gagggtctcg ccaggggaga ccctgtgcag ggagactgtt atcatggtga   2040

tggatttctg cttcattcat ttctttttcc agacagcatc atatagaatg agttgtgggg   2100

tggcagtcag caggtttggg tttatcctct attctgccac ttattactta aaaaaacccc   2160

aaaaaaccca acttatatag tataagctat atccagaaaa gtgcaaatat catacaagta   2220

ccatttgatg aatcttctga tatccccaca taaccaacac ccagaacctc ttcttgtctc   2280

attccaggat aaccactaac ctgacttcta acagcatcag tcagttttgt ctgtttttgt   2340

acattatata tgtgatggtt tgaatgtgtc ccccaaattt catgtgctgg aaacttaatc   2400

cttcaattca tatgttgatg gtttttggag gaagggcctt tgggaagtaa ttaggattag   2460

ataaggtcat ggggtgaggt atgatggcac tggtgactta taagaagaga aagagaaatc   2520

tgagctggca tgctcttgcc ctctcactgt gtgatgactt ctccatgtca tgatgcagca   2580

agaaggccct caccagatgg tggcaccatg cttttggact tcccagcctc tagaactgtg   2640

agctaaatca atttatttc tttataatca cccagtttga tattttgtca tagcaacaga   2700

atatggacaa agaaagaaaa ttaatgcaag aagtagagtt tttactgtaa cagattcctg   2760

aaaatgtgga agtggctttg gaactgggtg atgggaatag gttggaagag ttttgaggag   2820

caggctagaa aaagcctgta ttgtcaagaa tggagcatta tgccaggcac ggtgtctcag   2880

gcttataatc ccagcacttt gggaggccaa agcaggtgga tcacctgagg tcaggagttc   2940

gagaccagcc tagctaacat ggtgaaacgc tgtttctacc aaaaatacaa aaaattagct   3000

gggcgtggtg gcgcacacct                                               3020
```

```
<210> SEQ ID NO 2
<211> LENGTH: 3013
<212> TYPE: DNA
<213> ORGANISM: Homo sapiens

<400> SEQUENCE: 2
```

```
gcttgggatg aggaggggat gagctgtgtg aagcaaggtg cctctgtaat gggttccagt     60

gatgtgtctg ccactgtctt aataactgtg caattctaag cagaaccttt cctgtctctg    120

ggcctgagag ttcccctctg taagatgagg acttgaccta gcaaggtcct actcagatgc    180

ctgtagagaa caggcagggg aagttagaaa aaaaaaaagc cagtgaagga agggagctct    240

tcagcttgca cccaccatca cagtgcaggg acccaggctc agtgttgcca gatccaatga    300

cttctcaaga gctcaaaatc tagagttttg catgtgctct cccaagtact ggcagaaaat    360

tcaagattgt tagtaacact gtgtggctaa attctgcttg tgggctgcct agattcccaa    420

ttctgtgatt ctgtggttct ctggaagcat tggttctcca cagcacctgc atcacttgga    480

aacttgttag aaatgcaagc cctacctacg gccccacccc agacctaccc agttagaaat    540

ctgggggtgg gacctatcag tccatgtttg aacaagcccc acaagtgttc tcttgcaagc    600

tcaagtttta gaaccactga cctatagcca aaaaagaaaa agccaatcag tggtttgctg    660

gtagaggatt aacttaacaa ctggctttcc atgaaaataa agccttgatt ggtagcactt    720

gcaatttcta tggtacaaac gcttcccaca tgactgagtt caagctatca aggagacgtc    780

actgcacatg gacttgggaa gagatgagaa caatcagccc actgagccta tgggaactgg    840
```

```
ctccagcaca tccctgcaag tcaactctca tcagggtgag tgagttgagg accaagaagc    900
agttatcctc ttgcctttgc aggacccagg caaagggaag ggcatagtga cagtgatgat    960
ctctcttccg gaagtctttg gtttgctgag agtaaaaggc gtgggcttca ccagtggtga   1020
agccagtcat gcagccttag tcctggtact caaactccct aaatctcagt tttctatctg   1080
taaaatggga aaataagtcc tatgtcacag ggttgctgtg cagatttagc aatagaacat   1140
agccccgttc tttatgatga ctgatgctgc atcagtatgg ggacatctct atgtaatgga   1200
aagatggaga gaggattaag tgcaaagtca cagcacttaa tgggaactgt ggattagcta   1260
cttggtggca ttgggcaagt cagttgactt tgcattaatt ccacaaacaa tatttcccaa   1320
tttcctattc agatgagcat atgtgactga gtcagatgct gtgatcagag ccaggatgga   1380
gcatttccca caaactgtgg gatttttaag tgatgggaag gcacactgaa atggcattga   1440
atcatgcagt tgcagatact ctttttcaat tctcagtcct ttgattacat cagggagaaa   1500
agaaagtccc cacttgggct gagaatctct gcacccttct agctcttgtt aaccactctt   1560
ttgaatagca gagaaaacct cagactgcca tatctgggag agattttagc aacattttgt   1620
tttcattgta tctcttttta cagctacctc ccatttccct tctatttcaa gctagtaaca   1680
cagtttcttt ttaaattcat ttatttaaat gtaaaaataa gtctatttgg agaaaaaaaa   1740
tttttaatag catctctgga atgccagtat ggctaaattc atgaatgttg tcctcaaatg   1800
ctgaaatctg ggaagcatct ggccaagctt tgtggacagg ccttcctagt ttgaatccca   1860
agagccactc attccgagcc acaaaacatt ggaattcttg gttcacttcc ctaacctgaa   1920
cttgtcctct gtgaaatagg gacattaata gctcactcac agggctgctg tgaggacatg   1980
tgttgagctg agggtctggc caggggagac cctgtgcagg gagactgtta tcatggtgat   2040
ggatttctgc ttcattcatt tctttttcca gacagcatca tatagaatga gttgtggggt   2100
ggcagtcagc aggtttgggt ttatcctcta ttctgccact tattacttaa aaaaaaaaac   2160
ccaacttata tagtataagc tatatccaga aaagtgcaaa tatcatacaa gtaccatttg   2220
atgaatcttc tgatatcccc acataaccaa cacccagaac ctcttcttgt ctcattccag   2280
gataaccact aacctgactt ctaacagcat cagtcagttt tgtctgtttt tgtacattat   2340
atatgtgatg gtttgaatgt gtcccccaaa tttcatgtgc tagaaactta atccttcaat   2400
tcatatgttg atgctatttg gaggaagggc ctttgggaag taattaggat tagataaggt   2460
catggggtga ggtatgatgg cactggtgac ttataagaag agaaagagaa atctgagctg   2520
gcatgctctt gccctctcac cgtgtgatga cttctccatg tcatgatgca gcaagaaggc   2580
cctcaccaga tggtggcacc atgcttttgg acttcccagc ctctagaact gtgagctaaa   2640
tcaatttatt ttctttataa tcacccagtt tgatattttg tcatagcaac agaatatgga   2700
caaagaaaga aaattaatgc aagaagtaga gtttttactg taacagattc ctgaaaatgt   2760
ggaagtggct ttggaactgg gtgatgggaa taggttggaa gagttttgag gagcaggcta   2820
gaaaaagcct gtattgtcaa gaatggagca ttaggccagg cacggtggct cagacttata   2880
atcccagcac tttgggaggc caaagcaggt ggatcacctg aggtcaggag ttcgagacca   2940
gcctggctaa catggtgaaa cgctgtttct accaaaaata caaaaaatta gctgggcact   3000
ctggcgcaca cct                                                      3013
```

<210> SEQ ID NO 3
<211> LENGTH: 64956
<212> TYPE: DNA
<213> ORGANISM: Homo sapiens

<400> SEQUENCE: 3
gacaccccag ccacgccaag ccgggaagtc cccgcctcct ggagctgaac ccgcccctct 60
cccagaggtg gagctgcggg gggcgggaac aggcacggag aaaataaaca agactaaaaa 120
gtcctgagta gcgctgtgtg gccgcaaacc tgaacccacc ttttgcacca cgcgggaccc 180
ggcacgcttc ctgccaccca cccctgagag ggctgcgcgg ccgaccccag tactagaaaa 240
cactcgtcac ctcaatcaag acgggtacga aggccaacgg acgccttcct ttagaacgct 300
cagcacacag agcaacttct cacgcctact ctcaaatggc gtactccaaa ctagcactcc 360
cgacgtccag ctgtgaaccc agagcggcgg aaagcccctg aacccagcgc ccgggcatgc 420
gcagacgcgt tgttgtggtg ggcgtggctc cctccggacc cggcgccccg ccctccgccc 480
cgtgtccgca tgcgcgactg agccgcgggg gtggtactgc tgcatccggg tgtctgaaga 540
tccgatgaaa taacatatgc aaaatgattg ggtccgtgat tggcattcca gaaatggtag 600
ctgttattca gccaacaaat atttattgag cacctactat ggacttccct ggtgctgagg 660
atacaacagc aaccacagca gtcaaaagtc cctgtcttca tgttgctcag attctcatag 720
gggaaagcaa ataatgaaca aatacacggc cgggcgcagt ggctcacgcc tgtaatccca 780
gtactttgcg aggccaaggt gggcaagtca cctgaggtca ggagttcgag accagactag 840
ccaacgtggt gaaaccctgt cactactaaa aatacaaaaa ttagcgcggt gtggtggctc 900
atgcctgtag tcccagctac ttgggaggct gaggaaggag aatcgcttga acctaaaagg 960
cagaagttgc aatgagccaa gatcgtgcca ctgcattcca gcctgggtga cagagtactc 1020
cgtctaaaaa aaaaacctaa atacacaagt aaaaatatag acctcgtcag atgctagtaa 1080
gtgctgtgaa ggaaactaaa aggggaacac aaggaaccct tgtcaagggg agaagaaagg 1140
ggagttgatg ctgtcctttt aaatagggca gtcagaggcc gggcacagtg gttcacacct 1200
ataatcccag cactttggga ggttgaggtg ggtggatcac ttgaggtcag gagttcaaga 1260
ccagcctggc caacctggtg aaatcctgtc tctactaaaa aaacaaaaac tagccgggtg 1320
tggtatcacg cgcctataat cccagctact cgggaggctg aggcgggaga atcacttgaa 1380
cctgggaggt ggaggttgca gtgagccgag attgtgccat tgcagtccag cctaggcaac 1440
aagagcaaaa cttcatctca aaaaaaaaaa aaaaaaatagg gcagtcaggg aaaactttcc 1500
tgagaagggg atggtggagg atccagggag gtgaggtggg gagcaagcca gtacagttgt 1560
tccttgactt tcgatggggt tatgtcctga taaagccatg gtaagtagga aatattgtaa 1620
gtcaaaaatg catttaatac atctaaccta cggaacatca tagcttagtc tcacctacct 1680
taaacatgct tagaacactt acattagcct acagttgggc aaaatcctct aacacaaagc 1740
ctattttatg ataaagtatt gaatatctca tgtaatgtac tgagtactgt acggaaagtg 1800
aaagacggag tggtgggatg ggaactctaa gcgcggcttc cactgcatgt gtgttgcttt 1860
cgcgccatca taaagttgaa aagcgttaag tcaaaccatc gtacgtcgga ggccatctgt 1920
atctggtagg aggagtgttt cagacagaga gaacagcagg tgcacagagt gcttttttcc 1980
cagcatttta ttatgaaaaa tttcaaacat ctaccaaaaa aagttgaaag acttgtacag 2040
tgaaaagcca tacatctcac agctagaatc aacaattaac attttactgt atttggtttt 2100
tgacttatct atcctagatc ccttgtgctt tctgtagcag gtgacctgcc ttgaagattt 2160
aaagacagaa tatcaggaaa tgtagtcaga aaatggggcc ttttataaga gtcagagggg 2220
aagagcaaaa cctctgcttt tgacaaatct gttgggagag gccaactgca gggatacctc 2280

-continued

```
cctttttaa tgaaagcatt tctgttctgc gaggagcggg atcctcttgt caagcagtca   2340
gtccctgctg cttccttact ggggcaggat caggacgcac agggatttgg agtgccttgg   2400
aaccaaccac cacccacgcc gtttgccagc tggtaaacat gcccatcagg tccgggggtt   2460
ggcattgcct ggacatcttt agtgttcatc ttgctgacat ctggtgccct cgggcaggta   2520
ggtgcagttg gctgcctggt ttacagagct tgtactgggc ccaggttagc agaggtcaca   2580
tccatttatc ccactgcgca gaggagttcc ttctcaggaa acccagttta taagaagtac   2640
tgactgccag aaatagagca gaaatgagaa ccaggaggca attgtgagag gaatggagac   2700
ttctgacctc tggggattgg ggtaccctcc cccttaattg ctgttggggt agcagagggc   2760
ttagaagccc atgttcctag acttttagaa ttggaagaag acttagaagt aatctaggct   2820
gggggtcccc aacccccagg ctgtggcccg ttaggaacct gaccgcacag catgagggat   2880
aggccagcga gcactaccgc ctgagctccg cctcctgtca gatcagcagc ggcattagat   2940
tctcataggg gcacaaaccc tattgggaac cgcgcatgag agggatctag gttgcgtgct   3000
ccttaggaga atctaactaa tgcctgatga tctgaggtgg aacagtttca tccccaaacc   3060
atccctccaa cctcaccccg gtccatggaa aaattgtctt ttacaaaacc cgtccctggt   3120
gccaaaaagc ttggggaccc ctgatctagg ctacagttaa gtggtcaaac acccaggtcc   3180
tgaagttagg ctgcctgggt ttaaatccca gctctactgc ttactagccc tgtgaccttg   3240
agcaagtcac ttagtttttc tgtgcctcag ttcactcatt tgtaataaat cctaatagta   3300
cccatcccag tgtcatgaac taagttcata tatgtaaagt acttagaatg gtgcctagca   3360
agtacttaat aacagttagc tctgaaaatg tataaagcaa aattaaccaa tgttttagtg   3420
gtttgcagcc aactttttc tatgcgtgtg ctaacatatt attttataag agtgggaata   3480
tattgtacat gctgttatat aacttgcttt ttcactaaac agtctatcct ctgtgtcagt   3540
tttgataaaa gcgttttcct cttgcttttc ctgcatatgt tcagaaccat catattggta   3600
gcaagtttca tgtcctgtag ttttcttaac caaccccctg ctagtggaca tttaggttag   3660
tctcagtttt ttccttctgt aaataaagct gcactgagca agaagtgact gatgccaagt   3720
gactagatga ccttaggtat gacctctctg ggtcttggtt tcttggtcta aaaacaaaat   3780
gacaggattc gactgggtga ttaaaatctc ctctgatcta cataggaatt gttttcaaga   3840
catttctgca ttcctctagt gacagggtgc tcactacctc atgagtattt cagtggacaa   3900
ctgtaatggt caataaagta tccactttcc acctccctgc agctcctggc cctggcttta   3960
ttctctgggg ctccacacat tcagtttaca ctcagtggcc agtggctggg accattgtag   4020
aaaataagga aactccaatt ccttccttct tttcttcctc tttcatctct tcctccctct   4080
ctacatccct ctctctcttc cttccttcct cgacacttac catgtaccag accttctgcc   4140
aggcacatgg atgggagcac aggggaagtt ggctgcaggg ttagaactaa gtcccaagcc   4200
ccctaaagct catgccaggg gactggactg tccagtactg agggatgggg atgctgaggc   4260
tggtggcctt cctcaaatgc actgtagtgc cccaggcaga gtcctgggct gccctgtgag   4320
gaggtgacca gaggtagagc aacttcaccc taaggctgga tcaggatccc ctccaggttt   4380
ttactagagc caaacccaca tctcctttct cttctgccac cccccttaa aatgcttaga   4440
aacacataga tttaaataca aattcaaatg taagtaattt caactgtgta actatgagga   4500
gtcagttcta cgtgggtcct atctgtatcc tccccagggc tcagctccat tctttgcttt   4560
cattcattct cattcaatac attgttgtta agagctcact gggtgccctc tctgtcatgt   4620
agtaaggttt taaaaagaaa gcctcttctg agcttcagtt tccttattca taaaatagga   4680
```

gtattgatcc attccttgct tttcttacaa ggatatgctg aagatgactg aagtacagag 4740
taaagaagga ttatgtttgg gtgtcaaagg aatagaatgc cctctttcaa actgagcaca 4800
gcaggaacct gtaacaggaa cacagcaact tgttgaatga atgacaatat tggaaaacat 4860
acatttcctc ccctccccat catagtccct ctgcttccgt gttaactcca tagagaggcc 4920
agcacaacca gccttgcagc ctgagataag gcctttggcg ggtgtctccc ctatcgctcc 4980
ctcaagccct caagtaggtg ttggagagag gggtgatgcc tggtgctggt ggaacccctg 5040
cacagagacg gacacaggat gagctctaag tacccgcggt ctgtccggcg ctgcctgccc 5100
ctctgggccc taacactgga agcagctctc attctcctct tctatttttt tacccactat 5160
gacgcttcct tagaggatca aaaggggctc gtggcatcct atcaaggtga gagttcattg 5220
gaaaagtggt cacaggagca aatagcaggg gcaggggcgg gggaggcctg tggttctcca 5280
ggggcacaga tgttcctttc tacaaaatcc caaggaaaaa gattccccca tcttcttccg 5340
tagattgcac cgaaattcag ccaacaatgt aagctttcct ttagaagcag cctgggcatg 5400
ccctcttctg tgaagcctgc cttgattttt cagcacagtg agaggcatcc tctttggtgt 5460
tcctcaaatt ccctctacca aatggtcttc ataattctct gcttctctgc ttccccttct 5520
ctctcctcag tggcaaggaa ttttttttatt tttatagatt taggggatac aagtgcagct 5580
atcttatgca agcaatttca tgttgttggg tttttggttt ttgtttcctt tttgtggcct 5640
ctcgctcatt tcttatttct ttttgaggca gggtctcact ctgttgccca ggctgaagtg 5700
cagtggcatg atcatggttc actgcagcct tgacctccta gtctcaagca atcttcccac 5760
ctcagcctcc caagaagctg ggaccacagg agggcaccac catgcctggc taattttttt 5820
tttttttttt tttggtagag atgtgggtct ccctgtgttt cccagactgg tctcaaactc 5880
ctggacacaa gcgatcctcc agcctcagtc tcccaaagtg ctggaattac aggcgtgaag 5940
cactgtgccc agctctcttg ctcatatcta tactagtttt cttttggaag cttcagcctg 6000
ttgctacccc ccaccccccac ccccaccgac cccagctttc ttctcactta ggggctggga 6060
agtctgcatg ctgtctataa atccagaacc agaaggtatg gctgaagggg agggtaggat 6120
gatggttatt ttatattcag ctaaaaatat tcccagactg tgatgagaca actgtaaata 6180
agacagatgt ccacaatggt gtgactttgc ttttttaaaa atattgaaat gagtttcagg 6240
catctcagtg ggctgatagg ttgttgataa tagacagggc ctccttgaag aatgtccctg 6300
agacaaagtt gaagcttgag cctggttgag tccttgcttg ttcctaggtt gatatgaacg 6360
gctagttaac tggaagcaaa gagaagtcat cctgggggcc atggcagtga caagtaggac 6420
ttagggaggg aagcccttat accatttaag gtgctggccc agagaggagc cttcagtgac 6480
agacaaacaa gagctggcac aattttaatt cacttcaatt tactctaatt catttcaatc 6540
caatacaatt caatgcattc cattcattca accatgtatg acatccaatg tgggatccag 6600
actcatgatg attagagctg atatttatga gcacttacta tgtaccaggc actattctac 6660
atgctttaca ttgaaccctc acaataaccc aatgaggtgg gtactattat gatcttcgtt 6720
tttcatatga ggaaactagg catatggatg ttgagtaatt tgcccacggt cgctcagcta 6780
gcaatagcac agcgtattta aatttagcca ccctggattt agtttcctta cacttaacca 6840
ttatgcatca tggccccatt ttacagtggg cttgagtctt tgtcatataa cccagtaggt 6900
tagcagccac tattccaacc ctgtagattg actctagggt ccatgttctt taccccctgca 6960
ccgtgctact aacgtaggta caaaatgtcc tcagaaactc actttatacg gaagctcaga 7020

-continued

```
ggagggtcca caacccaggc aggggagacg atggtgtcag gggagggagg tgactgccca   7080
gccaggtctt gaaggctcag taggaattac ctgtgggaca aaggagggtc atccaagtga   7140
gggcacagtg ggtgccatgg cgtgcacaca caatagagca gactgagcct gggcttaaca   7200
ttgcattgcc ctggagccta aaaggggaaa caaagggccg ggcgacgtgg ctcacgcctg   7260
taatcccggc acattgggag gccaaggctg gagaatcacc tgaggttagg agttcgagac   7320
cagcctggcc aacatggcaa aaccgcatct ctactaaaat tataaaaact ggctgggtgt   7380
ggtggcacac gtctataatc cgagctactt gggaggccat tacactccag cctgggcgcc   7440
agagtgagac ttcatctcaa aaaaccaaac aacaaaaaca acaacaagaa caacaaaaaa   7500
acaaagagga gagcagggac tgggtgtggt gactcatgcc tgtaatccca aacactttgg   7560
gagaccaagg caggcagatc acctgaggtc aggagttcga gaccagcctg gccaacatgg   7620
taaaaccctg tctctactaa aaatacaaaa attagccgga tgtggtggca cgtgcctgta   7680
gtcccagctg cttgggaagc tgagggagga gaattgcttg aacccaggag gcagaggttg   7740
ctgagctgag aacatgccac tgcactccac cctgggtgac agagtgggac tctgtctgaa   7800
aaaaataata gtaataaata aaaataaaga gggaagcagc gggtggcaga ctcactgggc   7860
tgcatacgaa gtttggcttc agtctgaggt ccgaatagta aacagcagcg agacaagttt   7920
gggtttgggt catggaggaa gccatgccag ggctggtgtt gggcacaggg aaaggggcat   7980
ggcttgagac accagaccag cgtggaggct gtagtgtagt attgacctga ggacttcaac   8040
attctgatgg tgtacacacg attttttgag catgtaccat ggttatatat tacactttaa   8100
gtattacttt aagtattact acattaatat attttgtatg ttacaataaa tacatacaaa   8160
ttaggaaaat tgaaagagat caaaatgaaa tatataatat tttcaaatta ctaatcataa   8220
tggtgtcaat ctccaggcag ggtccattgc tacagttgac gatagtggat gaaaattcac   8280
tcctcagagt cttcttgata atttgaaatt gtcttgattg acttgtcaga tctgattaga   8340
tcaacatgtt ttaaatctcg aatgtgactg acagcttgta cgaggagaag tttcactctg   8400
ccttttccct tttgttcact tgactgccat tatttctatg cttccaatct gtgtttttct   8460
gcacgagttg gttaagccat tacttcattt tgtgaaagtt tgttgagtta aacttaggta   8520
acttaatctg tcaatccact taattgaatt cagtcctggt aaactataat agattattca   8580
aacctgccaa ttctaaaaag acattttgag acaatcagga aatctgaata tagcatgaat   8640
atcttacgat atacaaggat tattgttaat tttgttaggt atgataaaag catggtgggt   8700
tgtttttgtt tttgtttttt aagtctccat ctgttagaga ggcacattga aatggcatga   8760
tatctggggt ttgcttttat gccagaaaaa agaaaaagta cagaaggatt atagaaacaa   8820
gattggtctc atgtgacaat catcagagtt tggagatggg cacgtagggt catcgtgctg   8880
ttctctctgt tttcgtatat gctttaaaag ttctgtaata gttaattaaa aaaaaaaaaa   8940
aacaccctgg ctgagcattt agggaggcca agtggggagg atcgcttaaa ccaaggagtt   9000
caagacgagc ctaggaaaca tagggagacc cccccccatc tctaaaaaaa aaaaaaaaaa   9060
aaaaaacttt aaaatttaac ccagtgtggt ggcacatgcc tatagtccca gctactcagt   9120
aggctgaggt gagaggcttg cttgagcctg ggagcttgag gctgcagtgg gacgggattg   9180
taccacttca ctccagcatg ggcgacagag caagaccctg tctcaaaaaa aataaaaata   9240
tttgaggtga agcgaggctg taataacaaa tttaaaaata taaataaaac ataaaggctg   9300
ggtgtagtgg ctcacgcctg taatcccagc actttgggag gccaaagcag gcagatcacg   9360
aggtctggag atggagacca tcctggctaa cacgatgaaa ccccatctct accaaaaata   9420
```

caaaaaaatt agccgggtgt ggtggcgggt gcctgtagtc ccagctactt gggaggctga 9480
ggcaggagaa tggcgtgaac ccaggaggcg gagctttcag tgagctgaga ttacgccact 9540
gcactccagc ctgggcaaca gagcgagact ccgtctaaaa aaaaatgaaa ataaaaataa 9600
atgaaacata aaaccctgcc attagttgca atatgaagaa tatagagaaa tgcatatcaa 9660
atccttctca ttggaccaat attcccttag ggcaccttcc aaagctagga gactcaaggc 9720
tgtatgacat cctgagcaag tgaggggtgg cttctgggtg aatctgaata ttaaatattt 9780
gcagaattga aaacttcaca aagtaccttt agagatagaa tagcctagat ccatgtttct 9840
caaagtgtgg tccccagacc tgctgcctca gcatctcctg gaaatttagt agaaatgcag 9900
attctcaggc cctaggccag acctactgat cagaagctct gggcctgggg cccagcagtc 9960
tgtgttttca caagccctct tggtgattct tctgtgcatg aaagttcgag aattcctgga 10020
gctagactga ttcaaatctt gcctctgtat cttagagacc ttgggcagat tagtcaacct 10080
ctttctgcct ctgtttctac ttctgtcaga ggatgatagt acttgtttca ttaagttgtt 10140
gaaaggataa atgaattgac acacataaag agtattagct tttattatca aaagcttttt 10200
ttttgagaca gagttttgct cttattgccc aggggagtgc agtggtgcga tcttggctca 10260
ccgcaacctc cacctcccag gttcaagtaa ttctcctgcc tcagcctccc gagtagctgg 10320
gattacaggc atgcgccacc acgcccggct aattttgtat ttttagtaga gatggggttt 10380
ctccatgttg gtgaggctgg tctcgaactc ccaacctcag gtgatgcacc cgccttggcc 10440
tcccaaagtg ctgggattac aggcgtgagc caccgcgcct ggcccaaaag ctttaatttc 10500
ttaatttttt aaataaaata aataaaacta gaattgcttg ttttcttcca gctaccctgg 10560
tgattgtatt gagcattttc tggggtgtgt gttctttgct gtaatgacta ctggtctgga 10620
tgacctgtga tgagaccaga tgggcagggg cagtggagga gattctagag atatttagga 10680
gataagtcag ctgtacttga tgaaaagagt ggggagttaa ggctggctgc agatgtatga 10740
tttggcatag agaggtgcca gttcctgaga tgagagacag aaggggaggg acaggttgtg 10800
aggatgaatg aacaatgata tgttcattct gggcttggag ttaaggggcc tatgatatgc 10860
ttaggggaag cagagagtat caattaccta ttgctgcata acagccaccc caaacttagt 10920
ggcttaaaat agtaaccttt taatttactc atgatcatga ttctgtggtg caacaactgg 10980
gctgggttca gctgggcagt tcttctgtta gtttcaccca gggtcattca tgcatctgca 11040
gtttggggtg ggatggcctc agatgacctc attcacgtgt ttggcagttg gtgattcact 11100
gggggccatt actgtaacaa tcgcctacca ggcagagctt ccctaaggct tccaaactag 11160
gagactatcc tgggtcctgt gctgtggata ccactcagtc ccccatcccc accccatatt 11220
cctcaaaggc agagagaggg gctactagaa gacagaggag ttttcccagt gacatgtaaa 11280
cactccaaac cctggcacct tccacactgc agctttggtc tgcccctttg ggaaatctct 11340
gtttttcttc ccaggctgct ggaggggtga gagtcgccgg tagagtagag gctgtgggcg 11400
aggaggtggc ggcctcctga ggctgcagtg gtctttccag gcagcagtgg gagcacaggg 11460
tggaggtcaa ccctagagcc tgggagagtg aagctgggtg tgacttcaga gctgttggtg 11520
ctgaagtttc tgcaggccag aaggagggc aagagtggga gggggcgcag atccagaatc 11580
acggaggcag ctgaccggag gaggcagctg cccaagggga tggactcaga aggccaaagt 11640
gctgttatcc aaacgaactc tttgcaagtg gtctctttgc aacaggcctg ggggagagca 11700
gtcttgccta aagtcacacc gctaatcagc ggccggcacg gggtaacagt tactaacact 11760

```
cactacgtac ccaatgctgg gcgaagtgac ttgcatgagc cagcgagctc aatgctcatg  11820
gcaatcctct gagcagctgg cattgtttca tctcaatttt acagctcagg aagctgggac  11880
acagaggaag agccaggctc tgaacactga caacctgatt gagagaccca cactgttcat  11940
caccgttacg ctatatatgc tgtatagaaa ggcaggatgg cataatggtt aaacctaggt  12000
aggtagggtt tgaatcctcc tgctaccatt tactagctct gtgacttgga ctagttatag  12060
cacctctctg tgcctccctt tccccatctc taaaatgggg ataataaatc gtacctccta  12120
cctgaggctg ttgtgggcta agtctgtaag gcacgtagaa cagtgcctgg aacgtggggt  12180
actgtctatc tgtgtgcctg ctgttacaac aatggtgagt attgccttat ctctcgctgc  12240
tgaactacca ggttagactt ctttctgcaa gtcatgaggc tttcataaac ttttcctgaa  12300
ggctttccgt agaatgtaca attcccctct gggtccaggc atgggcgccc gggtagcaca  12360
tccacttctt atcacccctg aacaccttag agcccatcag cttatcaaac cagcagctga  12420
tgtgagtgca gagcagactg tgagaggtgg aggctgatac cagtgaggat gctccaagct  12480
gggacccagc cctgaagcgg gagcccagat aatggatggg tggaaatggg cctggagccc  12540
aggagaagtg ggaggatgag ggggcagggg gaggagaagc ctgaaatcaa atgttatttc  12600
ctgaccagtt tggggtgcat gagctctgtc aacagctcat ggaaactgct gccctaattt  12660
catcttgttg gctgaggcac aattcctctc tcagggacag tgtagagcct tggggaggaa  12720
ggccctgagc gcgtatacct ggaatcaggg aatcgggatc aggggcagca gctgtgccca  12780
ataaagcccc cacccaggat cctctgactt cctcatctct tttttttttt ttttgagctg  12840
cagtctcact ctgtcatcca ggctggagta cagtggtgcg atctcggctc actgcaacct  12900
cagccttctg ggttcaagcg attctcctgc ctcagcctcc tgagtagctg ggattacagg  12960
catgcgccac catgccaggc taatttttgt atttttagta gagacggggt ttcaccatgt  13020
tggccaggct ggtctcaaac tcctgacttc aagtgatctg cccacctcag cctcccaaag  13080
tgctaggatt acagacataa gccactgtgc ctggcctttt tttttttttt tttttgtaa  13140
acagggtctc cctctgtcac ccaggctgct ggagtgtagt ggtgtgaccg cagctcactg  13200
cagccttaac cttctaggca caagccatcc tcctacctca ccctcctgag tagctgggac  13260
tacaggcact cgccaccacg cccaagtaat tttgtatttt ttgtagagac aaggtcttgc  13320
tatgttgcct aggctggtct tgaactcctc agctcaagca atcctccctc cttggcctcc  13380
caaagtgctg ggattgtgct gggattacag gtgtgagcca ccatacctgg tctgacttcc  13440
taatctttag ggccccaact ctgcccttat ccaggcaact ctcctctccc catcttccac  13500
taacttcttt ggaatattcc agagctgtaa aagccttaga gagtatcaag tccaactcct  13560
atgtgttaca gacagggaaa ctgaggccta aagagggtaa tggacttgcc taagatcact  13620
tagtgaggtg agagaagaaa gagctagaga cagcctagcc tgtgcaagga catagttcca  13680
ggcattcaga gctgggctct gctgccggca tgtttggggc ctggtagtta gttcactgct  13740
gaactaccag gttagatttt ctttctccaa gttgtggagc tttcataaac ttttcctgaa  13800
ggtcttcctt acaatgtaca attctcctct gggcccggtc atgagcgccc ctcacaggct  13860
ctctctggtc cccttctgta aaatgagagg aaaatggaag aattgctcta ctcatggaat  13920
cttcaataag tctgggccct atgcatatag cattgctaca aaatggcaga tgcactttaa  13980
caatcgtgtt taataaaagg ttggatttgc atatctgaag tggggcatgc agtctccaac  14040
tgaacacaag cctcactgct cccgcatgtg cactgcacct tcatatacat atttcctgct  14100
tggctcctga gggaatttga gtaatcccaa gaggaacccc tgtagaaaat gtcccctggc  14160
```

cacacacccc cattcctaag gatgcaagca ggagatagaa acattccctg cacctccctc 14220
cttgttgtca gaagaagtgc aaagagttga atccttccta atgcccactt ctcacccacg 14280
ccccaaatcc ccaggtccca tggaggtcct tgggggcctc ctatatcctg gtggtgtcag 14340
gttgatttgg aaatgtcagt gtcctccctt gtcctctctg gcagaccctg ggtatgtgta 14400
tgtttcaatg gaagtgaatt taaatgtact ttataaatca aagacttttt ctgagacttt 14460
ggagagttcc agtaatgaga gcttctcatt gttatcaagg ccagggctgg agaccagtgg 14520
caggtgagtt cctattgctg tgattgtcat gatgatgttg atgaacagtc actatttatt 14580
gagcgttctc catgtgccag tcactgtact aaacattatt tcctttggat ttcccagaaa 14640
cctctcaggt gggtctaatt acccttattc agctgataag gaaagtaagc aacttacaag 14700
accacagggc tatgaagtgg aaacacataa attgatattt cattttattt atttatttat 14760
tttgagacag agtctcactg tgtcgcccag gctggagtgc agtggtgcgg tctcagctca 14820
ctgcaacctc tgcctcccgg gttcaagcga ttctcctgcc tgcctcccga gtagctggga 14880
ttacaggtgc ccaccaccac atccagctaa ttttttgta attttagtag agacggggtt 14940
tcaccatgtt ggccaggcta gtctcgaact gctgacttca tgatctgccc acctcatcct 15000
cctaaattgg tatctttata tgtccaaaag agtcaactgg tggcaattta gtgaggttta 15060
atctaatagg aaatgataga gctgggatcg aacagagcca tgtgaactca aaacctatgc 15120
ttccccttcc accttttga aaaacattgt ctaggctggg cacgatggct catgcctgta 15180
atcccagcac tttgggagac ggaggtgggt ggattacatg aggtcaggag ttcgagacca 15240
gcttggccaa aaattagcca ggcgtggtgg cgcgcgcctg tggttcccac tgaagcacag 15300
gaggctgaag cacaagaatc acttgaaccc gggaggtgga ggttgcagcg agccgagatc 15360
gcaccactgc actccaacct gggcaacaga gagactctgt ctcgaaaaaa aaaaattgtc 15420
tacatgctgg ttgcagaaaa tttaaacact aaaactaaaa aagtaaaaca cctcccaaac 15480
ttagagacaa tattaatgac ggaaaaaaaa ttcttcaaga tctctctctc tccagtcatt 15540
tattcatgtg cgaaaacagt tggtgattat tgataaaata gcttttagag tttggagcaa 15600
ttatgtgcat tacatatacc atttgattct ggcaacctaa tgaaggagta tgatcatttc 15660
ccctatttaa cagacaagaa caagaagagg gagggcagat ggtgtggtag tctaaggcac 15720
aggctccagc agattatcta ggtgtaaatc ttggctgtag gccaggccct gtggctcatg 15780
tctgtaatcc catcactttg ggaaaccgag gtgggcagat cacttgaggt caggagttcg 15840
agaccagctt ggccaacata gcgaaacccc ttctctatta aaaatacaaa aattagccgg 15900
gcacggtggc aggcacctgt aatcccagct acttgggagg ctgaggcagg agaatcactt 15960
gaacccagga ggcagaggtt gcagtgagcc aagatcttgc cactgtactc cagcctgggt 16020
gacgagtgaa actctatctc gatattaaaa aaaaaaatct tagctctacc caccggggca 16080
agttacgtaa cgcctctgtg ccttggtttt catatctgta aaatggtgac agtaacagca 16140
cccacgtcaa agtgtggttg tgagaacgaa acaagatagt ctatgtaaag tgattaaaac 16200
agcgtaggca catggtaaac gcttaggaaa tgtaggctgt tataaagctc agagatgtta 16260
agtaactaga tcaagatcac acagttagag ggtgccagag tcctgatttg aacccaagtt 16320
tgtctcgttc tggagctcaa gctgctaacc ctttttcaaa actggaatta aaccaaagtg 16380
ctcaccctcc gctttgctgg gcccctccct gccctcaggt gcgtctcttc cactcacctg 16440
ccacagcagc ctctgctcag ggtctgagac cgggaaaggt gagggctacc caggtggccc 16500

-continued

```
tgatgttttc tgccagccag ctcaccaggt ccctcgcagc aggcggcaaa gggagggagg  16560
tttgctgtga agattatgtg gttcccaaca acaagagcgc tgggcctatc tctgccctct  16620
cttttctgtg tgtcctggga caagtcactt ggcttctgtg gcttcatttt ctcatgtgcc  16680
cagccagggg gttggccctc atatgcaata acagcagcaa tgacctttac tgagtgtcca  16740
tgtgcgtcaa gcacgtgtgc tttacacttg ttcttattat taggtttaat aatagaataa  16800
ttgccacatt tactgagcac tcattatggg ccaggccctg ccctaagtgc ttaattagct  16860
ttagctcctc taatccttat cttatcccca cacggcatgt tatgttatcc ccattattca  16920
gttgagaaca ttgaggctca aagaggcaaa gtaacttgac caaatacttg taaacgatct  16980
tgcatgcccc ttccagctgc catttagtaa gactctaatt tcataccacc ctaaatctcg  17040
tctgcttccc cctcgtcctt ctcgccatct ccccaccgag cagttggcca agatctgacc  17100
gtgatggcgg ccattggctt gggcttcctc acctcgagtt tccggagaca cagctggagc  17160
agtgtggcct tcaacctctt catgctggcg cttggtgtgc agtgggcaat cctgctggac  17220
ggcttcctga gccagttccc ttctgggaag gtggtcatca cactgttcag gtattgggat  17280
ggtggctgga tcacttctgg gtcatagagg gaatggaccc cgaaaggaca ggttccagaa  17340
gatctgggat attgcccccct ctctgtctag caccagtgct gtgcaatatt taggacatcc  17400
ttatactaaa agattattca ttgtttaaaa ttcaaattaa ctgggcatcc tgtattttac  17460
tggacagccc tactccgtgt atcacaagga atccaggcct acattcctcc tgcatccttt  17520
ctttcctgtt attgtcgatt atgattttgt aaagttacat aatcaatata agtttatgga  17580
aaacgtaaga aggaaacacg ttagacagag agaaatagac atgccacacc tagagagaca  17640
ttctattttt tttttttttt ttgagacgga gtttcacttt tgttgcccag gctggagtgc  17700
aatggcgcta tctcggcaca ccacaacctc agccttctgg gttcaagcga ttctcctgcc  17760
tcagccgcct gagtagctgg gattacaggc atgtgccacc gcgcctggct gatttttgtat  17820
ttttagtaga gatagggttt ctccgtgttg gtcaggctag tctcaaactc ctgacctcag  17880
gtgatccgcc cgcctcggcc tcccaaagtg ctgggattac agacatgagc caccgcgtcc  17940
agcctgagag acattctctt gaaaagaaag gactttcagc cccctaatgc tgctagacaa  18000
taaatagcca tgcctttatt ttcattaaat tacctgtgct ttgtttacat gcatttgtgt  18060
gaaatgctaa gaaccatcac aactaatgta tggtgccaga agtcagaata gttgttacct  18120
gggcaggagg tggatattga ttaggaagga acacaaaata accgcatggg gtgcagaaaa  18180
tgttctctat gttcacctgg gtgatgatta cacatcaagc tatacacgtt ttaaaagggc  18240
attggcactt aataggagga agtaggctaa attttttcct gaaacattgt tttgttttgt  18300
tcaaacctct gaatccctgt gctgcccaga tgatggtaaa cgtcatccta ggcatcttag  18360
ggacctctca aggccattcc agcctcccct tctaagaccc tgctaaacct ctgggcactg  18420
ctgttaaaca tttctctatg agccaggaac tgtgctgagc actccacaaa tattattttg  18480
tttaactctt ccgggtaggg atctaacctg gtatacaggt aaggaagtgg aagctcagag  18540
agggcaaggc acttgcctag ggccacacag ctaagtggtg gagatggctc caacttttta  18600
ttataacctt ttccacatgc tccagagtgc tcagaacatg aaacacagtc tagccagctc  18660
ccgattggcc ctggagggaa aaaactttat atatttttct tttttaaaag gtttagaggc  18720
tgggcatggt ggttcacacc tgtaatccca gtacttttgg gaaccgaggt gggcagatca  18780
cttgagccca gaagtttaag accagcctga ctaacacagt gagatcctgt ctctgcagaa  18840
aatagaaaaa tcagctaggc gtggtggtgt gcacccacag tcccagctac ttgggaggct  18900
```

-continued

```
gaggcaggag gatcacctga acccagtgag gttgaggctg agtgagccat gatcgtgcca  18960
cttcactcca gcctggacaa cagagtgaga ccctgtctca aaaaacagtt ttaggggccg  19020
ggcgcagtgg ttcatgcctg taatcccagc actttgggag gccaaggcgg ggggatcatg  19080
aggtcaggag atcgagacca tcctggctaa ctcggagaaa ccctgtctct actaaaaata  19140
caaaaaatta gccgggcgtg gtggtgggcg cctgtagtcc cagccactcg ggaggctgag  19200
gcaggagaat ggcgtgaacc cgggaggcgg agtttgcagt gaaccgagat ggtgccactg  19260
cactccagcc tgggtgacag agcgagactc cgtctcaaaa aaaaaaaaca aaaacagttt  19320
taggccaggc gcggtggttc atgcctgtaa tcctagtact ttaggaggcc tagcaggtgg  19380
attacctgag gtcaggagtc cgagaccaac ctgagcaaca tggtgaaatc ctgtctctac  19440
taaaaacaca aaaattagct gggtgtggcg gcaggcacct gtaatcccag ctacttggga  19500
ggctgaggca ggcgaatcac ttgaacccgg gaggcggagg ctatagtgag ccgagatcgc  19560
accattgcac tgtagcctgg gcgacagagt gaggctctgt ctcaaaaaca aaacaaaaca  19620
aaaacagtct atgagttaat tcccaccaga attcaataca cacacgcaca catgcacgca  19680
tacacacact gtgtccacct gggaagtgac aaagggcacc ctgggggatt tcaaatggtg  19740
gtggccctgg tttggtgttg ctgccttagc ttaaggtcac accagccttc agcctcctgc  19800
cccacagtct agggctgctc ccctcatctg atgtccacag ggacctgttt gttcttgact  19860
caatctagaa agacgagaag ggagagaagt cactcgcagc ctgagtgaac tcccctgccc  19920
cacccctgac tgcttggatc cccctagggg tgacccctgc tgaaactggc tccttcctga  19980
ccggttcccg tcagggctgt gctgatgggt ggtgcccagg cctgcccctg gggacggggt  20040
actctccctt ggcaacactc cagcttgtgc cacttgactt gggactgatt tggttctgtt  20100
ttgagtccct tcaggggagg ggcctatctt attcaacgtt gttgtttgtt ttcctcacat  20160
actgataact tagcaaatgg ctattggagc aaaaatgaaa ataaacggaa ctctgaagtg  20220
ggatgtttta aaattttatt tatttttta gagacagggt cttgctctgt tgcccagtct  20280
ggagtgcagt ggtacaatca tagctcattg cagcctgtgc ctcctgggct caagtgatcc  20340
tcccacctca gcctcctgag ttaaattttt ttacaggcgc ctgctaccat gccctgctaa  20400
tttttgtatt tttagtagac aaggggtttc accaggtggg tcaggttggt ctggaactcc  20460
cgacctcaag tgatccacct gcctaggcct cccaaagtac tgggattaca ggcgtgagcc  20520
actgtgtcca gcctaaaact gtttttgaga cagggtctca ctctgttgtc caggctggag  20580
tgaagtggca tgttcatggc tcactcagcc tcaacctcac tgggttcagg tgatcctcct  20640
gcctcagcct cccaagtagc tgggactgtg ggtgcacacc accacgccta gctgattttt  20700
ctattttctg cagagacagg acctcactgt gttgctcagg ctggtctcaa actcctgggc  20760
tcaagtgatc tgcccacctc ggctctgaaa agtactggaa ttacagcctc ctgagtagct  20820
gagaccacag gcacacacca ccacacctag cttttttttt ttttgctttt tgtagagatg  20880
gagtctcact atgttgccca ggctggtctc aaactccagg ccttaagcaa tcctcccacc  20940
tcagcctccc aaagtgcgaa gattacaggt gtgagccacc attcctggcc ttaaaagtgt  21000
gatattttta atgtattttg aaatctgcag gactctccct agaagataat agcaataacc  21060
aactccttta ttgtgcttga cgtatatcaa ctcactttgc ccttaccgtg gctccagagg  21120
cattgggtcc accttataaa tggaggcacc aaggcacaga gtgattaaat aaattgccca  21180
ggatcacaca gccagaaagt gtctgagtca agattccagc ccaggcagcc tagacctgag  21240
```

-continued

```
agcacgctcc taaccactgc acatcactgt cttagcacct cctcagcaca aactggccct  21300
tgaggaatga aataccgccg ccggcacaca cgctcctgag ttaagccttt gtcaatgaaa  21360
tgaacaccca cttaaaagga ataacctgtc caggcacgat ggaacattga gtaacccctt  21420
attctaaatt cctggtccct gtaagactcc ttccccatgc ccttgccctt ttctgacctt  21480
cccctaaagt ccttgaggct taagcgggca tagtctgcag caaacactgg ggaagctgag  21540
tccagacttc agagcacagg ctttggatct aggccagctg gatttgaacc tcacatttgt  21600
gatcagctgg catgactgtt tccaaaaagt ccattttaat cctctacgtg accctctgta  21660
aaatgggata ctgaatggtg agctagcacg attttacaga gagtgaattt tttttgtgtg  21720
tgtgtgaggc agtcttactc tgttgcccag gctggagtgc agtggtgcag tctcggccca  21780
ctgaaacctc tgcctcccgg gttcaagcga ctgccatgcc tcagcctcga gagtggctgg  21840
gattacaagc atgcaccacc atgcccgggt aatttttgta tttttagttg agacagagtt  21900
tcaccatgtt ggccaggcca ctcttgaacc cctggcctca agtgatccac ctgccttggc  21960
ctcccaaagt gctgggagta caggcatgag ccactgcacc cagccttata gggttaaaat  22020
ttaaaagagg tgatgctgtt acaagcctgt tttacaaaat gctcttataa taaatcatta  22080
tcatcactgt tgctgtggtt gtagcatcat catcattaac tcccagaggg aggagggagt  22140
ctcagagcaa gctgctcagg ggagactgga tgtccatgga ttgtccagct cagtaccact  22200
tcctccagga agtcctccct gataagtcca gtcagcatca ccctctcctt ccaatgaacc  22260
ccactagcct tgtgatatca cagatattct tagttgacag gctcatggtg tagcctgtct  22320
agatcataag tacatttttt tttttttgg atcataagta tcttcaagac caaaataatt  22380
ttctactcct gagcatgctc attggtcaaa ggaaggaagg aatcataata gcgttaataa  22440
ggctagcgtc ttttcagaag ttggttcttt gtgccagtct tggtgctaga cacaccgata  22500
ggaagaatac tccttcacat ccccaggaca ccaacatggg atacgtttga tcatcattct  22560
taatttgcag aaggagaaat aggctcagtg agatgaaata gccactccag tggcaaggct  22620
gggactggaa gccgggcttg tcctgattcc aaatccagtt tctttccact gccacggaga  22680
cggagagaag ggacagtggc cccagatggg gatggggtga ctggatgtgg gcaggcctgc  22740
gggggaagag tgccctctgt tgagcatccg aatgatggca gcagaaaaga agactgggca  22800
gaatcccagt tatcagatcc cctgagggaa cagtcacccc gatcaccctc agtcagatga  22860
gtgtgtgtag atcaatgcct catagatgaa ggcactgagg cacagagtgg ttaagtcatc  22920
tgccagacca catggctcag ggtgcagagg ccaccttaac gggagaagag atggtcactc  22980
cactctgcag catcagcgcc caggtgggta gaaatcttgt cttctattcc cacagaaagt  23040
aggtgcccaa cagtgtttgt tgaaagaatg aatgaatgaa tgaatgaatg aatgaatgag  23100
tgagaggcat ccttccttct cagtcgtcct ggctctccct ctctccccca gtattcggct  23160
ggccaccatg agtgctttgt cggtgctgat ctcagtggat gctgtcttgg ggaaggtcaa  23220
cttggcgcag ttggtggtga tggtgctggt ggaggtgaca gctttaggca acctgaggat  23280
ggtcatcagt aatatcttca acgtgagtca tggtgctggg aggagggacc tgggagaaaa  23340
gggccaaaag ctccatttgg tggggtttcc agggttttga aaaataaaga caacctgtaa  23400
tcccagctac ttgggaggtt gaggagggaa gatcacttga ggccaggagt ttgagaccag  23460
cctgggcatc atagcaagat cctcatctct aaaaagtaat tttttctaaa ttatccagtt  23520
gtggtggcat gcacctgtag tctcagttac tcaggaggct gaggtgtgag ttggaaggat  23580
tgtttgagcc caggagttag ggaccgagct gggcaacata gcaagacctc atctctaaat  23640
```

-continued

```
aaataggtag gtggatagac agatagatag atagacagac agacagacag acagacaggc  23700
tgggtacagt ggctcacacc tgtaatccca gcactttggg aggccaagga gggcagatca  23760
cctgaggtca ggagttcaag accagcctgg tcaacatggg ggaacctcat ctctactaaa  23820
aatacaaaat ttagctgggc atggtggcag gcgcctgtaa tcccagctac tcaggaggct  23880
gaggcaagag aatcgcttga acccgagagg tggaggttgc agtgaaccga gatcgcgcca  23940
ttgcactgca gcctggggga caagagcaag acttcatctc aaatttaaaa taaagaaaaa  24000
agaaaagaaa agattgatag atagatagat atccaaatga gtttacaaaa atgtggtctg  24060
tgcaaatgtt taaacacaac aaaccaatgc ctttaactac tacagtataa tcctgtagga  24120
ttgtgctatt catgatataa ttatggttat ataaaagtaa ttaattctca gagcctcacc  24180
agcagtgggt ccagcaagtt tgtacagcca gcatcttctt tcagtcagtg cgtgtcagta  24240
actgcatatg tcctctcatt gggagagcct gtcgaaagtc taaatttgaa ggcagctgtg  24300
aaggtaaggc caatccaaat ggctctccca gatcctctgc tgtaaccctg accctgagtg  24360
aggacatagc caaccttccc atctcatagg tgagaaagct gatgcctgga gaggggaagg  24420
gactgcccaa gatcacatag caagatagtg gcagaaccca agcgagaacc cacagttcca  24480
gcctggctta gaagaaagtg cactggactt ggagtcaaag gctggggttt gcatcccagc  24540
tctgccataa atccctgtgt gactctgggc aatttaacct cttagagctt tagtttcttc  24600
atctgtaata tgagggtagc agtactacca catagggttt tgagggagta attgaattaa  24660
tcacatgaga tgatgcatgt ttacaaaaaa aagcatgaag cccctttact gtgcctcagt  24720
gtcccaaagg actttggatt ttactctgag aaatacaggg agaactaggg agtgttgggc  24780
agaggagagc catgatctga cttatgtttt aagatactct ggcttctggg ttcagaaaag  24840
actgaagggg caagagagga agcaggtgga gaccagagcg gcagtgattg ccatcatcca  24900
gactcagact aggacaatag ctgtgagagt gatgggaagt ggttggatcc tgactgtatt  24960
ttaatagcag aattgacagg atttgctgat agactgcacg tggggtggga gagggtcaag  25020
atgacttcaa ggttctcatc tggcacaact cagcggctgc tggtgccatt tactgagatg  25080
gggaatgttg gggtgggata gatctgggag ggaaaaccca gagttcagtg tcgaatgtgg  25140
tagcgttagg gttaaggttg ggggaggggg ggtagagatg tgtatgaaac atcccagtgg  25200
agacactgaa tggagatgta caagtctgaa gcttagtgga aaggttaggg ctagggatat  25260
aaatttggga gttgttacaa tacagatggt gtttaaagcc atgagaccca aggagatcac  25320
tcaggagtga ggataaagag agatgggaag aagtctgagg actgagtcct agaacaccct  25380
gcattttaga ggggggacat gtgtaagagc cagcaaagga gacagaattg tgcttggaga  25440
ggcaggagga agcccaggag agcgtgaggt cctggaaggc aaggaaagag agggccccag  25500
gtgggctgaa tgctgctgag aggtcaagtc ggatgagggc tgggaagtag ccattggatt  25560
tggccaggag accttggcat gcatggttgt agaggaggat gaaggcaaca gcctggcttg  25620
actgattcaa gagcaggaga tgagaaagtg gagacagcat gcaggggcag ctctgccaag  25680
gactttgcta taaaggggaa cagagaaatg gaggagaagc aggagggcaa taatccgata  25740
gagaggaaaa atctgatgat acagaagaga gatgaactgc aagagtcaag cctttgagtt  25800
ggaaagcagg agtgggattt tgagcactga tacctttagg ccgatgcagg gacagttcat  25860
cttttttttt tttttataca acattttatt taaaaaaatt attttcatag aatacatttt  25920
cacattagag attcccattg tgcggaaata acaatttatt acttatagtt ttatatttgt  25980
```

```
ggacagattg ttttagaaca agtagaatac atttgagaat taaatctcag tttacaatgg  26040
ataatatttt gatatgtctc tggggaaact tgcccttaaa tggaacttct gtatcttcag  26100
aagcactcca agcgtttctt cctaggattt agaaatttat aatatgagat agcagcattt  26160
cctaatttta aaatttccct agtatatgta accatcagta ggtggtatct actgactaga  26220
gagggaagtt tttgaaaatt aaacactgtc taattttctg caaagttttt attcatgaat  26280
taagagtatt tccctttgtc cattattccc aaggcaaata tggaaatttg atcatgtact  26340
aatcataata aagctggatt ctctttaaga gattgagaaa ttaaaaggca aaagctgata  26400
tatcatgttt agttatattg tgagtcttat aagaagctgg gaggcaaccc cattaactca  26460
ccagaataca gaactcagtc tcacaactta gatataattc ctctcaaacc ttttcctcaa  26520
agattaaatt ctgaaaataa tcttgtgatt aagagaagaa ggctgtccac caatgggctt  26580
atctgttatt tcttccttat tgtgagctta atggcatgac aaagcagagg caaagaggca  26640
tacatcaatt cttcaaagta ggaagtcaaa aaggtcagag cttccacagc atggcaacag  26700
ctttgcagat gcccacatcg tgatagttga aatagcaaag cccagcaaag gttaaagctg  26760
aaaatgccaa aagccctgcc ttggcagctt tctgcgaggc atccccatga acataatcag  26820
taacaacttg tccaaggccc cagtgaccat gaagagtgag ggctgcagcc agggaatagt  26880
ccgtcgcaga gcaaggattc aaataagcag ccggaagcag acccgggagc aaaacactga  26940
caaccctctc gctagtccag tggagagatg cagccttgga gccagaatgg tggctcggtg  27000
acaagtgtat gtgctgcact ccacaccatt ctgggatagg tcggtcctga agaaatgctg  27060
agatatgagc aggtctgacc actggagttc gcagcaacag agctcggcct ccttgggcac  27120
cgcaaacggc actcagcctc cagggaaccg ccatctcgtt cctgaggcgg agagttcatc  27180
ttaacgagag aaatggcagg gactgtgaat aggccggcag atttggtggc gggtgccaca  27240
ggttcagtct cctgcaggga gaggagaaaa tgccttacta attccttgta ttttctcaga  27300
gaaacaagag gcaccgtcat cagcctcatg tgagggtggg aaggagggat ggggtttgcg  27360
gagagggaaa gtgtggtatg gtcatctgtg ggagtggaag agagtgagag ggctgcaggg  27420
gtgcagcggg actgcaggct ggcaccaggg tccctagggc ttgtagttgg tggaaagtgc  27480
atcagtgacc agggctgtgt gcagctgctc caggcaggtg tggaagaagc agagttgaac  27540
ttgcccagcc tggagtgctg cccagagtga gcccaaagcc caggggagac cagagatggg  27600
gctgtttgca aaggaggaag tataacagta gcccacaaaa tctgagctgg ttaagaaagg  27660
agagagagtg aaaatgggga gcccagcctg gcagcctggg tacacatctc agctcaaccc  27720
acactagctg aatccatttg ggccccttcg ttgacctctc tgtgcctcag tttccctatc  27780
tatagaatgg ggataagaat aaggctactt cctagggctg ttgtgaggat tgaacaagtg  27840
accgaacact tgttcaattt tgaacactgt tctaaagcat ttaggacagt gcctggcatg  27900
gggtaagtgt tgcggcagtg ctgttatttt catcatcacc attgttctca ggctgcgttg  27960
attggagctg ctgaagggag gcaatttaag gaagtgagcc ggacagatag gaggtggtgg  28020
tggttatcag gtgcgatgct tgaaactgag gcttcggagg caacagttac tggtaatgac  28080
aaggtctaag gcttgacagt gggtggcaga agtgtaacgc agggaaagag acgagcggtc  28140
aaggagccga gagggaagga gttgggtgga ctaagatcat ttgtggaaga atgatggaga  28200
gaaaggctga agggcagggg ctgacatcat cagtgaccaa gaggcggccg ggaggctgag  28260
accacagcaa gaaagggaga gtgtgatggc atcttcttca agggagctgg ggatgtttgg  28320
ggtggaaaaa agaacaatgg tctgggaggg aatatgggaa attttttttt tttttttttt  28380
```

-continued

```
ttttttttt gagatggagt ttcgctgttg tcatccaggc tggattgcaa tgttgcaatc  28440
ttggctcact gcaacttctg ccttccaggt tcaagtgatt ctcctgtctc agcttcccga  28500
gtagctgaga ttacaggcac acaccaccac gcctggctta cttttgtatt tttagtagag  28560
acggagtttt gccatgttgg ccaggctggt ctcaaactcc tgacctcagg tgatccaccc  28620
gccttggcct cccaaagtgc tgggattaga ggtgtgagcc accgcgccca gcctggaagt  28680
ttgtatttat taatttttgg ttgtcttcat ctgtgtatgt gactttaacc cctaaatact  28740
tcagtgtaca tttcttttt ttttttcttt tgagacagag tcttgctcca tcaatcaccc  28800
aggctggagt gcggtggtgt gatctcggct cactgcaacc tccgcctcct ggattcaagc  28860
aattcttgtg cctcaccctc ccgagtagct gggattaggg gcatgccacc atgcccagtt  28920
aatttttgta tttttagtag agatggagtt tcaccatatt ggccaggctg gtcttgagct  28980
cctggcctca gttgatccac ctgtctcagc ctcccaaatt gctgagatta caggcgtggg  29040
ccaccataac cggcctcagt gtatatttct gatgcagttg ggttctgtat ccccctccaa  29100
tctcatctcg aattgtaatc cccacgtgtt gagggcatga cctcgtggga ggtgattgga  29160
tcacaggggt ggtttccccc atgctgttct tgtgacagtg agtgggtttt caggagagct  29220
gatggtttga aagtgtggca cttcctctct ctctttctct ctctctctca cctgacacca  29280
cgtaagatgt gccttgcttc cctttcacct tccaccatga ttgtaagttt cctgaggcct  29340
ccccggccat gccaaactgt gagtcaattc agcctctttt gtttataaat tacgcagtct  29400
caggaagtat ctttatagca gtgtgaaaac agactaacac aatttcctaa aacaagggga  29460
cattctctta cataaccttt tttcagttaa caaaaaatgag aaattgacat tgatatatta  29520
tgattacctt attctcattt caccaatttt ctcaataata tcttttctag aaaaaaatat  29580
atattttttg tggtcgagga ttacatcttg catttagttc tcatgtctta ttaaattcca  29640
tcaatctgga gcagtttctt catctttctt tatctttcat gaccttgaca tgttttgaag  29700
tttcgagcca gttcttttgt agaatgtggg tttgtctgct gttcctcatg attagattgt  29760
gggtatgcat ttttggtagg aattctccaa gagccgtgtg tgcccttctt agtatatcat  29820
atcagaagac atgctatcaa tttgccccat tactgggtgt gttaactgtg atcattgggt  29880
taagatggta cctgccagga tcttccactg caaagttact attttcccct ttgtaattaa  29940
taaacatctt gtgaggagat aatttcctat agaaatcctg ttgatcatcc aactttcacc  30000
cactgatttt agtgttcatt gattcttccc tgaataaatt agtactataa taattgccaa  30060
tggtggtttt ctaattccat ctttccttca gtagttggca ttcttctgta aggaaaagct  30120
ttcgcttctc tgttcatcca ctcatctatg tacttattta tatcaccatg ggctcctgga  30180
ttccggttta cacacttcca ttttctgcct tttctctctg cttaatataa ggattaatga  30240
gaactccctg attcccagga agaaaatgtc agcagagctt tcttaggcgg aatgaagaga  30300
attcagtgta agaaccataa aggtgtatct gtgtagtatg gacagtttta aaaaacaaac  30360
aaacacaaag aacctccaag ggcaggaggt gctgccagac tcaggagggc actagaactg  30420
gctatgagaa gccactgaga tcccaggtag tctgtgctct ccatcttttg gctcttattc  30480
tctccgtaca tctaacatct ctgtacacca gctttctctt tagcgaaaaa cgtgtcccct  30540
ccacccaccc atccacctcc acttgttcct gcatttctat gtcccagatc ctgcagaaaa  30600
caactctttt ctctcagtta gtctcaattc tgtagtccag ggagagagaa tctgatcagt  30660
cccctgggtc atttttccac tctggtccaa gcagctacag ctggcatggg aaatagttca  30720
```

cacagtaaaa acatggctgt caagaagagg agtaaatttc agaggcagaa cactccctgt 30780
gagcccgaac ctcttcctgc tttgttgcag tcttcataac gattgcttta aaagactgca 30840
ttgatataac atcatctctc ttctctgcat ctttgacttg ctagcttaac tggtctagag 30900
gagggcttag cactgatttt gagtattcat tttcctcaaa acttcaattc agcctgggtt 30960
tcttcagcag gagggcccgg gggaaccaga gccagggacc agagtcattt cagtgcacca 31020
gctcaagaaa tgaatattcc aggccaagaa tccccaagtg ttcttcctga actccttcct 31080
ggtggagttc aaagagatga aaaacacaag cccgcttttc agttcttatc aggaaactgc 31140
atagactttc ctctttatgt atgactgagg gctttttacc atcatttgtt cccttcacaa 31200
atatttattt ggtatttact atataccagg gactcttgtg gcagtggaaa atacaactct 31260
catggaacgt ctgttccaga aggaaagact gccaataaac aataaaatag gcaaaagata 31320
tagcatgtta gagagtggta agtaccacag ataaaaatga aatggagaaa agaaacacga 31380
aaagttgggg agagaggata actgtttgag agggtggcca ggggcagctt catcttatca 31440
agagggtgat tttttgagta cagacctgaa ggtaacgagt gcacaagcca tatgggtacc 31500
tgagaacagc ggcagaacaa tggcagggtg ctgggagggc tgtttaccag ccacgctgtt 31560
tagaattgtc agcacatggt gataaaaaaa aaaaaaaaaa aaaaaaaaca ggctgggagc 31620
agtggctcat gcctgtaatc ccagcgcttt gggaggccaa ggcggatgga tcacttgagg 31680
tcaggagttc gagaccaggc tggggaacat ggtgaaaccc cgtctctact aaaaatacaa 31740
aaattagccg ggcacggtgg tgggtgcctg taatcccagc tacttgggag gctgaagcag 31800
gagaatcgct tgaacccaac gggtggaggt tgcagtgagc caagatggca ccagtgcact 31860
ctagcctggc gacagagtga gactccgtct caaaaataaa taaataaata aatacaaata 31920
aaaagcagac agacttttta gttggcttta gaattcttag acaccctcta cagacaaggc 31980
accccgattg cttgcaccca gggtggacta ctccctccac cctgcccttg ttacaccctg 32040
gctgggggtc agcatttcag gcagctgaat gacccaaagt gggaacacgc tagtgggttt 32100
gaggatgagc aagtggagga gggcaatagg aggtgacgcc cgagaggtca ggtgagagtg 32160
gatcctgcag ggtcgtggca agaacctgga ccttgacttt gagtgacatg ggagccgctg 32220
gaggcttctg agcagaggag taacatgatc tgacttgcat tttattttat ttatttattt 32280
gacgcagtgt cactctgtcg ctgaagctgg agtgcagtgg cgacatctca gctcactata 32340
gcctccgcct cccaggttcc agtgaatctc ctgcatcagc ctcccaggta gataggatta 32400
caagcaagca tcaccacgcc tggctaattt ttgtattttt agtagagaca gggttttgcc 32460
atgttggcca ggctggtatc gaactcctga cctcaggtga tccacccacc tcagcctccc 32520
aaagtgctgg gattacaggc aaaattagaa tatatctaga atttcctgaa gaccttagtt 32580
tggtattata agaagtctgg ttgcttcatg ttgcaaaatt tatatcactc atcactcccg 32640
cagagttaaa attccgctga gaagtaggaa tcagtgaggt gcgtgtccat gtgggttttt 32700
gccacaccta agtgaacctt ggtcaaaagc atataagagc tactgatagg ccgggtgtgg 32760
tggctcatgc ctgtaatctc agcactttgg gagggaagga tctcttgagc ccaggagttc 32820
aagaccagcc tgagcaacat agcaagattc catctttaca caaaatttaa aaattggcca 32880
ggcatggttg tacattcctg taatcccagc tactcaggag gctgaggtgg gaggattgct 32940
tgagcctggg agttggagac tacagtgagc tgtggccaca ccactgcact ccagcttgag 33000
caatggagca agactctgtc tcaaaaaaaa aaaaaaaagg ccaggcgcag tggctcatgc 33060
ctgtaatccc agcactttgg gaggccgagg cgggtggatc gcctgaggtc aggagtttga 33120
gaccagcctg gcaaacacgg tgaaacccca tctctactaa aaatacaaaa ttagcccagc 33180
gtagtggcgc atgcctgtaa tcccagctac tagggaagct gaggcaggag aatcgcgtga 33240
acctgggagg caaatgttcc agtgagccga gatcgtgcca ttgcactcca gcctgggcag 33300
agcctgctgg gttgggctgg gtaagctctg aacaccagtc tcatggcttc aagtcacacc 33360
tcctaagtga agctctgaac tttctccaag gactatcagg gcttgccccg ggcagaggat 33420
gccgacactc actgctctta ctgggtttta ttgcagacag actaccacat gaacatgatg 33480
cacatctacg tgttcgcagc ctattttggg ctgtctgtgg cctggtgcct gccaaagcct 33540
ctacccgagg gaacggagga taaagatcag acagcaacga tacccagttt gtctgccatg 33600
ctgggtaagg acaaggtggg gtgagtggtc tcctacttgg gctgagcaga atggctcaga 33660
aaaggctctg gctgaaaaaa tctccctcct ttaccaagtt cccctgggtg tctgaagccc 33720
ttccatcatg attcatttct ttgagtagtg tttgctaaat tcataccttt gaattaagca 33780
cttcacagag caggttcagg aggcctgggg tatgcagatt tcaaccctct tggcctttgt 33840
ttccttgtct gtaaaatgtg gttagctggt atcagcttga gagctcggag gggagacgtg 33900
acttccccat ctaactctaa gtgacaaggc tgagactctc cagccctagg attctcatcc 33960
aaaacccctc gaggctcaga cctttggagc aggagtgtga ttctggccaa ccaccctctc 34020
tggcccccag gcgccctctt cttgtggatg ttctggccaa gtttcaactc tgctctgctg 34080
agaagtccaa tcgaaaggaa gaatgccgtg ttcaacacct actatgctgt agcagtcagc 34140
gtggtgacag ccatctcagg gtcatccttg gctcaccccc aagggaagat cagcaaggtg 34200
agcagggcgc tgcccttggg cagcacttgg gtctaacagg actagcacac atatttatgc 34260
ccctccccac cccagggcca gcgtgggttg ggagagggca tgccgggtgg tggagctgtg 34320
cctgcctcta cagtggagct ctaggtagaa tgctgggtgg tcacagtggg cctgggactc 34380
aggagactgt ccagtgatca aaggctttct gggggtagtg attaaatcca tccatgctaa 34440
catgaaacag acctcagttt gaaccccatt tctgctagtt gctaaagtca gtcaccatga 34500
gcgagagtca gcagcaacag actagactag aattagccag cctctctctt ccccccaaca 34560
aatttcaaga atggaaccat cagaatcaga agtagagaag tatgtgacac tagccatgtg 34620
gctctggtca agccacttca acgttttgag tctcagtggc ctcatctgta aagtgggaat 34680
taagagatgg tgcatgtaaa gtgcttaacg gggagtaaat ggtaggcaaa cattagctgc 34740
tgctattagt aaagagagac gatggtgtgt gtgagtcttg tgggcagaga tgggtgagag 34800
gggagacaaa acaagttctc atgatgatgg gggaaggggc tccagctggt ggtgtcggag 34860
ggaagtctgg acagaccagt ggtggggctc gggtgggagg cactgggggg gctggagtgg 34920
aaagaatgtg gccacagatg acagcttcac agcagaattc agtgctaaga ggaagtgagt 34980
ggccatgagt tccatggtga cagaaagtct aagacaccca gcaaggcagg agtgggtgtc 35040
aactcaggga agcccagagg ctaatcctag gtgagagctg agggtgtcag ataagagcaa 35100
ggcaaggctc cggttctgga gcagtgaagg acatagcaga gctatgaccc aggaacaagg 35160
cccagcttat tgaaactggg cccagtcaca cagggtggca caggcaccaa gtagccaata 35220
ataataataa aaacaataac aatgatttgt gtctactggg catttattca tgttctatgc 35280
cagacactgg gctaagagct ttatatgtgg aaactcattt aatccttaca ataaccttat 35340
gaagaaggta catccaaaac cccattcttc taggccaggt gcagtggctc acacctgtaa 35400
tcccaatatt ttgggaggct gaggcaagag gattggttga ggccaggagt tcaagaccag 35460

```
cccaggcaac atagcaagac cctgtctcta aaaaataaaa caaaaaccca ttcttcccgc  35520
tgcccaggga cacaccacta atgagtgtga tgggtgccta ggatgctgag cacctggact  35580
tcccagctca ttccctaaat gctgcacaat cagggtaact gtgccctgag cctaagaggc  35640
agtagtgagc tggcccatca tgtccactga tgaaggacac gtagccccaa cacaggggag  35700
aagtggtttc aggatcagca aagcagggag gatgttacag ggttgccttg ttcccagcgt  35760
gctggtcact tgcagcaaga tggtgttctc tctctacctt gcttccttta cccacacgct  35820
atttctttgc agacttatgt gcacagtgcg gtgttggcag gaggcgtggc tgtgggtacc  35880
tcgtgtcacc tgatcccttc tccgtggctt gccatggtgc tgggtcttgt ggctgggctg  35940
atctccgtcg gggagccaa gtacctgccg gtaagaaact agacaactaa cctcctctgc  36000
tttggctgaa ggccagcagg acgctgggac ctgatgggcc actgtgcagt gcacagctgc  36060
attaggcagg tgtcggcgca ttctcttatt ggcttcaacg cctagtgagg gatccatcct  36120
ggctcggtgg cgcatttgtt aagatgctcg ggagcaggtg gcagaaccca tttgagcttg  36180
cttgggcatt ggggagaatt tgttatcagg ctactggggt gtcacagaac tcaaggacag  36240
ggactggagt gttgtgggga gccccgaagc ccctgtttta cttctttctt tgcttttcct  36300
gaatatctgc tttattctta ctctatagac atgcttcctc ctctttcacc ccacattgtg  36360
gggtgtagtc ttttgcttca agaaagcagc ctggtggatg gaatctcttg gccccaatcc  36420
caaattctct ggagaagggg ctctttggtt taacttggat aatgttgtct tcagctgggg  36480
gtgggcacat cgtgcatatg tggctgctgc cggggaacca cgtggatgat gtgagaggag  36540
cagcacccag aagagggagt gctgggctga tggtccaggt cgtgtccact tctgattgtt  36600
taattcttct tctaagtgga tggatctttc tccaatactc agcaaatcct gatcgttcca  36660
gaatacttca ttatagccaa ttggttataa tgtgcttctc taagagaaat atttagggac  36720
aacaaatctt catgggtttg aagacttgat ggaggaaaaa ggagtagatt ttcgaaggct  36780
ggatttggat gaacaggggc tattcaggga gtgcattcca acctaaaatt aggaaaaact  36840
ggctgggcgc agtggctcac gcgctttggg aggccgaggc gggcagatgg cctgaggtca  36900
ggagttcaag accagcctgg ccaacatggt gaaacccatc tctactaaaa gtacaaaaat  36960
tagccaggca tggtggcggg cacctgtcat cttagcgact caggaggctg agacacgaga  37020
atcacttgaa cctgggagac agagcttgca gtgagctgaa atcgtgccat ggcactccag  37080
cctgggcgac agaacaagac tctgtcttaa aaaaaaaaaa agtggtttat atacagagtg  37140
gaatattatt tagccataaa aagaatgaaa tcctgtcatt tgcagcaaca tggatggaac  37200
tggaggtaat taaaaaataa aattaaataa ggaaaaacgt atcaatactt cgattaacca  37260
aaaccagggc aaatctgatt ttcatctttg caaggggaac aaatttcttt tatctcctct  37320
ggctttgaaa ccctgaaatg aaaggaggaa gggcagaaaa aagaacacat agcaagttat  37380
catcagtctc agcgcccatc gcattccctg agcttgtttc cttgacttca tcactggcag  37440
gactattcaa aaatgattcg ctcattcatt catatattca ttcattcatc attccttcat  37500
tcaacacata cgttttaaca ctcatcttgc ttttcaagct atagtttagt gagcgaaatg  37560
gatacacaca atacagtgtg agaacagcaa gagggcacat ctgagctagc ctgggatggg  37620
tctggaaatg cttcctggag cagaggaaac ggttgacagc caagtgttga cagagaagta  37680
gtattagcca ggcagagaca tggggaatgt attccaggca gaaggcacag tgtgtatgaa  37740
agcttattgt taagaagagt gtgtggccca accaggaaac agacattcta aaggcatagg  37800
gtccacccag gagcatggtg gacccagatc cctgaaagat gggaggtgct caggcacact  37860
```

-continued

```
tcctgggcta gttgaggagt ctggatattt atttatttat ttatttattt atttatttat  37920
ttattgagac agagtctcat tctgtcaccc aggctggagt gcagtggtgc aatctcagct  37980
cactgcaacc tccacctcct gggttcaagt gattctccta cctcagcctc ctgagtagct  38040
gggattacag gtgcccacca ccatgcctgg ctaattttcg tgtgtgtatg tattttgttg  38100
ttgttgttgt tgttgttgtt gttgttgttg agacggtgtc tcgctctttt gcccaggctg  38160
gagtgcagtg gcgccatctc agcttactgc aagctccgcc tcccgggttc acaccattct  38220
cctgcctcag cctcctgagt agctgggtct acaggcgccc accaccacgc ccagctaatt  38280
ttttgtgttt ttagtagaga cggggtttca ccatgttggc cctgctggtc ttgaactccc  38340
gacttcaggt gatccaccca tgtcggcctc ccaaagtgct gggattacag gcatgagcca  38400
ccgtgcccaa cctggatttt tattctgaag actaataggg attctaagga aggaaccagc  38460
ctgattgaat ttgcatatgt gtccacatct gctggctcac ggctgtgtgg gaggctgagt  38520
gatggggagg aaggattact gagtagggat ctgaaggtgt ggcctcatgc tttctttcta  38580
accagctgtg ttgtctttgg gatggtgctt aaatttgggc tagaccagtg ggtcttggtc  38640
accccccagg ggacatctta caatgtctgg aggcgttctt ggttgacaca gtggggtgag  38700
ggctgctact ggcagctcgt ggggagagac cagggatgct gcttaacatc ctacagtaca  38760
cagggcagcc cccaccacaa ggaattatca gctgaaattg tgaacagtgt ctacactaga  38820
cccttgctac tcatagtgtg gtccgtagac cagcagcatt ggcatcacct gggaccttgt  38880
tagaaatgct gttagacccc accccacatc cactaaagcc agctcttcat ttcaacaaac  38940
tccccgatga tgtgagtgca cattcaagtc tgagaagggc ttctttgagg tgagccttag  39000
tgcccatccc cctttggtgg ccccggatac caagggtgtg tgaaaggggt gggtagggaa  39060
tatgggtctc acctgccaat ctgcttataa taacacttgt ccacaggggt gttgtaaccg  39120
agtgctgggg attccccaca gctccatcat gggctacaac ttcagcttgc tgggtctgct  39180
tggagagatc atctacattg tgctgctggt gcttgatacc gtcggagccg gcaatggcat  39240
gtgggtcact gggcttaccc cccatcccct taacactccc ctccaactca ggaagaaatg  39300
tgtgcagagt ccttagctgg ggcgtgtgca ctcggggcca ggtgctcagt aggcttcggt  39360
gaatatttgt tggctgattt attcagaaat tctgtccagc ccctaccttg gatggattta  39420
tcacctctcc aggccacctc ttctttccaa atagggccac ctaggtatag accaaagaca  39480
cgaaatcttt tgtgatccca caaacacaga gcaggtcaaa taggcccaag ccaattgaga  39540
ctgtggttca ggtcgtgatg cagagctttg ctgtggacgt gctcccactg cgtactagct  39600
gggcatgtgg cttaaccttt ctcagcctca gtcgccccat tgtaaatgga gataatgata  39660
ctatctcccc tcacaggact gttgggatgc tactggattt aataagctaa tgcagggaca  39720
tgctaagcac aacccatccc tgaggcccag agaggggtgg gccttggctg aggtctcact  39780
gcgaggtggg aatgtgggcc tccagaccag aggtaggtcc tgtggcccct agacagtgga  39840
cagcaatggt cagtttgaca caccagagcc ctagccatta cttcctggat gttgtgtgaa  39900
tattttctgg acatggctta tataaaatga aaaagtgaat tgggcacgat acagggatag  39960
atttttagag atgaactggt agcatgatga taatcatatt cactgataac atttactact  40020
gttattgact gctttaaaag tgttgggcat tgtgctagaa accattatat gcattatctc  40080
cttgaattct cacaaccgcc tactgaggta ttctcagact ctaagaaatg agatttaaga  40140
gaagttatct gcccaaggtc actcggctgg aacctggctg taaaaatggc tgaagcaggt  40200
```

```
gatgaggagc tgatgcgttt ggacgtgtct cagagaaatc atggaggcgc tgcggttcct  40260
accggttctt ggatgccttc tacagagaca accatagccc caaattatag ggatcacata  40320
tcagtgggtg agacatcctt gcttgggatg aggaggggat gagctgtgtg aagcaaggcg  40380
cctctgtgat gggttccagt gatgtgtctg ccactgtctt aataactgtg caattctaag  40440
cagaaccttt cctgtctctg ggcctgagag ttcccctctg aaagatgagg acttgaccta  40500
gcaaggtcct actcacatgc ctgtagagaa caggcagggg aagttagaaa aaaaaaaaag  40560
ccagtgaagg aagggagctc ttcagcttgc acccatcatc acagtgcagg gacccaggct  40620
cagtgttgcc agatccaatg acttctcaag agctcaaaat ctagagtttt gcatgtgctc  40680
tcccaagtac tggcagaaaa ttcaagattg ttagtaacac tgtgtggcta aattctgctt  40740
gtgggctgcc tagattccca attctgtgat tctgtggttc tctggaagca ttggttctcc  40800
acagcacctg catcacttgg aaacttgtta gaaatgcaag ccctacctac ggccccaccc  40860
cagacctacc cagttagaaa tctgggggtg ggacctatca gtccatgttt gaacaagccc  40920
cacaagtgtt ctcttgcaag ctcaagtttt agaaccactg acctatagcc aaaaaagaaa  40980
aagccaatca gtggttttct ggtaaaggat taacttaaca aactggcttt ccaagaaaat  41040
aaagccttga ttggtagcac ttgcaatttc tatggtacaa acgcttcccg catgactgag  41100
ttcaagctgt caaggagaca tcactataca tggacttggg aagagatgag aacaatcagc  41160
ccactgagcc tatgggaact ggctccagca catccctgca agtcaactct catcagggtg  41220
agtgagttga ggaccaagaa gcagttatcc tcttgccttt gcaggaccca ggcaaaggga  41280
agggcatagt gacagtgatg atctctcttc cggaagtctt tggtttgctg agagtaaaag  41340
gcgtgggctt caccagtggt gaagccagtc atgcagcctt agtcctggta ctgaaactct  41400
ctaaatctca gttttctatc tgtaaaatgg gaaaataaga cctatgtcac agggttgctg  41460
tgcagattta gcaacagaac atagccccgt tctttatgat gactgatgct gcatccgtat  41520
gaggacatct ctatgtaatg gaaagatgga gagaggatta agcgcaaagt cacaacactt  41580
aatgggaact gtggattagc tacttggtgg cattgggcaa gtcagttgac tttgcattaa  41640
ttccacaaac aatatttccc aatttcctat tcagatgagc atatgtgatt gagtcagatg  41700
ctgtgatcag aaccaggatg gagcatttcc cacaaactgt gggattttta agtaatggga  41760
aggcacactg aaatggcact gaatcatgca gttgcagata ctctttttca attctcagtc  41820
ctttgattac gtcagggaga aaagaaagtc cccacttggc ctgagaatct ctgcacccctt  41880
ctagctcttg ttaaccactc ttttgaatag cagagaaaac ctcagactgc catatctggg  41940
agagatttta gcaacatttt gttttcattg tatctctttt tacagctacc tcccatttcc  42000
cttctatttc aagctagtaa ctcagttttc ttttaaattc aattatttaa atgtaaaaat  42060
aagtctattt ggagaaaaaa aattttaata gcatctctgg aatgccagta tggctaaatt  42120
catgaatgtt gtcctcaaat gctgaaatct gggaagcatc tggccaagct ttgtggacag  42180
gcctgcctag tttgaatccc aagagccacc cagtccaagc cacaaaacat tggaattctt  42240
ggttcacttc cctaacctga acttgccctc tgtgaaatag ggacactaat agctcactca  42300
cagggctgct gtgaggacat gtgttgagct gagggtctcg ccaggggaga ccctgtgcag  42360
ggagactgtt atcatggtga tggatttctg cttcattcat ttctttttcc agacagcatc  42420
atatagaatg agttgtgggg tggcagtcag caggtttggg tttatcctct attctgccac  42480
ttattactta aaaaaacccc aaaaaaccca acttatatag tataagctat atccagaaaa  42540
gtgcaaatat catacaagta ccatttgatg aatcttctga tatccccaca taaccaacac  42600
```

-continued

```
ccagaacctc ttcttgtctc attccaggat aaccactaac ctgacttcta acagcatcag  42660
tcagttttgt ctgtttttgt acattatata tgtgatggtt tgaatgtgtc ccccaaattt  42720
catgtgctgg aaacttaatc cttcaattca tatgttgatg gtttttggag gaagggcctt  42780
tgggaagtaa ttaggattag ataaggtcat ggggtgaggt atgatggcac tggtgactta  42840
taagaagaga aagagaaatc tgagctggca tgctcttgcc ctctcactgt gtgatgactt  42900
ctccatgtca tgatgcagca agaaggccct caccagatgg tggcaccatg cttttggact  42960
tcccagcctc tagaactgtg agctaaatca atttattttc tttataatca cccagtttga  43020
tattttgtca tagcaacaga atatggacaa agaaagaaaa ttaatgcaag aagtagagtt  43080
tttactgtaa cagattcctg aaaatgtgga agtggctttg gaactgggtg atgggaatag  43140
gttggaagag ttttgaggag caggctagaa aaagcctgta ttgtcaagaa tggagcatta  43200
tgccaggcac ggtgtctcag gcttataatc ccagcacttt gggaggccaa agcaggtgga  43260
tcacctgagg tcaggagttc gagaccagcc tagctaacat ggtgaaacgc tgtttctacc  43320
aaaaatacaa aaaattagct gggcgtggtg gcgcacacct gtaatctcag ctactcagga  43380
ggctgaagca ggagaatcac ttgaacccag gaggcagagg ttgcagtgag ctgagatcgt  43440
gctattgcac tccagcttgg gcaacaagag caaaactcca tctcaaaaaa aaaaaaaaag  43500
aaagaaaaag aatggagcat taaagacagt tctgcagttc tggtgagggc ttaaaggaag  43560
accccagaac tagggaaagt ctggaacttc ttaatggtta ctgaagtcgt tgagatcaga  43620
gtgctgatag aaatatggct ggtaaaggcc attctgatga ggtctcagat agaactgaag  43680
aaccacgtgt tggaaactgg agcaaaggtc atcctttta taaagaagca aagatcttag  43740
ctgaactttt tctgtgccag agtcatttat ggaaggcaga aaatctgtag gtcagccatg  43800
ttgtagggaa tgaaagaaca ttttcagctg agaacactga gagtgtgaca caactaccga  43860
ctgataagaa aactagtaca cataaattag ccaggcgtgg tggtgggcgc ctgtattccc  43920
agctacctgg gaggctgagg caggagaatg gcatgaaccc gggaggcaga gcttgcagtg  43980
agccaagatc gcgccactgc actccagcct gggcgacaga gcaaaactcc gtctcaaaaa  44040
gaaaaaaaaa aggaagaaag aaaattagta cacatagaac aaagccagag gctgttcatc  44100
aggacaaggg agaaaaactc caaagccatt tcagagatct tcaagactgc ccctcccatt  44160
actggcccag agctctaaga gggcagaatg gtttggaatg accagctgct gcccagggct  44220
gccttgggtc tctgctcccc acatttctgg tgcagcattc ctcagccatc ccagctgtgg  44280
ttcaggtggc cacaggtgtg atgtggaagg taaaagtcat aaaccttggc agcatacaca  44340
tggcactaat tttgcaggtg tgcagaatgc aaaagctgag gggcatgcc ttcttccacc  44400
tacatttcaa agggtgctgt gaacagccac cccagagagc ccctagtaga gcagggtcta  44460
gtggagctac aagggtgggg ccaccgccaa gaccccagaa tggtagagct atcatagtgc  44520
aatgccagct tgggagaact gcaggcatga gactccaacc tgtgcgaagt gcaacatggg  44580
cagaacccag caaaaccaca ggggcagagc tccccgaagc ttcgggggtc caaattccat  44640
agtgtgtcca ggaggtggca cacagagtaa aagatcattc tgaaggttta aggtttaatg  44700
ttgttttcta tgttgggttt tgtactttcc tggaaccagt taccctttt cccttgcctc  44760
tttttccttt tagaatggga atgtctgtcc tatgcctgtt ccactgttgt attttggaag  44820
tcaataactt gttttgactt tacaggctta cagccagagg gaatctccca tagaatgaat  44880
tgtaccttaa gtctcaccca catctgattt agatgagacc atggactttg gaattttgag  44940
```

-continued ttggtgctgg aacaagttaa gactttgggg gttgtctaag tgtggtgttt catgcctgta 45000
atcccagtga tttgggaggt tgaggtggga ggattgcttg agcccaggag ctcaagacca 45060
gcctgggcaa catagtgaga cctgtctcta caaaaaataa aaataaaaaa attagccagg 45120
tattgtggca tatacctgta attctagcta ctcaggaggc tgaggtgaga ggatcacttg 45180
agcccaggag tttgaggctg cagtgagcta tggtcgtgcc actgcattcc agccagggca 45240
acagagtgag actctgtctc tacaaataaa attaaataaa cttagctgga tatggtggca 45300
cacatctgta gtcctagcta ctcaggaggc tgagacagga ggattacttg agccaaggag 45360
tttgaggctg cagtgagcta tgatcatgcc actgcattcc agcctggatg atagagcaaa 45420
atcccatctc taaaaaaaaa aaaaaaaaaa aaaaaaaaaa aaaaaacttt agtgctattg 45480
gaatgaattt tgcatgtaag aaggacatgc attttggggg ctggggcagg atgctgtggt 45540
ttgaatgcat ccctcaaatt tcatgtgttg gaaacttaat ctccaaattc atatgttgat 45600
gaaattggag gtgaagcctt tgggaggtaa ctaggattag ataaagtcat cagggtgggg 45660
cccctatgat gagactggtg gcttacaaga ggaagagaga actgagctga catgctcttg 45720
ccctcttgcc atgtgatacc ctctgccatg taatggcagg cacagcaaga aggtcctcaa 45780
cagatgccag cagcatgttc ttggacttcc cagcctccag aaccatgagc tatatatact 45840
tattttacaa attacccatt ctgtggtatt ctgttatagc aatagaaaat gaactgagat 45900
aatatacatg gaatcataca gtaagtctgt gcttttgtat gcttctttta ctcaacattg 45960
tagttgtgag attcatccag gttgttaagc attgctgtac cctttttcca ctgggatata 46020
gtgttctgtc atgcttgggt cttaatttat aaaggtgact gagtggcatt ttcttccagt 46080
attattggaa ggaaagtttt gttgttcaca gttcccctgt aaacaagagg cagaacacgt 46140
catgcagggc cacacaaaac tgtatcatcc agggaccagg cagcagaaag agagggggaa 46200
ctgggactat gcctttatga aaaagagtgg tgggagagta actgggtgag ggcatccact 46260
aatgggcagg aagtgaaaac acatatgtta gaatttgtag ctgaggggtt tataatatga 46320
gtttcctatg cctgagaaag ctgacttgca agaaaatgag ataaacaact ttggccatta 46380
gtgtggccct gtcataaatg aatgccagat aggcaaatag agaatctaag aaaagatagt 46440
tggaacaagt gttccattgt gtgaatgcag cagaatttat ttatccatta ttgaggagga 46500
tttgggtagt ttccagtttg gagctattat gaatattcta gtattgctcc tatgaacatt 46560
ctagcacttt tatttttgga gcacacgaat gcacttctgt tgattatatg cctagaagtg 46620
aaattgttga attatacagt attcacacag tcagctttag tggctactgc taaacaattt 46680
tctctagtag tttgcgccaa tctaatcacc agtagtgtat agaagctcct tttactccac 46740
atttgccaa cacttggtgt tttccttctt tttgattagt catttagcaa tcaaacctat 46800
tgtttacatt ttgatatctc caataactaa ctaaatggag cacttttaat atgctttttg 46860
gacagttgaa tatcttttct tgtgaaatgt ctattcaagt tagtttgccc attttctatt 46920
gtggtgttct gtctttttct tattgatttg taggaattcc ttacgtatcc tggatatgaa 46980
tcccactttg tgcgttacct ttttccttct ttctttcttt ttgaaacaga gtctccttct 47040
gtcacccagg ctggaatgca gtggcgctat ctcagcccac tacaacctct gcctcccagc 47100
ttcaagcaat tctcatactt catcctcctg agtagcttag attacaggcg catgccacca 47160
tgcccagcta acttctgtat agacaaaata atttttggta gagacagggt tttgccatgt 47220
tggacaggct gatcttggac tcctggcctc aactttggcc caccttggcc tcccaaagtg 47280
ccaggattac aggtgtgagc caccatgccc agcccacctt ttactttctt aatggtgtct 47340

-continued

```
tttgaacaag agaggttctt aattttaata tagcccaatt tatcattgtt ccctttatgt  47400
ttagttcttt tatgtccttt ttaagaattt ttgcagccag cgcggtggct cacacctgta  47460
atcccagcac tttgggaggc tgaggctggc ggatcacaag gtcaagagat cgagatcatc  47520
ctggccaaca tggtgaagcc ctgtgcctac taaaaataca aaaaattagc tgggcgttgt  47580
ggctcttgcc tgtagtctca gctactcggg aggctgagat cacgccactg cactccagcc  47640
tggtgacaca gcaagactcc atctcaaaaa aaaatttttt ttgcaaggtc atgcatatgt  47700
ccccctgatt tttttcctaa aaatcactta ttattagatc aatgaattga gtaattgact  47760
acatttttca gtcattcaac aaatatttcc ctgaggtttt gataacctga actgtgtttg  47820
gagctgggga ggaagcaaac tattgaagat atacaaagat ggcaaagatg agggcctgga  47880
gcttgccaca cggaaggggg gatggctgcc tgaatggttg ggcaggtagt tgttgacatc  47940
tgcactccct acatgagcag cagggtggca actcttttta tctttttaat ttatttttct  48000
tttctttctt tctttttttt tttttgagat ggagtctcgc tgtgttgccc aggctggagt  48060
gcagtggcgt gatctcagct cactgcaaac tccacctccc aggttcacgc cgttctcctg  48120
cctcagcctc ctgagtagct gggactacag gcgcctgcca ccactcccgg ctaatgtttt  48180
gtatttttag tagagaaggg gtttcactgt gttagccagg atggtctcca tctcctgacc  48240
tcatgatctg cccgcctcgg cctcccaaag tgtggggatt acaggtgtga gccaccacac  48300
ccggccttaa tttatttttc tagtctgcag gtaattcttt ttaattctct ccactctcct  48360
atgatcttat gaggtaggga ctgtcattat ttctcccact ttataatgaa caatcagtaa  48420
agacagggaa gataaccaaa tgacatacaa ggtggggtcc accccatgag gctgcaggct  48480
tggagctttg ctttgtctta aaaatgagaa catgagctgc ccacctgttg agacaagaaa  48540
caggaaaggc ttaaaaaact ggcttgttat gtacaactat ccgtggggct gcagtgaacg  48600
ggctggcagt gcccaggtgc aggctgaacc ctgggacaat cacattcagc atccaagggc  48660
ccccgtaata gcttaatgtt tgaattgaac ccctggggtt gccttgaagg agagaggtcg  48720
tggaagtatg ttcaaggggt agggatgggc aggggagatg ggtctgaaag ccaagctcta  48780
ccccacccac cttgccccaa gagaaataga accttcatct ttaattgcct aacgagaaaa  48840
ctggggctgg ccagatgtgg tggctcatgt ctgtaatccc agcactttgg gaggccgagg  48900
cgggcagatc acttgaggtc aggagttcga gatcaccctg gtcaacatgg tgaaaccccg  48960
tctctattaa taatacaaaa attatccagg tatggtggcg catgcctgta gtcccagcta  49020
cttgaggcac aagaatcgct tgaacctggg ggacagaggt tgcagtgagc cgaccactgc  49080
actccagtct ggacgacaga gtgagactcc atctcacaaa caaaaacaga aaaaaaaaaa  49140
aaaaaaagag agagagagaa aactggaggc tctgagaggt tgagggactt gcccagggtc  49200
ttgcagctag taagtgacag agctgggact tgagcttggg ttttctgact cctggtctgg  49260
ttcattatcc atgaggtgct gggaactaaa ataagccaca atcttggaat ctccgtcgcc  49320
tccctccctc ccacatgtct gcgtggcttt ttgggaaaat gccaggggaa tgtaccagcc  49380
agggagagga ccccttgtttt cctcatggcc cttcctggca atggcactac tgacaccgac  49440
agtccttttt gtccctgatg acctctgctg cctgatgccc aagtgaccac ctctgctttg  49500
tcatttctag gattggcttc caggtcctcc tcagcattgg ggaactcagc ttggccatcg  49560
tgatagctct cacgtctggt ctcctgacag gtcagtgtga ggccaccttt cttccaccat  49620
tgccaggaca cagcacccac gtccagagcg caccctgccg tgtggctgga tgtctatgtg  49680
```

-continued ccccatctcc ttccctgagg atcacataat ttcagaattg gaaaggttct tagaggtcac 49740
ctgctgctaa tgtggactgt gaggccaggg cagggaaggg acatccctga ggttataagt 49800
agggtgagtg gcaacgttgc agacttttga acccagggct ggtgatcaca ctcagttttg 49860
cacagaagcc cgagaaaatc cttacaccca aaagcctacc ttttatttct gaggacaccc 49920
ataatactat tttattcaac agatatttat tcaatatcca ctatgagcca ggcactgggg 49980
acacagcagt gagcaaaaca aattccctga ccccatggaa ttgaccttct agtgggggaa 50040
ggtattagca ataaatagac aaataagtgt ctactacgcc agatgggaag aagtggctgt 50100
gaagacagag caaactagag aaacatagag tcaatgtggg atggggtgtt cttttagggg 50160
ggtggtcagg gaaagcttat ctgagtagtt agcttttaag cagagacccc aatgaagagg 50220
agggagatat gcgatgcatt tagttagggg aagaacattc catgaaaata ggatagcaag 50280
tgcaaaggcc ctgagacagc agcatgcttt gtgtgttgag ggaacagtaa ggagaccagt 50340
gtggttggtg tgaatggagt gagaaggagc agcaggggtt gagggcagaa tggtagtgag 50400
gagcaggccc ttataaaaga tgggaagcca ctggagatct ttcaacaaag gggaaaagta 50460
tgtttctgtt cttgcaataa aatagaacag caaaaaatct aggggagttg ctaattagcc 50520
agttttactt atatgccagg tgaaaatatg tggctaggtg cagtggctca tacctgtaat 50580
tgcagcagtt tgggagaccg aagtgggcag atcatctgag atcaggattc aagaccagca 50640
tggccaacat ggtgaaaccc catctctact aaaaattaaa aaataagcca ggcgtggtgt 50700
tggatcccag ctacttggga ggctgaggca gtagaattgc ttgaacccgg gaggcagagg 50760
ttgcagtgag ccgagactct gtctaaaaaa aaagaaaaaa agaaaataca cattcaggcc 50820
aggtgcagtg gctcacgcct gtaatcccag cactttggga ggctgagaca ggtagatcac 50880
ttgaggtcag gagttcgaga ccagcctgac caacatggca aaaccctgtc tctaccagaa 50940
atacaaaaat tagccaggcg tggtggcgtg tgcctgtagt cccagctact ggggaggctg 51000
aagtagggga atggcttgac cccaggaggt ggaggttata gtgagtcgag gttgcaccac 51060
tgccctccag cctaggtgac agagtgagac tgtctcaaaa aaaaaagaaa gaaaatatac 51120
attccatcca gaactgttca cctttattct acaagcaaac atcttttatt ggttagacac 51180
ccatatatgt gtccctaagc aggaggtgaa tgccaaataa gagacaaatg gcgtaagaca 51240
ctatgagttg tgtgacgttg ggcatgtcac tttactccct ctgagccttg gttagcttct 51300
ctgtaaaatg aaaggattat ggtaactaag ctggcttcct tccagcttta acaaactgta 51360
tggaggtact ttttggagtt acctgggtaa tttttgagtg tgagattggc tagaattgct 51420
ttaatatacc atgtctggcc ttagcttttt gcagagtctt tgtgaagaag cagaggcgga 51480
gtagcgttaa ttccgtaagt taacgttcag ttcgtggcag ctggcaatcc aaccctggga 51540
aaggctgccg gatttagcaa aaatgcaagg tgtctgtttt taaatttgaa atgaattggg 51600
tatcctgcat tttatttggc aaccctgtcc tgggactcac actattcact gttatcactg 51660
gtatgttcaa agtggtgctg acttgccctc tgtcttgcaa agtaccagga ggtcttttct 51720
tattcttcac tggagtcaaa aaagagaata gaggaaaaga caatcatatt gttcctttaa 51780
gagttaagac caacaagttt tcttctttac atgttgtttt tgacatgagc aaactggtga 51840
ttaaaaacaa cttgggtggc tcatacttgt aatcccagca ccttgggaag ctgaggtggg 51900
agaatagctt gaggccagga gttcaagcca gggcaacata gtgagacccc atctctacaa 51960
aagatacaaa aattagccag gcgtggtggt acacctgtag tcccagctgc tctggaggct 52020
gagatgggag gatcagttga gcttgggagg cagaagttgc agtgagctga gatcatgcca 52080

```
ctgcactcca gcctggacaa cagagcaaga ccctgtctca aaaaaggaaa caaaacaact  52140
tggacaatgg aagggggaaa aagttcctca agcagccaaa attgcaccaa atggactccc  52200
agaagacaag catttaattt gttaattgag ccctctatgg gcctgtctgt atttatttaa  52260
gaaacaatcc tatcaagcat agttattggg tttctcagcc caggtagatt agaaatagca  52320
gattagaggt gggctaggtt tctagaggta aagtacacca gcagaagtta gaagtgaaag  52380
caaagagcct aacagaggaa gagaaattct tttttttttc tttttttaga cgcagttttg  52440
ctcttgttgc ccaggctgga gtgcaatggc gctatctcgg ctcactacaa cctcagcctc  52500
ctgggttcaa gtgattctcc tgcctcagcc tcccgagtag ctgggattac aggcatgcac  52560
caccacaccc ggctaatttt gtatttttag tagagacagg gtttctccat gttggtcatg  52620
ctggtctcga actcctgacc tcaggtgatc cgcccacctt ggcctcccaa agtgctggga  52680
ttacagggat aagccactgc gaccggccga caaattctta aaactggaca caagaacaca  52740
aaacgcttgg gctgctgaga gattagaaca acaaccctcc acagctacac accttttcca  52800
cgttatatgg cacgttataa gtgggtgttc ctagtgatgg ttctgatttt ttttaaaaaa  52860
agtctaaata tgtttaatgt tgtctcagaa gacaaaatat attttagaca gatattcctc  52920
agtgatgagt aagcctcagc tatctggaaa attcatgcag gcgccagaga tcgttactga  52980
gtaattcaag ctaactgcgt catgctggtt gtaccctgca tgccaatatc agctaaaagc  53040
agcaccacga aagggaaata cgaatctcac taagcactcg cccattcttg ttaacgacac  53100
tggaactgat catccttaat aatacacaga taaatctatc aggagcattt ccttgcttcc  53160
tgtgaaagga agcactcatt ccatgtgtcc tgtgaaattc atccaacttc aggaagctgg  53220
aggaatacat atggccaagc tatctgggca gagagtagac agggaatgga ggttgggcac  53280
agtggctcac acctgtaatc gcagccattt agaaggcaaa ggcgggcaga tcacttgagc  53340
tcaggtgttc aagaccagcc tgggcaacat ggctaagtcc tgtctctgca aaaaatacca  53400
aaaactgagc tggatatggt agcacacacc tgtggtccca gctacttggg aggctgaggt  53460
gggagggttg cttgaccccg ggagtttgag gctgcaatga gctgtgattg tgccactgca  53520
ctccagcctg gataacagaa tgagactctg tcccaaaaat aaaaaataaa atcaaagaca  53580
cttaaaaaga tggggaaaag gaaggacagg cacttaagca agttataagc tactttccta  53640
actacacaag tggaatctta agctgaggtt cccaggagtt gactggagcc agagaagaca  53700
gacctatagg agcacccaat tggagtcacc ctccatagta gcccatatgt cttacatgga  53760
tcagctttcg tggggccctt ttactccatc tggggaaggg cgtcagatct gtggctctca  53820
tgtactgctc agtacactgc cattcccagt tcttttttc aaaaaaaaaa aaaaaatgtc  53880
tacagaatcg gccaggtgtg gtggctcatg cctgtaatac tagcactttg gaaggctgag  53940
gtgggtggat cacctgaggt cgggagttcg agaccagcct ggccaacatg gtgaaactcc  54000
atctctacta aaaaaaaaaa aaaaaaaaaa attagctgga tgtggtggca ggcgcctata  54060
atctcagcta cttgggaggc tgaggcagga taatcgcttg aacctgggag gcagaggctg  54120
cagtgagccg agatcacgcc attgtactcc agcctgggcg atagagtgag actctgtctc  54180
aaaataaata aaataaaata aaataaaata aaataaaata ggctacagaa ttaagctggt  54240
ccaggaatga cagggcttcc atttatttgt ctttcaattg tgggagaaaa aggatttctg  54300
ttgagatact gtcgttttga cacacaatat ttcgattaat cttgagatta aaaatcctgt  54360
gctccaaatc ttttaacatt aaattatgca tttaaacagg tttgctccta aatcttaaaa  54420
```

-continued

```
tatggaaagc acctcatgag gctaaatatt ttgatgacca agttttctgg aaggtaagat  54480
ttttcaccta ttaacgtgat agattttgag tgcatgaact taaaaacata cctgagtata  54540
tatgttgact tgctgtttat gagtaaaaca aaaacaaaaa tggagtaagg agcattgcag  54600
gaggaactag aggagaaaca aatccatgat atgcatgtgt gtgggggagg gtggcgggga  54660
ggtggtaaag gtcaccattt ccctgatacc tcaaattcat tcagagtcag ggatgagaca  54720
gctttcactg gccacacttc ccctccccct atctgcagtc ctcagcgtag ccaaatagtc  54780
tgacatgcgg gtgacagaac cccacaatgc aaaagctgga agaaacctca agccttggag  54840
tccaacccct tttttgacag atgctaagag tggagacatg acttatcaag atcttacaac  54900
tggctgggca cggtggctca cgcctgtgat cccagcactt tgggaggctg aggtggggcg  54960
atcacctgag gccaggagtt cgagaccagc ctggccaacg tgtcgaaacc ccatctctac  55020
taaaaataca aaagttagct gggtgtggtg gcacatgcct gtaatcccag ttactcagga  55080
ggctgaggca ggagaatcac ttgaacctgg gaagcgaagt ttgcagtgat ctgagatcat  55140
gccactgcac tccagcctgg gtgacagagc gagactttgc ctcaaaaaca aaacaaaaca  55200
attgtacata tttaaagtgt tgtaaccaag tgagttacag agaaacacca cactttgagc  55260
ctaattcagg agtcctttat tagccggcga cctagagacg actagtgctc aaaattctct  55320
cggccccaaa gaaggggcta gattttcttt tataccttgg tttagaaagg ggagcgggaa  55380
ttgagctgaa gcaatcttac agaagtaaaa caggcaaaaa agttaaaaag acaaatggtt  55440
acaggaaaac aaacagttcc aggtgcagga gctttaaagc catcacaagg tgacaggtgc  55500
gggggctctg ggtgctatct gccggacaca aacgcagggg cactagagta ctatcacccg  55560
ggcaaattcc tgggaactgc ggacacagct tgccacagta ccttatcagc taattgcact  55620
ctttgatgtg ctgggagtca gcttgcacaa gttaagtcct tgaggaaggg ggtgggtaag  55680
gagcccttaa cgtcttgcaa atgaaggagc cgaatggaat ccctccggct ttcttagcta  55740
agagagagtc aatcaagtta atacaagtta gggtatcaca aaagtatata atttgataca  55800
ttttaacgta tttatacact gaagagacca tcaccaccat caagacaagg agcacaccca  55860
tcacttccac acacttcctc ctgctccttt gaaattcctc cctccctacc cacctggtcc  55920
cacccaaagg caaccactga actactttct gtcactaagg tttgcatttt ctgtaatttt  55980
tttgtttgag acagggtctc actccgccac ccacaccgta atgcagtggc accatcatgg  56040
ctcactgtag cctcaacctc cccaggctca ggagatcctc ccccctcagc ctcctgagta  56100
gctaggacca caggtgtagg ccaccatggc aggctaattt ttgtattttt ttgtagagat  56160
ggggtttcac cgtattacct aggctggtct cgaactcatg ggttcaagca atcctcctgc  56220
cttggcctct caaagtgctg ggattatagg catgagccac tgtgcccagc cctctgtaat  56280
gttacacaaa gggaatcatg cagcacgtac tgcccttggt ctggcttctt ttgctcagca  56340
tgattattct gagaatcatc cgtgttgttg cgtgtaactg acttcatcag cttctctctg  56400
cagctgtcag ctcttggctt ctcccaacag ccaatctctc tttatcccct gcaagtgttc  56460
ttgcctattt agcagaatca aggtactcta tcgaaaagac tcggaaaatt ggtttaatct  56520
attcattcat tcctcaggta tttatcgaat aactattcta taccaagtac tatgctaatc  56580
aaccaaggac agcacaaaca ggagaaatct ccagctcagt cacttgagtt gcaataaata  56640
tttgctggat aggtcaggtg cagtggctca cacttgtaat cccagcactt tggggattac  56700
tgagacggga ggatctcttg agcccaggag gccaaggctg cagagaacca tgatcatgcc  56760
actgcactcc agcctgggtg acagagtgag atcctgtctc tgaaaaaaaa tatttgctgg  56820
```

ataaattaag gaaatctgac gaaccccatc agtagccatt gcagcaacag gtaaactaga 56880
acgagtgtga atttggaatg aggaaacccg atgttggcca tcattctgta atgtcatgta 56940
ttatgtaatg tattatatat taatgtatgt attatgtagg caagttcctt gacctctctc 57000
actggtaaca taagagtagt aatctttgtg ctacttcact gggttatttt aaagatcaag 57060
tgaggtaata atgtctgtaa caacattctg taaaatgcaa accgccacat gaatgtgaaa 57120
gtttattact agggatttag ccaaccacaa gggaatgtgt gagcataaga gctatcatat 57180
tgcaagccta cagtttctga ttttgtgcta ggtgcttttc cacattacct gattttatcc 57240
tcacaacagc cctgcataaa agtaagtatg tcgcccaggt gcggtggctc atgcctataa 57300
tcccagcact ttgggagccc gaggtgggca aatcacttga gatcaggagt ttgaaaccag 57360
cctggtcaac gtggtgcaac cctgtctcta ctaaaaatac aaaaaaaaat tagacaggcg 57420
tggtggtgga tgcctgtaat cccagctact tgggaagctg aggcaggaga atggcttgag 57480
cccgggagat ggagattgca gtgagatgag attgcgccac tgcactccag cctgggtgac 57540
agagcaaggc tatgtctcaa aagagaaaaa aaaagtaagt atctcagtct tgaagatgat 57600
gaaatggagg cctagagaga ttaagtaact tgcccaaaat gacagaacta atgcatagaa 57660
aagaagaaat gtgatgtctt ttggctccaa agacacccca catatgcgtt ggttacagtt 57720
actagagaaa agttattcca cccccacccc acccccagaa atcttctgac ttgttttctc 57780
gcagttgagt aggaccattt attcggcagt gtaccattct cagcttgcag ttgaaagcca 57840
aatatccatt aaagaggcaa ggatgcaaac ttgctaagct gataaatcca ggggtgattt 57900
ttttttttt tgcaaaccat ccaacaagac attttaaata ctcattgaat ttcatagaac 57960
tgactgccag gattggaaag acattaaagc cagctcagcc actgcctcgc tggttggcca 58020
gaccacgcct ggcacttctg ggagggagca ctcaccaccc cccaagggca cccatctcat 58080
cctccgaagg tttatgaaaa tgcactcatc atttgctaat tcattccact acgtgtatta 58140
cctaatttgt gacacgatgt gaagtaccag agagataatt ctaaataaaa tatagttatg 58200
ggtctcaagg agccagatat gctaatctcc tatcctcctg cagtttacag tggtcctcac 58260
cagatactta tttacaaaaa ttcagtttat tatttatttt tttgagacag agtcttgctc 58320
tatagctcag gctagagtgt aatggtgtga tctcggctca cttcaacctc tgcctcccag 58380
gttcaagtga ttctcctgcc tcaacctccc aagtagctgg gactacaggc acctgccacc 58440
acggctaatt tttggagttt tagtagagac agggtttcac cacgttggcc aggctggcct 58500
cgaactcctg acctcaggtg atctgcccac atcagcctcc caaaatgttg ggattacagg 58560
cgtgagccac catgcccggc caaaacttca gtttataaca caatctttca cgtgtcttct 58620
gctttcatta aaagaataga cagttccctt ctttatttca gtttaataaa ccatggattt 58680
tatttcatgc tttgcaaaac acaagggctc actgacatgc acttcttaaa ctaattctgg 58740
ctggtcgcct gtaattccag cactttggga ggctgaggcc gacagatcac ttcaagtcag 58800
gagttcaaga ccagcctggc caatatggtg aaaccacgtc tctaccaaaa atataaaaaa 58860
ttagccaggt gtggtggtgc gtgactataa tcccagctac tcaggggcct gaggcagaaa 58920
aatcacttga acccgggagg cggaggttac agtgagctga gatcgcgcca ctgcactcca 58980
gcctgggcga cagagtgaga ctctgtctca aaaaataaat aaatacaaat aatgtaaaat 59040
acgaaacaag caatcctggc agtagctgct ggaatgagag gagggagagg tcatagggag 59100
gtcggggaca atggagcatg gagttgtgtt ggatttggct aagcagcagg aagtgcaagg 59160

-continued

```
cattccaagc aagaggaggg gggcaggtgg ggagcatctg caagaacaga agcagcatga  59220
gcaacctggc tcggcagtgt gtgaaaaggc tgaaaggtgg ctagagccac ttcaatttca  59280
tccttcaggc aaatgggaaa ttcccaaagg tttgagtggg gaagcaatgc ctacaatgaa  59340
agtttgagag tgaagcagag tgatcgaatt aagcatgtag gccgagttct gaaataactg  59400
caatgtgctg aagatcatcc attggcttct gaatgagtat ttgcagttta tttttaaaa  59460
tgattttatt gccaagaaag ataaacacta ctgttttggt acaaaaacat aacaaaatgt  59520
gttgagtccc tcttgctgtt ttacgcgaag ttttaaaaat ctactcttgt cacagtggta  59580
tcacccctac ttctgatttc aaataaatgt tctagagaca cagtaagggc ccaacaaacg  59640
cttgttcaac aacacaagga gagccagctt ttaaagtagg aaaacaggcc gggcgccgtg  59700
gctcacacct gtaatcccaa cactttggga ggctgaggtg ggcagatcac ttgaggtcag  59760
gagttcaaga acagcttggc caacatggtg aaaccctgtc tctactaaaa acacaaacat  59820
tagccaggcg tggtggtgca caccagtagt cccagctatt caggaggctg aggcaggaaa  59880
atggcttgaa ctggggaggc agtggttgca gtgagccgag atcgtgccac tgcactccag  59940
cctgggggac agagggagac tccatctcaa aataaaacaa aacaaaacca aatcatacaa  60000
aaacattagc tgggtgtggt ggtgcatacc tgtaatccca gctacttggg aagctgaggc  60060
agaattactt gaacccctgg ggggaggttg cagtgagctg agatcttgcc actacactcc  60120
agcctgggca acagagtgag gagactctgt ctcaaaaaat atatatatta aaaaaaagaa  60180
aaaaaaaagt aaactaggaa aacacatcag cagcctgcca acagactccc ctagcctcgg  60240
tgagggccag tgttctggga ggcagatctg aattctagtc ctagttcacc cactggcagg  60300
ctggtgccct tgggcaggtc gcttctctgg ggctcagttt cttcctctat aaaatgagat  60360
caaatcccat gttctaagag tttgtgctct ggagtcagac agatctgggt tctaccactg  60420
ccagctctgt gatcttgtag cttcagtctc gtcatctgac atggagataa cagtaactgt  60480
ctcactgtgt tgttagggtt taaaggagat aatgtatgtg aaatgttagc aaacaagtgt  60540
tagctaccct gatttccggt ttcagagttc tgtggtccca gtttatgcca catgcagtga  60600
cgttgtatgg taggctgtgg tgtggcacca cttcagaact cagcgcatgc acagcttgca  60660
gaagagaagg ccagaggaga cctaagaagg ctcttcgaac acttgaaaga ccggcatgta  60720
ggccgggcgc agtgactcac gcctgtaatc ccagcagttt tggaggtcga ggcgggtgga  60780
tcacctgagt ttgggagttt gataccagcc tgaccaacaa ggtgaaaccc cgtctctact  60840
aaaaaataca aacattagct gggcatggtg gcgggtgcct gtaatcccag ctactccggt  60900
ggttgaggca gaattgcttg aacccgggag gcagaggttg cagtgagctg agattgcatc  60960
actgcactcc agcctgagac aagagcgaaa ctccatctca aacaaaacaa acaaccaacc  61020
aaacaaaacc aaaaaaaaaa ctggcatgta gaagaaaaat actttttctc tacacttctc  61080
caaagaattt aactaggccc aggggaggtg cagtataaat ttctaacaat ctcaactgtc  61140
tgccaaatgg aatgagctac ttcatatggc agtagtgagt cctctgtctt tggaggcatt  61200
caaataaaag ccagatggcc atttatcaac aatccatgta aaacgttaga tgaaataaaa  61260
cctatatatc caagatctct tccaattcag attttatgaa agaatttcta aggtctttgt  61320
aatgagacat ttaggctgtt tcaagagatc aagccaaaat cagtatgtgg gttcatctgc  61380
aataaaaatg tttgttttgc ttttacagtt tcctcatttg gctgttggat tttaagcaaa  61440
agcatccaag aaaaacaagg cctgttcaaa aacaagacaa cttcctctca ctgttgcctg  61500
catttgtacg tgagaaacgc tcatgacagc aaagtctcca atgttcgcgc aggcactgga  61560
```

gtcagagaaa atggagttga atcctttctc tgccactctt tgaggagaat ctcaccattt 61620
attatgcact gtagaataca acaataaaat acagccatgt accacataac aacatcttgg 61680
taaacaacag actgcatata tgatggtggt catccagtaa gctaaggtta atttattatt 61740
attccttgtt tttttttttt tttttttttt tttgagatgt agtcttactc tgtcacccag 61800
gctagagtgc aatggcacca tcttggctca ctgcaacctc tacctcctgg gttcaagcaa 61860
atctcctgcc tcagcctcca aagtagctgg gattacaggc acccaccaca tctggctaat 61920
tttttgtatt tttagtaaag atggggtttc accatgttgg ccaggctgat ctcaaactcc 61980
tgacctcaag tgatctgccc gcctcggcct cccaaagtgc tggaaccaca ggcctgagcc 62040
actgtgccca gccttgtttg ctttttttaac agataacagt gtgctcatag aaactgcttt 62100
gacatgactg caatcatgtg cttcatagaa acttaattag attataccac tagagtcttc 62160
agatttttat actttttttt tttgaaacgg agtctcactc tgtcaccagg ctggagtgca 62220
gtgccgcaat ctcggctcac tgcaacctcc gcctcccagg ttcaagcaat tctcctgcct 62280
cagcctcccg agtagctgga attacaagtg cgcactacca cacccagcta atttttgcat 62340
ttttacttga cagggtttca ccatgttggc taggatagtt tcaccaggat ctcttggcct 62400
catgatcagc ctgcctcggc ctcccaaagt gctgggatta caggtgtgag ccaccgtgcc 62460
cagcctatac ttcccttttt gaataccatt tggtgttttg aagaattaac agctttgtga 62520
acgtggcagt gcttgtgatt caggcttcca ttgagaccaa ggggagaacc tggttgcagg 62580
acaaacagac ggacagcgtg tggcagtgtt taaatgctct tctgaaggct gatacgacag 62640
ctctctgtgc actgattgca tatgcatccc aagattatat tattgttttc tactgctatg 62700
tgtcacactt tgccaaacag gatgtggaaa atgaataagc ggttttctta ggcacttctt 62760
aacagacaat tggtcaaaat gaactccatt gcttaagaaa cacataaaca ccatttagtc 62820
actgaacata gctatatgta tggttgttac tatgggaaat cttgttttgc caattttctt 62880
tgaaaattct ggcagaccaa ggttcttttt gtttacataa tacttgaaaa ataaaaatga 62940
acaagctaac aaactaccaa gttttcactt acataaatgt agttgcatac agaaaatgtg 63000
actgtgaatt aatttttcta ggacttttaa actataagca ctatttgcac aaaagagaac 63060
caatctatca attacaaact cacataattt tacagatttt tttttcccta cacagcacat 63120
aaaacagaag gaatttgaag ccaccctcca aacacagggg aaggaggctg tgtgtatatc 63180
ctcattgtct ttcacattct aaggtggttc cactcagtga ctgaaatcct taagcgttgt 63240
attagtctgc ttgggctacc ataacagcag cttaaactgt tgtttagcca ctcagactta 63300
aacaacagaa atttatttcc ttatagttct ggaggctgga agttcaaggt gccggcaagg 63360
ttggtttctg gtgagacctc tctccctgtc ttgcagatgg ctgcctcctc cctgtgtcct 63420
catagagcct gtcttctgct tttacacttc tggtgtcatc ttcctttttt tttttttttt 63480
tttttttttt ttgagacaga gtctcgctct atcgcccagg ctggagtgca gtggcccgat 63540
ggatctcggc tcactgcaac ctctgcctcc caggttcaag caattctcct gcctcagcct 63600
cccaagtagc tgggactaca ggtgcccacc atcatgcctg gctaattttt gtatttttag 63660
tagagacagg gtttcaccat attggccagg ctggtctcga actcctgacc ttgtcatctg 63720
cctgcctcgg cctcccaaag tgctaggatt acaggcgtga gccaccgcac ccggcctctt 63780
cctcttctta taaggacacc agtcctatta gattagggct ccaccctcat aacctcattt 63840
gaccttaact attatttctt taaagcacct atttccaaat atagtcactt taggggttag 63900

-continued ggcttcaaaa gatgaatctg agggagctca attcagtaaa tagcagtagt cattaatgga 63960
caatgtatac aaagataatt tcgtgattac tgtccttatg cataaacgtc ctcagtgttc 64020
cactgcgttt atccagattt agtatcacaa agactttgct ctgagaaaaa tgtgattttt 64080
tttttttttt ttttttgaga cagagtcttg ctctgtcacc caggatggag tgcagtggtg 64140
caatctcggc tcactgaaac ctccgcctcc caggttcacg ccattctcct gcctcaatct 64200
cccgagtagc tgggactaca ggcgtccgcc aagatgccca gctaattttt tttttttttt 64260 tttttttga gacggagtct cgctctgtta cccaggctgg agtgcagtgg cgcgatctcg 64320
gctcactgca agctccgcct cccgggttca cgccattctc ctgcctcagc ctccggagta 64380
gctgggacta caggcgcccg ccactacgcc cggctaactt ttttgtattt ttagtagaga 64440
cggggtttca ccatgttagc caggatggtc tcaatctcct gacctcgtga tccacctgcc 64500
tcagcctccc aaagtgctgg gattacaggc atgagccacc gcgcccagca gatttttttt 64560
tttttttttg agatggagtc ttgctctgtt gcccaacctg gagtgcagtg ttatgatttt 64620
ggctcactgc aacctctacc atgttcaagc gattctccca cctctgcctc ccgtgtagct 64680
gggatcacag gcacacgcca ccacacctag ctactttttg tatttttagt agaaatgggg 64740
tttcaccatg ttggccagga tggtcccgaa ctcctgacct caagtgatcc tcctgcctcg 64800
gccttccaaa gtgctgggat tacaggtgtg agccactgtg cctggccaaa aatgtgattt 64860
cttatttccc acattgccaa ttccatttca attaactata atagctatgt ctattgagca 64920
ctcaagcgta ttctagaaac tgttcctgat tctggg 64956

<210> SEQ ID NO 4
<211> LENGTH: 65624
<212> TYPE: DNA
<213> ORGANISM: Homo sapiens

<400> SEQUENCE: 4
acccttggcg tggacacatt tccagggagg gaccggagga cctcctacct cattggtcac 60
tgccagtgac tgagcttgac tcaggtagga gggcatggca ggtattctca gggagtctgg 120
tgtttacaga aaagtcatga ttacacgtga aagctgtggg ctccctggct tgattcacca 180
cacctgcagg aagcctggct gctcagacca gcacgccgtg gacatagcac cacttgctca 240
gcttcatttc cgtaactcag gctgccaggc ctgctgacaa attttcacgt ttgtaataac 300
cctgtgagga gaccagagta catcttactt gactcataag gaaattgaga ctgggtgatt 360
tagtaacttg ggaggcagaa ttgcaaagtg attagcaaca caagccatgg tgtcagatgg 420
atctgggtta ggtcccacct ctgccgttta ttagctgtgt ggctttgggt actcacgcca 480
cctctctgag cagcagtttc ctcttttgta agcgtaatga tgcctacact cacaggcttg 540
agaggaagat ccgatgaaat agcatatgca aaatgattgg ttccgtgctt ggcattccag 600
aaatggtagc tgttattcag ccaacaaata tttattgagc acctactatg gacttccctg 660
gtgctgagga tacaacagca accacagcag tcaaaagtcc ctgtctttat gttgctcaga 720
ttctcatagg ggaaagcaga taatgaacaa atacacggcc agacgcagtg gctcacgcct 780
gtaatcccag tactttgcga ggccaaggtg ggcaagtcac ctgaggtcag gagttcgaga 840
ccagcctagc caacatggtg aaaccctgtc actactaaaa atacaaaaat tagcgcagtg 900
tggtggctca tgcctgtagt cccagctact tgggaggctg aggaaggaga atcgcttgaa 960
cctaaaaggc agaagttgca atgagccaag atcgtgccac tgcattccag cctgggtgac 1020
agagtactcc atctaaaaaa aaaacctaaa tacacaagta aaaatataga cttcgtcaga 1080

```
tgctagtaag tgctgtgaag gaaactaaaa ggggaacaca aggaaccctt gtcaagggga   1140
gcagaaaggg gagttgatgc tgtcctttta aatagggcaa tcagaggcca ggcacagtgg   1200
ctcacactta taatcccagc actttgggag ttcgaggcag gtggatcact tgaggtcagg   1260
agttcaagac cagccaggcc aatgtggtga aaccctgtct ctactaaaac tacaaaaact   1320
agccaggtgt ggtatcgcgt gcctataatc ccagctactc gggaggctga ggcgggagaa   1380
tcgcttgaac ctgggaggcg gaggttgcag tgagccgaga ttgtgccatt gcagtccagc   1440
ctgggcaaca agagcaaaac ttcatctaaa aaaaaaacac agcaaaaaag ggcagtcagg   1500
gaaaacttcc ctgagaaggg gatggtggag tacagatcca gggaggtgag gtggggagca   1560
agccagtaca gttgttcctt gactttcgat gaggttatgt cctgataaag ccatggtaag   1620
taggaaatat tgtaagtcaa aaatgcattt aatacaccta acctacggaa catcatagct   1680
tagtgtcacc taccttaaac atgcttagaa cgcttacatt agcctacggt tgggcaaaat   1740
catctaacac aaagcctatt ttatgataaa gtattgaata tctcatgtaa tgtactgagt   1800
actgtacgga aagtgaaaga cggagtggtg ggatgggaac tctaagcacg gcttccactg   1860
catgtgtgtt gctttcgcgc catcataaag ttgaaaagcg ttaagtcaaa ccaccgtacg   1920
tcggaggcca tctgtatctg gtaggaggag tgtttcagac agagagaaca gcaggtgcaa   1980
tagagtgctt ttttcccagc attttattat gaaaaatttc aaacatctac caaaaaaagt   2040
tgaaagactt gtacggtgaa aagccataca tctcacagct agaatcaaca attaacattt   2100
tactgtattt ggtttttgac ttatctatcc tagatccctt gtgctttctg tagcaggtga   2160
cctgccttga agatttaaag acagaatatc gggaaatgta gtcagaaaat ggggcctttt   2220
ataagagtca gaggggaaga gcaaaaactc tgctttcgag aaatctgtcg ggagaggcca   2280
actgcaggga tacctccctt ttttaatgaa agcatttctg ttctgcgagg agcgggatcc   2340
tcttgtcaag cagtcagtcc ctgctgcttc cttactgggg caggatcagg acgcacaggg   2400
atttggagtg ccttggaacc aaccaccacc cacgctgttt gccagctggt aaacatgcct   2460
gtcaggtcta ggggttggca ttgcctggaa atctttagtg ttcatcttgc tgacatctgg   2520
tgccctcggg taggtaggtg cagttggctg cctggtttac agagcttgta ctgggcccag   2580
gttagcaggg gtcacatccc tttatcccac tgtgcagggg agttccttct caggaaaccc   2640
agtttataag aagtactgac tgccagaaat agagcagaga tcagaaccag gaggcaattg   2700
tgagaggaat ggagacttct gacctctggg gattggggta ccctccccct taattgctgt   2760
tggggtagca gagggcttag aagcccatgt tcctagactt ttagaattgg aagaagactt   2820
agaagtaatc taggctgggg gtccccaacc cccaggctgt ggcccgttag gaacctgacc   2880
gcacagcatg aggggtaggc cagcgagcac taccgcctga gctccgcctc ctgtcagatc   2940
agcagcggca ttagattctc acaggggcac aaaccctatt gggaaccgcg catgagaggg   3000
atctaggttg cgtgctcctt aggagaatct aactaatgcc tgatgatctg aggtggaaca   3060
gtttcatccc cacaccatcc ctccaacctc accccggtcc atggaaaaat tgtcttctac   3120
aaaacccgtc cctggtgcca aataggttgg ggacccctga tctaggctac agttaagtgg   3180
tcaaacaccc aggtcctgaa gttaggctgc ctgggtttaa atcccagctc tactgcttac   3240
tagccctgtg accttgagca agtcacttag tttttctgtg cctcagttta ctcatttgta   3300
ataaaagctt aatagtaccc atcccagtgt catgaactaa gttcatatat gtaaagtgct   3360
tagaatggtg cctagcaagt acttagtaac agttagctct gaaaatgtat aaagcaaaat   3420
```

-continued

```
taaccaatgt tttagtggtt tgcagccaac ttttttctat gcgtgtgcta acatattatt   3480
ttataagagt gggaatatat tgtacatgct gttatataac ttgctttttc actaaacagt   3540
ctatcctctg tgtcagtttt gataaaagcg ttttcctctt gcttttcctg catatgttca   3600
gaaccatcat attggtagca agtttcatgt cctgcagttt tcttaaccaa ccccctgcta   3660
gcggacattt aggttagtct cagtttttc cttctgtaaa taaagctgca ctgagcaaga   3720
agtgaccgat gccaagtgac tagatgacct taggtatgac ctctctgggt cttggtttct   3780
tggtctaaaa acaaaatgac aggattcgac tgggtgatta aaatctcctc tgatctacat   3840
aggaattgtt ttcaagacat ttctgcattc ctctagtgac agggtgctca ctacctcatg   3900
agtatttcag tggacaactg taatggtcaa taaagtatcc actttccacc ttccacttcc   3960
ctgtagctcc tggccctggc tttattctct ggggctccac acattcagtt tacactcagt   4020
ggccagtggc tggggccatt gtagaaaatg aggaaactcc aattccttcc ttcttttctt   4080
cctctttcat cccttcctcc ctccctacat ccctctctct cttccttcct tccttgacac   4140
ttaccatgta ccagaccttc tgccaggcac atggatggga gcacagttcc gggaagttgg   4200
ctgcagggtt agaactaagt cccaagcccc gtaaagctca tgccagggga ctggactgtc   4260
cagtactgag ggatggggat gctgaggctg gtggccttcc tcagatgcac tgtagtgccc   4320
caggcagagt cctgggctgc cctgtgagga ggtgaccaga ggtagagcaa cttcacccta   4380
aggctggatc aggatcccct ccaggttttt actagagcca aacccacatc tcctttctct   4440
tctgccaccc cccttaaaa tgcttagaaa cacatagatt taaatacaag ttcaaatgta   4500
agtaatttca actgtgtaac tatgaggagt caattctacg tgggtcctat ctgtatcctc   4560
cccagggctc agctccattc tttgctttca ttcattctca ttcaatacat tgttgttaag   4620
agctcactgg gtgccctctc tgtcatgtag taaggtttta aaaagaaagc ctcttctgag   4680
cttcagtttc cttatttata aaataggagt attgatccgt tccttgcttt tcttacaagg   4740
atatgctgaa gatgactgaa gtacagagta aagaaggatt atgtttgggt gtcaaaggaa   4800
tagaatgccc tctttcaaac tgagcacagc aggaacctgt aacaggaaca cagcaacttg   4860
ttgaatgaat gacaatattg gaaaacatac atttcctccc ctccccatca tagtccctct   4920
gcttccgtgt taactccata gacaggccag cacagccagc cttgcagcct gagataaggc   4980
ctttggcggg tgtctcccct atcgctccct caagccctca agtaggtgtt ggagagaggg   5040
gtgatgcctg gtgctggtgg aacccctgca cagagacgga cacaggatga gctctaagta   5100
cccgcggtct gtccggcgct gcctgcccct ctgggcccta acactggaag cagctctcat   5160
tctcctcttc tattttttta cccactatga cgcttcctta gaggatcaaa aggggctcgt   5220
ggcatcctat caaggtgaga gttcattgga acagtggtca caggagcaaa tagcaggggc   5280
aggggcgggg gaggcctatg gttctccagg ggcacagatg ttcctttcta caaaatcccg   5340
aggaaaagat tcccccatct tcttccgtag attgcaccga aattcagtca acaatgtaag   5400
ctttccttta gaagcagcct gggcatgccc tcttctgtga agcctgcctt gatttttcag   5460
cacagtgaga ggcatcctct ttggtgttcc tcaaattccc tctaccaaat ggtcttcata   5520
attctctgct tctctgcttc cccttctctc tccttagtgg caaggatttt ttttattttt   5580
atagatttag gggatacaag tgcagctagc ttatgcaagc aatttcatgt tgttgggttt   5640
tcgggttttg tttcctttt gtggcctctc gctcatttct tatttctttt tgagacaggg   5700
tctcactctg ttgcccaggc tgaagtgcag tggcatgatc atggttcact gcagccttga   5760
cctcctagtc tcaagcaatc ttcccacctc agcctcccaa gaagctggga ccacaggagg   5820
```

-continued

```
gcaccaccat gcctggctaa attttttttt ttttttggta gagatgtggg tctccctgtg   5880
tttcccagac tggtctcaaa ctcctggaca caagcgatcc tccagcctca gtctcccaaa   5940
gtgctggaat tacaggcgtg aagcactgtg cccagctctc ttgctcatat ctatactagt   6000
tttcttttgg aagcttcagc ctgttgctac cccccacccc cacccccacc gaccccagct   6060
ttcttctcac ttaggggctg ggaagtctgc atgctgtcta taaatccaga accagaaggt   6120
atggctgaag gggagggtag gatgatggtt attttatatt cagctaaaaa tattcccaga   6180
ctgtgatgag acaactgtaa ataagacaga tgtccacaat ggtgtgactt tgctttttta   6240
aaaatattga aatgagtttc aggcatctca gtgggctgat aggttgttga taatggacag   6300
ggcctccttg aagaatgtcc ctgagacaaa gttgaagctt gagcctggtt gagtgcttgc   6360
ttgttcctag gttgatatga acggctagtt aactggaagc aaagagaagt catcctgggg   6420
gccatggcag tgacaagtag gacttaggga gggaagccct tataccattt aaggtgctgg   6480
cccagagagg agccttcagt gacagacaaa caagagctgg cacaatttta attcatttca   6540
atttacttta attcatttca atccaataca attcaatgca ttccattcat tcaaccatgt   6600
atgacatcca atgtgggatc cagacacatg atgattagaa ctgatattta tgagcactta   6660
ctatgtacca ggcactattc tacatgcttt acattgaacc ctcacaataa cccaatgagg   6720
tgggtactat tatgatcttc gtttttcata tgaggaaact aggcatatgg atgttgagta   6780
atttgcccaa ggtcgctcag ctagcaatag cacagcgtat ttaaatttag ccaccctgga   6840
tttagtttcc ttacacttaa ccattatgca tcatggcccc attttacagt ggcgttgagt   6900
catttgtcat ataacccagt aggtgtagca gccactattc caaccctgta gattgactct   6960
agggtccatg ttctttaccc ctgcaccgtg ctactaacgt aggtacaaaa tgtcctcaga   7020
aactcacttt atatggaagc tcagaggagg gtccacaacc caggcagggg agacgatggt   7080
gtcaggggag gcttctggag ggaggtgcct gcccagccag ctcttgaagg ctcagtagga   7140
attacctgtg ggacaaaggc gggtcatcca agtgagggca cagtgggtgc cattgcgtgt   7200
gcacacacta gagcagactg agcttgggct taacattgca ttgccctgta gcctaaaaag   7260
agaagcaagg ggctgggcga ggtagctgac acctgtaatc ccagcacttt gggaggccaa   7320
ggctggagaa tcacctgagg ttaggagttc aagaccagcc tggccaacat ggcaaaaccc   7380
catctctact aaaattataa aaactagccg ggtgtggtgg cacacgtctg taatcccagc   7440
tacttgggag gccattacac tccagcctgg gcgacagagc aagacttcat ctcaaaaaac   7500
caaacaaaaa caacaacaac aacaaaaaac aaagaggaga gcagggactg ggtgtggtgg   7560
ctcatgcctg taatcccaaa cactttggga ggccaaggcg ggcagatcac ctgaggtcag   7620
gagttcgaga ccagcctggc ccatatggtg aaaccctgtc tctactaaaa atacaaaaat   7680
tagccggatg tggtggcacg tgcctgtagt cccagctgct tgggaagctg agggaggaga   7740
attgcttgaa cccaggaggt agaggtagct gagctgagaa tacgccactg cactccagcc   7800
tgggtgacag agtgggactc tgtctgaaaa aaataatagt aataaataaa aataaacagg   7860
gaagcagtgg gtggtagact cactgggctg catacggagt ttggcttcag tctgaggtcc   7920
gaatagtaaa caggagcgcg acaagtttgg gtttgggtca tggcggatgc catgccaggg   7980
ctggtgttgg gcacagggga aggggcatgg cttgagacac aagaccagcg tggaggctgt   8040
agtgtagtat tgacccgagg gcttcaacct tctgatggtg tacacaccat tttttgagca   8100
tgtaccatgg ttatatgtta cactttaagt attactacat taatatattt tgtatgttat   8160
```

```
aataaataca tacaaattag gaaaattgaa agagatcaga atgaaatata taatattttc   8220
aaattactaa tcataatggt gtcaatctcc aggcagggtc cattgctaca gttgacgata   8280
gtggatgaaa attcactcct cagagtcttc ttgataattt gaaattgtct tgattgactt   8340
gtcagatctg attagatcga catttttttaa atctcgaatg tgactgacag cttgtacaag   8400
gagaagtttc actctgcctt tcctttttgt tcacttgact gccattattt ctctgcttcc   8460
aatctgtgtt tttctgcacg agttggttaa gccattactt cattttgtga aagtttgttg   8520
agttaaactt aggtaactta atctgtcaat ccacttaatt gaattcagtc ctggtaaact   8580
ataatagatt attcaaacct gccaattcta aaaagacatt ttgagacaat caggaaatct   8640
gaatatagca tgaatatctt acgatataca aggattattg ttaattttgt taggtatgat   8700
aaaagcatgg tgggtttttt ttttgttttt gtttttaag gctctatctg ttagagaggc   8760
acattgaaat ggcatgatat ctggggtttg ctttcatacc agaaaaaaga aaaagtagag   8820
aaggattata gaaacaagat tggtctcatg tgacaatcat cagagtttgg agatgggcac   8880
gtagggtcat cgtgctgttc tctctgtttt catatatgct ttgaaagttc tgtaatagtt   8940
aattaaaaaa aaaaaaaaca ccctggctga gcacttaggg aggccaagtg gggaggattg   9000
cttaaaccaa gaagttcaag accagcctag gaaacatagg gagacccccc cccgccatct   9060
ctaaaaaaaa aaaaaaaaaa ctgtaaaatt taacccagtg tggtggcaca tgcctgtagt   9120
cccagctact cagtaggctg aggtgagagg cttgcttgag cctgggagct tgaggctgca   9180
gtgggacggg attgtaccac ttcactccag catgggcgac agagcaagac cctgtctcaa   9240
aaaaaaatga aaatatttga ggtgaagcga gactgtaata acaaatttaa aaatataaat   9300
aaaacataaa ggctgggtgc ggtggctcac gcctgtaatc ccagcacttt gggaggccaa   9360
ggcaggcaga tcacgaggtc tggagatgga gaccatcctg gctaacatga tgaaacccca   9420
tctctactaa aaatacaaaa aattagctgg gtatggtggc gggtgcctgt agtcccagct   9480
acttgggagg ctgaggcagg agaatggcgt gaacccagga ggcggagctt tcagtgagct   9540
gagattacac cactgcactc cagcctgggc aacagggcga gactccatct caaaaaaaaa   9600
atgaaaataa aaataaataa aacataaaac cctgccatta gttgcaacat gaagaatata   9660
gagaaatgcg tatcaaatcc ttctcattgg accaatattc ccttagggca ccttccaaag   9720
ctaggagact caaggctgta tgacatcctg agcaagtgag ggtggcttc tgggtgaatc   9780
tgaatattaa atatttgcag aattgaaaac ttcacaaagt acctttagag atagaatagc   9840
ctagatccat gtttctcaaa gtgtggtccc cagacctgct gcctcagcat ctcctggaaa   9900
tttagtagaa atgcagattc tcaggcccta ggccagacct actgatcaga agctctgggc   9960
ctggggccca gcaatctgtg ttttcacaag ccctctgggt gattcttctg tgcgtgaaag  10020
ttcgagaatt cctggagcta gactgattca aatcttgcct ctgtatctta gagaccttgg  10080
gcagattagt caacctcttt ctgcctctgt ttctacttct gtcagaggat gatagtactt  10140
gtttcattaa gttgttgaaa ggataaatga attgacacac ataaagagta ttagctttta  10200
ttatcaaaag cttttttttt ttgagacaga gttttgctct tattgcccag gggagtgcag  10260
tggtgcgatc ttggctcacc gcaacctccg cctcccaggt tcaagtaatt ctcctgcctc  10320
agcctcccga gtagctggga ttacaggcat gcgccaccac gcccggctaa ttttgtattt  10380
ttagtagaga cggggtttct ccatgttggt caggctggtc tcgaactccc aacctcaggt  10440
gatccacccg cctcggcctc ccaaagtgct gggattacag gcgtgagcca ccatgcctgg  10500
cccaaaagct ttaatttctt aattttttaa ataaaataaa taaaactaga attgcttgtt  10560
```

-continued ttcttccagc taccctggtg attgtattga gcattttctg ggtgtgtgt tctttgctgt 10620 aatgactact ggtctggatg acctgtgatg agaccagatg ggcaggggca gtggaggaga 10680
ttctagagat atttaggaga taaagtcagc tgtacttgat gaaaagagtg gggagttaag 10740
actggctgca gatgtatgat ttggcataga gaggtgccag ttcctgaggt gagagacaga 10800
aggggaggga caggttgtga ggatgaatga acaatgatat gttcattctg ggcttggagt 10860
taaggggcct atgatatgct taggggaagc agagagtatc aattacctat tgctgcataa 10920
cagccacccc aaacttagtg gcttaaaata gcaacctttt aatttactca tgatcatgat 10980
tctgtggtgc aacaactggg ctgggttcag ctgggcagtt cttctgttag tttcacccag 11040
ggtcattcat gcatctgcag tttggggtgg gatggcctca gatgacctca ttcacatgtt 11100
tggcaattgg tgattcactg ggggccatta ctgtaacaat cgcctaccag gcagagcttc 11160
cctaaggcta ccaaactggg agactatcct gggtcctgtg ctgtggatac cactcagtcc 11220
cccatcccca ccccatactc ctcaaaggca gagagagggg ctactagaag acagaggagt 11280
tttcccagtg acatgtaaac actccaaacc ctggcacctt ccacactgca gctttggtct 11340 gccccctttgg gaaatctctg tttttcttcc caggctgctg gaggggtgag agtcgccggt 11400
agagtagagg ctgtgggcga ggaggtggcg gcctcctgag gctgcagtgg tctttccagg 11460
cagcagtggg agcacagggt ggaggtcaac cctagagcct gggggagtga agctggttct 11520
gccttcagag ctcttggtgc tgaagtttct gcaggccaga gggaggggca agagtgggag 11580
ggggtgcaga tccagaatca cagaggcagc tgaccggagg aggcagctgc ccaaggggat 11640
ggactcagaa ggccaaagtg ctgttatcca aacgaactct ttgcaagtgg tctctttgca 11700
acaggcctgg gggagagcag tcttgcctaa agtcacaccg ctaatcagcg gccggcacgg 11760
ggtaacagtt actaacactc actacgtacc caatgctggg caaagtgact tgcatgagcc 11820
agcgagctca atgctcatgg caatcctctg agcagctggc attgtttcat ctcaatttta 11880
cagctcagga agctgggaca cagaggaaga gccaggctct gaacactgac aacctgattg 11940
agagacccac actgttcatc accgttacgc tatatatgct gtatagaaag gcaggatggc 12000
ataatggtta aacctaggta ggtagggttt gaatcctcct gctaccattt actagctctg 12060
tgacttggac tagttatagc acctctctgt gcctcccttt ccccctctct aaaatgggga 12120
taataaatcg tacctcctac ctgaggctgt tgtgggctaa gtctgtaagg cacgtagaac 12180
agtgcctgga acgtggggta ctgtctatct gtgtgcctgc tgttacaaca atggtgagta 12240
ttgccttatc tctcgctgct gaactaccag gttagacttc tttctgcaag tcatgaggct 12300
ttcataaact tttcctgaag gctttccgta gaatgtacaa ttcccctctg ggcccaggca 12360
tgggcgcccg ggtaggacat ccacttctta tcacccctga acaccttaga gcccatcagc 12420
ttatcaaacc agcagctgat gtgagtgcag agcagactgt gagaggtgga ggctgatacc 12480
agtgaggatg ctccaagctg ggacccagcc ctgaagcggg agcccagata atggacgggt 12540
ggaaatgggc ctggagccca agagaggtgg gaggatgagg gggcaggggg aggagaagcc 12600
tgaaatcaaa tgttatttcc tgaccagttt ggggtgcatg agctctgtca acagctcatg 12660
gaaactgctg ccctaatttc atcttgttgg ctgaggcaca attcctctct cagggacagt 12720
gtagagcctt ggggaggaag gccctgagcg catatacctg gaatcaggga atcgggatca 12780
ggggcagcag ctgtgcccga taaagccccc acccaggatc ctctgacttc ctcatctctc 12840 ttttttttg agccggagtc tcactctgtc atccaggctg gagtacagtg gtgcgatctc 12900

-continued

```
ggctcactgc aacctcagcc ttctgggttc aagcgattct cctgcctcag cctcctgagt  12960
agctgggatt acaggcatgc gccaccatgc caggctaatt ttgtattttt agtagagacg  13020
ggatttcacc atgttggcca ggctggtctc aaactcctga cttcaagtga tctgcccacc  13080
tcagcctccc aaagtgctag gattacaggc ataagccact gtgcccggcc ttttttttt  13140
ttttttttt tttttttaaa aaaagggtct ccctctgtcg cctaggctgc tggagtatag  13200
tgatgtgatc gtggctcact gcagccttaa ccttctaggc acaagccatc ctcccacctc  13260
accctcctga gtagctggga ctacaggcac ttgccaccac gcccaagtaa ttttgtattt  13320
tttgtagaga caaggtcttg ctatgttgcc taggctggtc ttgaactcct cagctcaagc  13380
aatcctcctt ccttggcctc ccaaagtgct gggattacag gtgtgagcca ccacacctgg  13440
tctgacttcc taatctttag ggccccaact ctgcccttat ccaggcaact ctcctctccc  13500
catcttccac taacttcttt ggaatattcc agagctgtaa aagccttaga gagtatcaag  13560
tccaactcct atgtgttaca gacagggaaa ctgaggccta aagagggtaa tggacttgcc  13620
taagatcgct tagtgaggtg agagaagaaa gagctagaga cagcctagcc tgtgcaagga  13680
catagttcca ggcattcaga gctgcgctct gctgccggca tgtttggggc ctggtagtta  13740
gttcactgct gaactaccag gttagatttt ctttctccaa gttgtggggc tttcataaac  13800
ttttcctgaa ggtcttcctt acaatgtaca attctcctct gggcccggtc atgagcgccc  13860
ctcacaggct ctctctggtc cccttctgta aaatgagagg aaaatggaag aattgctcta  13920
ctcatggaat cttcaataag tctggaccct atgcatatag cattgctaca aaatggcaga  13980
tgcactttaa caatcgtgtt taataaaagg ttggatttgc atatctgaag tggggcatgc  14040
agtctccaac tgaacacaag cctcactgct cccacatgtg cactgcacct tcatatacat  14100
atttcctgct tggctcctga gggaatttga gtaatcccaa gaggaacccc tgtagaaaat  14160
gtcccctggt cacacacccc cattcctaag gatgcaagca ggagatagaa acattccctg  14220
cacctccctc cttgctgtca gaagaagtgc aaagagttga atccttccta atgcccactt  14280
ctcacccacg ccccaaatcc ccaggtcccg tggaggtcct tgggggtctc ctatatcctg  14340
gtggtgtcag gttgatttgg aaatgtcagt gtcctccctt gtcctctctg gcagaccctg  14400
ggtgtgtgta cgtttcaatg gaagtgaatt taaatgtact ttataaatca aagacttttt  14460
ctgagacttt ggagagttcc agtaatgaga gcttctcatt gttatcaaag ccagggctgg  14520
agaccagtgg caggtgagtt cctattgctg tgattgtcat gatgatgttg atgaacagcc  14580
actatttatt gagtgttctc catgtgctag gcactgtact aaacattatt tccttcggat  14640
gtcccagaaa cctctcaggt ggctctaatt acccttattc tgttgataag gaaagtaagc  14700
aacttagaag accacagggc tatgaagttg aaacacgtaa attgatattt tattttattt  14760
atttatttat ttatttattt tgagacagag tctcactgtg tcgcccaggc tggagtgcag  14820
tggtgcggtc tcagctcact gcaacctccg cctcctgggt tcaagcgatt ctcctgcctc  14880
agcctcccga gtagctggga ttacaggtgc ccgccaccac atccagctaa tttttttgta  14940
attttagtag agacggggtt tcaccatgtt ggccaggcta gtctcgaact gctgacctca  15000
tgatctgccc acctcatcct cctaaattgg tatttttata tgtccaaaag agtcaactgg  15060
tggcaattta gtgaggttta atctaatagg aaatgataga gctgggatcg aacagagcta  15120
tgtgaactca aaacctatgc ttccccttcc accttttcga aaaacattgt ctaggctggg  15180
cacggtggct catgcctgta atcccagcac tttgggagac ggaggtgggt ggattacatg  15240
aggtcaggag ttcgagacca gcttggccaa aaattagcca ggcgtggtgg tgcgcgcctg  15300
```

-continued

```
tggttcccac tgaagcacag gaggctgaag cacaagaatc acttgaaccc gggaggcaga  15360
ggttgcagca aaccgagatc gcaccactgc actccaacct gggtaacaga gagactctgt  15420
ctcgaaaaaa aaaaaattgt ctacatgctg gttgcagaaa atttaaacac taaaactaaa  15480
aaagtaaaac atctcccaaa gttagagaca atattcatga tgggaaaaaa aaaattcttc  15540
aagatttctc tctctccagt catttattca tgtgcgaaaa cagttggtga ttattgataa  15600
gaagagggag ggcagatggt gtggtagtcc aaggcacagg ctccagcaga ttatctaggt  15660
ttaaatcttg gctgtaggcc aggccctgtg gctcatgtct gtaatcccat cactttggga  15720
aaccgaggtg ggcagatcac ttgaggtcag gagtttgaga ccagcttggc caacatagtg  15780
aaaccccttc tctattaaaa atacaaaaat tagccgggca cggtggtggg cacctgtaat  15840
cccagctact tgggaggctg atgcaggaga atcacttgaa cccaggaggc agaggttgca  15900
gtgagccaag atctcgccac tgtactccag cctgggtgac aagagtgaaa ctctatctca  15960
aaattaaaaa aaaaaaatct tagctctacc caccggggca agttacataa cgcctctgtg  16020
ccttggtttt catatctgta aaatggtgac agtaacagca cccatgtcaa agtgtggttg  16080
tgagaacgaa acaagatagt ctatgtaaag tgattaaaac agcgtaggca catggtaaac  16140
gcttaggaaa tgtaggctgt tataaagctc agagatgtta agtaactaga tcaagaccac  16200
acagttagag agtgccacag tcttgatttg aacccaaatt tgtctcgttc tggagctcaa  16260
gctgctaacc ctttttcaaa actggaatta aaccaaagtg ctcaccctcc gctttgctgg  16320
gcccctccct gccctcaggt gcatctcttc cactcacctg ccacagcagc ctctgctcag  16380
ggtctgagac tgggaaaggt gagggctacc caggtggccc tgatgttttc tgccagccag  16440
ctcaccaggt ccctcgcagc aggcggcaaa gggagggagg tttgctgtga agattatgtg  16500
gttcccaaca acaagagcac tggccctatc tctgccctct cttttctgtg tgtcctggga  16560
caagtcactt ggcttctgtg gctttatttt ctcatgtgcc cagccagggg gttggccctc  16620
atatgcaata acagcagcaa tgacctttac tgagtgtcca tgtgcatcaa gcacgtgtac  16680
tttacacttg ttcttattat taggtttaat aatagaataa ttgccacatt tactgagcac  16740
tcattatggg ccaggccctg ccctaagtgc ttaattagct ttagctcctc taatccttac  16800
cttatcccca cacggcatgt tatgttatcc ccattattca gttgagaaca ttgaggctca  16860
aagaggcaaa gtaacttgac caaatacttg taaacgatct tgcatgcccc ttccagctgc  16920
catttagtaa gactctaatt tcataccacc ctaaatctcg tctgcttccc cctcctcctt  16980
ctcaccatct ccccaccgag cagtcggcca agatctgacc gtgatggcgg cccttggctt  17040
gggcttcctc acctcaaatt tccggagaca cagctggagc agtgtggcct tcaacctctt  17100
catgctggcg cttggtgtgc agtgggcaat cctgctggac ggcttcctga gccagttccc  17160
tcctgggaag gtggtcatca cactgttcag gtattgggat ggtggctgga tcacttctgg  17220
gtcatagagg gaatggaccc cgaaaggaca ggttccagaa gatctgggat attgcccccct  17280
ctctgtctag caccagtgct gtgcaatatt taggacatcc ttatgctaaa agattattca  17340
ttgtttaaaa ttcaaattta actgggcatc ctgtatttta ctggacagcc ctactctgtg  17400
tatcacaagg aatccaggcc tacattcctc ctgcatcctt tctttcctgt tattgtcgat  17460
tatgattttg taaagttaca taatcagtat aagtttatgg aaaacgtaag aaggaaacac  17520
gttagacaga gagaaataga catgccacac ctagagagac attctatttt ttttttttct  17580
tttttgagac ggagtttcgc ttttgttgcc caggctggag tgcaatggcg ctatctcggc  17640
```

-continued

```
acaccacaac ctcagccttc tgggttcaag cgattctcct gcctcagcct cctgagtagc  17700
tgggattata ggcatgtgcc accacacctg gctgattttg tatttttagt agagataggg  17760
tttctctgtg ttggtcaggc tagtctcaaa ctcctgacct caggtgaccg gcctgcctcg  17820
gcctcccaaa gtgctgggat tacaggcatg agccaccgcg tccagcctga gagacattct  17880
cttgaaaaga aaggactttc agccccctaa agctactaga caagaaatag ccatgccttt  17940
attttcatta aattacctgt gctttgttta gatgcctttg tgtgaaatgc taagaaccat  18000
cacaactaat gtatggtgcc agaagtcaga atagtggtta cctgggcagg aggtggatat  18060
tgattaggaa ggaacacaaa atagccccat ggggtgcaga aaatgttctc tgtgttcacc  18120
tgggtgatga ttacacatca agctatacac attttaaaag ggcattggca cttaatagaa  18180
ggaactaggc taaatttttt cctgaaacat tgttttgttt tgttcaaacc tctgaatctc  18240
tcagctcccc agatgatggt aaacgtcatc ctaggcatct tagggacctc tcaaggcctc  18300
tcaaggccat tccagcctcc ccttctaaga ccctgctaaa cctctgggca ctgctgttaa  18360
acatttctct atgagccagg aactgtgctg agcactccac aaatattatt ttgtttaact  18420
cttccaggta gggatctaac ctggtataca ggtaaggaag tggaagctca gagagggcaa  18480
ggcacttgcc tagggccaca cagctaagtg gtggagatgg ctctaacttt tttttataac  18540
cttttccaca tgctccagag tggtcagaac atgaaacaca gtctagccag ctcctgactg  18600
gccctagagg aaaaaaactg tatgtatttt tctttttttaa aaggtttaga ggctgggcat  18660
ggtggttcac gcctgtaatc ccagtacttt tgggagctga ggtgggcaga tcacttgagc  18720
ccaggagttt gagaccagcc tgagcaacgc agtgagaccc tgtctctgca gaaaatagaa  18780
aaatcagcta ggcgtggtgg tgtgcaccca cagtcccagc tacttgggag gctgaggcag  18840
gaggatcacc tgaacccagt gaggctgagg ctgagtgagc catgatcgtg ccactttact  18900
ccagcctgga caacagagtg agaccctgtc tcaaaaaaca gttttagggg ccgggcgcgg  18960
tggctcatgc ctgtaatccc agcactttgg gaggtggggg tgggcagatc atgaggtcag  19020
gagatggaga ccatcctggc taactcggag aaaccctgtc tcgactaaac atacaaaaaa  19080
ttagctgggc gtggtggcgg gcgcctgtag tcccagccac tcgggaggct gaggcaggag  19140
aatggcgtga accttggagg cggagtttgc agtgagccga gatcgtgcca ctgcactcta  19200
gcctgggcga cagagcgaga ctctgtctca aaaaaaaaaa aaccaaaaac aacagtttta  19260
ggccaggcgc ggtggttcat gcctgtaatc ctagtacttt aggaggccta gacagatgga  19320
ttacctgagg tcaggagttc gagaccgacc tgagcaacat ggtgaaatcc tgtctctact  19380
aaaaacacaa aaattagctg ggcattgtgg caggcacctg taatcccagc tacttgggag  19440
gctgaggcag gcgaatcact tgaacccggg aggcggaggc tatagtgagc cgagatcgcg  19500
ccattgcact gtagcctggg cgacagagtg aggctccgtc tcaaaaacaa aacaaaacaa  19560
aaaccatctt agagttaatt cccaccggga ttcaatacac acacacacac acacacacac  19620
acgcacgcac gcacgcacgc ccgcatacac acactgcatc cacctggaaa gtgacaaagg  19680
gcaccctggg gggaattcaa atggtggtgg ccctggtttg gtgttgctgc cttagcttaa  19740
ggtcacacca gccttcagcc tcctgcccca cagtctaggg ctgctccctt catctgatgt  19800
ccacagggac ctgttcattc ttgactcaat ccaggaagat gagaagggag agaagtcact  19860
cgcagcctga gtgaactccc ttgctccacc cctgactgct tggatccccc taggggtgac  19920
ccctgctgaa actggctcct tcctgaccgg ttcccgtcag ggctgtgctg atgggtggtg  19980
cccaggcctg cccctgggga cggggtactc tcccttggca acactccagc ttgtgccact  20040
```

tgacttggga ctgatttggt tctgttttga gtcccttcag gggaggggcc tatcttattc 20100
aacgttgttg tttgttttcc tcacatactg ataacttagc aaatggctat tggaacaaaa 20160
atgaaaataa atggaaccct gaagtgggat gttttaaatt tttatttatt atttttttag 20220
agacagggtc ttgctctgtt gcccagtctg gagtgcagtg gtacaatcat agctcactgc 20280
agcctctgcc tcctgggctc aagtgatcct cccacctcag cctcctgagt taaatttttt 20340
tacagacgcc tgctaccatg cccggctaat ttttgtgttt ttagtagaga cggggtttca 20400
ccaggtgggt caggttggtc tcgaactcct gacctcaagt gatccacccg cctaggcctc 20460
ccaaagtact gggattacag gcgtgagcca ctgtgcccgg cctaaaactg tgtttgagac 20520
agggtctcac tctgttgtcc aggctggagt gaagtggcat gttcatggct cactcagcct 20580
cagcctcact gggttcaggt gatcctcctg cctcagcctc ctaagtagct gggactatgg 20640
gtgcacacca ccacgcctag ctgatttttc tgtcttctgc agagacagga cctcactgtg 20700
ttgctcaggc tggtctcaaa ctcctgggct caagtgatct gcccacctcg gctccgaaaa 20760
gtactggaat tacagcctcc tgagtagctg agaccacagg cacacaccac cacgcctagc 20820
tttttttttt ttttttttgc tttttgtaga gatggagtct cactatgttg cccaggctgg 20880
tctcaaactc caggccttaa gcaatcctcc cacctcagcc tcccaaagtg ctaagattac 20940
aggtgtgagc caccattcct ggccttaaaa gtgtgatatt tttaatgtat tttgaaatct 21000
gcaggactct ccctagaaga taatagcaat aaccaactcc tttattgtgc ttgacgtata 21060
tcaactcact ttgcccttac cgtggctcca gaggcattgg gtccacctta taaatggagg 21120
caccaaggca cagagtgatt aaataagttg cccaggatca cacagccaga aagtgtctga 21180
gtcaagattc cagcccaggc agcctagacc tgagagcacg ctcctaacca ctgcacatca 21240
ctgtcttagc acctcctcag cacaaactgg cccttgagga atgaaatacc gccgccggca 21300
cacacgctcc tgagttaagc ctttgtcaat gaaatgaaca cccacttaaa aggaataacc 21360
tgtccaggca cgatggaaca ttgaataacc ccttattcta aattcctggt ccctgtaaga 21420
ctccttcccc atgcccttgc ccttttatga ccttccccta aagtccttga ggcttaagcg 21480
ggcatagtct gcagcaaaca ctggggaagc tgagtccaga cttcagagca caggctttgg 21540
atctaggcca gctggatttg aacctcacat ttgtgatcag ctggcatgac tgtttccaaa 21600
aagtccattt taatcctcta cgtgaccctc tgtaaaatgg ggatactgaa cggtgagcta 21660
gcacgatttt acagagagtg aatttttttt tttttttttt tttgtgagac agagtcttac 21720
tctgtcgccc aggctggagt gcagtggtgc aatctcggct gactgcaacc tctgcctccc 21780
gggttcaagc gactgccatg cctcagcctc gagagtggct gggattacaa gcatgcacca 21840
ccatgcccgg gtaattttttg tatttttagt tgagacagag tttcaccatg ttggccaggc 21900
cactcttgaa cccctggcct caagtgatcc acctgccttg gcctcccaaa gtgctgggag 21960
tacaggcatg agccactgcg cccagcctta tagggttaaa atttaaaaga ggtgatgctg 22020
ttacaagcct gttttacaaa atgctcttat aataaatcat tatcatcact gttgctgtgg 22080
ttgtagcatc atcatcatta actcccagag ggaggaggga gtctcagagc aagctgctca 22140
ggggagactg gatgtccatg gattgtccag ctcagtacca cttcctccag gaagtcctcc 22200
ctgataagtc cagtcagcat caccctctcc ttccaatgaa ccccactagc cttgtgatat 22260
cacagatatt cttagttgac aggctcatgg tgtatgtagc ctgtctagat cataagtaca 22320
tttttttttt ttttggatca taagaacctt caagaccaaa ataattttct cctcctgagc 22380

```
atgctcattg gtcaagggaa ggaaggaatc gtaatagtgt taataaggct agtgtctttt  22440
caggagttgg ttctttgtgc cagtcttggt gctagacaca ccgataggaa gaatactcct  22500
tcacatcccc aggacaccaa catgggatac gtttgatcat cattcttaat ttgcagaagg  22560
agaaataggc tcagtgagat gaaatagcca ctccagtggc aaggctggga ctggaagccg  22620
ggcttgtcct gattccaaat ccagtttctt tccactgcca cggagaggga gagaagggac  22680
agtggcccca gatgaggatg gggtgactgg atgtgggcag gcctgcgggg gaagagtgcc  22740
ctctgttgag catccgaatg atggcagcag aaaagaagac tgggcagaat cccagttatc  22800
agatcccctg agggaacagt caccccgatc accctcagtc agatgagtgt gtgtagatca  22860
atgcctcata gatgaaggca ctgaggcaca gagtggttaa gtcatctgcc agaccacatg  22920
gctcagggtg cagaggccac cttaacggga gaagagatgg tcactccact ctgcagcatc  22980
agcgcccagg tgggtagaaa tcttgtcttc tatttccaca gaaagtaagg tgcccaacag  23040
tgtttgttga atgaatgaat gaatgaatga atgagtgaga ggcatccttc cttctcagtc  23100
atcctggctc tccttctcac ccccagtatt cggctggcca ccatgagtgc tatgtcggtg  23160
ctgatctcag cgggtgctgt cttggggaag gtcaacttgg cgcagttggt ggtgatggtg  23220
ctggtggagg tgacagcttt aggcaccctg aggatggtca tcagtaatat cttcaacgtg  23280
agtcatggtg ctgggaggag ggacctggga gaaaagggcc aaaagctcca tttggtgggg  23340
cttccggggt tttgaaaaat aaagacaacc tgtaatccca gctacttggg aggttgagga  23400
gggaagatca cttgaggcca ggagtttgag acccgcctgg gcatcatagc aagatcctca  23460
tctctaaaaa gtaatttttt ctaaattatc cagttgtggt ggcatgcacc tgtagtgtca  23520
gttactcagg aggctgaggt gtgagttgga aggattgctt gagcccagga gttagagatg  23580
aacctgggca atatagcaag acctcatctc taaataaata ggtaggtgga tagatagata  23640
gatagataga tagatagata gatagacaga cagacagaca gacagacaga cagacaggct  23700
gggtacagtg gctcacacct gtaatcccag cactttggga ggccaaggag ggcagatcac  23760
ctgaggtcag gagttcaaga ccagcctggt caacatgggg gaacctcatc tctactaaaa  23820
atacaaaatt tagctgcgca tggtggcagg tgcctgtaat cccagctact caggaggctg  23880
aggcaagaga atcgcttgaa cccggagggt ggaggttgca gtgaactgag atcgcgccat  23940
tgcactgcag cctgggggac aagagcaaga cttcatctcc aataaaaaaa aaagaaaaaa  24000
gaaaagaaaa gattgataga tagatagata cccaaatgag gttacaaaag tgtggtctgt  24060
gcaaatgttt aaacacaaca aaccagtgcc tttaactact acagtataat cctgtaggat  24120
tgtgctattc atgatgtaat tatggttgta taaaagtaat taattctcag agcctcacca  24180
gcagtgggtc cagcaagttt gtacagccag catcttcttt cagtcagtgc gtgtcagtaa  24240
ctgcacatgt cctctcattg ggagagcctg tcgaaagtct aagtttgaag gcagctgtga  24300
aggtaaggcc aatccaaatg gctctcccag ctcctctgct gtaaccctga ccctgagtga  24360
ggacatagcc aaccttccca tctcataggt gagaaggctg atgcctggag aggggaaggg  24420
actgcccaag atcacatagc aagatagtgg cagaacccaa gcgagaaccc acagttccag  24480
cctggcttag aagaaagtgc actggacttg gagtcaaagg ctggggtgtg catcccagct  24540
ctgccataaa tccctgtgtg actctgggca atttaacctc ttagagcttt agtttcttcg  24600
tctgtaatat gagggtagca gtactaccac atagggtttt gagggagtaa ttgaattaat  24660
cacatgaaat gatgcacgtt tacaaaaaaa agcatgaagc ccctttactg tgcctcagta  24720
tcccaaagga ctttggattt actctgagaa atacagggag aactagggag tgttgggcag  24780
```

```
aggagagcta tgatctgact tatgttttaa gatactctgg cttctgggtt cagaaaagac  24840
tgaaggggca agagaggaag caggtggaga ccagagcagc agtgatggcc atcatccaga  24900
ctcagactag gacaatagct gtgagggtgg tgggaagtga ttggatcctg actatatttt  24960
aatagcagaa ttgacaggat ttgctgatag actgcacgtg gggtgggaga gggtcaagat  25020
gacttcaagg ttctcatctg gcacaactca gcagctgctg gtgccattta ctgagatggg  25080
gaacattggg gtgggataga tctgggaggg aaaacccaga gttcagtgtc gaatgtggta  25140
gcgttagggt taaggttggg gcgggtagag atgtgtatga aacatcccag tggagacact  25200
gaatggagat gtacaagtct gaagcttagt ggaaaggtta gggctaggga tataaatttg  25260
ggagttgtta caatacagat ggtgtttaaa gccatgagac ccaaggagat cactcaggag  25320
tgaggataaa gagagatggg aagaagtctg aggactgagt cctagaacac cctgcatttt  25380
agaggggga catgtgtaag agccagcaaa ggagacagaa ttgtgcttgg agaggcagga  25440
ggaagcccag gagagcgtga ggtcctggaa ggcaaggaaa gagagggccc caggtgggct  25500
gaatgctgct gagaggtcaa gtcggatgag ggctgggaag tagccattgg atttgacaag  25560
gagaccttgg catgcatggt tgtagaggag gatgaaggca aaagcctggc ttgactgatt  25620
caagagcagg agatgagaaa gtggagacag catgcagggg cagccctgcc aaggactttg  25680
ctctaaaggg gaacagagaa atggaggaga agcaggaggg caataatccg atagagagga  25740
aaaatctgat gatacagaag agagatgaac tgcaagagtc aagcctttga gttggaaagc  25800
aggagtggga ttttgagcac tgataccttt aggccgatgc agggacagtt catctttttt  25860
aaaattatta ttattataca acattttatt taaaaattta ttttcacaga atacattttc  25920
acattagaga ttcccattgt gcgaaaataa caatttatta cttatagttt tatatttgtg  25980
gacagattgt tttagaacaa gtagaataca tttgagaatt aaatctcagt ttacaatggg  26040
taatattttg atacgtctat ggggaaactt gcccttaaat ggaacttctg tatcttcaga  26100
agcactccaa gcgtttcttc ctaggattta gaaatttata atatgagata tcagcatttc  26160
ctaattttaa aatttcccta gtatatgtaa ccatcggtag gtggtatcta ccgactagag  26220
agggaagttt ttgaaaatta aacactgtct aattttctgc aaagttttta ttcatgaatt  26280
aagagtattt cccttagtcc attattccca aggcaaatat ggaagtttga tcatatgcta  26340
atcatactaa agctggattc tctttaagag attgagaaat taaaaggcaa aagctgatat  26400
atcatgttta gttatactgt gagtcttata agaagctggg aggcaacccc attaactcac  26460
cagaatacag aactcagtct cacaacttaa atataattcc tctcaaacct tttcctcaaa  26520
gttaaattct gaaaataatc ttgtgattaa gagaagaagg ctgtccacca atggacttat  26580
ctgttatttc ttccttattg tgagcttaat ggcatgacaa agcagaggca aagaggcata  26640
catcaattct tcaaagtagg aagtcaaaaa ggtcagagct tccacagcat ggcaacagct  26700
ttgcagatgc ccacatcgtg atagttgaaa tagcaaagcc cagcaaaggt taaagctgaa  26760
aatgccaaaa gccctgcctt ggcagctttc tgcgaggcat ccccatgaac atagtcagta  26820
acaacttgtc caaggcccca gtgaccatga agagtgaggg ctgcagccag ggaatagtcc  26880
gtcgcagagc aaggattcaa ataagcagcc ggaagcagac ccgggagcaa aacactgaca  26940
accctctcgc tagtccagtg gagagatgca gccttggagc cagaatggtg gctcggtgac  27000
aagtgtatgt gctgcactcc acaccattct gggataggtc ggtcctgaag aaatgctgag  27060
atatgagcag gtctgaccac tggagttcgc agcaacagag ctcggcctcc ttgggcaccg  27120
```

caaacggcac tcagcctcca gagaaccgcc atctcgttcc tgaggcggag agttcatctt 27180
aacgagagaa atggcaggga ctgtgaatag gccggcagat ttggtggcgg gtgccacagg 27240
ttcagtctcc tgcagggaga ggagaaaatg ccttactaat tccttgtatt ttctcagaga 27300
aacaagaggc accgtcatca gcctcatgtg agggtgggaa ggagggatgg ggtttgcgga 27360
gagggaaagt gtggtatggt catctgtggg agtggaagag agtgagaggg ctgcaggggt 27420
gcagcgggac tgcaggctgg caccagggtc cctagggctt gtagttggtg gaaagtgcat 27480
cagtgaccag ggctgtgtgc agctgctcca ggcaggtgtg gaagaagcag agttgaactt 27540
gcccagcctg gagtgctgcc cagagtgagc ccaaagccca agggagacca gagatggggc 27600
tgtttgcaaa ggaggaagta taacagtagc ccacaaaatc tgagctggtt aagaaaggag 27660
agagagtgaa aatggggagc ccagcctggc agcctgggta cacatctcag ctcaacccac 27720
actagctgaa tccatttggg ccccttcgtt gacctctctg tgcctcagtt tccctatcta 27780
tagaatgggg ataagaataa ggctacttcc tagggctgtt gtgaggattg aacaagtgac 27840
cgaacacttg ttcaattttg aatactgttc taaagcattt aggacagtgc ctggcatggg 27900
gtaagtgttg cggcagtgct gttattttca tcatcaccat tgttctcagg ctgcgttgat 27960
tggagctgct gaagggaggc aatttaagga agtgagccgg acagatagga ggtggtggtg 28020
gttatcaggt gcgatgcttg aaactgaggc ttcggaggca acagttactg gtaatgacaa 28080
ggtctaaggc ttgacagtgg gtggcagaag tgtaacgcag ggaaagagac gagcggtcaa 28140
ggagccgaga gggaaggagt tgggtggact aagatcattt gtggaagaat gatggagaga 28200
aaggctgaag ggcaggaact gacatcatca gtgaccaagg ggcggccagg aggctgagac 28260
cgcagcaaga aagggagagt gtgatggcat cttcttcaag ggagctgggg atgtttgggg 28320
tggaaaaaag aacaatggtc tgggagggaa tatgggaagt tttttttttt tttttcagat 28380
ggagtttcgc tgttgtcacc caggctggat ggcaatgttg caatctcggc tcactgcaac 28440
ctctgccttc caggttcaag tgattctcct gtctcagctt cccgagtagc tgagattaca 28500
ggcacacacc accacgcctg gcttactttt gtatttttag tagagacgga gttttgccat 28560
gttggccagg ctggtctcaa actcctgacc tcaggtgatc cacccgcctt ggcctcccaa 28620
agtgctggga ttagaggtgt gagccaccgc gcccagcctg gaagtttgta tttattaatt 28680
tttggttgtc ttcatctgtg tatgtgactt taacccctaa atacttcagt gtacatttct 28740
tttttttttt tttttttttt tgagacagag tcttgctcca tcacccaggc tggagtgcag 28800
tggtgtgatc tcggctcact gcaacctccg cctcctggat tcaagcaatt cttgtgcctc 28860
accctcccga gtagctggga ttaggggcat gccaccatgc ccagttaatt tttgtatttt 28920
tagtagagat ggagtttcac catattggcc aggctggtct tgagctcctg gcctcagttg 28980
atccacctgt ctcagcctcc caaattgctg agattacagg cgtgggccac cataaccggc 29040
ctcagtgtat atttctgatg cagttgggtt ctgtatcccc ctccaatctc atctcgaatt 29100
gtaatctcca cgtgttgagg gcaggacctt gtgggaggtg atgggatcac aggggtggtt 29160
tcccccatgc tgttcttgtg acagtgagtg ggttttcagg agagctgatg gtttgaaagt 29220
gtggcacttc ctctctctct ttctctctct ctctcacctg ccaccacgta agatgtgcct 29280
tgcttccctt tcaccttcca ccatgattgt aagtttcctg aggcctctcc ggccatgcca 29340
aactgtgagt caattcagcc tcttttgttt ataaattacg cagtctcagg aagtatcttt 29400
atagcagtgt gaaaacagac taacacaatt tcctaaaaca aggggacatt ctcttacata 29460
accattgttc agttaacaaa aatgagaaat tgacattgat atattatgat taccttattc 29520
tcatttcacc aattttttca ataatatcct ttctagaaaa aaatacatat tttttgtggt 29580
cgaggattac atcttgcatt tagttctcat gtcttattaa attccatcaa tctggaacag 29640
tttcttcatc tttctttatc tttcatgacc ttgacatgtt ttgaagtttc gagccagttc 29700
ttttgtagaa tgtgggtttg tctgctgttc ctcatgatta gattgtgggt atgcattttt 29760
ggtaggaatt ctccaagagc cgtgtgtgcc cttcttagta tatcatatca gaagacatgc 29820
tatcaatttg ccccattact gggtgtgtta actgtgatca ttgggttaag atggtacctg 29880
ccaggatctt ccactgcaaa gttactattt tcccctttgt aattaataaa catcttgtga 29940
ggagataatt tcctatagaa atcctgttga tcatccaact ttcacccact gatttagtg 30000
ttcattgatt cttccctgaa taaattagta ctataataat tgccaatggt ggttttctaa 30060
ttccatcttt ccttcaatag ttggcattct cctgtaagga aaagctttcg cttctctgtt 30120
catccactca tctatgtatt tgtttatatt accatggact cctggattcc ggtttacaca 30180
cttccatttt ctgccttttc tctctgctta atataaggat taatgagaac tccctgattc 30240
ccaggaagaa aatgtcacca gagctttctt aggtggaatg aagagaattc agtgtaagaa 30300
ccataaaggt gtatctgtgt agtatggaca gttttaaaaa acaaacaaac aaaaagaacc 30360
tccaagggca ggaagtgctg ccagactcag gagggcacta gaactgacta tgagaagcca 30420
ctgagatccc aggtagtctg tgctctccat cttttggctc tgattctctc tgtacatcta 30480
acatctctgt acaccagctt tctctttagc gaaaaacgtg tcccctccac ccacccatcc 30540
acctccactt gttcctgcat ttctatgtcc cagatcctgc agaaaacaac tcttttctct 30600
cagttagtct caattctgta gtccagggag agagaatctg atcagtcccc tgggtcattt 30660
ttccactctg gtccaagcag ctacagctgg catgggaaat agttcacaca gtaaaaacat 30720
ggctgtcaag aagaggagta aatttcagag gcagaacact ccctgtgagc ccgaacctct 30780
tcctgctttg ttgcagtctt cataacgatt gctttaaaag actgcattga tataacatca 30840
tctctcttct ctgcatcttt gacttgctag cttaactggt ctagaggagg gcttagcact 30900
gattttcagt attcattttc ctcaaaactt caattcagcc tgggtttctt cagcaggagg 30960
gctcggggga accagagcca gggaccagag tcatttcagt gcaccagctc aagaaatgaa 31020
tattccaggc caagaatccc caagtgttct ttctgaagtc cttcctggtg gagctcaaag 31080
agatgaaaaa cgcaagcccg cttttcagtt cttatcagga aactgcatag actttcctct 31140
ttatgtatga ctgagggctt tttaccatca tttgttcact tcacagatat ttatttggta 31200
tttactatat accaggcact cttgtggcag tggaaaatac aactctcgtg gaacatctgt 31260
tccagaagga aagactgcca ataagcaata aaataggcaa aagatatagc atgttagaga 31320
gtggtaagta ccacagagaa aaataaaatg gagaaaagaa acacgaaaag ttggggagag 31380
aggacaactg tttgaggggg tggccagggg cagcttcatc tcatcaaggg ggtgattttt 31440
tttgagtaca gacctgaagg taacgagtgc acaagccaca tgggtacctg agaacagcgg 31500
cagaacaatg gcagggtgct gggagggcta tttaccaccc atgctgttta gaattgtcag 31560
cacatggtga taaaaaaaaa aataggctgg gtgcggtggc tcatgcctgt aatcccagcg 31620
ctttgggagg ccaaggcgga tggatcactt gaggtcagga gttcgagacc aggctgggga 31680
acatggtgaa accccgtctc tactaaaaat acaaaaatta gccgggcaca gtggtgggcg 31740
cctgtaatcc cagctacatg ggaggctgaa gcaggagaat cgcttgaacc cagtgggtga 31800
agtttgcagt gagccaagat ggcaccactg cactccagcc tggcgacaga gcgagactcc 31860

-continued

```
gtctcaaaaa taaataaata aataaataaa aataaaaagc agacagactt tttagttggc  31920
tttagaattg ttagacaccc tctgcagaca aggcaccccg attgcttgca cccagggtgg  31980
actactccct ccatcctgcc cttgttacac cctggctggg ggtcagcatt tcaggcagct  32040
gaatgaccca aagtgggaac acgctagtgg gtttgaggat gagcaagtgg aggagtgcaa  32100
taggaggtga cgcccgagag gtcaggtgag agtggatcct gcagggtcgt ggcaagaacc  32160
tggaccttga ctttgagtga catgggagcc gctggaggct tctgagcaga ggagtaacat  32220
gatctgactt gcattttatt ttatttattt atttgacgca gtctcactct gtcgccgaag  32280
ctggagtgca gtggcgccat ctcagctcac tacagcctct gcctcccagg ttccagtgaa  32340
tctcctgcct cagcctccca ggtagatggg attacaagca agcatcacca cgcctggcta  32400
atttttgtat ttttagtaga gacagggttt tgccatgttg gccaggctgg tatcgaactc  32460
ctgacctcag gtgatccacc cacctcagcc tcccaaagtg ctgagattac aggcttgagc  32520
caccacgccc ggcctgactt gcattttaac agggtcactc tgtctgctgt gtggagaaca  32580
gtccgcagga agacaagggt ggaaatgggg agaccagtta ggaggttact gtaacaattt  32640
ggggtagcgg tgatggtggc ttaaaccaag atggggtcag tgggaaatgg tgctaaaaat  32700
cctgccaatt ctgggtattt ttagaaagca cagctgacag ctttctccag tagcccacta  32760
aataagttat gaagcattac taaaatgtga tagtcatgat gcaaaattag aatatatcta  32820
gaatctcccg aagaccttag tttggtatta caagaagtct ggttgcttca tgttgcaaaa  32880
tttatatcac tcatcactcc tgcagagtta aaattccgct gagaagtagg aatcagtgaa  32940
gtgcgtgtcc atgtgggttt ttgccacacc taagtgaacc ttggtcaaaa gcatataaga  33000
gctactgata ggccgggcgt ggtggctcat gcctgtaatc tcagcacttt gggagggaag  33060
gatctcttga gcccaggagt tcgagaccag cctgagcaac atagtgagat tccatcttta  33120
cacaaaattt aaaaattggc caggcatggt tgtgcactcc tgtaatccca gctacttagg  33180
aggctgaggt gggaggattg cttgagcctg ggagttggag actacagtga gctgtggcca  33240
caccactgca ctccagcttg agcaatggag caagactctg tctcaaaaaa aaaaaaaaaa  33300
aaaaaaaaaa gaggccgggc acagtggctc atgcctgtaa tcccagcact ttgggaggcc  33360
gaggcgggtg gatcgcctga ggtcaggagt ttgagaccag cctggcaaac acggtgaaac  33420
cccatctcta ctaaaaatac aaaattagcc cagcgtagtg gcgcatgcct gtaatcccag  33480
ctactaggga agctgaggca ggagaatcgc gtgaacctgg gaggcaaatg ttccagtgag  33540
ccgagatcgt gccattgcac tccagcctgg gcaaagcctg ctgggttggg ctgggtaagc  33600
tctgaacacc agtctcgtgg cttcaagtca cacctcctaa gtgaagctct gaactttctc  33660
caaggaccat cagggctttc ccctgggcag aggatgccga cactcactgc tcttactggg  33720
ttttattgca gacagactac cacatgaacc tgaggcactt ctacgtgttc gcagcctatt  33780
ttgggctgac tgtggcctgg tgcctgccaa agcctctacc caagggaacg gaggataatg  33840
atcagagagc aacgataccc agtttgtctg ccatgctggg taaggacaag gtggggtgag  33900
tggtctcata cttgggctga gcagaatggc tcagaaaagg ctctggctga aaaaatctcc  33960
ctcctttacc aacttcccct gggtgtctga agcccttcca tcatgattca cttctttgag  34020
tagtgtttgc taaattcata cctttgaatt aagcacttcc ttttagggac ctctcttcat  34080
taatatccac tagaaaggag agactcatta tgtgtgagtt tcaataagtt tatccaatcc  34140
ctttgttttc aactgaaagg agggaaacgg acaagtgaag aaggtagggc ccaggagtga  34200
aggaacaagg gtgggaatag taataatgtt gtactttgaa aatctactgg gaaaatgatg  34260
```

aacttagact gctgggagag gctaatagaa aatcgggcag tgagcttgat agtaggcaaa 34320
ggactatcag gccacggggt caagttaaag cagcacattc attaaaaaaa aaaaaataag 34380
cgtttgggcc aggcgtggtg gctcaagcct gtaatcccag cactttggga ggccaaggtg 34440
ggtggatcac ctgaggtcag gagttcgaga ccagcctggc caacagggcg aaaccccatc 34500
tctactaaaa atacaaacaa atcagctggg catggtggtg cacgcctgta atcccagcta 34560
cttgggaggc tgaggcagga gaatcttttg aatccaggtg gtggaggttg cagtgagcca 34620
agatcgcgcc actgcactcc agcctgggca acagagcaag agtccatctc aattaaaaag 34680
aaaaaaaaat taaaataagc atttgaccat cacagagcag gttcaggagg cctggggtat 34740
gcagatttca accctcttgg cctttgtttc cttgtctgta aaatgtggtt agctggtatc 34800
agcttgagag ctcggagggg agacgtgact tccccatcta actctaagtg acaaggctga 34860
gactctccag ccctaggatt ctcatccaaa acccctcgag gctcagacct ttggagcagg 34920
agtgtgattc tggccaacca ccctctctgg cccccaggcg ccctcttctt gtggatgttc 34980
tggccaagtg tcaactctgc tctgctgaga agtccaatcc aaaggaagaa tgccatgttc 35040
aacacctact atgctctagc agtcagtgtg gtgacagcca tctcagggtc atccttggct 35100
cacccccaaa ggaagatcag catggtgagc agggcgctgc ccttgggcag cacttgggtc 35160
taacaggact agcacacata tttatgcccc tccccacccc agggccagcg tgggttggga 35220
gagggcatgc cgggtggtgg agctgtgcct gcctctacag tggagctcta ggaagaatgc 35280
tgggtggtca caggggggcct gggactcagg agactgtcca gtgatcaaag gctttctggg 35340
gggagtgatt aaatccatcc atgctaacat gaaacagacc tgagtttgaa ccccgtttct 35400
gctagttgct caagtcagtc accatgagcg agagtcagca gcaacagact agactagaat 35460
tagccagcct ctctcttccc cccaacaaat ttcaagaatg gaaccatcag aatcagaagt 35520
agagaagtat gtgacactag ccatgtggct ctggtcaagc cacttcaacg ttttgagtct 35580
cagtggcctc atctgtaaag tgagaattaa gagatggtgc atgtaaagtg cttaacgggg 35640
agtaaatggt aggcaaacat tagctgctgc tattagtaca gagagacaat ggtgtgtgtg 35700
agtcttgtgg gcagagatgg gtgagagggg agacaaaaca agttctcatg atgatggggg 35760
caggggggtcc agctggtggt gtcggaggga agtctggaca gaccagtggt ggggctcggg 35820
tgggaggcac tggggggggct ggagtggaaa gaatgtggcc acagatgaca gcttcacagc 35880
agaattcagt gctaagagga agtgagtggc catgagttcc atggtgacag aaagtctaag 35940
acacctagca aggcaggagt gggtgtcagc tcagggaagc tcagaggcta aacctaggtg 36000
agagctgagg gtgtcagata agagcaaggc aaggctccgg ttctggagta gtgaaggaca 36060
tagcagagct ataacccagg aacaaggccc agcttattgg aactgggacc agtcacacag 36120
ggtggcacag gcaccaagta gccaataata ataataaaaa caataacaat gatttatgtc 36180
tattgggcat ttattcatgt tctatgccag acactggact aagagcttta tatgtggaaa 36240
ctcatttaat ccttacaata accttatgaa gaaggtacat ccaaaacccc attcttctag 36300
gccaggtgca gtggctcaca cctgtaatcc caatattttg gaaagctgag gcaagaggat 36360
tggttgaggc caggagttca agaccagccc aggcaacata gcaagaccct gtctctaaaa 36420
aataaaacaa aaacccattc ttcccgctgt ccagggacac accactaatg agtgtgatgg 36480
gtgcctagga tgctgagcac ctggacttcc cagctcattc cctaaatgct gcacaatcag 36540
ggtaactgtg ccctgagcct aagaggcagt agtgagctgg cccaccgtgt ccactgatga 36600
aggacacgta gccccaacac aggggagagg tggtttcagg atcagcaaag cagggaggat 36660
gttacagggt tgccttgttc ccagcgtgct ggtcacttgc agcaagatgg tgttctctct 36720
ctaccttgct tcctttaccc acacgctatt tctttgcaga cttatgtgca cagtgcggtg 36780
ttggcaggag gcgtggctgt gggtacctcg tgtcacctga tcccttctcc gtggcttgcc 36840
atggtgctgg gtcttgtggc tgggctgatc tccatcgggg gagccaagtg cctgccggta 36900
agaaactaga caactaatgc tctctgcttt ggctgaaggc cagcaggacg ctgggacctg 36960
atgggccact gtgcagtgca cagctgcatt aggcaggtgt tggtgcattc tcttattggc 37020
ttcaacgcct agcgagggat ccatcctggc tcggtggcac atttgttaag atgctgggga 37080
gcaggtggca gaacccattt gagcttgctt gggcactggg gagaatttgt taccaggcta 37140
caggggtgtc acagaactca aggacaggga ctggagtgtt gtggggagcc cagaagcccc 37200
tgttttactt ctttctttgc ttttcctgaa tatctgcttt attcttactc tatagacctg 37260
cttcctcctc tttcacccca cattgtgggg tgtagtcttt tgcttcaaga aagcagcctg 37320
gtggatggaa tctcttggcc ccaatcccaa attctctgga gaaggggctc tttggtttaa 37380
cttggataat gttgtcttca gctgggggtg ggcacatcgt gcatatgtgg ctgctgccgg 37440
ggaaccacgt ggatgatgtg agaggagcag cacccagaag agggagtgct gggctgatgg 37500
tccaggtcgt gtccacttct gattgtttaa ttcttcttct aagtggatgg atctttctcc 37560
aatactcagc aaatcctgat cgttccagaa tacttcatta tagccaattg gttataatgt 37620
gcttctctaa gagaaatatt tagggacaac aaatcttcat gggtttgaag acttgatgga 37680
ggaaaaagga gtagattttc gaaggctgga tttggatgaa caggggctat tcagggagtg 37740
cattccaacc taaaattagg aaaaactggc tgggcgcagt ggctcacgcg ctttgggagg 37800
ccgaggcggg cagatggcct gaggtcagga gttcaagacc agcctggcca acatggtgaa 37860
accatctcta ctaaaagtac aaaaattagc caggcgtggt ggcgggcacc tgtcatctta 37920
gctactcagg aggctgagat gcgagaatca cttgaacctg ggagacagag cttgcagtga 37980
gccgaaattg cgccactgca ctccagcctg ggcgacagaa caagactctg tcttaaaaaa 38040
aaaaaagtgt tttatataca gagtggaata ttatttagcc ataaaaagaa tgaaatcctg 38100
tcatttgcag caacatggat ggaactggag gtcattaaaa aataaaataa aataaataag 38160
gaaaaacgta tcaatacttc gattgaccaa aaccagggca aatctgattt tcatctttgc 38220
aaggggaaca aatttctttt atctcctctg gctttgaaac cctgaaatga aaggaggaag 38280
ggcagaaaaa agaacacata gcaagttacc atcaggctca gcgcccatcg cattccctga 38340
gcttgtttcc ttgacttcat cactggcagg actattcaaa aatgattccc tcattcattc 38400
atatattcat tcattcatca ttccttcatt caacacatac gttttaacac tcatcttgct 38460
tttcaagcta tagtttagtg agcgaaatgg atacacagaa tacagtgtga gaacagctac 38520
agggcacatc tgagctagcc tgggatgggt ccggaaatgc ttcctggagc agaggaaacg 38580
gttgacagcc aagtgttgac agagaagtag tattagccag gcagagacat ggggaatgta 38640
ttccaggcag aaggcacagt gtgtatgaaa gcttattggt aagaagagtg tgtggcccaa 38700
ccaggaaaca gacattctga aggcataggg tccacccagg agcatggtga acccagatcc 38760
ctgaaagatg ggaggtgctc aggcacactt cctgggctag ttgaggggtc tggattttta 38820
tttacttatt tttttattta ttgagacaga gtctcgttct gtcacccagg ctggagtgca 38880
gtggtgcaat ctcagctcac tgcaacctcc acctcctggg ttcaagtgat tctcctacct 38940
cagcctcctg agtagctggg attacaggtg cccaccacca tgcctggcta atttgtgtgt 39000
gtgtgtgtgt gtgtgtgtgt gtgtgtgtgt tttgttgttg ttgttgttgt tgagacggtg 39060
tctcgctctt ttgcccaggc tggagtgcag tggcgccatc ttggcttact gcaagctctg 39120
cctcccgggt tcacaccatt ctcctgcctc agcctcctga gtagctggga ctacaggcgc 39180
cctccaccac gcccagctaa tttttgtgt ttttagtaga gacggggttt cgccatgttg 39240
gccatgctgg tcttgaactc ttgacttcag gtgatccacc cacgttggcc tcccaaagtg 39300
ctgggattac aggcatgagc caccgtgccc gacctggatt tttattctga agactaatgg 39360
ggatcctaag gaaggaacca gcctgactga atttgcatat gtgtccacat ctgctggctc 39420
atggctgtgt gggaggctga gtgatgggga ggaaggatta ctgagtaggg atctagaggt 39480
gtggcctcat gctttctttc taaccagctg tgttgtcttt gggatggtgc ttaaatttgg 39540
gctagaccag tgggtcttgg tcacccccca ggggacatct gacaatgtct ggaggcgttc 39600
ttggttgaca cagtggggtg agggctgcta ctggcagctc gtggggagag accaggaatg 39660
atgcttaaca tcctacagtg cacagggcag cccccatcac aaggaattat cagctgaaat 39720
tgtgaatagt gcctacacta gacccttgct actcatagtg tggtccgtag atgagcagca 39780
ttggcatcac ctgggacctt gttagaaatg ctcttagacc ccaccccaca tccactaaag 39840
ccagctcttc atttcaacaa actccccatt gatgtgagta cacattcaag tctgagaagg 39900
gcttctttga ggtgagcctt agtgcccatc cccatttggt ggcgccggat accaagggtg 39960
tgtgaaaggg gtgggtaggg aatatgggtc tcacctgcca atctgcttat aataacactt 40020
gtccacaggt gtgttgtaac cgagtgctgg ggattcacca catctccgtc atgcactcca 40080
tcttcagctt gctgggtctg cttggagaga tcacctacat tgtgctgctg gtgcttcata 40140
ctgtctggaa cggcaatggc atgtgggtca ctgggcttac cccccatccc cttaacactc 40200
ccctccaact caggaagaaa tgtgtgcaga gtccttagct ggggcgtgtg cactcggggc 40260
caggtgctca gtaggcttcg gtgaatattt gttggctgat ttattcagaa attatgtcca 40320
gcccctacct tggatggatt tatcacctct ccaggccacc tcttctttcc aaataggacc 40380
acctaggtat agaccaaaga cacgaaatct tctgtgaccc cacaaacaca gagcaggtca 40440
aataggccca agccaattga gactgtggtt caggtcgtga tgcagagctt tgctgtggac 40500
gtgctcccac tgcgtactag ctgggcatgc ggcttaacct ttctcagcct cagtcgcccc 40560
cttgtaaatg gagataagga tactatctcc cctcacaggg ctgttgggat gctactggat 40620
ttaataagct aatgcaggga catgctaagc acaacccatc cctgaggccc agagaagggt 40680
gggcctcggc tgaggtctca ctgtgaggtg ggaatgtggg cctccagacc agaggtaggt 40740
cctgtggccc ctagacagtg gacagcaatg gtcagtttga cacaccagag ccctagccat 40800
tacttcctgg atgttgtgtg aatattttct ggacatggct tatataaaat gaaaaagtga 40860
attgggcacg atatagggat agatttttag agatgaactg atagcatgat gataatcata 40920
ttcactgata acatttacta ctgttattga ctgctttaaa agtgttgggc attgtgctag 40980
aaaccattat atgcattatc tccttgaatt ctcacaaccg cctactgagg tattctcaga 41040
ctctaagaaa tgagatttaa gagaagttat ctgcccaagg tcacccggct ggaacctggc 41100
tgtaaaaatg gctgaagcag gtgatgagga gctgatgtgt ttggacgtgt ctcagagaaa 41160
tcatggaggc gctggggttc cttccggttc ttggatgcct tctacagaga caaccatagc 41220
cccaaattat agggatcaca tatcagtggg tgagacatcc ttgcttggga tgaggagggg 41280
atgagctgtg tgaagcaagg tgcctctgta atgggttcca gtgatgtgtc tgccactgtc 41340

-continued

```
ttaataactg tgcaattcta agcagaacct ttcctgtctc tgggcctgag agttcccctc  41400
tgtaagatga ggacttgacc tagcaaggtc ctactcagat gcctgtagag aacaggcagg  41460
ggaagttaga aaaaaaaaaa gccagtgaag gaagggagct cttcagcttg cacccaccat  41520
cacagtgcag ggacccaggc tcagtgttgc cagatccaat gacttctcaa gagctcaaaa  41580
tctagagttt tgcatgtgct ctcccaagta ctggcagaaa attcaagatt gttagtaaca  41640
ctgtgtggct aaattctgct tgtgggctgc ctagattccc aattctgtga ttctgtggtt  41700
ctctggaagc attggttctc cacagcacct gcatcacttg gaaacttgtt agaaatgcaa  41760
gccctaccta cggccccacc ccagacctac ccagttagaa atctggggt gggacctatc  41820
agtccatgtt tgaacaagcc ccacaagtgt tctcttgcaa gctcaagttt tagaaccact  41880
gacctatagc caaaaaagaa aaagccaatc agtggtttgc tggtagagga ttaacttaac  41940
aactggcttt ccatgaaaat aaagccttga ttggtagcac ttgcaatttc tatggtacaa  42000
acgcttccca catgactgag ttcaagctat caaggagacg tcactgcaca tggacttggg  42060
aagagatgag aacaatcagc ccactgagcc tatgggaact ggctccagca catccctgca  42120
agtcaactct catcagggtg agtgagttga ggaccaagaa gcagttatcc tcttgccttt  42180
gcaggaccca ggcaaaggga agggcatagt gacagtgatg atctctcttc cggaagtctt  42240
tggtttgctg agagtaaaag gcgtgggctt caccagtggt gaagccagtc atgcagcctt  42300
agtcctggta ctcaaactcc ctaaatctca gttttctatc tgtaaaatgg gaaaataagt  42360
cctatgtcac agggttgctg tgcagattta gcaatagaac atagccccgt tctttatgat  42420
gactgatgct gcatcagtat ggggacatct ctatgtaatg gaaagatgga gagaggatta  42480
agtgcaaagt cacagcactt aatgggaact gtggattagc tacttggtgg cattgggcaa  42540
gtcagttgac tttgcattaa ttccacaaac aatatttccc aatttcctat tcagatgagc  42600
atatgtgact gagtcagatg ctgtgatcag agccaggatg gagcatttcc cacaaactgt  42660
gggattttta agtgatggga aggcacactg aaatggcatt gaatcatgca gttgcagata  42720
ctctttttca attctcagtc ctttgattac atcagggaga aaagaaagtc cccacttggg  42780
ctgagaatct ctgcaccctt ctagctcttg ttaaccactc ttttgaatag cagagaaaac  42840
ctcagactgc catatctggg agagatttta gcaacatttt gttttcattg tatctctttt  42900
tacagctacc tcccatttcc cttctatttc aagctagtaa cacagttttc ttttaaattc  42960
atttatttaa atgtaaaaat aagtctattt ggagaaaaaa aatttttaat agcatctctg  43020
gaatgccagt atggctaaat tcatgaatgt tgtcctcaaa tgctgaaatc tgggaagcat  43080
ctggccaagc tttgtggaca ggccttccta gtttgaatcc caagagccac tcattccgag  43140
ccacaaaaca ttggaattct tggttcactt ccctaacctg aacttgtcct ctgtgaaata  43200
gggacattaa tagctcactc acagggctgc tgtgaggaca tgtgttgagc tgagggtctg  43260
gccaggggag accctgtgca gggagactgt tatcatggtg atggatttct gcttcattca  43320
tttctttttc cagacagcat catatagaat gagttgtggg gtggcagtca gcaggtttgg  43380
gtttatcctc tattctgcca cttattactt aaaaaaaaaa acccaactta tatagtataa  43440
gctatatcca gaaaagtgca aatatcatac aagtaccatt tgatgaatct tctgatatcc  43500
ccacataacc aacacccaga acctcttctt gtctcattcc aggataacca ctaacctgac  43560
ttctaacagc atcagtcagt tttgtctgtt tttgtacatt atatatgtga tggtttgaat  43620
gtgtccccca aatttcatgt gctagaaact taatccttca attcatatgt tgatgctatt  43680
tggaggaagg gcctttggga agtaattagg attagataag gtcatggggt gaggtatgat  43740
```

ggcactggtg acttataaga agagaaagag aaatctgagc tggcatgctc ttgccctctc 43800
accgtgtgat gacttctcca tgtcatgatg cagcaagaag gccctcacca gatggtggca 43860
ccatgctttt ggacttccca gcctctagaa ctgtgagcta aatcaattta ttttctttat 43920
aatcacccag tttgatattt tgtcatagca acagaatatg gacaaagaaa gaaaattaat 43980
gcaagaagta gagtttttac tgtaacagat tcctgaaaat gtggaagtgg ctttggaact 44040
gggtgatggg aataggttgg aagagttttg aggagcaggc tagaaaaagc ctgtattgtc 44100
aagaatggag cattaggcca ggcacggtgg ctcagactta taatcccagc actttgggag 44160
gccaaagcag gtggatcacc tgaggtcagg agttcgagac cagcctggct aacatggtga 44220
aacgctgttt ctaccaaaaa tacaaaaaat tagctgggca ctctggcgca cacctgtaat 44280
cccagctact caggaggctg aagcaggaga atcacttgaa cccaggaggc agaggttgca 44340
gtgagctgag atcgtgctat tgcactccag cttgggcaac aagagcaaaa ctccaactca 44400
aaaaaaaaaa aaaaagaaaa agaaaaagaa tggagcatta aagacagttc tacagttctg 44460
gtgagggctt aaaagaagac cccagaacta gggaaagtct ggaacttctt aatggttact 44520
gaagtcgttg agatcagaat gctgatagaa atgtggctgg tgaaggccat tctgatgagg 44580
tctcagatgg aactgaagaa ccacgtgttg gaaactggag caaaggtcat cctttttata 44640
aagaagcaaa gatcttagct gaactttgtc tgtgccagag tcatttatgg aaagcagaaa 44700
atccgtaggt cacccatgtt gtagagaatg aaagaacatt ttcagctgag aaaactgaga 44760
gtgtgaccaa gctaccgatt gataagaaaa ctagtacaca taaattagcc aggcgtggtg 44820
gtgggcgcct gtagtcccag ctacatggga ggctgaggca ggagaatggc atgaacccgg 44880
gaggcagagc ttgcagtgag ccgagatcgc gccactgcac tccagcctgg gcgacaaagc 44940
gagactccat ctcaaaaaaa aaaaaaaaaa aaaggaagaa agaaaattag tacacataga 45000
acaaagccag aggctgttca tcaggacaag ggagaaaaac tccaaagcca tttcagagat 45060
cttcaagact gcccctccca ttactggccc agagctctaa gagggcagaa tggtttggaa 45120
tgaccagctg ctgcccaggg ctgccttggg tctctgctcc ccacatttct ggtgcagcat 45180
tcctcagcca tcccagctgt ggttcaagtg gccacaggtg tgatgtggaa ggtaaaagtc 45240
ataaaccttg gcagcataca catggcacta attttgcagg tgtgcagaat gcaaaagctg 45300
agggggcatg ccttctccca cctacatttc aaagggtgct gtgaacggcc accccagaga 45360
gcccctagta gagcaaggtc tagtggagct acaagggtgg ggccaccgcc aagaccccag 45420
aatggtagag ctatcatagt gcaatgccag cttgggagaa ctgcaggcat gagactccaa 45480
cctgtgcgaa gtgcaacatg ggcagaaccc agcaaaacca caggggcaga gctccccgaa 45540
gcttcggggg tccaaattcc atagtgtgtc caggaggtgg cacacagagt aaaagatcat 45600
tctgaaggtt taaggtttaa tgttgttttc tatgttgggt tttgtacttt cctggaacca 45660
gttacccttt ttcccttgcc tctttttcct tttagaatgg gaatgtctgt cctatgcctg 45720
ttccactgtt gtattttgga agtcaataac ttgttttgac tttacaggct tacagccaga 45780
gggaatctcc catagaatga attgtacctt aagtctcacc cacatctgat ttagatgaga 45840
ccatggactt tggaattttg agttggtgct ggaacaagtt aagactttgg gggttgtcta 45900
agtgtggtgt ttcatgcctg taatcccagt gatttgggag gctgaggtgg gaggattgct 45960
tgagcccagg agttcaagac cagcctaggc aacatagtga gacctgtctc tacaaaaata 46020
aaaataaaaa gttagccagg tattgtggca tgtgcctgta attctagcta ctcaggaggc 46080

-continued

```
tgaggtgaga ggatcacttg agcccaggag tttgaggctg cagtgagcta tggtcgtgcc  46140
actgcattcc agccagggca acagagtgag actctgtctc tacaaataag attaaataaa  46200
cgtagctgga gatggtggca cacgtctgta gtcctagcta ctcaggaggc tgagacagga  46260
ggattacttg agccaaggag tttgaggctg cagtgagcta tgatcatgcc actgcattcc  46320
agcctggatg atagagcaaa atcccatctt taaaaaaaaa aaaaaaaaaa aaaaaaatat  46380
atatatatat atatatatat atatatatat atatatatat actttggtgc tattgggatg  46440
aattttgcat gtacgaagga catgcatttt gggggctggg gcagaatgct atggtttgaa  46500
tgcatccctc aaatttcatg tgttggagac ttaatctcca aattcatatg ttgatgaaat  46560
tggaggtgaa gcctttggga ggtaactagg attagataaa gtcatcaggg tggggcccct  46620
atgatgagac tggtggctta caagaggaag agagacctga gctgacatgc tcttgccctc  46680
ttgccatgtg ataccctctg ccatgttatg gcacagcaag aaggtcctca acagatgcca  46740
gcagcatgct cttagacttc ccagcctcca gaaccatgag ctatatataa ttattttata  46800
aattacccat tctgtggtat tctgttatag caacagaaag tgaactgaga taatatacat  46860
ggaatcatac agtaagtctg tgcttttgta tgcttctttt actcaacatt gtagttgtga  46920
gattcatcca ggttgttaag cattgctgta cttttttttcc actgggatat agtgttctgt  46980
catgcttggg tcttaattta taaaggtgac tgagtggcat tttcttccag tattattgga  47040
aggaaagttt tgttgttcac agttcccctg taaaaaagag gcagaacacg tcttgcaggg  47100
ccacacaaaa ctgtgtcatc cagggaccag gcagcagaaa gagaggggga actgggccta  47160
tgcctttatg aaaaagagtg gtgggagagt aactgggtga gggcatccac taatgggcag  47220
gaagtgaaaa cacatatgtt ggaatttgta gctgaggggt ttataatatg agtttcccat  47280
gcctgagaaa gctgacttgc aagaaaacga gataaacaac tttggccatt agtgtggccc  47340
tgtcataaat gaatgccgga tagacaaatc gagaatctaa gaaaagatag ttggaacaag  47400
tgttccattg tgtgaatgca gcagaattta tttatccatt attgaggagg atttgggtag  47460
tttccagttt ggagctatta tgaatattct agtattgctc ctctgaacat tctagcactt  47520
ttgtttttgg agcacacgaa tgcacttctg ttgattatat gcctagaagt gaaattgttg  47580
agttatacag tattcacaca gtcagcctta gtggctactg ctaaacagtt ttctctagta  47640
gtttgcgcca atctaatcac cagtagtgta tagaagctcc ttttactcca catttgttta  47700
acacttggtg ttttccttct ttttgattag tcatttagca gtgaaaccta ttttttacat  47760
tttgatatct ccaataacta actaaatgga gcacttttaa tatgcttttt ggacagttga  47820
atatcttttc ttgtgaaatg tctattcaag ttagtttgcc cattttctat tgtggtgttc  47880
tgtctttttc ttattgattt taggaattcc ttacatatcc tggatatgaa tcccactatg  47940
tggcttacct ttttccttct ttctttttga aacagagtct ccttctgtca cccaggctgg  48000
aatgcagtgg cgctatctca gctcactaca acctctgcct cccaggttca agcaattctc  48060
atacttcagc ctcctgagta gcttagatta caggtgcatg ccaccatgcc caccgaattt  48120
ttgtatagac aaaataattt ttggtagaga cagggttttg ccatgttggc caggctgatc  48180
ttgaatccta gcctcaactt tggcccacct tggcctccca aagtgccagg attacaggtg  48240
tgagccacca tgcccagccc accttttact ttcttaatgg tgtcttttga acaaggaggt  48300
tcttaatttt aatatagccc aatttatcat tgttcccttt atgcttagtt cttttatgtc  48360
ctgtttaaga atttttgcag ccagctcggt ggctcacacc tgtaatccca gcactttggg  48420
aggctgaggc tggcagatca caaggtcaag agatcgagat catcctggcc aacatggtga  48480
```

-continued

```
aaccctgtcc ttactaaaaa tacaaaaaat tagctgggcg ttgtggctct tgcctgtagt  48540
ctcagctact cgggaggctg agatcacgcc actgcactcc agcctggtga cacagcaaga  48600
ctccatctaa aaaaaaaaga aatttgcaag gtcatgcata tgtccccctg aatttttttc  48660
taaaaatcac ttaattttag atcaatgaat tgagtaattg actccatttt tcagtcattc  48720
aacaaacatt tccctgaggt tttgataacc tgaactgtgt ttggagctgg ggaggaagca  48780
aactattgaa tatatacaaa gatggcaaag atgagggcct ggagcttgcc acacggaagg  48840
ggggatggct gcctgaatgg ttgggcaggt agttgttgac atctgcactc cctacaagag  48900
cagcagggtg gcaactcttt ttatcttttt aatttatttt tcttttctct tttttttttg  48960
agatggagtc ttgctctgtt gcccaggctg gagtgcagtg gcgtgatctc agctcactgc  49020
aaactccacc tcctgggttc acaccgttct cctgcctcag cctcctgagt agctgggact  49080
gcaggcacct gccaccactc ccggctaatg ttttgtattt ttagtagaga aggggtttca  49140
ctgtgttagc caggatggtc tccatctcct gacctcatga tccacccgcc tcggcctccc  49200
aaagtgcggg gattacaggt gtgagccacc acacccggcc ttaatttatt tttctagtct  49260
gcaggtaatt ctttttaatt ctctccactc tcctatgatc ttatgaggta gggactgtga  49320
ttatttctcc cactttataa tgaacaatca gtaaagacag ggaagataac caaatgacat  49380
acaaggtggg gtccacccca tgaggctgca ggcttggagc tttcctttgt cttaaaaatg  49440
agaacatgag ctgcccacct gttgagacaa gaaataggaa aggcttaaaa aactggcttg  49500
ttgtgtacaa ctatccgtgg ggctgcagtg aacgggctgg cagtgcccag gtgcatgctg  49560
aaccctggga caatcacatt cagcatccag gggcccccgt aatagcttaa tgtttgaatt  49620
gaacccctgg ggttgccttg aaggagagag atcctggaag tatgttcaag gggtagggat  49680
gggcagggga gatgggtctg aaagccaagc tctaccccac ccaccttgcc ccaagagaaa  49740
tagaaccttc atctttaatt gcctaacgag aaaactgggg ctggccagat gtggtggctc  49800
atgtctgtaa tcccagcaat ttgggaggcc aaggcgggca gatcacttga ggtcaggagt  49860
tcgagttcag cctggtcaac atggtgaaac cccgtctcta ttaataatac aaaaattatc  49920
caggtatggt ggcgcatgcc tgtagtccca gctacttgag gcacaagaat cgcttgaacc  49980
tgggggacag aggttgcagt gagccgacca ctgcactcca gtctggacga cagagtgaga  50040
ctccatctca caaacaaaaa cagaaaaaaa aaaaaaaaaa agagagagag agaaaactgg  50100
aggctctgag aggttaaagg acttgcccag ggtcttgcag ctagtaagtg acagagctgg  50160
gacttgagct tgggttttct gactcctggt ctggttcatt atccatgagg tgctgggaac  50220
taaaataagc cacaatcttg gaatctccgt cgcctccctc cctcccacat gtctgcgtgg  50280
ctttttggga aaatgccagg ggaatgtacc agccagggag aggacccttg ttttcctcat  50340
ggcccttcct ggcaatggca ctactgacac cgacagtcct ttttgtccct gatgacctct  50400
gctgcctgat gcccaagtga ccacctctgc tttgtcattt ctaggattgg cttccaggtc  50460
ctcctcagca ttggggaact cagcttggcc atcgtgatag ctctcacgtc tggtctcctg  50520
acaggtcagt gtgaggccac ctttcttcca ccattgccag gacacagcac ccacgtccag  50580
agcgcaccct gccgtgtggc tggatgtcta tgtgccccat ctccttccct gaggatcaca  50640
taatttcaga attggaaagg ttcttagagg tcacctgctg ctaatgtgga ctgtgaggcc  50700
agggcaggga agggacatcc ctgaggttat aagtagggtg agtggcaacg ttgcagactt  50760
ttgaacccag ggctggtgat cacactcagt tttgcacaga agcccgagaa aatccttaca  50820
```

-continued

```
cccaaaagcc tacctttat ttctgaggac acccataata ctattttatt caacagatat  50880
ttattcaata tccactatga gccaggcact ggggacacag cagtgagcaa aacaaattcc  50940
ctgaccccat ggaattgacc ttctagtggg ggaaggtatt agcaataaat agacaaataa  51000
gtgtctacta cgccagatgg gaagaagtgg ctgtgaagac agagcaaact agagaaacat  51060
agagtcaatg tgggatgggg tgttctttta ggggggtggt cagggaaagc ttatctgagt  51120
agttagcttt taagcagaga ccccaatgaa gaggagggag atatgcgatg catttagtta  51180
ggggaagaac attccatgaa aataggatag caagtgcaaa ggccctgaga cagcagcatg  51240
ctttgtgtgt tgagggaaca gtaaggagac cagtgtggtt ggtgtgaatg gagtgagaag  51300
gagcagcagg ggttgagggc agaatggtag tgaggagcag gcccttataa aagatgggaa  51360
gccactggag atctttcaac aaaggggaaa agtatgtttc tgttcttgca atacaataga  51420
aaagcaaaaa atctagggga gttgctaatt agccagtttt acttatatgc caggtgaaaa  51480
tatgtggcta ggtgcagtgg ctcatacctg taattgcagc agtttgggag accgaagtgg  51540
gcagatcatc tgaggtcagg attcaagacc agcctggcca acatggtgaa accctgtctc  51600
tactaaaaat taaaaaatta gccaggcgtg gtggtgggca cctgtaatcc cagctacttg  51660
ggaggctgag gcaggagaat tgcttaaacc cgggaggcag aggttgcagt gggccgagac  51720
tctgtctaaa aaaaaaagaa aatacacatt caggccaggc acagtggctc acgcctgtaa  51780
tcccagcact ttgggaggct gaggcaggta gatcacctga ggtcaggagt tcgagaccag  51840
cctgaccaac atgggaaaac cctgtctctg ccagaaatac aaaaattagc caggcgtggt  51900
ggtgtgtgcc tgtagtccca gctactcggg aggctgaagt aggggaatgg cttgacccca  51960
ggaggtggag gttatagtga gccaaggttg caccagccta ggtgacagag tgagactgtc  52020
tcaaaaaaaa aaaaaagaaa gaaaatatac attccatcca gaacttgtta ttctacaagc  52080
aaacatcttt tattggttag acacccatat atgtgtccct aagcaggagg tggatgccaa  52140
ataagagaca aatggcgtaa gacactatga gttgtgtggt gacattgggc atgtcacttc  52200
actccctctg agccttggtt agcttctctg taaaatgaaa ggattatggt aactaagctg  52260
gcttccttcc agctttaaca aactgtatgg aggtacattt tggagttact tgggtaattt  52320
ttgagtgtga gattggctag aattgcttta atataccaat gtctggcctt agcttttggc  52380
agagtctgtg tgaagaagca gaggcggagt agagttaatt ccgtaagtta acgttcagtt  52440
cgtggcagct ggcaatccaa ccctgggaaa ggctgccgga tttagcaaaa atgcaaggtg  52500
tctgttttta aattcgcaat gaattgggta tcctgcattt tatttggcaa ccctgtcctg  52560
ggactcacac tattcactgt tatcactggt atattcgaag tggtgctgac ttgccctctg  52620
tcttgcaaag tacccggggg tcttttctta tgcttcactg gagtcaaaaa agagaataga  52680
ggaaaagaca atcatattgt tcctttaaga gttaagacca acaagctttc ttctttacat  52740
gttgtttttg acatgagcaa actggtgatt aaaaacaact tgggtggctc atacttgtaa  52800
tcccagcact ttggaaagct gaggtgggag aatagcttga ggccaggagt tcaagccagg  52860
gcaatcctat agtgagaccc catctctaca aaagatacaa aaattagcca ggtgtggtgg  52920
tacacctgta gtcccagctg ctccggaggc tgagatggga ggatcagttg agcttgggag  52980
gcagaagttg cagtgagctg agatcgtgcc actgcactcc agcctggaca acagagcaag  53040
accctgtctc aaaaaaggaa acaaaacaac ttggacaatg gaagggggag aaagttcctc  53100
aagaagccaa aattgcacca aatggactcc cagaagccaa gcatttaact tgttaattga  53160
gccctctgtg ggcctgtcta tacttattta aggaacaatc ctatcaagca tagttattgg  53220
```

gtttctcagc ccaggtagat tagaaatagc agattagagg tgggctaggt ttctagaggt 53280
aaagtacacc agcagaagtt agaagtgaaa gcaaagagcc taacagagga agagaaattc 53340 ttttttttt tttagacgg agttttgctc ttgttgccca ggctggagtg caatggcgct 53400
atctcggctc aacgcaacct ccgcctcctg ggttcaagtg attctcctgc ctcagcctcc 53460
tgagtagctg ggattacagg catgcaccac cacgcccggc taattttgta tttttagtag 53520
agacagggtt tctccatgtt ggtcatgctg gtctcgaact cctgacctca ggtgatccgc 53580
ccaccttggc ctcccaaagt gctgggatta caggcataag ccactgtgcc cggccaacaa 53640
attcttaaaa ctggacacaa gaacacaaaa cgcttgggct gctgagagat tagaccaaca 53700
accctccacg gctacaaacc ttttccacgt tatatggcac gttataagtg ggtgttccta 53760
gtgatggttc tgattttttt tttaaaaagt ctaaatatgt ttaatgttgt ctcagaagac 53820
aaaatatatt ttagacagat attcctcagt gatgagtaag cctcagctat ctggaaaatt 53880
catgcaggcg ccagagatca ttactgagta attcaagcta ataactgcgt catgctggtt 53940
gtaccctgca tgccaatatc tgctaaaagc agcaccacga aagggaaata cgaatctcac 54000
taagcactca cccattcttg ttaacgacac tggaactgat catccttaat aatacacaga 54060
taaatctatc aggagcattt ccttgcttcc tgtgaaagga agtactcatt ccatgtgtcc 54120
tgtgaaattc agccagcttc gggaagctgg aggaatacat atggccaagc tacctgggca 54180
gagagtagac agggaatgga ggttgggcac agtggctcac acctgtaatt gcagcccttt 54240
agaaggcaaa ggcgggcaga tcacttgagc tcaggtgttc aagaccagcc tgggcaacat 54300
ggctaaaccc cgtctctgca aaaaatacaa aaaaatgagc tggtatggt agcacacact 54360 tgtggtccca gctacttggg aggctgaggt ggggggttg cttgtgcctg ggagtttgag 54420
gctgcaatga gctgtgattg tgccactgca ctccagcctg gataacagaa tgagaccctg 54480
ttccaaaaat aaaaaataaa atcaaagaca cttaaaaaga tggggaaaag gaaggacagg 54540
cacttaagca agttataagc tactttccta actacacaag tggaatctta agctgaggtt 54600
cccaggagtt gactggagcc agagaagaca gacctatagg agcacccaac tggagtcgcc 54660
ctccatagta gcccatatgt cttacatgga tcagctttcg tggggccctt ctactccgtc 54720
tggggaaggg cgtcagatct gtggctctca tgtactgctc agtacactgc cattcccagt 54780
tctttttttc aaaaaaaaaa aaattgttta cagaatcggc cgggtgtggt ggcttatgcc 54840
tataatacta gcaatttgga aggctgaggt gggtggatca cctgaggtca ggagttcgag 54900
accagcctgg ccaacatggt gaaaccccat cctactaaaa aaaaaaaaaa aaaaaaatta 54960
gctggatgtg gtggcaggcg cctataatct tagctacttg ggaggctgag gcaggagaat 55020
cgcttgaacc tgggaggcag aggctgcagt gagccgagat catgccacgg tactccagcc 55080
tgggtgatag agtgagactc tgtctcaaaa taaataaaat aaaataaaat aaaataaaat 55140
aaaataaaat agtctacaga attaagctgg tccaggaatg acagggcgtc catttatttg 55200
tctttcaatt gtgggagaaa aaggatttct gttgagacac tgtcgttttg acacacacaa 55260
tattttgatt aatcttgaga ttaaaaatcc tgtgctccaa atcttttaac attaaattat 55320
gcatttaaac aggtttgctc ctaaatctca aaatatggaa agcacctcat gtggctaaat 55380
attttgatga ccaagttttc tggaaggtaa gatttttcac ctattaacgt gatagatttt 55440
gagtgcatga acttaaaaac atacctgggt atatatgttg acttgctgtt tatgagtaaa 55500
acaaaaacaa aaatggagta aggagcattg caggaggaac tagaggagaa acaaatccat 55560

-continued gatatgcatg tgtgtggggg agggtggcgg ggaggtggta aaggtcacca tttccctgat 55620
acctcaaatt cattcagagt cagggatgag acagctttca ctggccacac ttcccctccc 55680
gctatctgca gtcctcagcg tagccaaata gtttgacatg cgggtgacag aaccccgcaa 55740
tgcaaaagct ggaagaaacc tcaagccttg gagtccaacc cctttttga cagatgctaa 55800 gagtggagac atgacttatc aagatcttac aactggctgg gcacggtggc tgacgcctgt 55860
aatcccagca ctttgggagg ctgaggtggg gcgatcacct gaggccagga gttcgagacc 55920
agcctggcca acgtgtcaaa accccatctc tactaaaaat acaaaagtta gctgggcgtg 55980
gtagcacatg cctgtaatcc cagttactca ggaggctgag gcaagagaat cgcttgaaat 56040
caggaggcag aggttgcagt gagctgagat tgcgccactg cactccagcc tgggtgacaa 56100
gagctgacac tctgtctcaa aaaaaaaaaa aaaaaaaaaa aattcttaca gtgtgtgagt 56160
atccaggctg agtcctgaac acagctcttg ataaatgata acaagcaggc acaaaaaaat 56220
tgtagtacag gagtctgagg tcacttagca aagggacata aagttcaaac agctcagcag 56280
ctgctgaggg tcccgtgtta cattgtagca tttgttgttg tgactgggct agaaagaagg 56340
tgaagaaggt tggagctcac tccctgcctc ccctcccact ctcctccctt tgacctacac 56400
tcatagttca cgcagcactc tgatgtgtcc ccttaggcca tcctctagtc aatgctgtgg 56460
gtaggctgga ccagcaggga ccagtattgt cacagcaagt ccaggccaac agtggtcagg 56520
ctgctgcccg gtgttgtgcc tttgtgagtg gcagatccaa gaccggaacc caggccttct 56580
gagtcccagg ccaatgcttg ccccacccag catccaagat gttgctcact aaagagacag 56640
agaagcagcc ttattatggg cctggacacc tgtgcatgag gggtcaagca gagaggacct 56700
ggggagagac cctgcccctt cttttccttc tccttcctct cctttctctt cttcttcctc 56760
ttcaaatagc tttttgaggt gtaactggca tacaatcaat tgtacatatt taggctgggt 56820
atggtggctc acgcctgtaa tcccagcact ttgggaggcc aaggcgggtg gatcacttga 56880
ggtcaggagt ttgagaccag cctgggcaac ccggtgaaac cccgtctcca ctaaaactac 56940
aaaaattagc caggcgtggt ggcagctgcc tgtaatcccg gctactcggg aggctgaggc 57000
aggagaatca cttgaacctg ggaagcgaag tttgcagtga tctgagatca tgccactgca 57060
ctccagcctg ggtgacagag cgagactttg cctcaaaaac aaaacaaaac aattgtacat 57120
atttaaagtg ttgtaaccaa gtgagttaca gagaaacacc acactttgag cctaattcag 57180
gagtccttta ttagccggcg acctagagac gactagtgct caaaattctc tcggccccaa 57240
agaaggggct agattttctt ttataccttg gtttagaaag gggaggggga attgagctga 57300
agcaatctta cagaagtaaa acaggcaaaa aagttaaaaa gacaaatggt tacaggaaaa 57360
caaacagttc caggtgcagg agctttaaag ccatcacaag gtgacaggtg cgggggctct 57420
gggtgctatc tgccggacac aaacgcaggg gcactagagt actatcaccc gggcaaattc 57480
ctgggaactg cggacacagc ttgccacagt accttatcag ctaattgcac tctttgatgt 57540
gctgggagtc agcttgcaca agttaagtcc ttgaggaagg gggtgggtaa ggagccctta 57600
acgtcttgca aatgaaggag ccgaatggaa tccctccggc tttcttagct aagagagagt 57660
caatcaagtt aatacaagtt agggtatcac aaaagtatat aatttgatac attttaacgt 57720
atttatacac tgaagagacc atcaccacca tcaagacaag gagcacaccc atcacttcca 57780
cacacttcct cctgctcctt tgaaattcct cccttcctac ccacctggtc ccacccaaag 57840
gcaaccactg aactactttc tgtcactaag gtttgcgttt tctgtaattt ttttgtttga 57900
gacagggtct cactccgcca cccacaccgt aatgcagtgg caccatcatg actcactgta 57960
gcctcaacct ccccaggctc aggagatcct cccccctcag cctcctgagt agctaggacc 58020
acaggtgtag gccaccatgg caggctaatt tttgtatttt tttgtagaga tggggtttca 58080
ccgtattacc taggctggtc tcgaactcat gggttcaagc aatcctcctg ccttggcctc 58140
tcaaagtgct gggattatag gcatgagcca ctgtgcccag ccctctgtaa tgttacacaa 58200
agggaatcat gcagcacgta ctgcccttgg tctggcctct tttgctcagc atgattattc 58260
tgagaatcat ccgtgttgtt gcgtgtaact gacttcatca gcttctctct gcagctgtca 58320
gctcttggct tctcccaaca gccaatctct ctttatcccc tgcaagtgtt cttgcctatt 58380
tagcagaatc aaggtactct atcgaaaaga ctcggaaaat tggtttaatc tattcattca 58440
ttcctcaggt atttatcgaa taactattct ataccaagta ctatgctaat caaccaagga 58500
cagcacaaac aggagaaatc tccagctcag tcacttgagt tgcaataaat atttgctgga 58560
taggtcaggt gcagtggctc acacttgtaa tcccagcact ttggggatta ctgagacggg 58620
aggatctctt gagcccagga ggccaaggct gcagagaacc atgatcatgc cactgcactc 58680
cagcctgggt gacagagtga gatcctgtct ctgaaaaaaa atatttgctg gataaattaa 58740
ggaaatctga cgaaccccat cagtagccat tgcagcaaca ggtaaactag aacgagtgtg 58800
aatttggaat gaggaaaccc gatgttggcc atcattctgt aatgtcatgt attatgtaat 58860
gtattatata ttaatgtatg tattatgtag gcaagttcct tgacctctct cactggtaac 58920
ataagagtag taatctttgt gctacttcac tgggttattt caaagatcaa gtgaggtaat 58980
aatgtctgta acaacattct gtaaaatgca aaccgccaca tgaatgtgaa agtttattac 59040
tagggattta gccaaccaca agggaatgtg tgagcataag agctatcata ttgcaagcct 59100
acagtttctg attttgtgct aggtgctttt ccacattacc tgattttatc ctcacaacag 59160
tcctgcataa aagtaagtat gtcgcccagg tgcggtggct catgcctata atcccagcac 59220
tttgggagcc cgaggtgggc aaatcacttg agatcaggag tttgaaacca gcctggtcaa 59280
cgtggtgcaa ccctgtctct actaaaaata caaaaaaaaa ttagacaggc gtggtggtgg 59340
atgcctgtaa tcccagctac ttgggaagct gaggcaggag aatggcttga gcccgggaga 59400
tggagattgc agtgagatga gattgcgcca ctgcactcca gcctgggtga cagagcaagg 59460
ctatgtctca aaagagaaaa aaaaagtaag tatctcagtc ttgaagatga tgaaatggag 59520
gcctagagag attaagtaac ttgcccaaaa tgacagaact aatgcataga aaagaagaaa 59580
tgtgatgtct tttggctcca aagacacccc acatatgcgt tggttacagt tactagagaa 59640
aagttattcc acccccaccc cacccccaga aatcttctga cttgttttct cgcagttgag 59700
taggaccatt tattcggcag tgtaccattc tcagcttgca gttgaaagcc aaatatccat 59760
taaagaggca aggatgcaaa cttgctaagc tgataaatcc aggggtgatt tttttttttt 59820
ttgcaaacca tccaacaaga cattttaaat actcattgaa tttcatagaa ctgactgcca 59880
ggattggaaa gacattaaag ccagctcagc cactgcctcg ctggttggcc agaccacgcc 59940
tggcacttct gggagggagc actcaccacc ccccaagggc acccatctca tcctccgaag 60000
gtttatgaaa atgcactcat catttgctaa ttcattccac tacgtgtatt acctaatttg 60060
tgacacgatg tgaagtacca gagagataat tctaaataaa atatagttat gggtctcaag 60120
gagccagata tgctaatctc ctatcctcct gcagtttaca gtggtcctca ccagatactt 60180
atttacaaaa attcagttta ttatttattt ttttgagaca gagtcttgct ctatagctca 60240
ggctagagtg taatggtgtg atctcggctc acttcaacct ctgcctccca ggttcaagtg 60300

-continued

```
attctcctgc ctcaacctcc caagtagctg ggactacagg cacctgccac cacggctaat  60360
ttttggagtt ttagtagaga cagggtttca ccacgttggc caggctggcc tcgaactcct  60420
gacctcaggt gatctgccca catcagcctc ccaaaatgtt gggattacag gcgtgagcca  60480
ccatgcccgg ccaaaacttc agtttataac acaatctttc acgtgtcttc tgctttcatt  60540
aaaagaatag acagttccct tctttatttc agtttaataa accatggatt ttatttcatg  60600
ctttgcaaaa cacaagggct cactgacatg cacttcttaa actaattctg gctggtcgcc  60660
tgtaattcca gcactttggg aggctgaggc cgacagatca cttcaagtca ggagttcaag  60720
accagcctgg ccaatatggt gaaaccacgt ctctaccaaa aatataaaaa attagccagg  60780
tgtggtggtg cgtgactata atcccagcta ctcaggggcc tgaggcagaa aaatcacttg  60840
aacccgggag gcggaggtta cagtgagctg agatcgcgcc actgcactcc agcctgggcg  60900
acagagtgag actctgtctc aaaaaataaa taaatacaaa taatgtaaaa tacgaaacaa  60960
gcaatcctgg cagtagctgc tggaatgaga ggagggagag gtcataggga ggtcggggac  61020
aatggagcat ggagttgtgt tggatttggc taagcagcag gaagtgcaag gcattccaag  61080
caagaggagg ggggcaggtg gggagcatct gcaagaacag aagcagcatg agcaacctgg  61140
ctcggcagtg tgtgaaaagg ctgaaaggtg gctagagcca cttcaatttc atccttcagg  61200
caaatgggaa attcccaaag gtttgagtgg ggaagcaatg cctacaatga aagtttgaga  61260
gtgaagcaga gtgatcgaat taagcatgta ggccgagttc tgaaataact gcaatgtgct  61320
gaagatcatc cattggcttc tgaatgagta tttgcagttt attttttaaa atgattttat  61380
tgccaagaaa gataaacact actgttttgg tacaaaaaca taacaaaatg tgttgagtcc  61440
ctcttgctgt tttacgcgaa gttttaaaaa tctactcttg tcacagtggt atcaccccta  61500
cttctgattt caaataaatg ttctagagac acagtaaggg cccaacaaac gcttgttcaa  61560
caacacaagg agagccagct tttaaagtag gaaaacaggc cgggcgccgt ggctcacacc  61620
tgtaatccca acactttggg aggctgaggt gggcagatca cttgaggtca ggagttcaag  61680
aacagcttgg ccaacatggt gaaaccctgt ctctactaaa aacacaaaca ttagccaggc  61740
gtggtggtgc acaccagtag tcccagctat tcaggaggct gaggcaggaa aatggcttga  61800
actggggagg cagtggttgc agtgagccga gatcgtgcca ctgcactcca gcctggggga  61860
cagagggaga ctccatctca aaataaaaca aaacaaaacc aaatcataca aaaacattag  61920
ctgggtgtgg tggtgcatac ctgtaatccc agctacttgg gaagctgagg cagaattact  61980
tgaacccctg gggggaggtt gcagtgagct gagatcttgc cactacactc cagcctgggc  62040
aacagagtga ggagactctg tctcaaaaaa tatatatatt aaaaaaaaga aaaaaaaaag  62100
taaactagga aaacacatca gcagcctgcc aacagactcc cctagcctcg gtgagggcca  62160
gtgttctggg aggcagatct gaattctagt cctagttcac ccactggcag gctggtgccc  62220
ttgggcaggt cgcttctctg gggctcagtt tcttcctcta taaaatgaga tcaaatccca  62280
tgttctaaga gtttgtgctc tggagtcaga cagatctggg ttctaccact gccagctctg  62340
tgatcttgta gcttcagtct cgtcatctga catggagata acagtaactg tctcactgtg  62400
ttgttagggt ttaaaggaga taatgtatgt gaaatgttag caaacaagtg ttagctaccc  62460
tgatttccgg tttcagagtt ctgtggtccc agtttatgcc acatgcagtg acgttgtatg  62520
gtaggctgtg gtgtggcacc acttcagaac tcagcgcatg cacagcttgc agaagagaag  62580
gccagaggag acctaagaag gctcttcgaa cacttgaaag accggcatgt aggccgggcg  62640
cagtgactca cgcctgtaat cccagcagtt ttggaggtcg aggcgggtgg atcacctgag  62700
```

tttgggagtt tgataccagc ctgaccaaca aggtgaaacc ccgtctctac taaaaaatac 62760
aaacattagc tgggcatggt ggcgggtgcc tgtaatccca gctactccgg tggttgaggc 62820
agaattgctt gaacccggga ggcagaggtt gcagtgagct gagattgcat cactgcactc 62880
cagcctgaga caagagcgaa actccatctc aaacaaaaca aacaaccaac caaacaaaac 62940
caaaaaaaaa actggcatgt agaagaaaaa tactttttct ctacacttct ccaaagaatt 63000
taactaggcc caggggaggt gcagtataaa tttctaacaa tctcaactgt ctgccaaatg 63060
gaatgagcta cttcatatgg cagtagtgag tcctctgtct ttggaggcat tcaaataaaa 63120
gccagatggc catttatcaa caatccatgt aaaacgttag atgaaataaa acctatatat 63180
ccaagatctc ttccaattca gattttatga aagaatttct aaggtctttg taatgagaca 63240
tttaggctgt ttcaagagat caagccaaaa tcagtatgtg ggttcatctg caataaaaat 63300
gtttgttttg cttttacagt ttcctcattt ggctgttgga ttttaagcaa aagcatccaa 63360
gaaaaacaag gcctgttcaa aaacaagaca acttcctctc actgttgcct gcatttgtac 63420
gtgagaaacg ctcatgacag caaagtctcc ttatgtataa tgaaacaagg tcagagacag 63480
atttgatatt aaaaaattaa agactaaaaa cttagtttaa gagtcaattt aataagttta 63540
aaataaatgt ttagtttcat taggatgatg ctatcaatat tttcttggtt acagacacat 63600
tattaaagtt ttgggttaat tttattgaca attcttaaga ttctttctca tgcttaataa 63660
agcatgctac tcagttaact cttgtctaca tcagcaaagc agataataca aaacaggaaa 63720
attacaaatc actgatactt agtccttgtg ggaatcatgc ttttctccca gcagttttac 63780
aaggtggctg gcattccctg agcatattct gaattgcact gtggggaaag aggttgtgct 63840
cagttgtagg gtggggggat gcactgcctg aggattaaaa aactagttct gtgaccgtga 63900
ggaagtcgtt taaatttcca tggtctgttc cctcctatgt gaaaagagaa ggtgggcttc 63960
aacctctaag atcttctcca gttttcacat tttatggact tttgtagaaa aaacatcagg 64020
agttcatgtg ggatgacagc aagtcatttc tttgaggaga gtcttgatca ccaggcaata 64080
ttcacagtgt agagactgtc agatgaccat ggctagcatg gaaatgagac ccacacattt 64140
aaatcaccca gcaaatattc cgaaggctaa ttgtagcaca ttttatgaaa gacatttcaa 64200
actgtggtcc tgaagagtgt atcccatctt gcagaggtgg ggagcctggg gggacaagag 64260
ttctgaagag gaagagacaa caagagttcc cagtagctaa tgtttgtcat tctagttgac 64320
cgtgctggtc tattaggcta gtggttcagt acacagatga aatgcaacat ggaacccagt 64380
ttattatcag aacaactaca aagaaattgt cccctgtcta agactggagt gtcaagtctc 64440
tgcccttttt tcctttcctt caatggtgga tgtggagtga ctgtgcatcc caccagaacc 64500
acgtgtcatg gctgagtcac atcttcctgc ccttggaatg agaggcacag cggaagacct 64560
tcccatggaa gggacacagg gagcctggtg gctggaccat ggtgcttctc tcttccaaca 64620
cgtccactca ccccttggga gaccctcaaa agccagttac attacatgtt cacagaattt 64680
ttggtaaaag taaataccaa ttatagtgag gaagaatttt gaccacggaa tattttaaaa 64740
actaaaaaat gtttatattt catttaacat ttgacacaga agagaccaca tttgaataaa 64800
cacattaaat cttcagagca ctttcattgt ggttttggac ctcagatatg acaaatactt 64860
acattgacaa atccataatt tcttttgtaa tttcttttta tttttacaaa ttataccatg 64920
ataaaatttg acaaaaatta ttcatgtgaa agtttcctct aacattttat aagttaatca 64980
agtgcatacc acaatagatt tttggttgtt gtttaggtgt tctcgtgatt ttagtattac 65040

```
acaactttaa gctgagacta cactcagaaa taagtttaga aaatggcatt acaaaaggtt  65100

gggagtgagc agtaaaaaaa caaacaaacc catgcagggc tgttgtgctg tgggaaatca  65160

gatgtgttca ctgccataag tcttcagtgc ggccaaactt aaaaaccagc cctctgtgaa  65220

taaaacaaga aatatcacat gactccctga atttgagaaa agagtatgtg agatttcgag  65280

aatggtgtga aacaaacaac gaagaataat tgatgagttg tagaagaaat tttggtacga  65340

aatgtatcaa aacagaaact gatcattcta aggtagtgaa ttcttccatt atgttcaact  65400

gtgctattaa ccaccatatt cccaacaacc ttaactttca agtactgaat acacatgtga  65460

cttttaaaaa gttaccagtg tttactatgt aaccattata tgtctgattt tttttttttt  65520

ttttgagaca gagtcttgct ctgtcgccca ggctggagtg cagtggcgtg atctcggctc  65580

actgcaagct ctgcctcccg ggttcatgcc attctcctgc ctct                   65624


<210> SEQ ID NO 5
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 5

cgtcctggct ctccctctct                                                 20


<210> SEQ ID NO 6
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 6

tatttttcaa aaccccggaa g                                               21


<210> SEQ ID NO 7
<211> LENGTH: 23
<212> TYPE: DNA
<213> ORGANISM: Artificial sequence
<220> FEATURE:
<223> OTHER INFORMATION: Synthetic sequence: RHD/RHCE hybrid exon 3-
      specific probe

<400> SEQUENCE: 7

ggtcaacttg gtgcagttgg tgg                                             23


<210> SEQ ID NO 8
<211> LENGTH: 23
<212> TYPE: DNA
<213> ORGANISM: Artificial sequence
<220> FEATURE:
<223> OTHER INFORMATION: Synthetic sequence: reference RHD/RHCE specific
      probe

<400> SEQUENCE: 8

ggtcaacttg gcgcagttgg tgg                                             23


<210> SEQ ID NO 9
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 9
```

caagctgtca aggagacatc actat 25

<210> SEQ ID NO 10
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 10
cattacatag agatgtcccc atact 25

<210> SEQ ID NO 11
<211> LENGTH: 27
<212> TYPE: DNA
<213> ORGANISM: Artificial sequence
<220> FEATURE:
<223> OTHER INFORMATION: Synthetic sequence: Probe

<400> SEQUENCE: 11
cctggtactc aaactcccta aatctca 27

<210> SEQ ID NO 12
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 12
gccacttatt acttaaaaaa acccc 25

<210> SEQ ID NO 13
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 13
aaggcccttc ctccaaatag 20

<210> SEQ ID NO 14
<211> LENGTH: 27
<212> TYPE: DNA
<213> ORGANISM: Artificial sequence
<220> FEATURE:
<223> OTHER INFORMATION: Synthetic sequence: Probe

<400> SEQUENCE: 14
aatttcatgt gctggaaact taatcct 27

<210> SEQ ID NO 15
<211> LENGTH: 25
<212> TYPE: DNA
<213> ORGANISM: Artificial sequence
<220> FEATURE:
<223> OTHER INFORMATION: Synthetic sequence: Probe

<400> SEQUENCE: 15
atttcatgtg ctggaaactt aatcc 25

<210> SEQ ID NO 16
<211> LENGTH: 18
<212> TYPE: DNA

<213> ORGANISM: Artificial sequence
<220> FEATURE:
<223> OTHER INFORMATION: Synthetic sequence: Primer

<400> SEQUENCE: 16
caagagccac ccagtcca 18

<210> SEQ ID NO 17
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 17
ccaagagcca ctcattccg 19

<210> SEQ ID NO 18
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 18
acatggagaa gtcatcacac a 21

<210> SEQ ID NO 19
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 19
catggagaag tcatcacacg 20

<210> SEQ ID NO 20
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 20
tgttgagctg agggtctggt 20

<210> SEQ ID NO 21
<211> LENGTH: 18
<212> TYPE: DNA
<213> ORGANISM: Artificial sequence
<220> FEATURE:
<223> OTHER INFORMATION: Synthetic sequence: Primer

<400> SEQUENCE: 21
ttgagctgag ggtctggc 18

<210> SEQ ID NO 22
<211> LENGTH: 18
<212> TYPE: DNA
<213> ORGANISM: Artificial sequence
<220> FEATURE:
<223> OTHER INFORMATION: Synthetic sequence: Primer

<400> SEQUENCE: 22
ttgagctgag ggtctcgc 18

<210> SEQ ID NO 23
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 23
gaatcttctg atatccccat 20

<210> SEQ ID NO 24
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 24
gaatcttctg atatccccac 20

<210> SEQ ID NO 25
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 25
ggttctgggt gttggttata 20

<210> SEQ ID NO 26
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 26
ggttctgggt gttggttatg 20

<210> SEQ ID NO 27
<211> LENGTH: 18
<212> TYPE: DNA
<213> ORGANISM: Artificial sequence
<220> FEATURE:
<223> OTHER INFORMATION: Synthetic sequence: Primer

<400> SEQUENCE: 27
caaaggccct tcctccac 18

<210> SEQ ID NO 28
<211> LENGTH: 18
<212> TYPE: DNA
<213> ORGANISM: Artificial sequence
<220> FEATURE:
<223> OTHER INFORMATION: Synthetic sequence: Primer

<400> SEQUENCE: 28
caaaggccct tcctccaa 18

<210> SEQ ID NO 29
<211> LENGTH: 21
<212> TYPE: DNA
<213> ORGANISM: Artificial sequence
<220> FEATURE:

<223> OTHER INFORMATION: Synthetic sequence: Primer

<400> SEQUENCE: 29
aaaggccctt cctccaaaaa c 21

<210> SEQ ID NO 30
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 30
agattacagg tgtgcgccac cac 23

<210> SEQ ID NO 31
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 31
aaaggccctt cctccacaaa c 21

<210> SEQ ID NO 32
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 32
ttctggtaaa ggattaactt aacaaa 26

<210> SEQ ID NO 33
<211> LENGTH: 27
<212> TYPE: DNA
<213> ORGANISM: Artificial sequence
<220> FEATURE:
<223> OTHER INFORMATION: Synthetic sequence: Primer

<400> SEQUENCE: 33
atagaaaact gagatttagg gagtttg 27

<210> SEQ ID NO 34
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 34
ggattacagg tgtgcgccag agt 23

<210> SEQ ID NO 35
<211> LENGTH: 27
<212> TYPE: DNA
<213> ORGANISM: Artificial sequence
<220> FEATURE:
<223> OTHER INFORMATION: Synthetic sequence: Primer

<400> SEQUENCE: 35
tgctggtaga ggattaactt aacaact 27

-continued

<210> SEQ ID NO 36
<211> LENGTH: 28
<212> TYPE: DNA
<213> ORGANISM: Artificial sequence
<220> FEATURE:
<223> OTHER INFORMATION: Synthetic sequence: Primer

<400> SEQUENCE: 36
tgctggtaga ggattaactt aacaactg 28

<210> SEQ ID NO 37
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 37
caactggctt tccaagaaaa taa 23

<210> SEQ ID NO 38
<211> LENGTH: 27
<212> TYPE: DNA
<213> ORGANISM: Artificial sequence
<220> FEATURE:
<223> OTHER INFORMATION: Synthetic sequence: Primer

<400> SEQUENCE: 38
gccacttatt acttaaaaaa accccaa 27

<210> SEQ ID NO 39
<211> LENGTH: 29
<212> TYPE: DNA
<213> ORGANISM: Artificial sequence
<220> FEATURE:
<223> OTHER INFORMATION: Synthetic sequence: Primer

<400> SEQUENCE: 39
ttaatccttc aattcatatg ttgatgcta 29

<210> SEQ ID NO 40
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 40
gattataagc ctgagacacc gtgcctggca 30

<210> SEQ ID NO 41
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 41
gtgaagcaag gtgcctctgt a 21

<210> SEQ ID NO 42
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 42
atctcttccc aagtccatgt gc 22

<210> SEQ ID NO 43
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 43
gaagcaaggc gcctctgtg 19

<210> SEQ ID NO 44
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 44
tctcatctct tcccaagtcc atgtat 26

<210> SEQ ID NO 45
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 45
tttccctagt atatgtaacc atca 24

<210> SEQ ID NO 46
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 46
ggaaaaggtt tgagaggaat tatac 25

<210> SEQ ID NO 47
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 47
tttccctagt atatgtaacc atcg 24

<210> SEQ ID NO 48
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 48
ggaaaaggtt tgagaggaat tatat 25

<210> SEQ ID NO 49
<211> LENGTH: 21

<212> TYPE: DNA
<213> ORGANISM: Artificial sequence
<220> FEATURE:
<223> OTHER INFORMATION: Synthetic sequence: Probe

<400> SEQUENCE: 49
ggtactcaaa ctccctaaat c 21

<210> SEQ ID NO 50
<211> LENGTH: 21
<212> TYPE: DNA
<213> ORGANISM: Artificial sequence
<220> FEATURE:
<223> OTHER INFORMATION: Synthetic sequence: Probe

<400> SEQUENCE: 50
gatttaggga gtttgagtac c 21

<210> SEQ ID NO 51
<211> LENGTH: 19
<212> TYPE: DNA
<213> ORGANISM: Artificial sequence
<220> FEATURE:
<223> OTHER INFORMATION: Synthetic sequence: Probe

<400> SEQUENCE: 51
gtactcaaac tccctaaat 19

<210> SEQ ID NO 52
<211> LENGTH: 19
<212> TYPE: DNA
<213> ORGANISM: Artificial sequence
<220> FEATURE:
<223> OTHER INFORMATION: Synthetic sequence: Probe

<400> SEQUENCE: 52
atttagggag tttgagtac 19

<210> SEQ ID NO 53
<211> LENGTH: 17
<212> TYPE: DNA
<213> ORGANISM: Artificial sequence
<220> FEATURE:
<223> OTHER INFORMATION: Synthetic sequence: Probe

<400> SEQUENCE: 53
tactcaaact ccctaaa 17

<210> SEQ ID NO 54
<211> LENGTH: 17
<212> TYPE: DNA
<213> ORGANISM: Artificial sequence
<220> FEATURE:
<223> OTHER INFORMATION: Synthetic sequence: Probe

<400> SEQUENCE: 54
tttagggagt ttgagta 17

<210> SEQ ID NO 55
<211> LENGTH: 23
<212> TYPE: DNA
<213> ORGANISM: Artificial sequence
<220> FEATURE:
<223> OTHER INFORMATION: Synthetic sequence: Probe

<400> SEQUENCE: 55

-continued tggtactcaa actccctaaa tct 23

<210> SEQ ID NO 56
<211> LENGTH: 25
<212> TYPE: DNA
<213> ORGANISM: Artificial sequence
<220> FEATURE:
<223> OTHER INFORMATION: Synthetic sequence: Probe

<400> SEQUENCE: 56
ctggtactca aactccctaa atctc 25

<210> SEQ ID NO 57
<211> LENGTH: 23
<212> TYPE: DNA
<213> ORGANISM: Artificial sequence
<220> FEATURE:
<223> OTHER INFORMATION: Synthetic sequence: Probe

<400> SEQUENCE: 57
tgccaggcac ggtgtctcag gct 23

<210> SEQ ID NO 58
<211> LENGTH: 21
<212> TYPE: DNA
<213> ORGANISM: Artificial sequence
<220> FEATURE:
<223> OTHER INFORMATION: Synthetic sequence: Probe

<400> SEQUENCE: 58
tgccaggcac ggtgtctcag g 21

<210> SEQ ID NO 59
<211> LENGTH: 23
<212> TYPE: DNA
<213> ORGANISM: Artificial sequence
<220> FEATURE:
<223> OTHER INFORMATION: Synthetic sequence: Probe

<400> SEQUENCE: 59
agcctgagac accgtgcctg gca 23

<210> SEQ ID NO 60
<211> LENGTH: 21
<212> TYPE: DNA
<213> ORGANISM: Artificial sequence
<220> FEATURE:
<223> OTHER INFORMATION: Synthetic sequence: Probe

<400> SEQUENCE: 60
cctgagacac cgtgcctggc a 21

<210> SEQ ID NO 61
<211> LENGTH: 23
<212> TYPE: DNA
<213> ORGANISM: Artificial sequence
<220> FEATURE:
<223> OTHER INFORMATION: Synthetic sequence: Probe

<400> SEQUENCE: 61
tgccctctca ctgtgtgatg act 23

<210> SEQ ID NO 62
<211> LENGTH: 21
<212> TYPE: DNA
<213> ORGANISM: Artificial sequence
<220> FEATURE:
<223> OTHER INFORMATION: Synthetic sequence: Probe

<400> SEQUENCE: 62
gccctctcac tgtgtgatga c 21

<210> SEQ ID NO 63
<211> LENGTH: 23
<212> TYPE: DNA
<213> ORGANISM: Artificial sequence
<220> FEATURE:
<223> OTHER INFORMATION: Synthetic sequence: Probe

<400> SEQUENCE: 63
agtcatcaca cagtgagagg gca 23

<210> SEQ ID NO 64
<211> LENGTH: 21
<212> TYPE: DNA
<213> ORGANISM: Artificial sequence
<220> FEATURE:
<223> OTHER INFORMATION: Synthetic sequence: Probe

<400> SEQUENCE: 64
gtcatcacac agtgagaggg c 21

<210> SEQ ID NO 65
<211> LENGTH: 27
<212> TYPE: DNA
<213> ORGANISM: Artificial sequence
<220> FEATURE:
<223> OTHER INFORMATION: Synthetic sequence: Probe

<400> SEQUENCE: 65
ttatgccagg cacggtgtct caggctt 27

<210> SEQ ID NO 66
<211> LENGTH: 27
<212> TYPE: DNA
<213> ORGANISM: Artificial sequence
<220> FEATURE:
<223> OTHER INFORMATION: Synthetic sequence: Probe

<400> SEQUENCE: 66
gaagtcatca cacagtgaga gggcaga 27

<210> SEQ ID NO 67
<211> LENGTH: 25
<212> TYPE: DNA
<213> ORGANISM: Artificial sequence
<220> FEATURE:
<223> OTHER INFORMATION: Synthetic sequence: Probe

<400> SEQUENCE: 67
aggcacggtg tctcaggctt ataat 25

<210> SEQ ID NO 68
<211> LENGTH: 27
<212> TYPE: DNA
<213> ORGANISM: Artificial sequence
<220> FEATURE:
<223> OTHER INFORMATION: Synthetic sequence: Probe

<400> SEQUENCE: 68
tctgatatcc ccatataacc aacaccc 27

<210> SEQ ID NO 69
<211> LENGTH: 27
<212> TYPE: DNA
<213> ORGANISM: Artificial sequence
<220> FEATURE:
<223> OTHER INFORMATION: Synthetic sequence: Probe

<400> SEQUENCE: 69
gggtgttggt tatatgggga tatcaga 27

<210> SEQ ID NO 70
<211> LENGTH: 25
<212> TYPE: DNA
<213> ORGANISM: Artificial sequence
<220> FEATURE:
<223> OTHER INFORMATION: Synthetic sequence: Probe

<400> SEQUENCE: 70
ctgatatccc catataacca acacc 25

<210> SEQ ID NO 71
<211> LENGTH: 25
<212> TYPE: DNA
<213> ORGANISM: Artificial sequence
<220> FEATURE:
<223> OTHER INFORMATION: Synthetic sequence: Probe

<400> SEQUENCE: 71
ggtgttggtt atatggggat atcag 25

<210> SEQ ID NO 72
<211> LENGTH: 27
<212> TYPE: DNA
<213> ORGANISM: Artificial sequence
<220> FEATURE:
<223> OTHER INFORMATION: Synthetic sequence: Probe

<400> SEQUENCE: 72
cccccaaatt tcatgtgcta gaaactt 27

<210> SEQ ID NO 73
<211> LENGTH: 27
<212> TYPE: DNA
<213> ORGANISM: Artificial sequence
<220> FEATURE:
<223> OTHER INFORMATION: Synthetic sequence: Probe

<400> SEQUENCE: 73
aagtttctag cacatgaaat ttggggg 27

<210> SEQ ID NO 74
<211> LENGTH: 25
<212> TYPE: DNA
<213> ORGANISM: Artificial sequence
<220> FEATURE:
<223> OTHER INFORMATION: Synthetic sequence: Probe

<400> SEQUENCE: 74
cccaaatttc atgtgctaga aactt 25

<210> SEQ ID NO 75
<211> LENGTH: 25
<212> TYPE: DNA
<213> ORGANISM: Artificial sequence
<220> FEATURE:
<223> OTHER INFORMATION: Synthetic sequence: Probe

<400> SEQUENCE: 75
aagtttctag cacatgaaat ttggg 25

<210> SEQ ID NO 76
<211> LENGTH: 27
<212> TYPE: DNA
<213> ORGANISM: Artificial sequence
<220> FEATURE:
<223> OTHER INFORMATION: Synthetic sequence: Probe

<400> SEQUENCE: 76
aggattaagt ttccagcaca tgaaatt 27

<210> SEQ ID NO 77
<211> LENGTH: 25
<212> TYPE: DNA
<213> ORGANISM: Artificial sequence
<220> FEATURE:
<223> OTHER INFORMATION: Synthetic sequence: Probe

<400> SEQUENCE: 77
ggattaagtt tccagcacat gaaat 25

<210> SEQ ID NO 78
<211> LENGTH: 27
<212> TYPE: DNA
<213> ORGANISM: Artificial sequence
<220> FEATURE:
<223> OTHER INFORMATION: Synthetic sequence: Primer

<400> SEQUENCE: 78
cacattacat agagatgtcc ccatact 27

<210> SEQ ID NO 79
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 79
gccacttatt acttaaaaaa acccc 25

<210> SEQ ID NO 80
<211> LENGTH: 25
<212> TYPE: DNA
<213> ORGANISM: Artificial sequence
<220> FEATURE:
<223> OTHER INFORMATION: Synthetic sequence: Probe

<400> SEQUENCE: 80
atttcatgtg ctggaaactt aatcc 25

<210> SEQ ID NO 81
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 81
ctgagtcaga tgctgtgatc agag 24

DISCRIMINATION OF BLOOD TYPE VARIANTS

CROSS REFERENCE TO RELATED APPLICATIONS

This is the U.S. National Stage of International Application No. PCT/EP2012/061270, filed Jun. 14, 2012, which was published in English under PCT Article 21(2), which in turn claims the benefit of U.S. Provisional Application No. 61/498,317, filed Jun. 17, 2011, and U.S. Provisional Application No. 61/553,726, filed Oct. 31, 2011, both of which are incorporated by reference herein in their entirety.

FIELD OF THE INVENTION

The invention relates to methods for genotyping and blood cell antigen determination, which in particular may discriminate the RHD*r's or RHD*r's-like blood type variants, which encode C$^{+W}$ antigen and no D antigen, from RHD*DIIIa, RHD*DIVa-2 and other blood type variants. The invention also relates to products, in particular, probes, primers and kits for use in such methods.

BACKGROUND TO THE INVENTION

The success of blood transfusion often depends on the degree of compatibility between donor and recipient. The degree of compatibility, in turn, is a function of the similarity in Red Blood Cell (RBC) antigen content between donor and recipient. Expression of many RBC antigens in an individual can be predicted from the analysis of their genomic DNA. Therefore, analysis of donor and/or recipient DNA can be used to facilitate blood matching and thus enable proper blood transfusion practice.

Hemolytic reactions are more common in multi-transfused than in singly transfused individuals, not only because of the increased probability of such an event as the number of transfused units increases, but also because of the accumulative nature of the immune response in the recipient. An example of a condition whose treatment includes repeated blood transfusions is Sickle Cell Disease (SCD). From the above follows that a high degree of compatibility with donor blood is often critical for the long-term success of transfusion in SCD patients.

While SCD is more prevalent among individuals of African ancestry, the blood donor population in the USA and other Western countries is largely Caucasian. As a consequence of this disparity, differences in RBC antigens between both racial groups often become responsible for blood transfusion failures in SCD patients.

The genetic variant RHD*DIIIa-CE(4-7)-D, also known as RHD-CE-D$^{S}$, RHD-CE(4-7)-D, (C)ce$^{S}$, or r'$^{S}$, (RHD*r'$^{S}$ henceforth) can be found in up to 5-10% of the African-American population, but is extremely rare in Caucasians. This variant poses a special challenge to blood transfusion because it encodes a rather complex antigen profile, which includes absence of D antigen, altered forms of C (C$^{+W}$) and e antigens, expression of low-frequency VS antigen, no expression of V antigen, and absence of the high-frequency hr$^{B}$ antigen. Among them, D and C antigens are the clinically more relevant ones.

The antigenic complexity of RHD*r'$^{S}$ correlates with its genetic complexity, which includes a substitution of part of RHD exon 3, RHD exons 4-7, and the intervening introns by their RHCE counterparts, a G>T substitution at position 186 (exon 2), a C>T substitution at position 410 (hybrid exon 3), a C>G substitution at position 733 (exon 5), and a G>T substitution at position 1006 (exon 7). In addition to the changes in the RHD gene, RHD*r'$^{S}$ occurs in cis with RHCE*ce$^{S}$1006T, an RHCE gene that also encodes substitutions C>G at position 733 (exon 5) and G>T at position 1006 (exon 7).

To add to the antigenic and genetic complexity, knowledge about the molecular basis of RHD*r'$^{S}$ is incomplete. For instance, the precise points of RHCE/RHD recombination have not been reported to date. Furthermore, two types of RHD*r'$^{S}$ variant have been described and named Type 1 and Type 2, which differ not only in their genetic composition but also in their antigen profiles.

Several publications (Refs. 1-3) have uncovered the genetic similarity between RHD*r'$^{S}$ and other RHD variants, in particular RHD*DIIIa and RHD*DIVa/RHD*DIVa-2 (RHD*DIVa-2 henceforth). A number of molecular methods for the specific detection of RHD*r'$^{S}$ rely on the detection of single nucleotide polymorphisms (SNPs) located in hybrid exon 3. These SNPs are now known to be shared with variants RHD*DIIIa and RHD*DIVa-2. Consequently, to date, identification of RHD*r'$^{S}$ in a sample by DNA analysis requires detection of hybrid exon 3 SNPs and discrimination from RHD*DIIIa and RHD*DIVa-2. This discrimination is clinically relevant since the latter variants encode a different antigen profile, which includes expression of partial D and absence of C$^{+W}$.

Antibody reagents commonly used to detect C antigen do not discriminate between C$^{+W}$ and C$^{+}$. Therefore, the phenotype is often reported as C$^{+}$. In cases where the antibody reagent does discriminate between C$^{+W}$ and C$^{+}$ but the sample contains a normal RHCE*C allele in trans to a RHD*r'$^{S}$ allele, C$^{+W}$ is obscured by C$^{+}$, resulting in a C$^{+}$ phenotype for the sample. Therefore, RHCE*C needs to be tested for and shown absent prior to assignment of a C$^{+W}$ phenotype to a sample. Accordingly, there remains a need for further methods for distinguishing RHD*r's from RHD*DIIIa and RHD*DIVa-2. The present invention addresses these and other objects.

SUMMARY OF THE INVENTION

The present inventors have now found that intron 7 of the RHD locus and/or intron 7 of the RHCE locus find use in discriminating bloodtype variants. Genotyping at one or more polymorphic positions of intron 7 of said loci may, in some cases, be advantageously combined with genotyping positions elsewhere, such as in exon 3 of the RHD locus. In particular, the inventors have found that a determination of one or more genetic sequences in one or more regions of intron 7 of the RHD locus enables discrimination between blood type variants RHD*r'$^{S}$ or RHD*r'$^{S}$-like (i.e. blood type variants which express the C$^{+W}$ antigen and lack a D antigen) and other RHD/RHCE hybrid exon 3 variants, including but not limited to RHD*DIIIa, RHD*DIII_FN and RHD*DIVa-2. Knowledge about the sequence of each of these RHD and RHCE variants at polymorphic positions in the intron 7 regions enables the design and development of typing methods that exploit said polymorphisms, individually or in combination, to discriminate among variants. Discrimination among variants, in turn, enables determination of the genotype and prediction of the phenotype of a sample containing them with a high degree of accuracy, and resulting clinical utility.

As described herein in detail, the sequences of RHD variants RHD*r's, RHD*DIIIa, RHD*DIII_FN and RHD*DIVa-2 were determined at sixty single-nucleotide polymorphic positions located in a region of intron 7 of the RHD locus (see, in particular, Table 1). This region is delimited on the 5' end by position IVS7+1139, and on the 3' end by position IVS7+4108. The present invention also describes sequences of RHCE*ce variants RHCE*ce$^S$ and RHCE*ce733G at polymorphic positions of intron 7 of the RHCE locus. In particular, the region of RHCE intron 7 that is delimited on the 5' end by position IVS7+2970, and on the 3' end by position IVS7+4108 includes twenty seven informative single nucleotide polymorphisms. Intron 7 of RHD and intron 7 of RHCE are structurally similar and can be amplified together, e.g. in a PCR reaction. The present inventors believe that the informative use of sequences of intron 7 of the RHD/RHCE loci in the discrimination of blood variants (e.g. RHD*r's, RHD*DIIIa, RHD*DIII_FN, RHD*DIVa-2, RHCE*ce, RHCE*ce$^S$ and RHCE*ce733G) represents a significant unifying contribution over the prior art; there being a special technical relationship between intron 7 of RHD and RHCE. Moreover, the link between RHD*r's and the RHCE variants (these frequently being found in cis) results in a functional linkage.

Moreover, V and VS antigens and absence of hr$^B$ antigen are also encoded by RHCE variants that often present in cis with RHD*r's. The most prevalent among them are RHCE*ce$^S$ (and related variants), and RHD*733G. This responds to the genetic similarity between the RHD*r's portion that encodes antigens V, VS, hr$^B$ and the corresponding portion in RHCE variants RHCE*ce$^S$ and RHD*733G. As a consequence of this, discrimination of RHD*r's from other variants by genetic testing and for the purpose of predicting RHCE antigens, also benefits from the inclusion of polymorphisms that differ from those found in variants RHCE*ce$^S$ and RHD*733G.

The present inventors have characterized rearrangements in the sequence of intron 7. One such rearrangement, common to RHD*r'$^S$ and RHD*DIIIa, has its insertion point between positions IVS7+3101 and IVS7+3256, the sequence corresponding to RHCE 5' of IVS7+3101 and to RHD 3' of IVS7+3256 (with the sequence being indistinguishable between RHCE and RHD between both positions). A second rearrangement, which distinguishes RHD*r'$^S$ from RHD*DIIIa, has its insertion point between positions IVS7+1888 and IVS7+2152: The sequence corresponds to RHCE 5' of IVS7+1888 in the case of RHD*r'$^S$ and to RHD in the case of RHD*DIIIa. The sequence 3' of IVS7+2152 corresponds to RHCE for both RHD*r'$^S$ and RHD*DIIIa (with the sequence being indistinguishable between RHCE and RHD between both positions). This is depicted in FIG. 1A.

A further rearrangement has been identified that distinguishes RHD*DIIIa from RHD*DIII_FN (without wishing to be bound by any particular theory, the present inventors believe that RHD*DIII_FN likely corresponds to RHD*DIII-type 4, 6 or 7). This rearrangement can be seen in FIG. 1B (see also Table 1). In particular, RHD*DIIIa comprises RHCE sequence between positions IVS7+2153 and IVS7+2335, whereas RHD*DIII_FN comprises RHD sequence between positions IVS7+2153 and IVS7+2335.

Accordingly, in a first aspect the present invention provides a method for determining the presence or absence of, or for discriminating between, blood type alleles, which method comprises determining the identity of the nucleotide at one or more positions in intron 7 of the RHD locus and/or in intron 7 of the RHCE locus in a sample obtained from a human subject. The method may comprise genotyping the sample to determine the identity of the nucleotide at said one or more positions for one or more alleles.

Preferably, said blood type alleles are alleles which comprise an RHD/RHCE hybrid exon 3.

In some cases in accordance with the method of this aspect of the invention, said blood type alleles are selected from the group consisting of: RHD*r's; RHD*r's-like; RHD*r'$^S$ Type 1; RHD*r'$^S$ Type 2; RHD*DIIIa; RHD*III_FN; RHD*DIVa-2; RHD*DIVa; RHD*DIII-type4; RHD*DIII-type6; RHD*DIII-type7; RHD*DIII-type8; RHCE*ce$^S$; RHCE*ce$^S$1006T; RHCE*ce$^S$1006C RHCE*ce733G; RHCE*ce48C,733G,1025T; RHCE*ce48C,697G,733G; RHCE*ce340T,733G; and RHCE*ce48C,733G,748A.

In some cases in accordance with this aspect of the invention the method is for detecting the presence or absence of, or for discriminating between, blood type variants, said blood type variants comprising an RHD-RHCE hybrid exon 3, the method comprising: genotyping a sample obtained from a human subject at one or more polymorphic positions in intron 7 of the RHD gene locus, said one or more polymorphic positions being selected from:

(i) a first region of said intron 7 that is 5' of IVS7+1887, said first region including said position IVS7+1887;

(ii) a second region of said intron 7 that lies between IVS7+2153 and IVS7+3101, said second region including said positions IVS7+2153 and IVS7+3101; and (iii) a third region of said intron 7 that lies 3' of IVS7+3257, said third region including said position IVS+3257, wherein said positions are numbered according to the position numbering shown in FIG. 3.

In some cases, the method is for discriminating RHD*r's or RHD*r's-like from RHD*DIIIa, RHD*DIII_FN and/or RHD*DIVa-2, and wherein the method comprises genotyping the sample at one or more polymorphic positions in said first region of intron 7.

In some cases, the method is for discriminating RHD*r'$^S$ from RHCE variants, and wherein the method comprises genotyping the sample at one or more polymorphic positions in said first region of intron 7.

In some cases, the method is for discriminating RHD*r's, RHD*r's-like or RHD*DIIIa from RHD*DIVa-2, and wherein the method comprises genotyping the sample at one or more polymorphic positions in said second region and/or said third region of intron 7.

In some cases, the method is for discriminating between: (a) RHD*r's or RHD*r's-like; (b) RHD*DIIIa; and (c) RHD*DIVa-2, wherein the method comprises genotyping the sample at:

(i) one or more polymorphic positions in said first region of intron 7; and (ii) one or more polymorphic positions in said second or said third regions.

In cases where the identity of the nucleotide at said one or more polymorphic positions in said first region is that of RHCE, the sample may be classified as containing or having a high probability of containing an RHD*r's is allele. In certain cases, where the sample may have been previously determined to lack RHCE and RHCE variants, the classification as containing an RHD*r's allele may be made with even greater certainty.

In cases where the identity of the nucleotide at said one or more polymorphic positions in said first region is that of RHD, and sample is classified as being or having a high probability of being RHD*DIIIa or RHD*DIVa-2. In certain cases, where the sample may have been previously determined to lack RHD and RHD variants, the classification as containing an RHD*DIIIa or RHD*DIVa-2 allele may be made with even greater certainty.

In some cases, the method in accordance with the present invention comprises genotyping the sample at one or more polymorphic positions in intron 7 of the RHD gene locus, said one or more polymorphic positions being selected from:
(i) a first region of said intron 7 that is 5' of IVS7+1887, said first region including said position IVS7+1887;
(ii(a)) a second (a) region of said intron 7 that lies between IVS7+2153 and IVS7+2335, said second (a) region including said positions IVS7+2153 and IVS7+2335;
(ii(b)) a second (b) region of said intron 7 that lies between IVS7+2449 and IVS7+3101, said second (b) region including said positions IVS7+2449 and IVS7+3101; and
(iii) a third region of said intron 7 that lies 3' of IVS7+3257, said third region including said position IVS+3257, wherein said positions are numbered according to the position numbering shown in FIG. 3. In certain cases, in accordance with the present invention, the method is for discriminating between: (a) RHD*r's or RHD*r's-like; (b) RHD*DIIIa; (c) RHD*DIII_FN; and (d) RHD*DIVa-2, wherein the method comprises genotyping the sample at:
(i) one or more polymorphic positions in said first region of intron 7;
(ii) one or more polymorphic positions in said second (a) region;
(iii) one or more polymorphic positions in said second (b) region; and
(iv) one or more polymorphic positions in said third region.

In cases where the identity of the nucleotide at said one or more polymorphic positions in said second (a) region is the same as that of conventional RHD, and the identity of the nucleotide at said one or more polymorphic positions in said second (b) region (other than at positions IVS7+2945 and IVS7+3026) is the same at that of conventional RHCE, and the sample may be classified as having (or having a high probability of having) a RHD*DIII_FN allele.

In certain cases in accordance with the method of the invention, the method comprises genotyping the sample at one or more polymorphic positions in intron 7 of the RHCE locus, said polymorphic positions in intron 7 of the RHCE locus being located in a region that lies between IVS7+2970 and IVS7+4108, said region including said positions IVS7+2970 and IVS7+4108, and wherein said method is for detecting the presence or absence of, or for discriminating between, RHCE, RHCE*ce$^S$ and RHCE*ce733G, wherein said positions are numbered according to the numbering shown in FIG. 3.

In accordance with the method of this aspect of the invention, said polymorphic positions may be selected from the single nucleotide polymorphism (SNP) positions set forth in Table 1, the position numbering being as shown in FIG. 3. In some cases, the method may comprise genotyping the sample at, at least, 2, 3, 4, 5, 6, 7, 8, 9, 10 or more SNP positions selected from those set forth in Table 1. In certain cases, the genotype at the one or more SNP positions detected for the sample is used to classify the RHD and/or RHCE haplotypes present in the sample, according to the classification set forth in Table 1.

In some cases, the sample is a sample which has previously been determined to comprise an RHD-RHCE hybrid exon 3.

In some cases, the method further comprises determining whether the sample contains an RHD-RHCE hybrid exon 3.

The method may comprise genotyping the sample at one or more polymorphic positions selected from:
IVS2-26, IVS2-13, IVS2-8 in RHD intron 2;
IVS3+64, IVS3+69 in RHD intron 3; and
position 410 in RHD exon 3. In particular, the method may comprise genotyping the sample at position c.410 of the RHD locus, located in exon 3, wherein presence of T at said position in the context of upstream RHD and downstream RHCE sequences near that position indicates presence of an RHD/RHCE hybrid exon 3 variant in the sample.

In certain cases in accordance with the method of the present in invention, the method comprises genotyping not more than 50, such as not more than 40, 30, 25, 20, 15, or not more than 10, single nucleotide polymorphic positions in the RHD gene locus and/or the RHCE gene locus. Thus, the method of the invention may provide considerable efficiency savings when compared with, for example, complete sequencing of the entire gene(s) or gene region. The method of the present invention advantageously concentrates on those informative polymorphic positions that may be used to determine presence or absence of, or to discriminate between, blood type variants.

Preferably, the method of the present invention further comprises the use of genotyping data to predict the phenotype encoded by RHD allele(s), and the use of this prediction to enable the determination of an RhD phenotype and/or the RHCE phenotype for the subject based on the genotype of the sample.

In accordance with the present invention, the subject may be undergoing, or may be a candidate for, blood transfusion. In some cases, the subject may have SCD, or any other disease requiring repeated blood transfusions, such as Thalassemia major or certain blood cell malignancies.

In accordance with the present invention, the subject may be of non-Caucasian race. In particular, the subject may be of African ancestry (e.g. "Black persons"). In certain cases, the subject may have an ancestral origin in a Mediterranean country.

In accordance with the method of the invention, the sample may be any suitable biological sample from which it is possible to determine the genotype of the subject at one or more polymorphic positions in intron 7 of the RHD gene and/or the RHCE gene. In certain case, the sample may conveniently take the form of a blood sample.

In accordance with the method of the invention, the sample may, in some cases, be subjected to one or more treatments to extract and/or amplify a nucleic acid prior to or as part of said genotyping. In particular, the sample may be treated to extract genomic DNA. Furthermore, genomic DNA extracted from the sample may be subjected to a PCR reaction in order to amplify a region of interest, for example, all or part of intron 7 of the RHD gene and/or the RHCE gene.

In certain cases in accordance with the method of the invention, the method may comprise carrying out an Allele-Specific Polymerase Chain Reaction (ASP) and/or Allele-Specific Hybridization (ASH).

In certain cases in accordance with the method of the invention, the method may comprise labelling a nucleic acid obtained from the sample or labelling an amplicon derived from a nucleic acid obtained from the sample. The label is preferably a detectable label. In some cases, DNA derived from the sample, e.g. PCR product resulting from use of the DNA from the sample as template, may be labelled using a fluorescent label or dye (e.g. by conjugating said fluorescent label or dye to the PCR product before or after fragmentation of the PCR product).

In certain cases in accordance with the method of the invention, the method may further comprise carrying out serological analysis on a blood sample that has been obtained from the subject, combining the serological analysis with said genotype and thereby determining the blood type phenotype of the subject. Combining the genotype-based prediction of blood type with a serological-based prediction may be useful, e.g., to improve accuracy or to resolve ambiguous results.

However, it is specifically contemplated herein that the method in accordance with this aspect of the invention may in some cases avoid the use of any serological analysis. This may result in considerable savings in terms of labour, cost and time.

In certain cases in accordance with the method of the invention, DNA may be obtained from the sample and amplified using primers that are selective for RHD/RHCE hybrid intron 7. For example, the primers may be selected from: a primer comprising or consisting of the nucleotide sequence of SEQ ID NO: 9, a primer comprising or consisting of the nucleotide sequence of SEQ ID NO: 10, a primer comprising or consisting of the nucleotide sequence of SEQ ID NO: 12 and a primer comprising or consisting of the nucleotide sequence of SEQ ID NO: 13.

Preferably, said primers may be used in pairs, such as the primers of SEQ ID Nos: 9 and 10 as a pair, or the primers of SEQ ID Nos: 12 and 13 as a pair.

In certain cases, in accordance with the method of the present invention, one or more of the primers may be a variant of one or more of the primers of SEQ ID NOs: 9, 10, 12 and 13, having 1, 2, 3, 4 or 5 nucleotide alterations whether by addition, deletion or substitution ("variant primers"). Preferably, a primer variant of the primers of SEQ ID NO: 9, 10, 12 and 13, respectively, comprises one or more additional nucleotides at the 3' and/or 5' end of the sequence set forth in SEQ ID NOs: 9, 10, 12 and 13, respectively, wherein the one or more additional nucleotides provide an extension to the primer sequence, and wherein the extension sequence is complementary to a portion of the sequence of the RHD or RHCE locus (sense or antisense strand), preferably a portion that is contiguous with the portion of sequence recognised by the primer of SEQ ID NOs: 9, 10, 12 and 13, respectively. Specifically contemplated herein are primer variants that are essentially functionally equivalent to the exemplary primers disclosed herein.

In certain cases in accordance with the method of the invention, DNA may be obtained from the sample and amplified using primers that are selective for RHD/RHCE hybrid intron 7. For example, the primers may be selected from: a primer comprising or consisting of the nucleotide sequence set forth in Table 7.

In certain cases, in accordance with the method of the present invention, one or more of the primers may be a variant of one or more of the primers set forth in Table 7, having 1, 2, 3, 4 or 5 nucleotide alterations whether by addition, deletion or substitution ("variant primers"). Preferably, a primer variant of a primer set forth in Table 7, comprises one or more additional nucleotides at the 3' and/or 5' end of the sequence set forth in Table 7, wherein the one or more additional nucleotides provide an extension to the primer sequence, and wherein the extension sequence is complementary to a portion of the sequence of the RHD or RHCE locus (sense or antisense strand), preferably a portion that is contiguous with the portion of sequence recognised by the primer set forth in Table 7. Specifically contemplated herein are primer variants that are essentially functionally equivalent to the exemplary primers disclosed in Table 7 herein.

In certain cases in accordance with the method of the invention, the genotyping step may comprise an allele-specific hybridisation of DNA extracted from the sample, or an amplicon derived from DNA extracted from the sample, wherein the allele-specific hybridisation comprises contacting said extracted DNA, or said amplicon, with a probe that hybridises to a portion of intron 7 of the RHD gene and/or of the RHCE gene, said hybridisation being selective for one allele at a polymorphic position as set forth in Table 1. In preferred case, the probe may be selected from: a probe comprising or consisting of the sequence of SEQ ID NO: 11, a probe comprising or consisting of the sequence of SEQ ID NO: 14 and a probe comprising or consisting of the sequence of SEQ ID NO: 15.

In certain cases, in accordance with the method of the present invention, the probe may be a variant of the probe of SEQ ID NO: 11, 14 or 15 having 1, 2, 3, 4 or 5 nucleotide alterations whether by addition, deletion or substitution ("probe variants"). Preferably, a probe variant of the probe of SEQ ID NO: 11, 14 and 15, respectively, comprises one or more additional nucleotides at the 3' and/or 5' end of the sequence set forth in SEQ ID NO: 11, 14 and 15, respectively, wherein the one or more additional nucleotides provide an extension to the probe sequence, and wherein the extension sequence is complementary to a portion of the sequence of RHD/RHCE hybrid intron 7 (sense or antisense strand), preferably a portion that is contiguous with the portion of sequence recognised by the probe of SEQ ID NO: 11, 14 and 15, respectively. Specifically contemplated herein are probe variants that are essentially functionally equivalent to the exemplary probes disclosed herein.

In certain cases in accordance with the method of the invention, the genotyping step may comprise an allele-specific hybridisation of DNA extracted from the sample, or an amplicon derived from DNA extracted from the sample, wherein the allele-specific hybridisation comprises contacting said extracted DNA, or said amplicon, with a probe that hybridises to a portion of intron 7 of the RHD gene and/or of the RHCE gene, said hybridisation being selective for one allele at a polymorphic position as set forth in Table 1. In preferred case, the probe may be selected from a probe comprising or consisting of a nucleotide sequence set forth in Table 8.

In certain cases, in accordance with the method of the present invention, the probe may be a variant of a probe set forth in Table 8, said variant having 1, 2, 3, 4 or 5 nucleotide alterations whether by addition, deletion or substitution ("probe variants"). Preferably, a probe variant of a probe set forth in Table 8 comprises one or more additional nucleotides at the 3' and/or 5' end of a sequence set forth in Table 8, wherein the one or more additional nucleotides provide an extension to the probe sequence, and wherein the extension sequence is complementary to a portion of the sequence of RHD/RHCE hybrid intron 7 (sense or antisense strand), preferably a portion that is contiguous with the portion of sequence recognised by a probe set forth in Table 8. Specifically contemplated herein are probe variants that are essentially functionally equivalent to the exemplary probes disclosed in Table 8 herein.

In certain cases in accordance with the method of the invention, the method may further comprise determining whether the sample contains an RHD-RHCE hybrid exon 3. Accordingly, in certain cases, DNA obtained from the sample is amplified using primers that are selective for RHD/RHCE hybrid exon 3. Preferably, the primers that are selective for RHD/RHCE hybrid exon 3 are selected from: a primer comprising or consisting of the nucleotide sequence of SEQ ID NO: 5 and a primer comprising or consisting of the nucleotide sequence of SEQ ID NO: 6. In some cases, the primers that are selective for RHD/RHCE hybrid exon 3 are selected from: a primer variant having 1, 2, 3, 4 or 5 nucleotide alternations, whether by addition, deletion or substitution, compared with the primer sequence of SEQ ID NOs: 5 and 6, respectively. The method in accordance with this aspect of the invention may further comprise genotyping the sample at a polymorphic position in exon 3 of the RHD locus, wherein the method comprises an allele-specific hybridisation of DNA extracted from the sample, or an amplicon derived from DNA extracted from the sample, and wherein the allele-specific hybridisation comprises contacting said extracted DNA or said amplicon with a probe that is selective for an allele present in RHD/RHCE hybrid exon 3. In certain cases, the probe may be selected from: a probe comprising or consisting of the sequence of SEQ ID NO: 7 and a probe comprising or consisting of the sequence of SEQ ID NO: 8. In certain cases, the probe that is selective for an allele present in RHD/RHCE hybrid exon 3 may be a variant probe having 1, 2, 3, 4 or 5 nucleotide alternations, whether by addition, deletion or substitution, compared with the probe sequence of SEQ ID NOs: 7 and 8, respectively.

In a second aspect, the present invention provides one or more oligonucleotide probes and/or primers for use in the method of the invention, wherein the one or more oligonucleotide probes and/or primers span, or are able to be used to span, the polymorphic positions in intron 7 of the RHD gene and/or the RHCE gene, said probes and/or primers being hybridisable to a portion of the sense or antisense strand of said RHD and/or RHCE gene. Typically, said oligonucleotide probes and/or primers are not more than 50 bases in length, such as 10-50 nucleotides or 15-35 nucleotides or even 19-27 nucleotides in length. Advantageously, the probes and/or primers are perfectly complementary to a portion of the sense or antisense strand of intron 7 or the RHD and/or RHCE gene, which portion includes a polymorphic position such that the probe and/or primer hybridises more efficiently to one allele (i.e. sequence including one form of the polymorphism) compared with another allele at said positions (i.e. sequence including another or the other form of the polymorphism). In certain preferred cases, the one or more oligonucleotide probes and/or primers span one or more polymorphic positions set forth in Table 1. For example, the one or more oligonucleotide probes in accordance with this aspect of the invention may, in some cases, be selected from the probes comprising or consisting of the nucleotide sequence set forth in one or more of SEQ ID Nos: 11, 14 and 15, or a variant of one of said probes having 1, 2, 3, 4 or 5 nucleotide alternations, whether by addition, deletion or substitution, compared with the nucleotide sequence set forth in SEQ ID Nos: 11, 14 and 15, respectively. Alternatively or additionally, the one or more primers in accordance with this aspect of the invention may, in some cases, be selected from the primers comprising or consisting of the nucleotide sequence set forth in one or more of SEQ ID Nos: 9, 10, 12 and 13, or a variant of one of said primers having 1, 2, 3, 4 or 5 nucleotide alternations, whether by addition, deletion or substitution, compared with the nucleotide sequence set forth in SEQ ID Nos: 9, 10, 12 and 13, respectively.

Alternatively or additionally, the one or more oligonucleotide probes in accordance with this aspect of the invention may, in some cases, be selected from the probes comprising or consisting of a nucleotide sequence set forth in Table 8, or a variant of one of said probes having 1, 2, 3, 4 or 5 nucleotide alternations, whether by addition, deletion or substitution, compared with a nucleotide sequence set forth in Table 8.

Alternatively or additionally, the one or more primers in accordance with this aspect of the invention may, in some cases, be selected from the primers comprising or consisting of the nucleotide sequence set forth in Table 7, or a variant of one of said primers having 1, 2, 3, 4 or 5 nucleotide alternations, whether by addition, deletion or substitution, compared with the nucleotide sequence set forth in Table 7.

In a third aspect, the present invention provides a plurality of oligonucleotide probes in accordance with the second aspect of the invention, wherein the probes are coupled to a solid support. Preferably, the probes are covalently attached (directly or via a linker) to the solid support. In some cases the solid support may comprise a planar surface, such as a glass surface (e.g. in the form of a DNA chip or "microarray"). In some cases the solid support may comprise a particle, such as a microbead to which one or more of the probes are conjugated.

In a fourth aspect, the present invention provides a kit for assessing a subject's blood type, the kit comprising:

- one or more probes and/or primers as defined in accordance with the second aspect of the invention;
- optionally, one or more probes and/or primers that span one or more polymorphic positions in intron 2, exon 3 and/or intron 3 of the sense or antisense strand of the RHD gene;
- optionally, one or more reagents and/or standards for use in carrying out a method as defined in accordance with the first aspect of the invention; and
- optionally, instructions for carrying out a method as defined in accordance with the first aspect of the invention.

In some cases in accordance with this aspect of the invention, the kit comprises:

- one or more primers selected from the primers comprising or consisting of one or more nucleotide sequences set forth in SEQ ID Nos: 5 and 6; and/or
- one or more probes selected from the probes comprising or consisting of one or more nucleotide sequences set forth in of SEQ ID Nos: 7 and 8.

In a fifth aspect, the present invention provides a system for use in determining a subject's blood type, the system comprising:

- a kit as defined in accordance with the fourth aspect of the invention; and
- at least one detector arranged to detect a signal from detectably labelled DNA obtained from said subject or a detectably labelled amplicon (fragmented or unfragmented) derived from DNA obtained from said subject;
- at least one controller in communication with the at least one detector, the controller being programmed with computer-readable instructions to transform said signal into predicted blood type genotypes, and optionally, to transform said predicted blood type genotypes into a predicted blood type phenotype.

In a sixth aspect, the present invention provides a method of blood matching, the method comprising:

- carrying out the method in accordance with the first aspect of the invention on a recipient sample from a recipient subject in need of donor blood and a donor sample from a potential donor subject;

comparing the blood type alleles present in the recipient sample with those present in the donor subject and thereby determining the compatibility of the recipient subject to receive blood from the donor subject.

In some cases, the method in accordance with the sixth aspect of the invention may be carried out for a plurality of recipient subjects and a plurality of potential donor subjects.

The invention will now be described in more detail, by way of example and not limitation, by reference to the accompanying drawings. Many equivalent modifications and variations will be apparent to those skilled in the art when given this disclosure. Accordingly, the exemplary embodiments of the invention set forth are considered to be illustrative and not limiting. Various changes to the described embodiments may be made without departing from the scope of the invention. All documents cited herein are expressly incorporated by reference.

The Sequence Listing is submitted as an ASCII text file in the form of the file named Sequence_Listing.txt, which was created on Dec. 12, 2013, and is 189,145 bytes, which is incorporated by reference herein.

DESCRIPTION OF THE FIGURES

FIGS. 3A-F are a series of panels showing a sequence alignment of intron 7 of the RHD locus with intron 7 of the RHCE locus. Identical nucleotides are indicated by a dot, gaps are indicated by a dash. The numbered positions referred to herein, e.g. the SNP position numbers set forth in Table 1, are numbered in accordance with the position numbering shown in this sequence alignment. The upper row sequence shows intron 7 of the RHD gene, numbered positions 1101 to 4120 (SEQ ID NO: 1). The lower row sequence shows intron 7 of the RHCE gene numbered positions 1101 to 4120 (SEQ ID NO: 2), according to the alignment with SEQ ID NO: 1.

DETAILED DESCRIPTION OF THE INVENTION

The present invention finds use in the determination of the clinically relevant RHD- and RHCE-encoded antigen phenotypes of a blood sample. The invention provides a method for detecting the presence or absence of, or for discriminating between, blood type variants, which method comprises genotyping a sample obtained from a human subject at one or more positions in intron 7 of the RHD gene and/or in intron 7 of the RHCE gene. Advantageously, the method of the present invention may further comprise determining the presence or absence of an RHD/RHCE hybrid exon 3 in said sample.

The Rh blood group D antigen is encoded by the RHD gene, which comprises 10 exons. The complete RHD gene sequence is available at NCBI Reference Sequence: NG_007494.1 No. NG_007494.1, GI:171184448, (SEQ ID NO: 3), the entire contents of which is incorporated herein by reference.

The Rh blood group C antigen is encoded by the RHCE gene, which comprises 10 exons. The complete RHCE gene sequence is available at NCBI Reference Sequence: NG_009208.2, GI:301336136, (SEQ ID NO: 4), the entire contents of which is incorporated herein by reference.

Figure 1A:
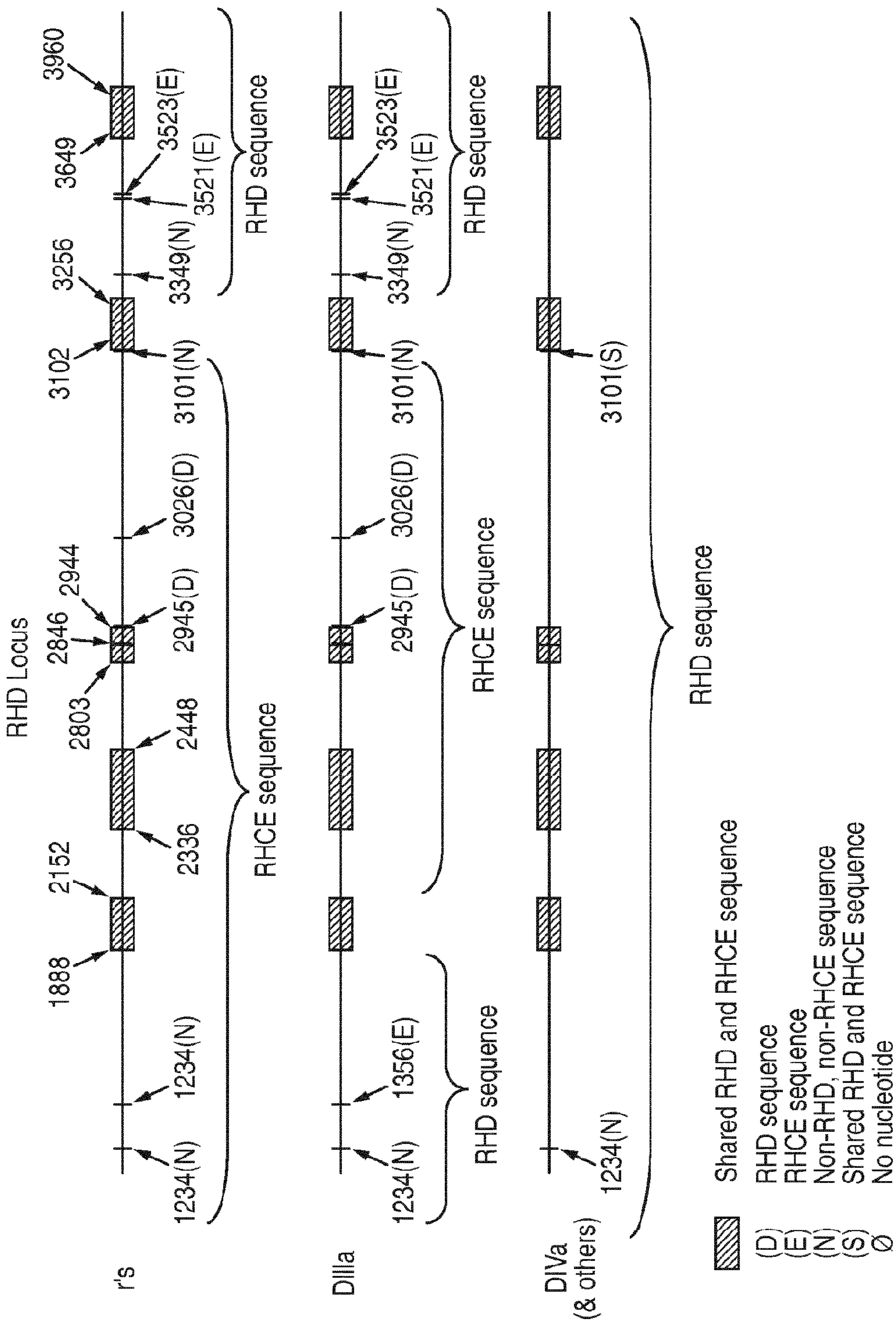
FIG. 1: A) shows a representation of the RHD locus for RHD*r'$^S$ (upper row), RHD*DIIIa (middle row) and RHD*DIVa (and others) (lower row), in which certain polymorphic positions are indicated and certain portions are labelled as being shared RHD and RHCE sequence (shaded box or (S)), RHD sequence (D), RHCE sequence (E), non-RHD, non-RHCE sequence (N) and no nucleotide present (Ø); B) shows a representation of the RHD locus for RHD*DIII_FN, in which certain polymorphic positions are indicated and certain portions are labelled as being shared RHD and RHCE sequence (shaded box or (S)), RHD sequence (D), RHCE sequence (E), non-RHD, non-RHCE sequence (N) and no nucleotide present (Ø)
Figure 1B:
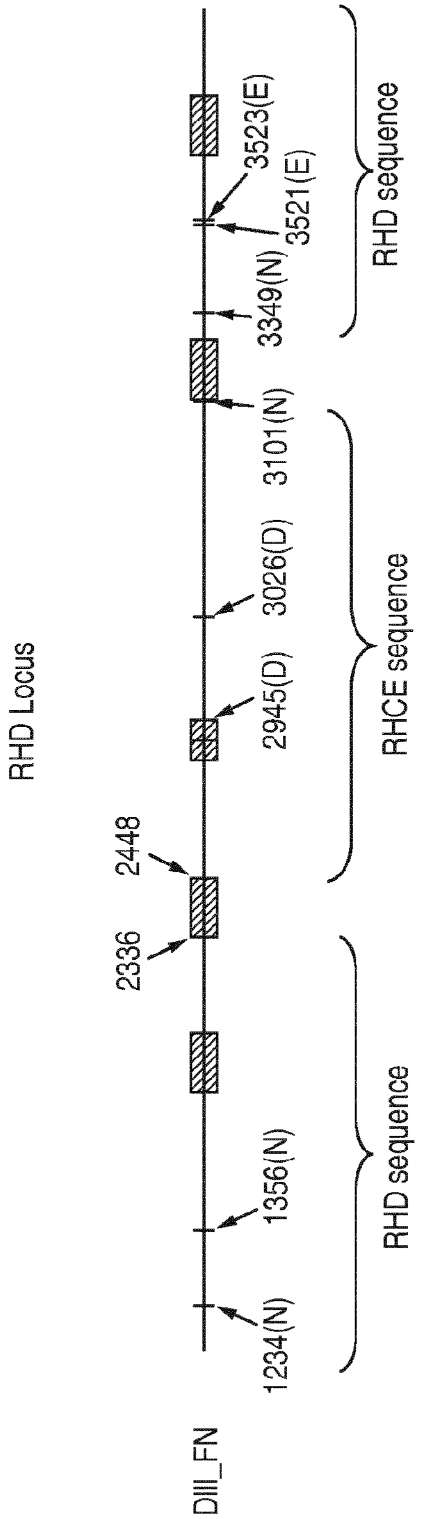
Figure 2:
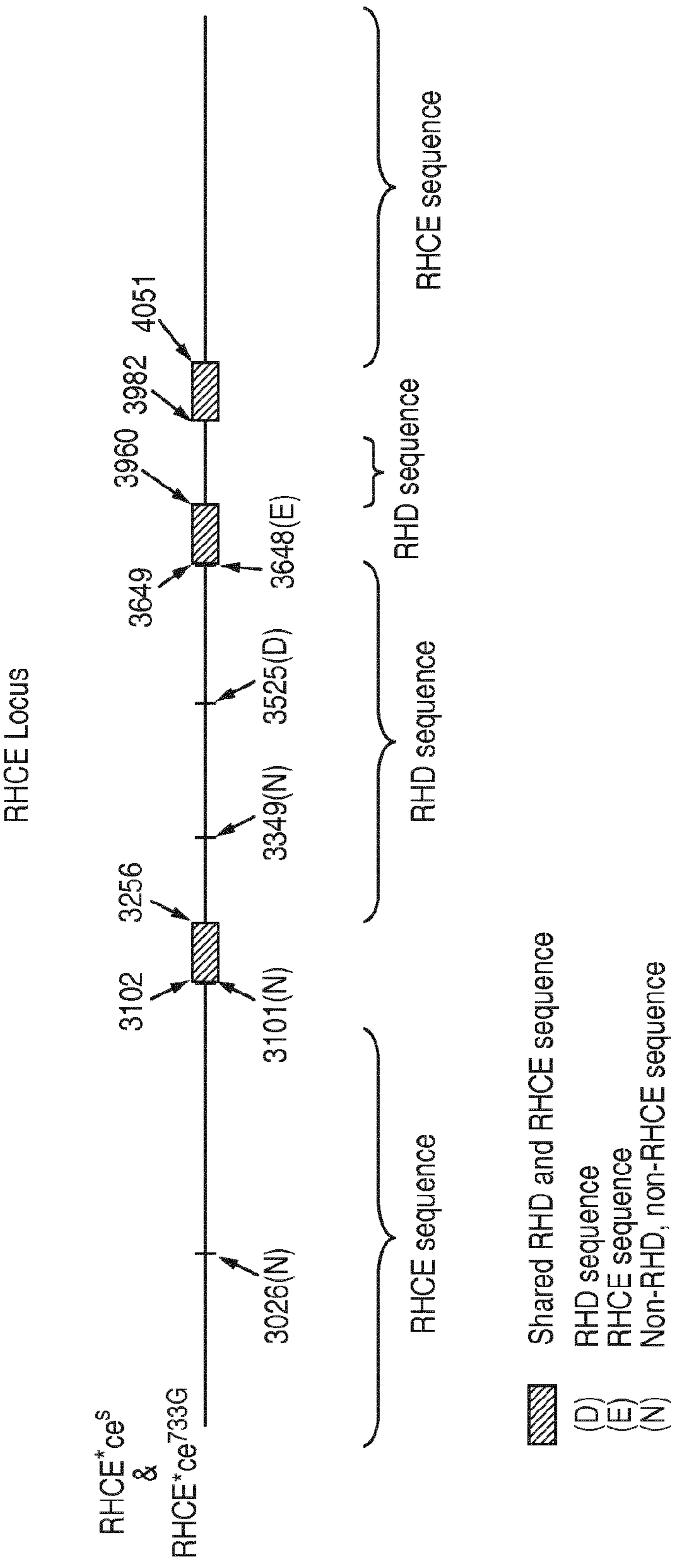
FIG. 2: shows a representation of the RHCE locus for RHCE*ce$^S$ and RHCE*ce733G, in which certain polymorphic positions are indicated and certain portions are labelled as being shared RHD and RHCE sequence (shaded box), RHD sequence (D), RHCE sequence (E) and non-RHD, non-RHCE sequence (N)

In certain cases in accordance with the present invention, the method may comprise: (1) determining the genotype of a sample at one or more positions between positions IVS7+2153 and IVS7+3101, (2) determining if the one or more positions from (1) corresponds to an RHD or RHCE sequence, (3) deducing from the genotype whether or not the sample contains or may contain a RHD*r'$^S$ haplotype, as indicated in FIG. 1.

Preferably, the method further comprises: (1 bis) determining the genotype of a sample at one or more positions on the 5' end of position IVS7+1887, (2 bis) determining if the one or more positions from (1 bis) correspond to an RHD or RHCE sequence.

Preferably, the method further comprises: (1 tri) determining the genotype of a sample at one or more positions on the 3' end of position IVS7+3257, (2 tri) determining if the one or more positions from (1 tri) correspond to an RHCE*ceS or RHCE*ce733G sequence, and (3) deducing from the genotype whether or not the sample contains or may contain a RHD*r'$^S$ haplotype, as indicated in Table 1.

Preferably, the method further comprises: (4) determining the genotype of a sample at one or more positions in exon 3, and deducing from the genotype whether or not the sample contains or may contain an RHD/RHCE hybrid exon 3.

Preferably, the method further comprises: determining the genotype of a sample at one or more polymorphic positions in the region between IVS7+2153 and IVS7+2335, said positions IVS7+2153 and IVS7+2335 being included in said region; determining if the one or more polymorphic positions correspond to an RHD or RHCE sequence; and deducing from the genotype determination whether the sample comprises a RHD*r'$^S$ haplotype or an RHD*RIII_FN haplotype, as indicated in Table 1.

The value of the new knowledge described herein is furthered by the fact that the aforementioned RHD variants are often found in cis or together in the same sample with the RHCE variants, which may confound determination of a genotype, and consequently determination of presence or absence of certain RH-encoded blood group antigens, in the sample harboring them. The confounding effect affects the more common genotyping methods in use, in particular methods whose source material is genomic DNA. Advantageously, the present invention mitigates this undesirable confounding effect.

The term "sample" as used herein is intended to encompass any material (solid, liquid or aspirate) obtained directly or indirectly from a human subject and from which the identity of one or more nucleotides in a relevant genomic locus (e.g. intron 7 or the RHD locus and/or intron 7 of the RHCE locus) can be determined. In particular, the term "sample" includes any biological fluid such as blood, plasma, urine, saliva, cerebrospinal fluid and interstitial fluid, any solid matter, such as tissue, bone and hair, any cell or cell extract, any derived cell line, such as an immortalised tumour cell line and stem cell line, an extract of any of the preceding sample types, such as fixed or paraffin-embedded tissue. In certain preferred embodiments, the sample is an extract of human genomic DNA, optionally amplified and/or purified.

As used herein, the term "genotyping" is intended to encompass any method for determining the identity of the nucleotide at a particular position such as a polymorphic position at a specified locus. Thus, genotyping includes identifying one or both alleles of a particular gene. Genotyping may employ any of a variety of techniques, including but not limited to, allele-specific hybridisation, allele-specific PCR, sequencing of all or part of a gene.

As described herein in detail, certain blood type alleles are less common and a typically referred to as "variants" (e.g. RHD*r'$^{S}$). Variant blood type alleles are in some cases referred to herein simply as "blood type variants".

TABLE 1

On the horizontal axis, the variants whose sequences are described in the present invention (RHD*r'$^{S}$, RHD*DIIIa, RHD*DIII_FN, RHD*DIVa-2, RHCE*ce$^{S}$, RHCE*ce733G), and their respective references (RHD, RHCE*ce). On the vertical axis, the relevant polymorphic positions in intron 7 of the RHD and RHCE loci (the region of interest). The SNP position numbering is as shown in the alignment of FIG. 3. The RHD reference sequence column shows the identity of the nucleotide at each of the indicated positions in intron 7 of the reference RHD gene. The RHCE*ce reference sequence column shows the identity of the nucleotide at each of the indicated positions in intron 7 of the reference RHCE gene. The RHD*r's variant sequence column shows the identity of the nucleotide at each of the indicated positions in intron 7 of the RHD*r's variant of the RHD gene (RHD locus). The RHD*DIIIa variant sequence column shows the identity of the nucleotide at each of the indicated positions in intron 7 of the RHD*DIIIa variant of the RHD gene (RHD locus). The RHD*DIII_FN variant sequence column shows the identity of the nucleotide at each of the indicated positions in intron 7 of the RHD*DIII_FN variant of the RHD gene (RHD locus). The RHD*DIVa-2 variant sequence column shows the identity of the nucleotide at each of the indicated positions in intron 7 of the RHD*DIVa-2 variant of the RHD gene (RHD locus). The RHCE*ce$^{s}$ variant sequence column shows the identity of the nucleotide at each of the indicated positions in intron 7 of the RHCE*ce$^{s}$ variant of the RHCE gene (RHCE locus). The RHCE*Ce733G variant sequence column shows the identity of the nucleotide at each of the indicated positions in intron 7 of the RHCE*ce733G variant of the RHCE gene (RHCE locus).

| | Reference Sequence | | Variant Sequence | | | | | |
|---|---|---|---|---|---|---|---|---|
| SNP position | RHD | RHCE*ce | RHD*r'$^{s}$ | RHD*DIIIa | RHD*DIII_FN | RHD*DIVa-2 | RHCE*ce$^{s}$ | RHCE*ce733G |
| IVS7 + 1139 | C | T | T | C | C | C | | |
| IVS7 + 1148 | G | A | A | G | G | G | | |
| IVS7 + 1234 | C | C | T | T | T | T | | |
| IVS7 + 1241 | A | T | T | A | A | A | | |
| IVS7 + 1276 | C | G | G | C | C | C | | |
| IVS7 + 1319 | A | Ø | A | A | A | A | | |
| IVS7 + 1356 | T | C | C | C | C | T | | |
| IVS7 + 1758 | T | G | G | T | T | T | | |
| IVS7 + 1765 | A | G | G | A | A | A | | |
| IVS7 + 1782 | A | Ø | Ø | A | A | A | | |
| IVS7 + 1850 | G | A | A | G | G | G | | |
| IVS7 + 1869 | G | A | A | G | G | G | | |
| IVS7 + 1880 | A | G | G | A | A | A | | |
| IVS7 + 1886 | A | G | G | A | A | A | | |
| IVS7 + 1887 | T | C | C | T | T | T | | |
| IVS7 + 2153 | G | C | C | C | G | G | | |
| IVS7 + 2160 | T | C | C | C | T | T | | |
| IVS7 + 2200 | A | T | T | T | A | A | | |
| IVS7 + 2235 | C | T | T | T | C | C | | |
| IVS7 + 2276 | C | A | A | A | C | C | | |
| IVS7 + 2282 | A | G | G | G | A | A | | |
| IVS7 + 2323 | C | T | T | T | C | C | | |
| IVS7 + 2335 | A | G | G | G | A | A | | |
| IVS7 + 2449 | T | C | C | C | C | T | | |
| IVS7 + 2472 | A | G | G | G | G | A | | |
| IVS7 + 2514 | A | G | G | G | G | A | | |
| IVS7 + 2539 | C | T | T | T | T | C | | |
| IVS7 + 2591 | G | A | A | A | A | G | | |
| IVS7 + 2620 | C | G | G | G | G | C | | |
| IVS7 + 2782 | T | A | A | A | A | T | | |
| IVS7 + 2802 | A | T | T | T | T | A | | |
| IVS7 + 2846 + 1 | Ø | T | T | T | T | Ø | | |
| IVS7 + 2945 | G | T | G | G | G | G | | |
| IVS7 + 2970 | C | T | T | T | T | C | T | T |
| IVS7 + 2973 | G | T | T | T | T | G | T | T |
| IVS7 + 2977 | A | G | G | G | G | A | G | G |
| IVS7 + 3026 | C | T | C | C | C | C | C | C |
| IVS7 + 3046 | C | T | T | T | T | C | T | T |
| IVS7 + 3099 | C | G | G | G | G | C | G | G |
| IVS7 + 3101 | C | C | T | T | T | C | T | T |
| IVS7 + 3257 | C | Ø | C | C | C | C | C | C |

TABLE 1-continued

On the horizontal axis, the variants whose sequences are described in the present invention (RHD*r'$^S$, RHD*DIIIa, RHD*DIII_FN, RHD*DIVa-2, RHCE*ce$^S$, RHCE*ce733G), and their respective references (RHD, RHCE*ce). On the vertical axis, the relevant polymorphic positions in intron 7 of the RHD and RHCE loci (the region of interest). The SNP position numbering is as shown in the alignment of FIG. 3. The RHD reference sequence column shows the identity of the nucleotide at each of the indicated positions in intron 7 of the reference RHD gene. The RHCE*ce reference sequence column shows the identity of the nucleotide at each of the indicated positions in intron 7 of the reference RHCE gene. The RHD*r's variant sequence column shows the identity of the nucleotide at each of the indicated positions in intron 7 of the RHD*r's variant of the RHD gene (RHD locus). The RHD*DIIIa variant sequence column shows the identity of the nucleotide at each of the indicated positions in intron 7 of the RHD*DIIIa variant of the RHD gene (RHD locus). The RHD*DIII_FN variant sequence column shows the identity of the nucleotide at each of the indicated positions in intron 7 of the RHD*DIII_FN variant of the RHD gene (RHD locus). The RHD*DIVa-2 variant sequence column shows the identity of the nucleotide at each of the indicated positions in intron 7 of the RHD*DIVa-2 variant of the RHD gene (RHD locus). The RHCE*ce$^s$ variant sequence column shows the identity of the nucleotide at each of the indicated positions in intron 7 of the RHCE*ce$^s$ variant of the RHCE gene (RHCE locus). The RHCE*Ce733G variant sequence column shows the identity of the nucleotide at each of the indicated positions in intron 7 of the RHCE*ce733G variant of the RHCE gene (RHCE locus).

| | Reference Sequence | | Variant Sequence | | | | | |
|---|---|---|---|---|---|---|---|---|
| SNP position | RHD | RHCE*ce | RHD*r'$^s$ | RHD*DIIIa | RHD*DIII_FN | RHD*DIVa-2 | RHCE*ce$^s$ | RHCE*ce733G |
| IVS7 + 3258 | C | Ø | C | C | C | C | C | C |
| IVS7 + 3259 | C | Ø | C | C | C | C | C | C |
| IVS7 + 3260 | C | Ø | C | C | C | C | C | C |
| IVS7 + 3261 | A | Ø | A | A | A | A | A | A |
| IVS7 + 3262 | A | Ø | A | A | A | A | A | A |
| IVS7 + 3349 | C | C | T | T | T | C | T | T |
| IVS7 + 3489 | G | A | G | G | G | G | G | G |
| IVS7 + 3521 | G | C | C | C | C | G | G | G |
| IVS7 + 3523 | T | A | A | A | A | T | T | T |
| IVS7 + 3525 | T | T | T | T | T | T | G | G |
| IVS7 + 3648 | T | C | T | T | T | T | C | C |
| IVS7 + 3961 | T | G | T | T | T | T | T | T |
| IVS7 + 3975 | T | G | T | T | T | T | T | T |
| IVS7 + 3981 | G | A | G | G | G | G | G | G |
| IVS7 + 4052 | A | G | A | A | A | A | G | G |
| IVS7 + 4105 | G | A | G | G | G | G | A | A |
| IVS7 + 4106 | T | C | T | T | T | T | C | C |
| IVS7 + 4107 | G | T | G | G | G | G | T | T |
| IVS7 + 4108 | G | C | G | G | G | G | C | C |

Key to Table 1

Ø: No nucleotide (position corresponds to a gap in the alignment set forth in FIG. 3).

Broadly, the present invention provides methods and products for the identification by molecular techniques of genetic variants RHD*r'$^S$ or RHD*r'$^S$-like, which encode no D antigen ($D^-$), an altered form of D antigen (partial D), altered C antigen ($C^{+W}$), altered e antigen ($e^{alt}$), VS antigen ($VS^+$), V antigen ($V^+$), and/or no hr$^B$ antigen (hr$^{B-}$) in blood cells. The present inventors have found that a determination of one or more genetic sequences in a region of intron 7 of the RHD locus enables discrimination between variants RHD*r'$^S$ or RHD*r'$^S$-like and other RHD/RHCE hybrid exon 3 variants, including but not limited to RHD*DIIIa, RHD*DIII_FN and RHD*DIVa-2. The present inventors have also found that a determination of one or more genetic sequences in a region of intron 7 of the RHCE locus enables discrimination between variants RHCE*ce$^S$ or RHCE*ce733G and conventional RHCE. Determination of said sequences in turn, enables prediction of the D antigen and C antigen phenotype for a large majority of samples containing RHD/RHCE hybrid exon 3, as well as prediction of e antigen, VS antigen, V antigen and hrB antigen for a large number of samples containing variants RHCE*ce$^S$ or RHCE*ce733G. In certain embodiments, the method of the invention provides considerable efficiency savings in comparison with, for example, full DNA sequencing, or genotyping of a large number of polymorphisms, or determining the phenotype by serological methods. Nevertheless, it is specifically contemplated that the method of the invention may, in some cases, involve DNA sequencing in order to genotype the sample obtained from the subject.

The RHD and RHCE variant sequences described herein have been determined by standard DNA sequencing, classified and consensuated from data for a set of samples known from serological and/or molecular typing methods to contain said variants. More specifically, the sample set consisted of seven samples containing the RHD*r'$^S$ variant, eleven samples containing the RHD*DIIIa variant, two samples containing the RHD*DIVa-2 variant, nine samples containing the RHCE*ce$^S$ variant, and three samples containing the RHCE*ce733G variant.

"Consensuated" as used herein specifically includes establishing by compilation and comparison of multiple highly-similar, non-identical sequences and selection of a single consensus sequence. "Consensuation" advantageously responds to the existence of sequence variations among samples containing the same variant.

In certain cases in accordance with the method of the invention, presence/absence of variant RHD*DIIIa or similar variants (including but not limited to RHD*DIII_FN, RHD*DIII-type4, RHD*DIII-type6, RHD*DIII-type7, RHD*DIII-type8) is determined by the combined identification of the nucleotide sequence at polymorphic positions IVS7+1887 and IVS7+2153, located in intron 7 of the RHD locus. Further determination of, e.g., one or more of the nucleotide sequence at one or more of polymorphic positions IVS7+2449, IVS7+2472, IVS7+2514, IVS7+2539, IVS7+2591, IVS7+2620, IVS7+2782, and IVS7+2802 may be employed in order to distinguish RHD*r'$^S$ from RHD*DIII_FN (in view of the fact that RHD*r'$^S$ and RHD*DIII_FN appear identical at the aforementioned positions IVS7+1887 and IVA7+2153 (see Table 1). As will be appreciated by reference to Table 1 and FIG. 1, the identification of the nucleotide at polymorphic position IVS+1887 may be substituted with a determination of the nucleotide sequence at one or more polymorphic positions located 5' of IVS7+1887, including but not limited to one or more of positions IVS7+1886, IVS7+1880, IVS7+1869, IVS7+1850 and IVS7+1782. Alternatively or additionally, the identification of the nucleotide at polymorphic position IVS7+2153 may be substituted with a determination of the nucleotide sequence at one or more polymorphic positions located 3' of IVS7+2153, including but not limited to one or more of positions IVS7+2160, IVS7+2200, IVS7+2235, IVS7+2276 and IVS7+2282. Each and every pair-wise or multiple combination of the polymorphic positions 5' of IVS7+1887 and 3' of IVS7+2153 is specifically contemplated herein. The determination that variant RHD*DIIIa or similar variants (including but not limited to RHD*DIII-type4, RHD*DIII-type6, RHD*DIII-type7, RHD*DIII-type8 and/or RHD*DIII_FN) is present in the sample may be made by positive identification of:

(i) RHD sequence at said position IVS7+1887 and/or at one or more polymorphic positions 5' of IVS7+1887 (including but not limited to one or more of positions IVS7+1886, IVS7+1880, IVS7+1869, IVS7+1850 and IVS7+1782); in combination with (ii) RHCE sequence at said position IVS7+2153 and/or at one or more polymorphic positions 3' of IVS7+2153 (including but not limited to one or more of positions IVS7+2160, IVS7+2200, IVS7+2235, IVS7+2276 and IVS7+2282).

Presence of RHD*DIII_FN may be distinguished from RHD*r'$^S$ by the presence of RHCE sequence at one or more polymorphic positions 3' of IVS7+2449 (including but not limited to one or more of positions IVS7+2449, IVS7+2472, IVS7+2514, IVS7+2539, IVS7+2591, IVS7+2620, IVS7+2782, IVS7+2802).

As will be appreciated by reference to FIG. 1 and Table 1, such pair-wise or multiple identification of (i) RHD sequence and (ii) RHCE sequence at the indicated intron 7 positions is characteristic of RHD*DIIIa and similar variants (including but not limited to RHD*DIII-type4, RHD*DIII-type6, RHD*DIII-type7, RHD*DIII-type8), but is not characteristic of RHD*r's or RHD*DIVa-2.

In certain cases in accordance with the method of the invention, presence/absence of variants RHD*r'$^S$ or RHD*DIIIa or similar variants (including but not limited to RHD*r'$^S$-like, RHD*DIII_FN, RHD*DIII-type4, RHD*DIII-type6, RHD*DIII-type7, RHD*DIII-type8) is determined by the combined identification of the nucleotide sequence at polymorphic positions IVS7+3523 and IVS7+3648, located in intron 7 of the RHD locus. As will be appreciated by reference to Table 1 and FIG. 1, the identification of the nucleotide at polymorphic positions IVS7+3523 and IVS7+3648 may be substituted by determination of the nucleotide sequence at one or more polymorphic positions located 5' of IVS7+3523 and 3' of IVS7+3648, respectively. The latter positions include but are not limited to IVS7+3521, IVS7+3099, IVS7+3046, IVS7+2977, IVS7+2973 on the 5' of IVS7+3523 and IVS7+3961, IVS7+3975, IVS7+3981, IVS7+4052, IVS7+4105 on the 3' of IVS7+3648. Each and every pair-wise combination of the polymorphic positions 5' of IVS7+3523 and 3' of IVS7+3648 is specifically contemplated herein.

In certain cases in accordance with the method of the invention, presence/absence of variants RHCE*ce$^S$ or RHCE*ce733G or similar variants (including but not limited to RHCE*ce48C,733G,1025T, RHCE*ce48C,697G,733G, RHCE*ce340T,733G, RHCE*ce48C,733G,748A) is determined by the combined identification of the nucleotide sequence at polymorphic positions IVS7+3981 and IVS7+4052, located in intron 7 of the RHCE locus. As will be appreciated by reference to Table 1 and FIG. 1, determination of the nucleotide sequence at polymorphic positions IVS7+3981 and IVS7+4052 may be substituted by determination of the nucleotide sequence at one or more polymorphic positions located 5' of IVS7+3981 and 3' of IVS7+4052, respectively. The latter positions include but are not limited to IVS7+3975, IVS7+3961, IVS7+3523, IVS7+3521, IVS7+3489 on the 5' of IVS7+3981 and IVS7+4105, IVS7+4106, IVS7+4107, IVS7+4108, IVS7+4127 on the 3' of IVS7+4052. Each and every pair-wise combination of the polymorphic positions 5' of IVS7+3981 and 3' of IVS7+4052 is specifically contemplated herein.

In certain cases in accordance with the method of the invention, presence/absence of variants RHD*r'$^S$, RHD*DIIIa, RHD*DIVa-2 or similar variants (including but not limited to RHD*r'$^S$-like, RHD*DIII_FN, RHD*DIII-type4, RHD*DIII-type6, RHD*DIII-type7, RHD*DIII-type8, RHD*DIVa) can be determined by the identification of the nucleotide sequence at a single polymorphic position, such as IVS7+1234, located in intron 7 of the RHD locus. As shown in Table 1 and FIG. 1, the identity of the nucleotide at position IVS7+1234 of the RHD locus (T in the case of the variants RHD*r'$^S$, RHD*DIIIa, RHD*DIII_FN, RHD*DIVa-2) differs from both the RHD reference sequence and the RHCE reference sequence. Therefore, the identification of a nucleotide that is non-RHD and non-RHCE at position IVS7+1234 of the RHD locus is indicative of the sample containing a variant selected from RHD*r'$^S$, RHD*DIIIa, RHD*DIVa-2 and similar variants (including but not limited to RHD*r'$^S$-like, RHD*DIII_FN, RHD*DIII-type4, RHD*DIII-type6, RHD*DIII-type7, RHD*DIII-type8 and RHD*DIVa).

In certain cases in accordance with the method of the invention, presence/absence of variants RHCE*ce$^S$ or RHCE*ce733G or similar variants (including but not limited to RHCE*ce48C,733G,1025T, RHCE*ce48C,697G,733G, RHCE*ce340T,733G, RHCE*ce48C,733G,748A) is determined by the identification of the nucleotide at a single polymorphic position, such as IVS7+3525, located in intron 7 of the RHCE locus. As shown in Table 1 and FIG. 1, the identity of the nucleotide at position IVS7+3525 of the RCE locus (G in the case of the variants RHCE*ce$^S$ and RHCE*ce733G) differs from both the RHD reference sequence and the RHCE reference sequence. Therefore, the identification of a nucleotide that is non-RHD and non-RHCE at position IVS7+3525 of the RHCE locus is indicative of the sample containing a variant selected from RHCE*ce$^S$, RHCE*ce733G and similar variants (including but not limited to RHCE*ce48C,733G,1025T, RHCE*ce48C,697G,733G, RHCE*ce340T,733G, RHCE*ce48C,733G,748A).

As will be apparent to the skilled person having regard to Table 1 and FIG. 1 herein, the RHD and RHCE variants exhibit characteristic and in some cases unique combinations of nucleotide identities at the specified SNP positions in intron 7 of RHD and of RHCE. These may be exploited to discriminate among RHD and/or RHCE variants, as required. The various combinations and variations that are made available by the information disclosed herein are within the scope of the present invention as set out in the appended claims.

A wide variety of techniques are suitable and may be used to detect these genetic sequences, e.g. to determine the identity of the nucleotide at one or more polymorphic positions in intron 7 of RHD and/or RHCE for a sample under consideration. The following are presented as non-limiting examples of such techniques. A suitable technique to detect the herein mentioned genetic sequences is mutation analysis by restriction digestion after a PCR reaction for amplifying the region of interest, if the genetic variant or polymorphism results in the creation or elimination of a restriction site. Sequence analysis, such as direct manual or fluorescent automated sequencing, directly or after selection of the region of interest by PCR, can also be used to detect specific sequences. Allele-specific oligonucleotides, for example, used in a competitive or non-competitive PCR (ASP henceforth), can also be used to detect genetic variants. Another suitable technique to detect specific sequences in a sample is testing that sample for the presence of a nucleic acid molecule comprising all or a portion of the region of interest, consisting in contacting said sample with a second nucleic acid molecule or probe under conditions for selective hybridization. In any of these techniques, all or a part of the region of interest can be amplified prior to performing the specific technique used for detection of the genetic variants.

The method makes use of the detection or lack of detection of one or more specific nucleotide sequences within the region of interest or within a "functional segment", such as an intron or an exon (e.g. intron 7 of RHD or RHCE) or part thereof.

In certain cases, the method of the invention makes use of Allele-Specific Hybridization (ASH henceforth), and may make use of synthetic oligonucleotide probes usually 10-50 nucleotides long, preferably 19-27 nucleotides long, the sequences of which are designed to be complementary to the interrogated sequence. Complementarity of sequences enables pairing of genomic DNA and oligonucleotide probe molecules. Specific pairing, i.e. pairing of probes to their complementary sequence and to no other sequence, can be made to occur under appropriate conditions, which include but are not limited to time of incubation, temperature of incubation, concentration of probe and complementary sequences, and mixing. Specific pairing to probes allows detection of sequences in a mix of sequences. Detection or lack of detection of specific sequences, in turn, allows determination of presence versus absence of functional segments or regions of interest.

Synthetic oligonucleotide probes can be used for the detection of particular conserved, non-variant regions and/or allelic variants in an individual's genomic DNA. Often, allelic variants are single nucleotide polymorphisms (SNPs), i.e. nucleotide positions at which the DNA composition may vary across individuals.

In some cases, the synthetic oligonucleotide probes described herein are designed and used to detect the presence or absence of functional nucleic acid segments and also, both to detect allelic variants located within sequences and to determine the presence or absence of functional segments or regions of interest.

Given a particular nucleotide at a particular position of a locus of genomic DNA, synthetic oligonucleotide molecules, or probes, can be designed to detect said nucleotide in a test sample. Probes can be designed in pairs such that one member of the probe pair is complementary to one strand of the sequence, whereas the other member of the probe pair is complementary to the other strand of the sequence. Probes can also be designed in sets so that they have different lengths and be complementary to one strand or the two strands of the sequence of interest.

In accordance with any aspect of the present invention, probes may be attached to a chemically-functionalized solid support. An example of a solid support is a flat glass surface, on which probe molecules are placed by contact deposition. Another example of a solid support is a micrometer-size polymer bead, to which probe molecules are attached by conjugation. Another example of a solid support is a nanometer-size particle to which probe molecules are attached by one of various means. An exemplary description herein relates to the procedure performed wherein the probes are immobilised on a flat glass surface. Attachment of probe molecules to the surface is performed at multiple individual locations referred to as replicate features or "replicates". The number of replicate features for each probe species is usually ten, although it may vary. Another exemplary description herein relates to the procedure performed wherein the probes are immobilised on a micron-size spherical surface. Attachment of probe molecules is performed at multiple individual spherical surfaces, referred to as replicate features or "replicates". The number of replicate features for each probe species is usually one hundred, although it may vary.

In accordance with any aspect of the present invention, functional segments or their portions may be amplified, for example by PCR, using as a template genomic DNA. Amplified functional segments or their portions can be labeled (e.g. with a fluorescent label) to allow for their detection, and optionally fragmented to facilitate their pairing with oligonucleotide probes.

In accordance with any aspect of the present invention, labelled and fragmented functional segments or their portions may be incubated under conditions that maximize the sensitivity and specificity of pairing with probes attached to the solid support. The presence of probe-paired functional segments or their portions may be determined indirectly from the measurement of label, usually a fluorochrome, attached to the solid support. This measurement is referred to herein as signal intensity. By way of example, the fluorescence emitted by the fluorochrome may be collected by means of a fluorescence detection device, such as a confocal scanner.

EXAMPLES

Example 1

Discrimination among genetic variants that share a RHD/RHCE hybrid exon 3 but encode different forms of D Ag (Partial D Ag vs. No D Ag) and RhC Ag (Normal C Ag vs. Altered/Weakened C Ag, sometimes abbreviated as $C^{+W}$)

The following example relates to a method of discriminating among RHD/RHCE hybrid exon 3 variants RHD*r's, RHD*DIIIa and RHD*DIVa-2. The method is based on the interrogation of the nucleotide composition of the genomic DNA of a sample at three locations in the RHD locus.

Identification of the nucleotide at a first location enables discrimination between variants RHD*r's/RHD*DIIIa and variant RHD*DIVa-2, and involves an ASP. In particular, this ASP interrogates polymorphic positions IVS7+3349, IVS7+4105, IVS7+4106, IVS7+4107, IVS7+4108, IVS7+4127 in RHD intron 7.

Identification of the nucleotide composition at a second location enables discrimination between variants RHD*r's and RHD*DIIIa, and involves an ASP. In particular, this ASP interrogates polymorphic positions IVS7+1869, IVS7+1880, IVS7+1886, IVS7+1887, IVS7+2276, IVS7+2282 in RHD intron 7.

Optionally, but in many cases very preferably, identification of the nucleotide composition at a third location may be carried out in order to determine the presence or absence of a RHD/RHCE hybrid exon 3 in the test sample, and involves molecular techniques known in the art as ASP and ASH. In particular, the RHD/RHCE hybrid exon 3 ASP interrogates polymorphic positions IVS2-26, IVS2-13, IVS2-8 in RHD intron 2 and polymorphic positions IVS3+64, IVS3+69 in RHD intron 3, while the ASH interrogates polymorphic position c.410 in RHD exon 3.

The method described above is applied to 252 samples selected to contain either no variant in either copy of the RHD gene, one variant in one copy of the RHD gene, or two variants, one on each copy of the RHD gene. Determination of the presence or absence of variants is made from DNA sequencing data as well as from genotyping data at polymorphisms in the RHD locus including certain positions shared with the present method and certain positions other than the ones described in the present method. Said samples are selected to include RHD variants encoding the major RhD phenotypes, namely RhD+, Partial D, Weak D, RhD⁻.

The process described below proceeds from the genotyping of said samples and the posterior analysis of said samples grouped by genotype and/or predicted phenotype. The serotype associated to a group corresponds to analysis performed only on a subset of the samples in said group.

Materials & Methods

Genomic DNA is extracted from nucleated cells in a blood sample by cell lysis. Extracted DNA is purified on an affinity column. Both, cell lysis and DNA purification are performed with a QIAamp Blood kit (Qiagen, Germany) by following manufacturer protocols and recommendations. Purity of DNA is determined by spectrophotometry on a Nanodrop instrument (Nanodrop, DE). Only DNA solutions with an $OD_{260}/OD_{280}$ 1.8±0.2 proceed to subsequent analysis.

Purified DNA is used as a template for multiplexed Polymerase Chain Reaction (PCR) amplification of the gene segments of interest in a GeneAmp 9700 thermal cycler (Perkin-Elmer, CA). Primer sequences for the different segments are listed in the Technical Description section. Cycling conditions consist of a denaturation/polymerase activation step at 95° C. for 15 min, followed by 38 cycles of denaturation at 95° C. for 45 sec, annealing at 60° C. for 60 sec, extension at 72° C. for 90 sec, and a final extension step at 72° C. for 10 min.

Amplified DNA is enzymatically fragmented by incubation with DNase I (Promega, WI) and alkaline phosphatase (Roche, Germany) at 37° C. for 30 min, followed by enzyme inactivation at 95° C. for 10 min.

Fragmented DNA is labeled by incubation with TdT enzyme (Roche, Germany) and biotin-ddUTP (Perkin-Elmer, CA) at 37° C. for 60 min.

Labelled DNA is placed on a proprietary microarray (Progenika Biopharma, S.A.). The microarray comprises a modified crystal surface to which allele-specific oligonucleotide probes are covalently attached. Probes are designed to interrogate multiple allelic variant positions in the amplified genomic segments. Each allelic variant is interrogated by 2 probes, for a total of 4 probes per SNP. Each probe is printed 10 times on the microarray, for a total of 40 features (spots) per SNP. Probe sequences are listed in the Technical Description section. The labelled DNA/microarray interface is placed in an incubation chamber of a HS 4800 Pro station (Tecan, Switzerland) and is incubated at 47° C. for 30 min and at 45° C. for 60 min in buffer containing SSPE, dextran, and deionized formamide to allow for probes to hybridize (bind) to their cognate sequences, when present. Unbound DNA is washed off by incubation at 23° C. for various times with buffer containing SSC with or without SDS. A streptavidin-Cy3 conjugate (Invitrogen, CA) diluted in buffer containing PBS and Tween-20 is added to the microarray surface and further incubated at 37° C. for 10 min. Unbound conjugate is washed off as before. The microarray is dried by flushing high-pressure liquid nitrogen through the incubation chamber.

Microarray-bound Cy3 fluorescence is detected on InnoScan 710, a confocal scanner (Innopsys, France) and is quantitated by ad hoc software.

Proprietary software (Progenika Biopharma, S.A.) is used to transform fluorescence intensity values for the particular allelic variants detected, singly or in combination, into blood group genotypes, and from genotypes into predicted blood group phenotypes.

Technical Description

Amplifications and hybridizations for determination of the three genetic sequences are performed as follows:

Amplification of RHD/RHCE Hybrid Exon 3 by ASP

Oligonucleotide primers that bind to intron 2 and intron 3 sequences in the RHD locus are used. The target sequence of the forward (upstream) primer, located in intron 2, is RHD-specific. The target sequence of the reverse (downstream) primer, located in intron 3, is RHCE-specific. The size of the PCR product is 270 base pairs when the following sequences are used:

```
                                      (SEQ ID NO: 5)
Forward primer:   5'-CGTCCTGGCTCTCCCTCTCT-3'

                                      (SEQ ID NO: 6)
Reverse primer:   5'-TATTTTTCAAAACCCCGGAAG-3'
```

In boldface, RHD-specific nucleotides (forward primer) and RHCE-specific nucleotides (reverse primer).

It is possible to use different primers provided that the primers enable specific, partial or complete, amplification of the RHD/RHCE hybrid exon 3 that characterizes variants RHD*r's, RHD*DIIIa, RHD*DIVa-2, among others.

Hybridization to RHD/RHCE Hybrid Exon 3 by ASH

Oligonucleotide probes that specifically bind to the non-coding strand of either RHD/RHCE hybrid exon 3 sequences or conventional RHD/RHCE exon 3 sequences are employed. The specificity of these probes hinges upon the allelic form present at a single polymorphic position, usually, but not necessarily, located at the center of the target sequence. One allelic form is detected by the RHD/RHCE hybrid exon 3-specific probe, the other by the consensus RHD/RHCE exon 3-specific probe. The size of the target sequence is 23 base pairs when the following sequences are used:

```
RHD/RHCE hybrid exon 3-specific probe:
5'-ggtcaacttggTgcagttggtgg-3'     (SEQ ID NO: 7)

reference RHD/RHCE-specific probe:
5'-ggtcaacttggCgcagttggtgg-3'     (SEQ ID NO: 8)
```

In boldface, the two allelic forms at the exon 3 polymorphic position.

It is possible to use oligonucleotide probes that differ from the previously described probes in sequence, length, or any other feature, provided that they enable specific, partial or complete, hybridization to the RHD/RHCE hybrid exon 3 that characterizes variants RHD*r's, RHD*DIIIa, RHD*DIVa-2.

Amplification of a Segment ("Segment #2") of RHCE/RHD Hybrid Intron 7 by ASP

Oligonucleotide primers that bind to intron 7 sequences in the RHD locus are used. The target sequence of the forward (upstream) primer is RHD specific. The target sequence of the reverse (downstream) primer is RHCE specific. The size of the PCR product is 438 base pairs when the following sequences are used:

```
                                           (SEQ ID NO: 9)
Forward primer:   5'-CAAGCTGTCAAGGAGACATCACTAT-3'

                                          (SEQ ID NO: 10)
Reverse primer:   5'-CATTACATAGAGATGTCCCCATACT-3'
```

In boldface, RHD-specific nucleotides (forward primer) and RHCE-specific nucleotides (reverse primer).

It is possible to use oligonucleotide primers that differ from the previously described primers in sequence, length, or any other feature, provided that they enable specific, partial or complete, amplification of the RHCE/RHD hybrid intron 7 that characterizes variants RHD*r's, RHD*DIIIa.

Hybridization to Segment #2 of RHCE/RHD Hybrid Intron 7 by ASH

An oligonucleotide probe that specifically binds to the non-coding strand of RHCE intron 7 sequences within the segment amplified by ASP is used. The specificity of this probe hinges upon the allelic forms present at two polymorphic positions, usually but not necessarily located around the center of the target sequence. The probe hybridizes to the target sequence when the appropriate allelic forms are present on it, but does not when replaced by other allelic forms, whether found in the population or not. The size of the target sequence is 27 base pairs when the following sequence is used:

```
Hybrid RHD/RHCE intron 7-specific probe:
                                          (SEQ ID NO: 11)
5'-CCTGGTACTCAAACTCCCTAAATCTCA-3'
```

It is possible to use an oligonucleotide probe or probes that differ from the previously described probe in sequence, length, or any other feature, as long as such probe or probes enable specific, partial or complete, hybridization to the RHD/RHCE hybrid intron 7 that characterizes variants RHD*r's, RHD*DIIIa, RHD*DIVa-2.

Amplification of a Further Segment ("Segment #4") of RHD/RHCE Hybrid Intron 7 by ASP Oligonucleotide primers that bind to intron 7 sequences in the RHD locus are used. The target sequence of the forward (upstream) primer is RHD specific. The target sequence of the reverse (downstream) primer is RHCE specific. The size of the PCR product is 305 base pairs when the following sequences were used:

```
Forward primer:
5'-GCCACTTATTACTTAAAAAAACCCC-3' (SEQ ID NO: 12)

Reverse primer:
5'-AAGGCCCTTCCTCCAAATAG-3'      (SEQ ID NO: 13)
```

In boldface, RHD-specific nucleotides (forward primer) and RHCE-specific nucleotides (reverse primer).

It is possible to use oligonucleotide primers that differ from the previously described primers in sequence, length, or any other feature, provided that they enable specific, partial or complete, amplification of the RHD/RHCE hybrid intron 7 that characterizes variants RHD*r's, RHD*DIIIa, RHD*DIVa-2.

Hybridization to Segment #4 of RHD/RHCE Hybrid Intron 7 by ASH

Oligonucleotide probes that specifically bind to the non-coding strand of hybrid RHCE/RHD intron 7 sequences within the segment amplified by ASP are used. The specificity of these probes hinges upon the particular allelic form usually but not necessarily located at the central position, which hybridizes to the target sequence when present on the probe, but does not when replaced by another allelic form, whether found in the population or not. The size of the target sequence is either 27 or 25 base pairs, respectively, when the following sequences are used:

```
RHD/RHCE hybrid intron 7-specific probe:
                                          (SEQ ID NO: 14)
5'-AATTTCATGTGCTGGAAACTTAATCCT-3'

RHD/RHCE hybrid intron 7-specific probe:
                                          (SEQ ID NO: 15)
5'-ATTTCATGTGCTGGAAACTTAATCC-3'
```

In boldface, the allelic form at the intron 7 polymorphic position.

It is possible to use oligonucleotide probes that differ from the previously described probes in sequence, length, or any other feature, provided that they enable specific, partial or complete, hybridization to the RHD/RHCE hybrid intron 7 that characterizes variants RHD*r's, RHD*DIIIa, RHD*DIVa-2.

A total of 252 selected samples known to contain consensus RHD, consensus RHCE, variant RHD or variant RHCE are analyzed as a test of the genotyping method described herein. The results can be shown in Table 2. Expected results correspond to data generated through the analysis of genomic DNA by one or more of the following:

A genotyping microarray that interrogates 72 polymorphic positions in the RHD locus and 8 polymorphic positions in the RHCE locus.

ASP to determine the presence or absence of Hybrid exon 3 (Hyb ex03).

ASP to determine the presence or absence of Hybrid intron 7 segment #2 ("Hyb in07 sg02").

ASP to determine the presence or absence of Hybrid intron 7 segment #4 ("Hyb in07 sg04").

Observed results correspond to data generated through the analysis of genomic DNA by a flow-cytometry-based genotyping test that combines ASP and ASH, as described in the Technical Description section above, to interrogate the three polymorphisms at Hyb ex03, Hyb in07 sg02, Hyb in07 sg04 that characterize variants RHD*r's, RHD*DIIIa, RHD*DIVa-2.

Table 2 lists samples alphabetically and includes for each one of them the following information:
RHD genotype at both alleles.
Known Hyb ex03 genotype.
Reference Method Hyb in07 sg02 genotype.
Method of the invention Hyb in07 sg02 genotype.
Reference Method Hyb in07 sg04 genotype.
Method of the invention Hyb in07 sg04 genotype.
Reference Method RHD*r's (r's) call.
Method of the invention r's call.

TABLE 2

| | | | | | Hyb in07 sg02 | | Hyb in07 sg04 | | RHD*r's | |
|---|---|---|---|---|---|---|---|---|---|---|
| # | Sample ID | RHD allele #1 | RHD allele #2 | Hyb ex03 | Reference | Method of the invention | Reference | Method of the invention | Reference | Method of the invention |
| 1 | A2Y53 | RHD | RHD/RHDdel | Absent | Absent | | Absent | | No r's | |
| 2 | AYU48 | RHD | RHD/RHDdel | Absent | Absent | | Absent | | No r's | |
| 3 | AYU53 | RHD | RHD/RHDdel | Absent | Absent | | Absent | | No r's | |
| 4 | AZJ10 | RHDdel | RHDdel | Absent | Absent | | Absent | | No r's | |
| 5 | BAT15 | RHD | RHD/RHDdel | Absent | Absent | | Absent | | No r's | |
| 6 | BBA07 | RHD | RHD/RHDdel | Absent | Absent | | Absent | | No r's | |
| 7 | BC0078 | wDt3 | wDt3/RHDdel | Absent | Absent | | Absent | | No r's | |
| 8 | BC0079 | DAR | DAR/RHDdel | Absent | Absent | | Absent | | No r's | |
| 9 | BC0080 | DAR | DAR/RHDdel | Absent | Absent | | Absent | | No r's | |
| 10 | BC0081 | DAR | DAR/RHDdel | Absent | Absent | | Absent | | No r's | |
| 11 | BC0082 | DAR | DAR/RHDdel | Absent | Absent | | Absent | | No r's | |
| 12 | BC0083 | r's | r's/RHDdel | Present | Absent | | Present | | r's | |
| 13 | BC0084 | r's | RHDdel | Present | Absent | | Present | | r's | |
| 14 | BC0085 | r's | r's/RHDdel | Present | Absent | | Present | | r's | |
| 15 | BC0086 | r's | RHD | Present | Absent | | Present | | r's | |
| 16 | BC0087 | r's | r's/RHDdel | Present | Absent | | Present | | r's | |
| 17 | BC0088 | RHDdel | RHDdel | Absent | Absent | | Absent | | No r's | |
| 18 | BC0089 | RHD | RHD/RHDdel | Absent | Absent | | Absent | | No r's | |
| 19 | BC0090 | RHD | RHD/RHDdel | Absent | Absent | | Absent | | No r's | |
| 20 | BC0091 | RHDdel | RHDdel | Absent | Absent | | Absent | | No r's | |
| 21 | BC0092 | RHDdel | RHDdel | Absent | Absent | | Absent | | No r's | |
| 22 | BC0093 | RHDdel | RHDdel | Absent | Absent | | Absent | | No r's | |
| 23 | BC0094 | DV | DV/RHDdel | Absent | Absent | | Absent | | No r's | |
| 24 | BC0095 | DV | DV/RHDdel | Absent | Absent | | Absent | | No r's | |
| 25 | BC0096 | DV | DV/RHDdel | Absent | Absent | | Absent | | No r's | |
| 26 | BC0097 | DV | DV/RHDdel | Absent | Absent | | Absent | | No r's | |
| 27 | BC0098 | RHD | RHD/RHDdel | Absent | Absent | | Absent | | No r's | |
| 28 | BC0099 | RHD | RHD/RHDdel | Absent | Absent | | Absent | | No r's | |
| 29 | BC0100 | RHD | RHD/RHDdel | Absent | Absent | | Absent | | No r's | |
| 30 | BC0101 | RHD | RHD/RHDdel | Absent | Absent | | Absent | | No r's | |
| 31 | BC0102 | RHD | RHD/RHDdel | Absent | Absent | | Absent | | No r's | |
| 32 | BC0103 | DIVa-2 | RHD | Present | Absent | | Absent | | No r's | |
| 33 | BC0104 | DIIIt4/DIIIt8 | RHD | Present | Absent | | Absent | | No r's | |
| 34 | BC0105 | DIVa-2 | Psi | Present | Absent | | Absent | | No r's | |
| 35 | BC0106 | DIVa-2 | DIVa-2/RHDdel | Present | Absent | | Absent | | No r's | |
| 36 | BC0107 | DIVa-2 | RHD | Present | Absent | | Absent | | No r's | |
| 37 | BC0108 | RHD | RHD/RHDdel | Absent | Absent | | Absent | | No r's | |
| 38 | BC0109 | RHD | RHD/RHDdel | Absent | Absent | | Absent | | No r's | |
| 39 | BC0110 | RHD Variant | RHDdel | Absent | Absent | | Absent | | No r's | |
| 40 | BC0111 | RHD | RHD/RHDdel | Absent | Absent | | Absent | | No r's | |
| 41 | BC0112 | RHD Variant | RHDdel | Absent | Absent | | Absent | | No r's | |
| 42 | BC0113 | wDt4.0/4.1 | RHD | Absent | Absent | | Present | | No r's | |
| 43 | BC0114 | RHD | RHD/RHDdel | Absent | Absent | | Absent | | No r's | |
| 44 | BC0115 | RHD | RHD/RHDdel | Absent | Absent | | Absent | | No r's | |
| 45 | BC0116 | RHD | RHD/RHDdel | Absent | Absent | | Absent | | No r's | |
| 46 | BC0117 | RHD | RHD/RHDdel | Absent | Absent | | Absent | | No r's | |
| 47 | BC0118 | RHD | RHD/RHDdel | Absent | Absent | | Absent | | No r's | |
| 48 | BC0119 | RHD | RHD/RHDdel | Absent | Absent | | Absent | | No r's | |
| 49 | BC0120 | RHD | RHD/RHDdel | Absent | Absent | | Absent | | No r's | |
| 50 | BC0121 | RHD | RHD/RHDdel | Absent | Absent | | Absent | | No r's | |
| 51 | BC0122 | RHD | RHD/RHDdel | Absent | Absent | | Absent | | No r's | |
| 52 | BC0123 | DAR | RHD | Absent | Absent | | Absent | | No r's | |
| 53 | BC0124 | RHD | RHD/RHDdel | Absent | Absent | | Absent | | No r's | |
| 54 | BC0125 | RHD | RHD/RHDdel | Absent | Absent | | Absent | | No r's | |
| 55 | BC0126 | RHD | RHD/RHDdel | Absent | Absent | | Absent | | No r's | |
| 56 | BC0127 | RHD | RHD/RHDdel | Absent | Absent | | Absent | | No r's | |
| 57 | BC0128 | RHD | RHD/RHDdel | Absent | Absent | | Absent | | No r's | |
| 58 | BC0129 | RHD | RHD/RHDdel | Absent | Absent | | Absent | | No r's | |
| 59 | BC0130 | DV | DV/RHDdel | Absent | Absent | | Absent | | No r's | |
| 60 | BC0131 | RHD | RHD/RHDdel | Absent | Absent | | Absent | | No r's | |
| 61 | BC0132 | RHD | RHD/RHDdel | Absent | Absent | | Absent | | No r's | |
| 62 | BCGEN446 | DIVa-2 | DIVa-2/RHDdel | Present | Absent | | Absent | | No r's | |
| 63 | BGG-09-0032 | DIIIa | DIIIa/RHDdel/r's | Present | Present | | Present | | | |
| 64 | BGG-09-0084 | r's | RHD | Present | Absent | | Present | | r's | |
| 65 | BGG-09-0216 | r's | RHD | Present | Absent | | Present | | r's | |
| 66 | BGG-09-0275 | DIIIa | RHD Variant | Present | Present | | Present | | No r's | |
| 67 | BGG-09-0281 | DIIIa | RHD | Present | Present | | Present | | No r's | |

TABLE 2-continued

| | | | | | Hyb in07 sg02 | | Hyb in07 sg04 | | RHD*r’s | |
|---|---|---|---|---|---|---|---|---|---|---|
| # | Sample ID | RHD allele #1 | RHD allele #2 | Hyb ex03 | Reference | Method of the invention | Reference | Method of the invention | Reference | Method of the invention |
| 68 | BGG-09-0287 | DIIIa | DAR | Present | Present | | Present | | No r’s | |
| 69 | BGG-09-0300 | DIIIa | RHD | Present | Present | | Present | | No r’s | |
| 70 | BGG-09-0333 | DIIIa/r’s | wDt4.0 | Present | Present | | Present | | | |
| 71 | BGG-10-0041 | DIIIa | Psi | Present | Present | | Present | | No r’s | |
| 72 | BGG-10-0052 | DIVa-2 | RHD | Present | Absent | | Present | | No r’s | |
| 73 | BGG-10-0056 | r’s | RHD | Present | Absent | | Present | | r’s | |
| 74 | BGG-10-0074 | DIIIa | RHD | Present | Present | | Present | | No r’s | |
| 75 | BGG-10-0075 | r’s | RHD | Present | Absent | | Present | | r’s | |
| 76 | BGG-10-0085 | r’s | r’s/RHDdel | Present | Absent | | Present | | r’s | |
| 77 | BGG-10-0097 | r’s | RHD | Present | Absent | | Present | | r’s | |
| 78 | BGG-10-0107 | DIIIa | RHD | Present | Present | | Present | | No r’s | |
| 79 | BGG-10-0118 | r’s | RHD | Present | Absent | | Present | | r’s | |
| 80 | BGG-10-0177 | r’s | r’s/RHDdel | Present | Absent | | Present | | r’s | |
| 81 | BGG-10-0187 | DIIIa | DIIIa/RHDdel/r’s | Present | Present | | Present | | | |
| 82 | BGG-10-0210 | r’s | RHD | Present | Absent | | Present | | r’s | |
| 83 | BGG-10-0280 | r’s | RHD | Present | Absent | | Present | | r’s | |
| 84 | BGG-10-0281 | DIIIa | DIIIa/RHDdel | Present | Present | | Present | | No r’s | |
| 85 | BGG-10-0284 | r’s | RHD Variant | Present | Absent | | Present | | r’s | |
| 86 | BGG-10-0367 | r’s | wDt2/2.1 | Present | Absent | | Present | | r’s | |
| 87 | BGG-10-0371 | r’s | RHD | Present | Absent | | Present | | r’s | |
| 88 | BGG-10-0373 | r’s | RHD | Present | Absent | | Present | | r’s | |
| 89 | BGG-10-0376 | r’s | RHD | Present | Absent | | Present | | r’s | |
| 90 | BGG-10-0380 | r’s | RHD | Present | Absent | | Present | | r’s | |
| 91 | BGG-10-0389 | r’s | RHD | Present | Absent | | Present | | r’s | |
| 92 | BGG-10-0396 | r’s | RHD | Present | Absent | | Present | | r’s | |
| 93 | BGG-10-0420 | DIIIa | RHD | Present | Present | | Present | | No r’s | |
| 94 | BGG-10-0425 | DIIIa | RHD | Present | Present | | Present | | No r’s | |
| 95 | BGG-10-0428 | r’s | RHD | Present | Absent | | Present | | r’s | |
| 96 | BGG-10-0443 | r’s | r’s/RHDdel | Present | Absent | | Present | | r’s | |
| 97 | BGG-10-0476 | r’s | RHD | Present | Absent | | Present | | r’s | |
| 98 | BGG-10-0481 | DIIIa | Psi | Present | Present | | Present | | No r’s | |
| 99 | BGG-10-0512 | DIIIa | RHD | Present | Present | | Present | | No r’s | |
| 100 | BGG-10-0523 | DIIIa | RHD | Present | Present | | Present | | No r’s | |
| 101 | BGG-10-0543 | DIIIa | RHD | Present | Present | | Present | | No r’s | |
| 102 | BGG-10-0575 | r’s | RHD | Present | Absent | | Present | | r’s | |
| 103 | BGG-10-0579 | DIIIa | RHD | Present | Present | | Present | | No r’s | |
| 104 | BGG-10-0590 | DIIIa | RHD | Present | Present | | Present | | No r’s | |
| 105 | BGG-10-0598 | r’s | RHD | Present | Absent | | Present | | r’s | |
| 106 | BGG-10-0628 | DIIIa | RHD | Present | Present | | Present | | No r’s | |
| 107 | BGG-10-0635 | r’s | RHD | Present | Absent | | Present | | r’s | |
| 108 | BGG-10-0638 | DIVa-2 | RHD | Present | Present | | Absent | | No r’s | |
| 109 | BGG-10-0642 | DIIIa | RHD | Present | Present | | Present | | No r’s | |
| 110 | BGG-10-0654 | r’s | RHD | Present | Absent | | Present | | r’s | |
| 111 | BGG-10-0656 | r’s | r’s/RHDdel | Present | Absent | | Present | | r’s | |
| 112 | BGG-10-0669 | DIIIa | Psi | Present | Present | | Present | | No r’s | |
| 113 | BGG-10-0715 | r’s | r’s/RHDdel | Present | Absent | | Present | | r’s | |
| 114 | BGG-10-0717 | DIIIa | RHD | Present | Present | | Present | | No r’s | |
| 115 | BGG-10-0723 | DIVa-2 | RHD | Present | Present | | Absent | | No r’s | |
| 116 | BGG-10-0735 | DIIIa | RHD | Present | Present | | Present | | No r’s | |
| 117 | BGG-10-0752 | r’s | RHD | Present | Absent | | Present | | r’s | |
| 118 | BGG-10-0770 | DIIIa | RHD | Present | Present | | Present | | No r’s | |
| 119 | BGG-10-0773 | r’s | RHD | Present | Absent | | Present | | r’s | |
| 120 | BGG-10-0790 | r’s | Psi | Present | Absent | | Present | | r’s | |
| 121 | BGG-10-0842 | DIIIa | RHD | Present | Present | | Present | | No r’s | |
| 122 | BGG-10-0847 | r’s | r’s/RHDdel | Present | Absent | | Present | | r’s | |
| 123 | BGG-10-0849 | r’s | DVt1/DAU5 | Present | Absent | | Present | | r’s | |
| 124 | BGG-10-0853 | r’s | r’s/RHDdel | Present | Absent | | Present | | r’s | |
| 125 | BGG-10-0867 | r’s | RHD | Present | Absent | | Present | | r’s | |
| 126 | BGG-10-0876 | DIVa-2 | RHD | Present | Absent | | Absent | | No r’s | |
| 127 | BGG-10-0900 | r’s | r’s/RHDdel | Present | Absent | | Present | | r’s | |
| 128 | BGG-10-0933 | r’s | RHD | Present | Absent | | Present | | r’s | |
| 129 | BGG-10-0942 | DIIIa | RHD | Present | Present | | Present | | No r’s | |
| 130 | BGG-10-0972 | r’s | RHD | Present | Absent | | Present | | r’s | |
| 131 | BGG-10-1233 | DIIIa | RHD | Present | Present | | Present | | No r’s | |
| 132 | BGG-10-1374 | r’s | r’s/RHDdel | Present | Absent | | Present | | r’s | |
| 133 | BGG-10-1379 | DIIIa | DIIIa/RHDdel | Present | Present | | Present | | No r’s | |
| 134 | BGG-10-1391 | r’s | RHD | Present | Absent | | Present | | r’s | |
| 135 | BGG-10-1413 | DIIIa | RHD | Present | Present | | Present | | No r’s | |
| 136 | BGG-10-1423 | r’s | RHD | Present | Absent | | Present | | r’s | |
| 137 | BGG-10-1455 | r’s | r’s/RHDdel | Present | Absent | | Present | | r’s | |
| 138 | BGG-10-1458 | DIIIa | RHD | Present | Present | | Present | | No r’s | |
| 139 | BGG-10-1468 | DIIIa | RHD | Present | Present | | Present | | No r’s | |
| 140 | BGG-10-1500 | r’s | RHD | Present | Absent | | Present | | r’s | |
| 141 | BGG-10-1532 | r’s | r’s/RHDdel | Present | Absent | | Present | | r’s | |

TABLE 2-continued

| # | Sample ID | RHD allele #1 | RHD allele #2 | Hyb ex03 | Hyb in07 sg02 | | Hyb in07 sg04 | | RHD*r's | |
|---|---|---|---|---|---|---|---|---|---|---|
| | | | | | Reference | Method of the invention | Reference | Method of the invention | Reference | Method of the invention |
| 142 | BGG-10-1574 | DIIIa | RHD | Present | Present | | Present | | No r's | |
| 143 | BGG-10-1577 | r's | r's/RHDdel | Present | Absent | | Present | | r's | |
| 144 | BGG-10-1588 | r's | r's/RHDdel | Present | Absent | | Present | | r's | |
| 145 | BGG-10-1591 | r's | RHD | Present | Absent | | Present | | r's | |
| 146 | BGG-10-1599 | r's | RHD Variant | Present | Absent | | Present | | r's | |
| 147 | BGG-10-1621 | DIIIa | DIIIa/RHDdel | Present | Present | | Present | | No r's | |
| 148 | BGG-10-1628 | DIIIa | DIIIa/RHDdel | Present | Present | | Present | | No r's | |
| 149 | BGG-10-1634 | DIIIa | RHD | Present | Present | | Present | | No r's | |
| 150 | BGG-10-1643 | r's | RHD | Present | Absent | | Present | | r's | |
| 151 | BGG-10-1649 | r's | r's/RHDdel | Present | Absent | | Present | | r's | |
| 152 | BGG-10-1653 | r's | RHD | Present | Absent | | Present | | r's | |
| 153 | BGG-10-1658 | DIIIa | RHD | Present | Present | | Present | | No r's | |
| 154 | BGG-10-1661 | r's | r's/RHDdel | Present | Absent | | Present | | r's | |
| 155 | BGG-10-1683 | DIIIa | RHD | Present | Present | | Present | | No r's | |
| 156 | BGG-10-2038 | r's | RHD | Present | Absent | | Present | | r's | |
| 157 | BGG-10-2142 | DIIIa | DIIIa/RHDdel | Present | Present | | Present | | No r's | |
| 158 | BGG-10-2144 | DIVa-2 | RHD | Present | Absent | | Absent | | No r's | |
| 159 | BGG-10-2153 | r's | RHD | Present | Absent | | Present | | r's | |
| 160 | BGG-10-2155 | r's | DVt1/DAU5 | Present | Absent | | Present | | r's | |
| 161 | BGG-10-2212 | r's | RHD | Present | Absent | | Present | | r's | |
| 162 | BGG-10-2215 | DIIIa/r's | Psi | Present | Present | | Present | | No r's | |
| 163 | BGG-10-2270 | DIIIa | RHD Variant | Present | Present | | Present | | No r's | |
| 164 | BGG-10-2335 | r's | r's/RHDdel | Present | Absent | | Present | | r's | |
| 165 | BGG-10-2347 | r's | RHD | Present | Absent | | Present | | r's | |
| 166 | BGG-10-2366 | r's | RHD | Present | Absent | | Present | | r's | |
| 167 | BGG-10-2379 | DIIIa | RHD | Present | Present | | Present | | No r's | |
| 168 | BGG-10-2391 | DIIIa | RHD | Present | Present | | Present | | No r's | |
| 169 | BGG-10-2433 | DIIIa | RHD | Present | Present | | Present | | No r's | |
| 170 | BGG-10-2435 | DIIIa | RHD | Present | Present | | Present | | No r's | |
| 171 | BGG-10-2456 | DIIIa | RHD | Present | Present | | Present | | No r's | |
| 172 | BGG-10-2470 | DIIIa | RHD | Present | Present | | Present | | No r's | |
| 173 | BGG-10-3386 | r's | r's/RHDdel | Present | Absent | | Present | | r's | |
| 174 | BGG-10-3387 | r's | RHD | Present | Absent | | Present | | r's | |
| 175 | BGG-10-3400 | r's | RHD | Present | Absent | | Present | | r's | |
| 176 | BGG-10-3409 | DIIIa | RHD | Present | Present | | Present | | No r's | |
| 177 | BGG-10-3417 | r's | RHD | Present | Absent | | Present | | r's | |
| 178 | BGG-10-3426 | r's | RHD | Present | Absent | | Present | | r's | |
| 179 | BGG-10-3427 | r's | r's/RHDdel | Present | Absent | | Present | | r's | |
| 180 | BGG-10-3461 | r's | r's/RHDdel | Present | Absent | | Present | | r's | |
| 181 | BGG-10-3486 | r's | RHD | Present | Absent | | Present | | r's | |
| 182 | BGG-10-3529 | RHD | RHD/RHDdel | Present | Absent | | Present | | No r's | |
| 183 | BGG-10-3539 | r's | r's/RHDdel | Present | Absent | | Present | | r's | |
| 184 | BGG-10-3545 | r's | RHD | Present | Absent | | Present | | r's | |
| 185 | BGG-10-3546 | DIIIa | RHD | Present | Present | | Present | | No r's | |
| 186 | BGG-10-3561 | r's | r's/RHDdel | Present | Absent | | Present | | r's | |
| 187 | BGG-10-3714 | DIVa-2 | DIVa-2/RHDdel/r's | Present | Present | | Absent | | | |
| 188 | BGG-10-3809 | r's | RHD | Present | Absent | | Present | | r's | |
| 189 | BGG-10-4060 | r's | r's/RHDdel | Present | Absent | | Present | | r's | |
| 190 | BGG-10-4080 | DIIIa | RHD | Present | Present | | Present | | No r's | |
| 191 | BGG-10-5191 | RHD | RHD/RHDdel | Absent | Absent | | Absent | | No r's | |
| 192 | BGG-10-5434 | | | | | | | | | |
| 193 | D114 | DVI | DVI/RHDdel | Absent | Absent | | Absent | | No r's | |
| 194 | D122 | DFR | DFR/RHDdel | Absent | Absent | | Absent | | No r's | |
| 195 | D123 | DIVa-2 | DIVa-2/RHDdel | Present | Absent | | Absent | | No r's | |
| 196 | D126 | r's | DVt1/DAU5 | Present | Absent | | Present | | r's | |
| 197 | D129 | Psi | Psi/RHDdel | Absent | Absent | | Absent | | No r's | |
| 198 | D131 | DOL | DOL/RHDdel | Absent | Absent | | Absent | | No r's | |
| 199 | D133 | DAU0 | DAU0/RHDdel | Absent | Absent | | Absent | | No r's | |
| 200 | D138 | RHD Variant | RHDdel | Absent | Absent | | Absent | | No r's | |
| 201 | D140 | wDt5 | wDt5/RHDdel | Absent | Absent | | Absent | | No r's | |
| 202 | D159 | RHD Variant | RHDdel | Absent | Absent | | Absent | | No r's | |
| 203 | D161 | RHD Variant | RHDdel | Absent | Absent | | Absent | | No r's | |
| 204 | D171 | r's | DAR | Present | Absent | | Present | | r's | |
| 205 | D190 | r's | DAR | Present | Absent | | Present | | r's | |
| 206 | D193 | DIVa-2 | DIVa-2/RHDdel | Present | Absent | | Absent | | No r's | |
| 207 | D195 | RHD | RHD/RHDdel | Absent | Absent | | Absent | | No r's | |
| 208 | D196 | DIVa-2 | DIVa-2/RHDdel | Present | Absent | | Absent | | No r's | |
| 209 | D202 | RHD | RHDdel | Absent | Absent | | Absent | | No r's | |
| 210 | D204 | RHDdel | RHDdel | Absent | Absent | | Absent | | No r's | |
| 211 | D213 | r's | r's/RHDdel | Present | Absent | | Present | | r's | |
| 212 | D214 | wDt15 | wDt15/RHDdel | Absent | Absent | | Absent | | No r's | |
| 213 | D221 | wDt4.0/4.1 | wDt4.0/4.1/RHDdel | Absent | Absent | | Present | | No r's | |
| 214 | D225 | RHD | RHD/RHDdel | Absent | Absent | | Absent | | No r's | |
| 215 | D226 | DAU5 | DAU5/RHDdel | Absent | Absent | | Absent | | No r's | |

TABLE 2-continued

| | | | | | Hyb in07 sg02 | | Hyb in07 sg04 | | RHD*r'^s | |
|---|---|---|---|---|---|---|---|---|---|---|
| # | Sample ID | RHD allele #1 | RHD allele #2 | Hyb ex03 | Reference | Method of the invention | Reference | Method of the invention | Reference | Method of the invention |
| 216 | D227 | DAU5 | DAU5/RHDdel | Absent | Absent | | Absent | | No r's | |
| 217 | D229 | DAU5 | DAU5/RHDdel | Absent | Absent | | Absent | | No r's | |
| 218 | D230 | wDt4.0/4.1 | wDt4.0/4.1/RHDdel | Absent | Absent | | Present | | No r's | |
| 219 | D231 | RHD | RHD/RHDdel | Absent | Absent | | Absent | | No r's | |
| 220 | D237 | RHD Variant | RHDdel | Absent | Absent | | Absent | | No r's | |
| 221 | D239 | DAU5 | DAU5/RHDdel | Absent | Absent | | Absent | | No r's | |
| 222 | D245 | wDt11 | wDt11/RHDdel | Absent | Absent | | Absent | | No r's | |
| 223 | D249 | RHD | RHD/RHDdel | Absent | Absent | | Absent | | No r's | |
| 224 | D261 | RHD | RHD/RHDdel | Absent | Absent | | Absent | | No r's | |
| 225 | D262 | wDt5 | wDt5/RHDdel | Absent | Absent | | Absent | | No r's | |
| 226 | D288 | DMH | DMH/RHDdel | Absent | Absent | | Absent | | No r's | |
| 227 | D289 | RHD Variant | RHDdel | Absent | Absent | | Absent | | No r's | |
| 228 | D290 | wDt1 | wDt1/RHDdel | Absent | Absent | | Absent | | No r's | |
| 229 | D291 | wDt2 | wDt2/RHDdel | Absent | Absent | | Absent | | No r's | |
| 230 | D298 | r's | DAR | Present | Absent | | Present | | r's | |
| 231 | D300 | RHD Variant | RHDdel | Absent | Absent | | Absent | | No r's | |
| 232 | D323 | DVI | DVI/RHDdel | Absent | Absent | | Absent | | No r's | |
| 233 | D328 | wDt4.0/4.1 | wDt4.0/4.1/RHDdel | Absent | Absent | | Present | | No r's | |
| 234 | D329 | wDt4.0/4.1 | wDt4.0/4.1/RHDdel | Absent | Absent | | Present | | No r's | |
| 235 | D330 | DAU5 | DAU5/RHDdel | Absent | Absent | | Absent | | No r's | |
| 236 | D331 | wDt4.0/4.1 | wDt4.0/4.1/RHDdel | Absent | Absent | | Present | | No r's | |
| 237 | GAL 10701360 | RHD | RHD/RHDdel | Absent | Absent | | Absent | | No r's | |
| 238 | GAL 10701364 | RHD | RHD/RHDdel | Absent | Absent | | Absent | | No r's | |
| 239 | GAL 10701365 | RHD | RHD/RHDdel | Absent | Absent | | Absent | | No r's | |
| 240 | GAL 10701366 | RHD | RHD/RHDdel | Absent | Absent | | Absent | | No r's | |
| 241 | GAL 10706636 | RHD | RHD/RHDdel | Absent | Absent | | Absent | | No r's | |
| 242 | GAL 10752569 | RHDdel | RHDdel | Absent | Absent | | Absent | | No r's | |
| 243 | GAL 10816074 | RHDdel | RHDdel | Absent | Absent | | Absent | | No r's | |
| 244 | GAL 10833160 | RHDdel | RHDdel | Absent | Absent | | Absent | | No r's | |
| 245 | GKO 10532283 | RHD | RHD/RHDdel | Absent | Absent | | Absent | | No r's | |
| 246 | GKO 32588 | RHD | RHD/RHDdel | Absent | Absent | | Absent | | No r's | |
| 247 | JCX33 | r's | RHD | Present | Absent | | Present | | r's | |
| 248 | L22 | RHD | RHD/RHDdel | Absent | Absent | | Absent | | No r's | |
| 249 | L23 | RHDdel | RHDdel | Absent | Absent | | Absent | | No r's | |
| 250 | L28 | RHD | RHD/RHDdel | Absent | Absent | | Absent | | No r's | |
| 251 | PGK53 | RHDdel | RHDdel | Absent | Absent | | Absent | | No r's | |
| 252 | ZGZ 51979 | r's | r's/RHDdel | Present | Absent | | Present | | r's | |
| 253 | ZGZ 52739 | DIIIa | RHD | Present | Present | | Present | | No r's | |

The above results can be summarized in Table 3.

TABLE 3

| | DIIIa | r's | DIVa-2 |
|---|---|---|---|
| Total | 49 | 82 | 14 |
| Called | 33 | 58 | 12 |
| 0K | 23 | 54 | 12 |
| FN | 10 | 4 | 0 |
| FN [sg02+ sg04+] | | | 0 |
| FN [sg02+ sg04−] | | 0 | |
| FN [sg02− sg04−] | 1 | | |
| FN [sg02+] | | 2 | 0 |
| FN [sg04+] | | | 0 |
| FN [sg02−] | 7 | | |
| FN [sg04−] | 2 | 2 | |
| Universe | 96 | 63 | 131 |
| Called | 70 | 45 | 91 |
| FP | 3 | 8 | 5 |

Key to Table 3
Shaded cells: does not apply
FN: false negative
FP: false positive
Universe: non-DIIIa, non-r'^S, non-DIVa-2
Called: calls made

Example 2

Discrimination among genetic variants that share a RHD/RHCE hybrid exon 3 but encode different forms of RhD Ag (Partial D Ag vs. No D Ag) and C Ag (Normal C Ag vs. Altered/Weakened C Ag, sometimes abbreviated as $C^{+W}$)

The following example relates to a method of discriminating among RHD/RHCE hybrid exon 3 variants RHD*r's, RHD*DIIIa and RHD*DIVa-2. The method is based on the interrogation of the nucleotide composition of the genomic DNA of a sample at three discrete and separate locations in the RHD locus by means of a molecular technique known in the art as Allele-Specific Polymerase Chain Reaction (ASP). Amplification of a DNA segment at one location enables determination of the presence of RHD/RHCE hybrid exon 3 in the test sample. Amplification of a DNA segment at another location enables determination of the presence of variants RHD*r's or RHD*DIIIa and absence of variant RHD*DIVa-2. Amplification of a DNA segment at yet another location enables determination of the presence of variant RHD*DIIIa and absence of variant RHD*r's.

The method outlined above and described in further detail below has been applied to 252 samples selected to contain in the RHD gene either no variant allele (i.e. two conventional alleles), one variant allele (and one conventional allele), or two variant alleles (i.e. no conventional allele). The samples were also selected to include RHD reference and RHD variant alleles encoding the major RhD phenotypes, namely $RhD^+$, Partial D, Weak D, $RhD^-$. In order to generate the reference dataset, presence vs. absence of variant allele(s) was determined for each sample by standard DNA sequencing and by genotyping, the latter following methods other than the method described herein. Polymorphic positions interrogated by the reference genotyping methods include positions shared with the present method as well as positions not shared with the present method.

Materials & Methods

According to the present example, genomic DNA was extracted from nucleated cells in a blood sample by cell lysis. Extracted DNA was purified on an affinity column. Both, cell lysis and DNA purification were performed with a QIAamp Blood kit (Qiagen, Germany) by following manufacturer protocols and recommendations. Purity of DNA was determined by spectrophotometry on a Nanodrop instrument (Nanodrop, DE). Only DNA solutions with an $OD_{260}/OD_{280}=1.8\pm0.2$ were used for subsequent analysis.

Purified DNA was used as a template for multiplexed Polymerase Chain Reaction (PCR) amplification of the gene segments of interest in a GeneAmp 9700 thermal cycler (Perkin-Elmer, CA). Primer sequences for the different segments are listed in the Technical Description section. Cycling conditions consisted of a polymerase activation step at 95° C. for 15 min, followed by 38 cycles of denaturation at 95° C. for 45 sec, annealing at 60° C. for 60 sec, extension at 72° C. for 90 sec, and a final extension step at 72° C. for 10 min.

Amplified DNA was separated by electrophoresis on a 2% agarose gel, stained with SYBR Safe dye (Invitrogen, OR), and photographed under UV illumination. Positive and negative control template DNA for each of the three DNA segments was included in every ASP assay. Amplification vs. No Amplification of a segment was determined visually by a trained laboratory technician.

Technical Description

According to the present example, amplification of each of the three DNA segments was performed as follows:

Amplification of RHD/RHCE Hybrid Exon 3 by ASP.

This step can make use of oligonucleotide primers that bind to intron 2 and intron 3 sequences in the RHD locus. The target sequence of the forward (upstream) primer, located in intron 2, is RHD specific. The target sequence of the reverse (downstream) primer, located in intron 3, is RHCE specific. The size of the PCR product was 270 base pairs when the following sequences were used:

```
                                     (SEQ ID NO: 5)
Forward primer:    5'-CGTCCTGGCTCTCCCTCTCT-3'

                                     (SEQ ID NO: 6)
Reverse primer:    5'-TATTTTTCAAAACCCCGGAAG-3'
```

In boldface, RHD-specific nucleotides (forward primer) and RHCE-specific nucleotides (reverse primer). Specifically, the polymorphic positions exploited by the oligonucleotide primers used in this ASP are IVS2-26, IVS2-13, IVS2-8 (forward primer) in RHD intron 2 and polymorphic positions IVS3+64, IVS3+69 (reverse primer) in RHD intron 3.

It is possible to use different primers provided that the primers enable specific, partial or complete, amplification of the RHD/RHCE hybrid exon 3 that characterizes variants RHD*r's, RHD*DIIIa, RHD*DIVa-2, among others.

Amplification of a Segment (Segment #2) of RHCE/RHD Hybrid Intron 7 by ASP.

Oligonucleotide primers that bind to intron 7 sequences in the RHD locus were used. The target sequence of the forward (upstream) primer is RHD specific. The target sequence of the reverse (downstream) primer is RHCE specific. The size of the PCR product was 438 base pairs when the following sequences were used:

```
Forward primer:
                                     (SEQ ID NO: 9)
5'-CAAGCTGTCAAGGAGACATCACTAT-3'

Reverse primer:
                                     (SEQ ID NO: 10)
5'-CATTACATAGAGATGTCCCCATACT-3'
```

In boldface, RHD-specific nucleotides (forward primer) and RHCE-specific nucleotides (reverse primer). Specifically, the polymorphic positions exploited by the oligonucleotide primers used in this ASP are IVS7+1869, IVS7+1880, IVS7+1886, IVS7+1887 (forward primer) and IVS7+2276, IVS7+2282 (reverse primer).

It is possible to use oligonucleotide primers that differ from the previously described primers in sequence, length, or any other feature, provided that they enable specific, partial or complete, amplification of the RHCE/RHD hybrid intron 7 that characterizes variants RHD*r's, RHD*DIIIa.

Amplification of Another Segment (Segment #4) of RHD/RHCE Hybrid Intron 7 by ASP.

Oligonucleotide primers that bind to intron 7 sequences in the RHD locus were used. The target sequence of the forward (upstream) primer is RHD specific. The target sequence of the reverse (downstream) primer is RHCE specific. The size of the PCR product was 305 base pairs when the following sequences were used:

```
Forward primer:
                                     (SEQ ID NO: 12)
5'-GCCACTTATTACTTAAAAAAACCCC-3'

Reverse primer:
                                     (SEQ ID NO: 13)
5'-AAGGCGCTTCCTCCAAATAG-3'
```

In boldface, RHD-specific nucleotides (forward primer) and RHCE-specific nucleotides (reverse primer). Specifically, the polymorphic positions exploited by the oligonucleotide primers used in this ASP are IVS7+3349 (forward primer) and IVS7+4105, IVS7+4106, IVS7+4107, IVS7+4108, IVS7+4127 (reverse primer).

It is possible to use oligonucleotide primers that differ from the previously described primers in sequence, length, or any other feature, provided that they enable specific, partial or complete, amplification of the RHD/RHCE hybrid intron 7 that characterizes variants RHD*r's, RHD*DIIIa, RHD*DIVa-2.

A total of 252 selected samples known to contain conventional RHD, conventional RHCE, variant RHD alleles or variant RHCE alleles were analyzed as a test of the genotyping method described herein. The results are shown in Table 4.

Reference results (Reference) correspond to data generated through the analysis of genomic DNA by one or more of the following:

A genotyping microarray that interrogates 72 polymorphic positions in the RHD locus and 8 polymorphic positions in the RHCE locus.

A microsphere- and flow cytometry-based genotyping test that interrogates 1 polymorphic position in the RHD locus and 7 polymorphic positions in the RHCE locus.

DNA sequencing by the standard Sanger dideoxy method

Method results (Method) correspond to data generated by the method described herein. Specifically, this dataset was obtained from the analysis of genomic DNA by ASP and agarose gel electrophoresis, as described in the Technical Description section of this document.

Table 4 lists samples alphabetically and includes for each one of them the following:

RHD genotype at both alleles.
Reference Hyb ex03 genotype.
Method Hyb ex03 genotype.
Reference Hyb in07 sg02 genotype.
Method Hyb in07 sg02 genotype.
Reference Hyb in07 sg04 genotype.
Method Hyb in07 sg04 genotype.
Reference RHD*r's Presence/Absence call.
Method RHD*r's Presence/Absence call.

RHD: conventional RHD
RHDdel: RHD deletion variant
RHD* has been omitted from the rest of RHD variants for simplicity

TABLE 4

| | | | | Hyb ex03 | | Hyb in07 sg02 | | Hyb in07 sg04 | | RHD*r's call | |
|---|---|---|---|---|---|---|---|---|---|---|---|
| # | Sample ID | RHO allele #1 | RHD allele #2 | Reference | Method | Reference | Method | Reference | Method | Reference | Method |
| 1 | A2Y53 | RHD | RHD/RHDdel | Absent | Absent | Absent | Absent | Absent | Absent | No r's | No r's |
| 2 | AYU48 | RHD | RHD/RHDdel | Absent | Absent | Absent | Absent | Absent | Absent | No r's | No r's |
| 3 | AYU53 | RHD | RHD/RHDdel | Absent | Absent | Absent | Absent | Absent | Absent | No r's | No r's |
| 4 | AZJ10 | RHDdel | RHDdel | Absent | Absent | Absent | Absent | Absent | Absent | No r's | No r's |
| 5 | BAT15 | RHD | RHD/RHDdel | Absent | Absent | Absent | Absent | Absent | Absent | No r's | No r's |
| 6 | BBA07 | RHD | RHD/RHDdel | Absent | Absent | Absent | Absent | Absent | Absent | No r's | No r's |
| 7 | BC0078 | wDt3 | wDt3/RHDdel | Absent | Absent | Absent | Absent | Absent | Absent | No r's | No r's |
| 8 | BC0079 | DAR | DAR/RHDdel | Absent | Absent | Absent | Absent | Absent | Absent | No r's | No r's |
| 9 | BC0080 | DAR | DAR/RHDdel | Absent | Absent | Absent | Absent | Absent | Absent | No r's | No r's |
| 10 | BC0081 | DAR | DAR/RHDdel | Absent | Absent | Absent | Absent | Absent | Absent | No r's | No r's |
| 11 | BC0082 | DAR | DAR/RHDdel | Absent | Absent | Absent | Absent | Absent | Absent | No r's | No r's |
| 12 | BC0083 | r's | r's/RHDdel | Present | Present | Absent | Absent | Present | Present | r's | r's |
| 13 | BC0084 | r's | RHDdel | Present | Present | Absent | Absent | Present | Present | r's | r's |
| 14 | BC0085 | r's | r's/RHDdel | Present | Present | Absent | Absent | Present | Present | r's | r's |
| 15 | BC0086 | r's | RHD | Present | Present | Absent | Absent | Present | Present | r's | r's |
| 16 | BC0087 | r's | r's/RHDdel | Present | Present | Absent | Absent | Present | Present | r's | r's |
| 17 | BC0088 | RHDdel | RHDdel | Absent | Absent | Absent | Absent | Absent | Absent | No r's | No r's |
| 18 | BC0089 | RHD | RHD/RHDdel | Absent | Absent | Absent | Absent | Absent | Absent | No r's | No r's |
| 19 | BC0090 | RHD | RHD/RHDdel | Absent | Absent | Absent | Absent | Absent | Absent | No r's | No r's |
| 20 | BC0091 | RHDdel | RHDdel | Absent | Absent | Absent | Absent | Absent | Absent | No r's | No r's |
| 21 | BC0092 | RHDdel | RHDdel | Absent | Absent | Absent | Absent | Absent | Absent | No r's | No r's |
| 22 | BC0093 | RHDdel | RHDdel | Absent | Absent | Absent | Absent | Absent | Absent | No r's | No r's |
| 23 | BC0094 | DV | DV/RHDdel | Absent | Absent | Absent | Absent | Absent | Absent | No r's | No r's |
| 24 | BC0095 | DV | DV/RHDdel | Absent | Absent | Absent | Absent | Absent | Absent | No r's | No r's |
| 25 | BC0096 | DV | DV/RHDdel | Absent | Absent | Absent | Absent | Absent | Absent | No r's | No r's |
| 26 | BC0097 | DV | DV/RHDdel | Absent | Absent | Absent | Absent | Absent | Absent | No r's | No r's |
| 27 | BC0098 | RHD | RHD/RHDdel | Absent | Absent | Absent | Absent | Absent | Absent | No r's | No r's |
| 28 | BC0099 | RHD | RHD/RHDdel | Absent | Absent | Absent | Absent | Absent | Absent | No r's | No r's |
| 29 | BC0100 | RHD | RHD/RHDdel | Absent | Absent | Absent | Absent | Absent | Absent | No r's | No r's |
| 30 | BC0101 | RHD | RHD/RHDdel | Absent | Absent | Absent | Absent | Absent | Absent | No r's | No r's |
| 31 | BC0102 | RHD | RHD/RHDdel | Absent | Absent | Absent | Absent | Absent | Absent | No r's | No r's |
| 32 | BC0103 | DIVa-2 | RHD | Present | Present | Absent | Absent | Absent | Absent | No r's | No r's |
| 33 | BC0104 | DIIIt4/DIIIt8 | RHD | Present | Present | Absent | Absent | Absent | Absent | No r's | No r's |
| 34 | BC0105 | DIVa-2 | Psi | Present | Present | Absent | Absent | Absent | Present | No r's | r's |
| 35 | BC0106 | DIVa-2 | DIVa-2/RHDdel | Present | Present | Absent | Absent | Absent | Absent | No r's | No r's |
| 36 | BC0107 | DIVa-2 | RHD | Present | Present | Absent | Absent | Absent | Absent | No r's | No r's |
| 37 | BC0108 | RHD | RHD/RHDdel | Absent | Absent | Absent | Absent | Absent | Absent | No r's | No r's |
| 38 | BC0109 | RHD | RHD/RHDdel | Absent | Absent | Absent | Absent | Absent | Absent | No r's | No r's |
| 39 | BC0110 | RHD Variant | RHDdel | Absent | Absent | Absent | Absent | Absent | Absent | No r's | No r's |
| 40 | BC0111 | RHD | RHD/RHDdel | Absent | Absent | Absent | Absent | Absent | Absent | No r's | No r's |
| 41 | BC0112 | RHD Variant | RHDdel | Absent | Absent | Absent | Absent | Absent | Absent | No r's | No r's |
| 42 | BC0113 | wDt4.0/4.1 | RHD | Absent | Absent | Absent | Absent | Present | Absent | No r's | No r's |
| 43 | BC0114 | RHD | RHD/RHDdel | Absent | Absent | Absent | Absent | Absent | Absent | No r's | No r's |
| 44 | BC0115 | RHD | RHD/RHDdel | Absent | Absent | Absent | Absent | Absent | Absent | No r's | No r's |
| 45 | BC0116 | RHD | RHD/RHDdel | Absent | Absent | Absent | Absent | Absent | Absent | No r's | No r's |
| 46 | BC0117 | RHD | RHD/RHDdel | Absent | Absent | Absent | Absent | Absent | Absent | No r's | No r's |
| 47 | BC0118 | RHD | RHD/RHDdel | Absent | Absent | Absent | Absent | Absent | Absent | No r's | No r's |
| 48 | BC0119 | RHD | RHD/RHDdel | Absent | Absent | Absent | Absent | Absent | Absent | No r's | No r's |
| 49 | BC0120 | RHD | RHD/RHDdel | Absent | Absent | Absent | Absent | Absent | Absent | No r's | No r's |
| 50 | BC0121 | RHD | RHD/RHDdel | Absent | Absent | Absent | Absent | Absent | Absent | No r's | No r's |
| 51 | BC0122 | RHD | RHD/RHDdel | Absent | Absent | Absent | Absent | Absent | Absent | No r's | No r's |
| 52 | BC0123 | DAR | RHD | Absent | Absent | Absent | Absent | Absent | Absent | No r's | No r's |
| 53 | BC0124 | RHD | RHD/RHDdel | Absent | Absent | Absent | Absent | Absent | Absent | No r's | No r's |
| 54 | BC0125 | RHD | RHD/RHDdel | Absent | Absent | Absent | Absent | Absent | Absent | No r's | No r's |
| 55 | BC0126 | RHD | RHD/RHDdel | Absent | Absent | Absent | Absent | Absent | Absent | No r's | No r's |
| 56 | BC0127 | RHD | RHD/RHDdel | Absent | Absent | Absent | Absent | Absent | Absent | No r's | No r's |
| 57 | BC0128 | RHD | RHD/RHDdel | Absent | Absent | Absent | Absent | Absent | Absent | No r's | No r's |
| 58 | BC0129 | RHD | RHD/RHDdel | Absent | Absent | Absent | Absent | Absent | Absent | No r's | No r's |
| 59 | BC0130 | DV | DV/RHDdel | Absent | Absent | Absent | Absent | Absent | Absent | No r's | No r's |
| 60 | BC0131 | RHD | RHD/RHDdel | Absent | Absent | Absent | Absent | Absent | Absent | No r's | No r's |
| 61 | BC0132 | RHD | RHD/RHDdel | Absent | Absent | Absent | Absent | Absent | Absent | No r's | No r's |
| 62 | BCGEN446 | DIVa-2 | DIVa-2/RHDdel | Present | Present | Absent | Absent | Absent | Absent | No r's | No r's |
| 63 | BGG-09-0032 | DIIIa | DIIIa/RHDdel/r's | Present | Present | Present | Present | Present | Present | No r's | No r's |
| 64 | BGG-09-0084 | r's | RHD | Present | Present | Absent | Absent | Present | Present | r's | r's |

TABLE 4-continued

| | | | | Hyb ex03 | | Hyb in07 sg02 | | Hyb in07 sg04 | | RHD*r's call | |
|---|---|---|---|---|---|---|---|---|---|---|---|
| # | Sample ID | RHO allele #1 | RHD allele #2 | Reference | Method | Reference | Method | Reference | Method | Reference | Method |
| 65 | BGG-09-0216 | r's | RHD | Present | Present | Absent | Absent | Present | Present | r's | r's |
| 66 | BGG-09-0275 | DIIIa | RHD Variant | Present | Present | Present | Absent | Present | Present | No r's | r's |
| 67 | BGG-09-0281 | DIIIa | RHD | Present | Present | Present | Present | Present | Present | No r's | No r's |
| 68 | BGG-09-0287 | DIIIa | DAR | Present | Present | Present | Absent | Present | Present | No r's | r's |
| 69 | BGG-09-0300 | DIIIa | RHD | Present | Present | Present | Absent | Present | Present | No r's | r's |
| 70 | BGG-10-0041 | DIIIa | Psi | Present | Present | Present | Absent | Present | Present | No r's | r's |
| 71 | BGG-10-0052 | DIVa-2 | RHD | Present | Present | Absent | Absent | Present | Present | No r's | No r's |
| 72 | BGG-10-0056 | r's | RHD | Present | Present | Absent | Absent | Present | Present | r's | r's |
| 73 | BGG-10-0074 | DIIIa | RHD | Present | Present | Present | Present | Present | Present | No r's | No r's |
| 74 | BGG-10-0075 | r's | RHD | Present | Present | Absent | Absent | Present | Present | r's | r's |
| 75 | BGG-10-0085 | r's | r's/RHDdel | Present | Present | Absent | Absent | Present | Present | r's | r's |
| 76 | BGG-10-0097 | r's | RHD | Present | Present | Absent | Absent | Present | Present | r's | r's |
| 77 | BGG-10-0107 | DIIIa | RHD | Present | Present | Present | Present | Present | Present | No r's | No r's |
| 78 | BGG-10-0118 | r's | RHD | Present | Present | Absent | Absent | Present | Present | r's | r's |
| 79 | BGG-10-0177 | r's | r's/RHDdel | Present | Present | Absent | Absent | Present | Present | r's | r's |
| 80 | BGG-10-0187 | DIIIa | DIIIa/RHDdel/r's | Present | Present | Present | Present | Present | Present | | |
| 81 | BGG-10-0210 | r's | RHD | Present | Present | Absent | Absent | Present | Present | r's | r's |
| 82 | BGG-10-0280 | r's | RHD | Present | Present | Absent | Absent | Present | Present | r's | r's |
| 83 | BGG-10-0281 | DIIIa | DIIIa/RHDdel | Present | Present | Present | Present | Present | Present | No r's | No r's |
| 84 | BGG-10-0284 | r's | RHD Variant | Present | Present | Absent | Absent | Present | Present | r's | r's |
| 85 | BGG-10-0367 | r's | wDt2/2.1 | Present | Present | Absent | Absent | Present | Present | r's | r's |
| 86 | BGG-10-0371 | r's | RHD | Present | Present | Absent | Absent | Present | Present | r's | r's |
| 87 | BGG-10-0373 | r's | RHD | Present | Present | Absent | Absent | Present | Present | r's | r's |
| 88 | BGG-10-0376 | r's | RHD | Present | Present | Absent | Absent | Present | Present | r's | r's |
| 89 | BGG-10-0380 | r's | RHD | Present | Present | Absent | Absent | Present | Present | r's | r's |
| 90 | BGG-10-0389 | r's | RHD | Present | Present | Absent | Absent | Present | Present | r's | r's |
| 91 | BGG-10-0396 | r's | RHD | Present | Present | Absent | Absent | Present | Present | r's | r's |
| 92 | BGG-10-0420 | DIIIa | RHD | Present | Present | Present | Present | Present | Present | No r's | No r's |
| 93 | BGG-10-0425 | DIIIa | RHD | Present | Present | Present | Present | Present | Present | No r's | No r's |
| 94 | BGG-10-0428 | r's | RHD | Present | Present | Absent | Absent | Present | Present | r's | r's |
| 95 | BGG-10-0443 | r's | r's/RHDdel | Present | Present | Absent | Absent | Present | Present | r's | r's |
| 96 | BGG-10-0476 | r's | RHD | Present | Present | Absent | Absent | Present | Present | r's | r's |
| 97 | BGG-10-0481 | DIIIa | Psi | Present | Present | Present | Present | Present | Present | No r's | No r's |
| 98 | BGG-10-0512 | DIIIa | RHD | Present | Present | Present | Absent | Present | Present | No r's | r's |
| 99 | BGG-10-0523 | DIIIa | RHD | Present | Present | Present | Present | Present | Present | No r's | No r's |
| 100 | BGG-10-0543 | DIIIa | RHD | Present | Present | Present | Present | Present | Present | No r's | No r's |
| 101 | BGG-10-0575 | r's | RHD | Present | Present | Absent | Absent | Present | Present | r's | r's |
| 102 | BGG-10-0579 | DIIIa | RHD | Present | Present | Present | Present | Present | Present | No r's | No r's |
| 103 | BGG-10-0590 | DIIIa | RHD | Present | Present | Present | Present | Present | Present | No r's | No r's |
| 104 | BGG-10-0598 | r's | RHD | Present | Present | Absent | Absent | Present | Present | r's | r's |
| 105 | BGG-10-0628 | DIIIa | RHD | Present | Present | Present | Present | Present | Present | No r's | No r's |
| 106 | BGG-10-0635 | r's | RHD | Present | Present | Absent | Absent | Present | Present | r's | r's |
| 107 | BGG-10-0638 | DIVa-2 | RHD | Present | Present | Present | Present | Absent | Absent | No r's | No r's |
| 108 | BGG-10-0642 | DIIIa | RHD | Present | Present | Present | Present | Present | Present | No r's | No r's |
| 109 | BGG-10-0654 | r's | RHD | Present | Present | Absent | Absent | Present | Present | r's | r's |
| 110 | BGG-10-0656 | r's | r's/RHDdel | Present | Present | Absent | Absent | Present | Present | r's | r's |
| 111 | BGG-10-0669 | DIIIa | Psi | Present | Present | Present | Present | Present | Present | No r's | No r's |
| 112 | BGG-10-0715 | r's | r's/RHDdel | Present | Present | Absent | Absent | Present | Present | r's | r's |
| 113 | BGG-10-0717 | DIIIa | RHD | Present | Present | Present | Present | Present | Present | No r's | No r's |
| 114 | BGG-10-0723 | DIVa-2 | RHD | Present | Present | Present | Present | Absent | Absent | No r's | No r's |
| 115 | BGG-10-0735 | DIIIa | RHD | Present | Present | Present | Present | Present | Present | No r's | No r's |
| 116 | BGG-10-0752 | r's | RHD | Present | Present | Absent | Absent | Present | Present | r's | r's |
| 117 | BGG-10-0770 | DIIIa | RHD | Present | Present | Present | Present | Present | Present | No r's | No r's |
| 118 | BGG-10-0773 | r's | RHD | Present | Present | Absent | Absent | Present | Present | r's | r's |
| 119 | BGG-10-0790 | r's | Psi | Present | Present | Absent | Absent | Present | Present | r's | r's |
| 120 | BGG-10-0842 | DIIIa | RHD | Present | Present | Present | Present | Present | Present | No r's | No r's |
| 121 | BGG-10-0847 | r's | r's/RHDdel | Present | Present | Absent | Absent | Present | Present | r's | r's |
| 122 | BGG-10-0849 | r's | DVt1/DAU5 | Present | Present | Absent | Absent | Present | Present | r's | r's |
| 123 | BGG-10-0853 | r's | r's/RHDdel | Present | Present | Absent | Absent | Present | Present | r's | r's |
| 124 | BGG-10-0867 | r's | RHD | Present | Present | Absent | Absent | Present | Present | r's | r's |
| 125 | BGG-10-0876 | DIVa-2 | RHD | Present | Present | Absent | Absent | Absent | Absent | No r's | No r's |
| 126 | BGG-10-0900 | r's | r's/RHDdel | Present | Present | Absent | Absent | Present | Present | r's | r's |
| 127 | BGG-10-0933 | r's | RHD | Present | Present | Absent | Absent | Present | Present | r's | r's |
| 128 | BGG-10-0942 | DIIIa | RHD | Present | Present | Present | Present | Present | Present | No r's | No r's |
| 129 | BGG-10-0972 | r's | RHD | Present | Present | Absent | Absent | Present | Present | r's | r's |
| 130 | BGG-10-1233 | DIIIa | RHD | Present | Present | Present | Absent | Present | Present | No r's | r's |
| 131 | BGG-10-1374 | r's | r's/RHDdel | Present | Present | Absent | Absent | Present | Present | r's | r's |
| 132 | BGG-10-1379 | DIIIa | DIIIa/RHDdel | Present | Present | Present | Present | Present | Present | No r's | No r's |
| 133 | BGG-10-1391 | r's | RHD | Present | Present | Absent | Absent | Present | Present | r's | r's |
| 134 | BGG-10-1413 | DIIIa | RHD | Present | Present | Present | Present | Present | Present | No r's | No r's |
| 135 | BGG-10-1423 | r's | RHD | Present | Present | Absent | Absent | Present | Present | r's | r's |
| 136 | BGG-10-1455 | r's | r's/RHDdel | Present | Present | Absent | Absent | Present | Present | r's | r's |
| 137 | BGG-10-1458 | DIIIa | RHD | Present | Present | Present | Present | Present | Present | No r's | No r's |
| 138 | BGG-10-1468 | DIIIa | RHD | Present | Present | Present | Present | Present | Present | No r's | No r's |
| 139 | BGG-10-1500 | r's | RHD | Present | Present | Absent | Absent | Present | Present | r's | r's |
| 140 | BGG-10-1532 | r's | r's/RHDdel | Present | Present | Absent | Absent | Present | Present | r's | r's |

TABLE 4-continued

| # | Sample ID | RHO allele #1 | RHD allele #2 | Hyb ex03 | | Hyb in07 sg02 | | Hyb in07 sg04 | | RHD*r’s call | |
|---|---|---|---|---|---|---|---|---|---|---|---|
| | | | | Reference | Method | Reference | Method | Reference | Method | Reference | Method |
| 141 | BGG-10-1574 | DIIIa | RHD | Present | Present | Present | Absent | Present | Present | No r’s | r’s |
| 142 | BGG-10-1577 | r’s | r’s/RHDdel | Present | Present | Absent | Absent | Present | Present | r’s | r’s |
| 143 | BGG-10-1588 | r’s | r’s/RHDdel | Present | Present | Absent | Absent | Present | Present | r’s | r’s |
| 144 | BGG-10-1591 | r’s | RHD | Present | Present | Absent | Absent | Present | Present | r’s | r’s |
| 145 | BGG-10-1599 | r’s | RHD Variant | Present | Present | Absent | Absent | Present | Present | r’s | r’s |
| 146 | BGG-10-1621 | DIIIa | DIIIa/RHDdel | Present | Present | Present | Present | Present | Present | No r’s | No r’s |
| 147 | BGG-10-1628 | DIIIa | DIIIa/RHDdel | Present | Present | Present | Present | Present | Present | No r’s | No r’s |
| 148 | BGG-10-1634 | DIIIa | RHD | Present | Present | Present | Present | Present | Present | No r’s | No r’s |
| 149 | BGG-10-1643 | r’s | RHD | Present | Present | Absent | Absent | Present | Present | r’s | r’s |
| 150 | BGG-10-1649 | r’s | r’s/RHDdel | Present | Present | Absent | Absent | Present | Present | r’s | r’s |
| 151 | BGG-10-1653 | r’s | RHD | Present | Present | Absent | Absent | Present | Present | r’s | r’s |
| 152 | BGG-10-1658 | DIIIa | RHD | Present | Present | Present | Absent | Present | Present | No r’s | r’s |
| 153 | BGG-10-1661 | r’s | r’s/RHDdel | Present | Present | Absent | Absent | Present | Present | r’s | r’s |
| 154 | BGG-10-1683 | DIIIa | RHD | Present | Present | Present | Present | Present | Present | No r’s | No r’s |
| 155 | BGG-10-2038 | r’s | RHD | Present | Present | Absent | Absent | Present | Present | r’s | r’s |
| 156 | BGG-10-2142 | DIIIa | DIIIa/RHDdel | Present | Present | Present | Present | Present | Present | No r’s | No r’s |
| 157 | BGG-10-2144 | DIVa-2 | RHD | Present | Present | Absent | Absent | Absent | Absent | No r’s | No r’s |
| 158 | BGG-10-2153 | r’s | RHD | Present | Present | Absent | Absent | Present | Present | r’s | r’s |
| 159 | BGG-10-2155 | r’s | DVt1/DAU5 | Present | Present | Absent | Absent | Present | Present | r’s | r’s |
| 160 | BGG-10-2212 | r’s | RHD | Present | Present | Absent | Absent | Present | Present | r’s | r’s |
| 161 | BGG-10-2215 | DIIIa | Psi | Present | Present | Present | Present | Present | Present | No r’s | No r’s |
| 162 | BGG-10-2270 | DIIIa | RHD Variant | Present | Present | Present | Present | Present | Present | No r’s | No r’s |
| 163 | BGG-10-2335 | r’s | r’s/RHDdel | Present | Present | Absent | Absent | Present | Present | r’s | r’s |
| 164 | BGG-10-2347 | r’s | RHD | Present | Present | Absent | Absent | Present | Present | r’s | r’s |
| 165 | BGG-10-2366 | r’s | RHD | Present | Present | Absent | Absent | Present | Present | r’s | r’s |
| 166 | BGG-10-2379 | DIIIa | RHD | Present | Present | Present | Present | Present | Present | No r’s | No r’s |
| 167 | BGG-10-2391 | DIIIa | RHD | Present | Present | Present | Present | Present | Present | No r’s | No r’s |
| 168 | BGG-10-2433 | DIIIa | RHD | Present | Present | Present | Absent | Present | Present | No r’s | r’s |
| 169 | BGG-10-2435 | DIIIa | RHD | Present | Present | Present | Present | Present | Present | No r’s | No r’s |
| 170 | BGG-10-2456 | DIIIa | RHD | Present | Present | Present | Present | Present | Present | No r’s | No r’s |
| 171 | BGG-10-2470 | DIIIa | RHD | Present | Present | Present | Present | Present | Present | No r’s | No r’s |
| 172 | BGG-10-3386 | r’s | r’s/RHDdel | Present | Present | Absent | Absent | Present | Present | r’s | r’s |
| 173 | BGG-10-3387 | r’s | RHD | Present | Present | Absent | Absent | Present | Present | r’s | r’s |
| 174 | BGG-10-3400 | r’s | RHD | Present | Present | Absent | Absent | Present | Present | r’s | r’s |
| 175 | BGG-10-3409 | DIIIa | RHD | Present | Present | Present | Present | Present | Present | No r’s | No r’s |
| 176 | BGG-10-3417 | r’s | RHD | Present | Present | Absent | Absent | Present | Present | r’s | r’s |
| 177 | BGG-10-3426 | r’s | RHD | Present | Present | Absent | Absent | Present | Present | r’s | r’s |
| 178 | BGG-10-3427 | r’s | r’s/RHDdel | Present | Present | Absent | Absent | Present | Present | r’s | r’s |
| 179 | BGG-10-3461 | r’s | r’s/RHDdel | Present | Present | Absent | Absent | Present | Present | r’s | r’s |
| 180 | BGG-10-3486 | r’s | RHD | Present | Present | Absent | Absent | Present | Present | r’s | r’s |
| 181 | BGG-10-3529 | RHD | RHD/RHDdel | Present | Present | Absent | Absent | Present | Present | No r’s | No r’s |
| 182 | BGG-10-3539 | r’s | r’s/RHDdel | Present | Present | Absent | Absent | Present | Present | r’s | r’s |
| 183 | BGG-10-3545 | r’s | RHD | Present | Present | Absent | Absent | Present | Present | r’s | r’s |
| 184 | BGG-10-3546 | DIIIa | RHD | Present | Present | Present | Present | Present | Present | No r’s | No r’s |
| 185 | BGG-10-3561 | r’s | r’s/RHDdel | Present | Present | Absent | Absent | Present | Present | r’s | r’s |
| 186 | BGG-10-3714 | DIVa-2 | DIVa-2/RHDdel | Present | Present | Present | Present | Absent | Absent | No r’s | No r’s |
| 187 | BGG-10-3809 | r’s | RHD | Present | Present | Absent | Absent | Present | Present | r’s | r’s |
| 188 | BGG-10-4060 | r’s | r’s/RHDdel | Present | Present | Absent | Absent | Present | Present | r’s | r’s |
| 189 | BGG-10-4080 | DIIIa | RHD | Present | Present | Present | Absent | Present | Present | No r’s | r’s |
| 190 | BGG-10-5191 | RHD | RHD/RHDdel | Absent | Absent | Absent | Absent | Absent | Absent | No r’s | No r’s |
| 191 | BGG-10-5434 | RHDdel | RHDdel | Absent | Absent | Absent | Absent | Absent | Absent | No r’s | No r’s |
| 192 | D114 | DVI | DVI/RHDdel | Absent | Absent | Absent | Absent | Absent | Absent | No r’s | No r’s |
| 193 | D122 | DFR | DFR/RHDdel | Absent | Absent | Absent | Absent | Absent | Absent | No r’s | No r’s |
| 194 | D123 | DIVa-2 | DIVa-2/RHDdel | Present | Present | Absent | Absent | Absent | Absent | No r’s | No r’s |
| 195 | D126 | r’s | DVt1/DAU5 | Present | Present | Absent | Absent | Present | Present | r’s | r’s |
| 196 | D129 | Psi | Psi/RHDdel | Absent | Absent | Absent | Absent | Absent | Absent | No r’s | No r’s |
| 197 | D131 | DOL | DOL/RHDdel | Absent | Absent | Absent | Absent | Absent | Absent | No r’s | No r’s |
| 198 | D133 | DAU0 | DAU0/RHDdel | Absent | Absent | Absent | Absent | Absent | Absent | No r’s | No r s |
| 199 | D138 | RHD Variant | RHDdel | Absent | Absent | Absent | Absent | Absent | Absent | No r’s | No r’s |
| 200 | D140 | wDt5 | wDt5/RHDdel | Absent | Absent | Absent | Absent | Absent | Absent | No r’s | No r’s |
| 201 | D159 | RHD Variant | RHDdel | Absent | Absent | Absent | Absent | Absent | Absent | No r’s | No r’s |
| 202 | D161 | RHD Variant | RHDdel | Absent | Absent | Absent | Absent | Absent | Absent | No r’s | No r’s |
| 203 | D171 | r’s | DAR | Present | Present | Absent | Absent | Present | Present | r’s | r’s |
| 204 | D190 | r’s | DAR | Present | Present | Absent | Absent | Present | Present | r’s | r’s |
| 205 | D193 | DIVa-2 | DIVa-2/RHDdel | Present | Present | Absent | Absent | Absent | Absent | No r’s | No r’s |
| 206 | D195 | RHD | RHD/RHDdel | Absent | Absent | Absent | Absent | Absent | Absent | No r’s | No r’s |
| 207 | D196 | DIVa-2 | DIVa-2/RHDdel | Present | Present | Absent | Absent | Absent | Absent | No r’s | No r’s |
| 208 | D202 | RHD | RHDdel | Absent | Absent | Absent | Absent | Absent | Absent | No r’s | No r’s |
| 209 | D204 | RHDdel | RHDdel | Absent | Absent | Absent | Absent | Absent | Absent | No r’s | No r’s |
| 210 | D213 | r’s | r’s/RHDdel | Present | Present | Absent | Absent | Present | Present | r’s | r’s |
| 211 | D214 | wDt15 | wDt15/RHDdel | Absent | Absent | Absent | Absent | Absent | Absent | No r’s | No r’s |
| 212 | D221 | wDt4.0/4.1 | wDt4.0/4.1/RHDdel | Absent | Absent | Absent | Absent | Present | Present | No r’s | No r’s |
| 213 | D225 | RHD | RHD/RHDdel | Absent | Absent | Absent | Absent | Absent | Absent | No r’s | No r’s |
| 214 | D226 | DAU5 | DAU5/RHDdel | Absent | Absent | Absent | Absent | Absent | Absent | No r’s | No r’s |
| 215 | D227 | DAU5 | DAU5/RHDdel | Absent | Absent | Absent | Absent | Absent | Absent | No r’s | No r’s |
| 216 | D229 | DAU5 | DAU5/RHDdel | Absent | Absent | Absent | Absent | Absent | Absent | No r s | No r’s |

TABLE 4-continued

| | | | | Hyb ex03 | | Hyb in07 sg02 | | Hyb in07 sg04 | | RHD*r's call | |
|---|---|---|---|---|---|---|---|---|---|---|---|
| # | Sample ID | RHO allele #1 | RHD allele #2 | Reference | Method | Reference | Method | Reference | Method | Reference | Method |
| 217 | D230 | wDt4.0/4.1 | wDt4.0/4.1/RHDdel | Absent | Absent | Absent | Absent | Present | Present | No r's | No r's |
| 218 | D231 | RHD | RHD/RHDdel | Absent | Absent | Absent | Absent | Absent | Absent | No r's | No r's |
| 219 | D237 | RHD Variant | RHDdel | Absent | Absent | Absent | Absent | Absent | Absent | No r's | No r's |
| 220 | D239 | DAU5 | DAU5/RHDdel | Absent | Absent | Absent | Absent | Absent | Absent | No r's | No r's |
| 221 | D245 | wDt11 | wDt11/RHDdel | Absent | Absent | Absent | Absent | Absent | Absent | No r's | No r's |
| 222 | D249 | RHD | RHD/RHDdel | Absent | Absent | Absent | Absent | Absent | Absent | No r's | No r's |
| 223 | D261 | RHD | RHD/RHDdel | Absent | Absent | Absent | Absent | Absent | Absent | No r's | No r's |
| 224 | D262 | wDt5 | wDt5/RHDdel | Absent | Absent | Absent | Absent | Absent | Absent | No r's | No r's |
| 225 | D288 | DMH | DMH/RHDdel | Absent | Absent | Absent | Absent | Absent | Absent | No r's | No r's |
| 226 | D289 | RHD Variant | RHDdel | Absent | Absent | Absent | Absent | Absent | Absent | No r's | No r's |
| 227 | D290 | wDt1 | wDt1/RHDdel | Absent | Absent | Absent | Absent | Absent | Absent | No r's | No r's |
| 228 | D291 | wDt2 | wDt2/RHDdel | Absent | Absent | Absent | Absent | Absent | Absent | No r's | No r's |
| 229 | D298 | r's | DAR | Present | Present | Absent | Absent | Present | Present | r's | r's |
| 230 | D300 | RHD Variant | RHDdel | Absent | Absent | Absent | Absent | Absent | Absent | No r's | No r's |
| 231 | D323 | DVI | DVI/RHDdel | Absent | Absent | Absent | Absent | Absent | Absent | No r's | No r's |
| 232 | D328 | wDt4.0/4.1 | wDt4.0/4.1/RHDdel | Absent | Absent | Absent | Absent | Present | Present | No r's | No r's |
| 233 | D329 | wDt4.0/4.1 | wDt4.0/4.1/RHDdel | Absent | Absent | Absent | Absent | Present | Present | No r's | No r's |
| 234 | D330 | DAU5 | DAU5/RHDdel | Absent | Absent | Absent | Absent | Absent | Absent | No r's | No r's |
| 235 | D331 | wDt4.0/4.1 | wDt4.0/4.1/RHDdel | Absent | Absent | Absent | Absent | Present | Present | No r's | No r's |
| 236 | GAL 10701360 | RHD | RHD/RHDdel | Absent | Absent | Absent | Absent | Absent | Absent | No r's | No r's |
| 237 | GAL 10701364 | RHD | RHD/RHDdel | Absent | Absent | Absent | Absent | Absent | Absent | No r's | No r's |
| 238 | GAL 10701365 | RHD | RHD/RHDdel | Absent | Absent | Absent | Absent | Absent | Absent | No r's | No r's |
| 239 | GAL 10701366 | RHD | RHD/RHDdel | Absent | Absent | Absent | Absent | Absent | Absent | No r's | No r's |
| 240 | GAL 10706636 | RHD | RHD/RHDdel | Absent | Absent | Absent | Absent | Absent | Absent | No r's | No r's |
| 241 | GAL 10752569 | RHDdel | RHDdel | Absent | Absent | Absent | Absent | Absent | Absent | No r's | No r's |
| 242 | GAL 10816074 | RHDdel | RHDdel | Absent | Absent | Absent | Absent | Absent | Absent | No r's | No r's |
| 243 | GAL 10833160 | RHDdel | RHDdel | Absent | Absent | Absent | Absent | Absent | Absent | No r's | No r's |
| 244 | GKO 10532283 | RHD | RHD/RHDdel | Absent | Absent | Absent | Absent | Absent | Absent | No r's | No r's |
| 245 | GKO 32588 | RHD | RHD/RHDdel | Absent | Absent | Absent | Absent | Absent | Absent | No r's | No r's |
| 246 | JCX33 | r's | RHD | Present | Present | Absent | Absent | Present | Present | r's | r's |
| 247 | L22 | RHD | RHD/RHDdel | Absent | Absent | Absent | Absent | Absent | Absent | No r's | No r's |
| 248 | L23 | RHDdel | RHDdel | Absent | Absent | Absent | Absent | Absent | Absent | No r's | No r's |
| 249 | L28 | RHD | RHD/RHDdel | Absent | Absent | Absent | Absent | Absent | Absent | No r's | No r's |
| 250 | PGK53 | RHDdel | RHDdel | Absent | Absent | Absent | Absent | Absent | Absent | No r's | No r's |
| 251 | ZGZ 51979 | r's | r's/RHDdel | Present | Present | Absent | Absent | Present | Present | r's | r's |
| 252 | ZGZ 52739 | DIIIa | RHD | Present | Present | Present | Present | Present | Present | No r's | No r's |

For the subset of RHD*r's samples analyzed by ASP in this example, Table 5 shows:

- Number of samples
- Number of genotype calls made
- Number of correct calls made, as determined by comparison to the reference dataset
- Number of False Negative (FN) calls, total
- Number of FN calls, by type:
  - Amplification of segment #2 (sg02)
  - No amplification of segment #4 (sg04)
  - Amplification of sg02 and no amplification of sg04
- FN rate in the detection of the RHD*r's variant.

TABLE 5

False Negative (FN) calls and rate for the determination of RHD*r's.

| | RHD*r'S |
|---|---|
| Samples Analyzed | 82 |
| Calls Made | 82 |
| Correct Calls | 82 |
| FN Calls | 0 |
| FN [sg02+ sg04−] | 0 |
| FN [sg02+] | 0 |
| FN [sg04−] | 0 |
| FN Rate | 0.000 |

For the subsets of non-RHD*r's samples, Hybrid exon 3 (Hex03) samples, and non-RHD*r's & Hex03 samples analyzed by ASP in this example, Table 6 shows the following:

- Number of samples
- Number of genotype calls made
- Number of correct calls made, as determined by comparison to the reference dataset
- Number of false positive (FP) calls
- FP rate in the detection of the RHD*r's variant.

TABLE 6

False Positive (FP) calls and rates for the determination of RHD*r's.

| | non-RHD*r's | Hex03 | Hex03 & non-RHD*r's |
|---|---|---|---|
| Samples Analyzed | 170 | 146 | 64 |
| Calls Made | 170 | 146 | 64 |
| Correct Calls | 159 | 135 | 53 |
| FP Calls | 11 | 11 | 11 |
| FP Rate | 0.065 | 0.075 | 0.172 |

TABLE 7

Primer Sequences

| Primer No. | Sequence | SEQ ID NO: |
|---|---|---|
| 1 | CAAGAGCCACCCAGTCCA | 16 |
| 2 | CCAAGAGCCACTCATTCCG | 17 |
| 3 | ACATGGAGAAGTCATCACACA | 18 |

TABLE 7-continued

Primer Sequences

| Primer No. | Sequence | SEQ ID NO: |
|---|---|---|
| 4 | CATGGAGAAGTCATCACACG | 19 |
| 5 | TGTTGAGCTGAGGGTCTGGT | 20 |
| 6 | TTGAGCTGAGGGTCTGGC | 21 |
| 7 | TTGAGCTGAGGGTCTCGC | 22 |
| 8 | GAATCTTCTGATATCCCCAT | 23 |
| 9 | GAATCTTCTGATATCCCCAC | 24 |
| 10 | GGTTCTGGGTGTTGGTTATA | 25 |
| 11 | GGTTCTGGGTGTTGGTTATG | 26 |
| 12 | CAAAGGCCCTTCCTCCAC | 27 |
| 13 | CAAAGGCCCTTCCTCCAA | 28 |
| 14 | AAAGGCCCTTCCTCCAAAAAC | 29 |
| 15 | AGATTACAGGTGTGCGCCACCAC | 30 |
| 16 | AAAGGCCCTTCCTCCACAAAC | 31 |
| 17 | CAAGCTGTCAAGGAGACATCACTAT | 9 |
| 18 | TTCTGGTAAAGGATTAACTTAACAAA | 32 |
| 19 | ATAGAAAACTGAGATTTAGGGAGTTTG | 33 |
| 20 | CATTACATAGAGATGTCCCCATACT | 10 |
| 21 | GGATTACAGGTGTGCGCCAGAGT | 34 |
| 22 | TGCTGGTAGAGGATTAACTTAACAACT | 35 |
| 23 | TGCTGGTAGAGGATTAACTTAACAACTG | 36 |
| 24 | CAACTGGCTTTCCAAGAAAATAA | 37 |
| 25 | GCCACTTATTACTTAAAAAAACCCCAA | 38 |
| 26 | AAGGCCCTTCCTCCAAATAG | 13 |
| 27 | TTAATCCTTCAATTCATATGTTGATGCTA | 39 |
| 28 | GCCACTTATTACTTAAAAAAACCCC | 12 |
| 29 | GATTATAAGCCTGAGACACCGTGCCTGGCA | 40 |
| 30 | GTGAAGCAAGGTGCCTCTGTA | 41 |
| 31 | ATCTCTTCCCAAGTCCATGTGC | 42 |
| 32 | GAAGCAAGGCGCCTCTGTG | 43 |
| 33 | TCTCATCTCTTCCCAAGTCCATGTAT | 44 |
| 34 | TTTCCCTAGTATATGTAACCATCA | 45 |
| 35 | GGAAAAGGTTTGAGAGGAATTATAC | 46 |
| 36 | TTTCCCTAGTATATGTAACCATCG | 47 |
| 37 | GGAAAAGGTTTGAGAGGAATTATAT | 48 |
| 38 | CACATTACATAGAGATGTCCCCATACT | 78 |
| 39 | GCCACTTATTACTTAAAAAAACCCC | 79 |
| 40 | CTGAGTCAGATGCTGTGATCAGAG | 81 |

TABLE 8

Probe Sequences

| Probe No. | Sequence | SEQ ID NO: |
|---|---|---|
| 1 | GGTACTCAAACTCCCTAAATC | 49 |
| 2 | GATTTAGGGAGTTTGAGTACC | 50 |
| 3 | GTACTCAAACTCCCTAAAT | 51 |
| 4 | ATTTAGGGAGTTTGAGTAC | 52 |
| 5 | TACTCAAACTCCCTAAA | 53 |
| 6 | TTTAGGGAGTTTGAGTA | 54 |
| 7 | TGGTACTCAAACTCCCTAAATCT | 55 |
| 8 | CTGGTACTCAAACTCCCTAAATCTC | 56 |
| 9 | CCTGGTACTCAAACTCCCTAAATCTCA | 11 |
| 10 | TGCCAGGCACGGTGTCTCAGGCT | 57 |
| 11 | TGCCAGGCACGGTGTCTCAGG | 58 |
| 12 | AGCCTGAGACACCGTGCCTGGCA | 59 |
| 13 | CCTGAGACACCGTGCCTGGCA | 60 |
| 14 | TGCCCTCTCACTGTGTGATGACT | 61 |
| 15 | GCCCTCTCACTGTGTGATGAC | 62 |
| 16 | AGTCATCACACAGTGAGAGGGCA | 63 |
| 17 | GTCATCACACAGTGAGAGGGC | 64 |
| 18 | TTATGCCAGGCACGGTGTCTCAGGCTT | 65 |
| 19 | GAAGTCATCACACAGTGAGAGGGCAGA | 66 |
| 20 | AGGCACGGTGTCTCAGGCTTATAAT | 67 |
| 21 | TCTGATATCCCCATATAACCAACACCC | 68 |
| 22 | GGGTGTTGGTTATATGGGGATATCAGA | 69 |
| 23 | CTGATATCCCCATATAACCAACACC | 70 |
| 24 | GGTGTTGGTTATATGGGGATATCAG | 71 |
| 25 | CCCCCAAATTTCATGTGCTAGAAACTT | 72 |
| 26 | AAGTTTCTAGCACATGAAATTTGGGGG | 73 |
| 27 | CCCAAATTTCATGTGCTAGAAACTT | 74 |
| 28 | AAGTTTCTAGCACATGAAATTTGGG | 75 |
| 29 | AATTTCATGTGCTGGAAACTTAATCCT | 14 |
| 30 | AGGATTAAGTTTCCAGCACATGAAATT | 76 |
| 31 | ATTTCATGTGCTGGAAACTTAATCC | 15 |
| 32 | GGATTAAGTTTCCAGCACATGAAAT | 77 |
| 33 | ATTTCATGTGCTGGAAACTTAATCC | 80 |

REFERENCES

1. DIIIa and DIII Type 5 are encoded by the same allele and are associated with altered RHCE*ce alleles: clinical implications. Connie M. Westhoff, Sunitha Vege, Christine Halter-Hipsky, Trina Whorley, Kim Hue-Roye, Christine Lomas-Francis, and Marion E. Reid. Transfusion (2010) 50, pp. 1303-1311.

2. Heterogeneous molecular background of the weak C, VS+, hrB−, HrB− phenotype in black persons. Bach-Nga Pham, Thierry Peyrard, Genevieve Juszczak, Isabelle Dubeaux, Dominique Gien, Antoine Blancher, Jean-Pierre Cartron, Philippe Rouger, and Pierre-Yves Le Pennec. Transfusion (2009) 49, pp. 495-504.

3. RHC and RHc genotyping in different ethnic groups. Martine G. H. M. Tax, C. Ellen van der Schoot, Rene' van Doorn, Lotte Douglas-Berger, Dick J. van Rhenen, and Petra A. Maaskant-van Wijk. Transfusion (2002) 42, pp. 6234-644.

The invention claimed is:

1. A method for determining the presence or absence of, or for discriminating between, blood type alleles, which method comprises:

providing a DNA-containing sample obtained from a human subject;

amplifying a first segment of intron 7 of the RHD locus by allele-specific polymerase chain reaction (PCR) using a first primer comprising the nucleotide sequence of SEQ ID NO: 9 and a second primer comprising the nucleotide sequence of SEQ ID NO: 10, thereby genotyping the sample at at least the TIC polymorphic site at IVS7+1887 and at the C/A polymorphic site at IVS7+2276;

amplifying a second segment of intron 7 of the RHD locus by allele-specific PCR using a first primer comprising the nucleotide sequence of SEQ ID NO: 12 and a second primer comprising the nucleotide sequence of SEQ ID NO: 13;

probing said amplified second segment by allele-specific hybridization using an oligonucleotide probe having the nucleotide sequence of SEQ ID NO: 70, thereby genotyping the sample at at least the C/T polymorphic site at IVS7+3349; and predicting the blood type allele of the human subject using the genotype of the sample at said polymorphic positions at IVS7+1887, IVS7+2276 and IVS7+3349.

2. The method according to claim 1, wherein said blood type alleles are alleles that comprise an RHD/RHCE hybrid exon 3.

3. The method according to claim 1, wherein said blood type alleles are selected from the group consisting of: RHD*r's; RHD*DIIIa; RHD*DIII_FN; RHD*DIVa-2; and RHCE*ce$^S$.

4. The method according to claim 1, wherein said method further comprises genotyping the sample at one or more polymorphic positions in intron 7 of the RHD gene locus, said one or more polymorphic positions being selected from: IVS7+1869, IVS7+1880, IVS7+1886, IVS7+2282, IVS7+3257, IVS7+3258, IVS7+3259, IVS7+3260, IVS7+3489, IVS7+3521, IVS7+3523, and IVS7+3525.

5. The method according to claim 1, wherein the method further comprises determining whether the sample contains an RHD-RHCE hybrid exon 3.

6. The method according to claim 5, wherein the method comprises genotyping the sample at one or more polymorphic positions selected from:

IVS2-26, IVS2-13, IVS2-8 in RHD intron 2;

IVS3+64, IVS3+69 in RHD intron 3; and position 410 in RHD exon 3.

7. The method according to claim 1, wherein the method comprises genotyping not more than 50, 40, 30, 25, 20, 15, or not more than 10, single nucleotide polymorphic positions in the RHD gene locus and/or the RHCE gene locus.

8. The method according to claim 1, wherein the method further comprises predicting an RHD phenotype and/or an RHCE phenotype for the subject based on the genotype of the sample.

9. The method according to claim 1, wherein the method further comprises determining whether the sample contains an RHD-RHCE hybrid exon 3, and wherein DNA obtained from said sample is amplified using primers that are selective for RHD/RHCE hybrid exon 3 and wherein said primers that are selective for RHD/RHCE hybrid exon 3 are selected from: a primer comprising the nucleotide sequence of SEQ ID NO: 5 and a primer comprising the nucleotide sequence of SEQ ID NO: 6.

10. The method according to claim 9, wherein said method further comprises genotyping the sample at a polymorphic position in exon 3 of the RHD locus, and wherein the method comprises an allele-specific hybridisation of DNA extracted from the sample, or an amplicon derived from DNA extracted from the sample, and wherein the allele-specific hybridisation comprises contacting said extracted DNA or said amplicon with a probe selected from: a probe comprising the sequence of SEQ ID NO: 7 and a probe comprising the sequence of SEQ ID NO: 8.

11. The method according to claim 1, further comprising genotyping the sample at one or more additional positions selected from the group consisting of IVS7+1869, IVS7+1880, IVS7+1886, IVS7+2276, IVS7+2282, and IVS7+3489.

12. The method according to claim 1, wherein the sample is determined to comprise C at position IVS7+1887, A at position IVS7+2276 and T at position IVS7+3349 and wherein the subject is predicted to have at least one RHD*r'$^S$ blood type allele.

13. The method according to claim 1, wherein the sample is determined to comprise T at position IVS7+1887, A at position IVS7+2276 and T at position IVS7+3349 and wherein the subject is predicted to have at least one RHD*DIIIa blood type allele.

14. The method according to claim 1, wherein the sample is determined to comprise T at position IVS7+1887, C at position IVS7+2276 and T at position IVS7+3349 and wherein the subject is predicted to have at least one RHD*DIII_FN blood type allele.

15. The method according to claim 1, wherein the sample is determined to comprise T at position IVS7+1887, C at position IVS7+2276 and C at position IVS7+3349 and wherein the subject is predicted to have at least one RHD*DIVa-2 blood type allele.

* * * * *